United States Patent
Seidel, III et al.

(10) Patent No.: US 12,029,782 B2
(45) Date of Patent: Jul. 9, 2024

(54) MHC CLASS II T-CELL MODULATORY MULTIMERIC POLYPEPTIDES FOR TREATING TYPE 1 DIABETES MELLITUS (T1D) AND METHODS OF USE THEREOF

(71) Applicant: Cue Biopharma, Inc., Boston, MA (US)

(72) Inventors: Ronald D. Seidel, III, Boston, MA (US); Rodolfo J. Chaparro, Cambridge, MA (US); John F. Ross, Boston, MA (US); Chee Meng Low, Boston, MA (US)

(73) Assignee: Cue Biopharma, Inc., Boston, MA (US)

( * ) Notice: Subject to any disclaimer, the term of this patent is extended or adjusted under 35 U.S.C. 154(b) by 0 days.

(21) Appl. No.: 18/218,943

(22) Filed: Jul. 6, 2023

(65) Prior Publication Data

US 2023/0346900 A1 Nov. 2, 2023

Related U.S. Application Data

(63) Continuation of application No. 18/107,244, filed on Feb. 8, 2023, which is a continuation of application No. PCT/US2021/049485, filed on Sep. 8, 2021.

(60) Provisional application No. 63/076,310, filed on Sep. 9, 2020.

(51) Int. Cl.
| | |
|---|---|
| C07K 14/62 | (2006.01) |
| A61K 39/00 | (2006.01) |
| A61P 3/10 | (2006.01) |
| A61P 37/06 | (2006.01) |
| C07K 7/08 | (2006.01) |
| C07K 14/495 | (2006.01) |
| C07K 14/525 | (2006.01) |
| C07K 14/55 | (2006.01) |
| C07K 14/705 | (2006.01) |
| C07K 14/74 | (2006.01) |
| C12N 9/88 | (2006.01) |

(52) U.S. Cl.
CPC ............ *A61K 39/0008* (2013.01); *A61P 3/10* (2018.01); *A61P 37/06* (2018.01); *C07K 7/08* (2013.01); *C07K 14/495* (2013.01); *C07K 14/525* (2013.01); *C07K 14/55* (2013.01); *C07K 14/62* (2013.01); *C07K 14/70532* (2013.01); *C07K 14/70539* (2013.01); *C12N 9/88* (2013.01); *C12Y 401/01015* (2013.01); *A61K 2039/577* (2013.01); *A61K 2039/605* (2013.01); *A61K 2039/645* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,635,363 A | 6/1997 | Altman et al. |
| 6,197,302 B1 | 3/2001 | Hirsch et al. |
| 6,211,342 B1 | 4/2001 | Hirsch et al. |
| 6,268,411 B1 | 7/2001 | Schneck et al. |
| 6,322,789 B1 | 11/2001 | Vitiello et al. |
| 6,600,012 B1 | 7/2003 | Agrawal et al. |
| 6,696,304 B1 | 2/2004 | Davies |
| 7,098,306 B2 | 8/2006 | Economou et al. |
| 7,186,804 B2 | 3/2007 | Gillies et al. |
| 7,432,351 B1 | 10/2008 | Chen |
| 7,670,595 B2 | 3/2010 | Gillies et al. |
| 8,435,494 B2 | 5/2013 | Gelfand |
| 8,992,937 B2 | 3/2015 | Hansen et al. |
| 9,284,349 B2 | 3/2016 | Tsunoda et al. |
| 9,359,424 B2 | 6/2016 | Maoult et al. |
| 9,494,588 B2 | 11/2016 | Springer et al. |
| 10,059,750 B2 | 8/2018 | Davis et al. |
| 10,272,042 B2 | 4/2019 | Daftarian et al. |
| 10,501,521 B2 | 12/2019 | Georges et al. |
| 10,927,158 B2 | 2/2021 | Seidel et al. |
| 10,927,161 B2 | 2/2021 | Seidel et al. |
| 11,117,945 B2 | 9/2021 | Seidel et al. |
| 11,370,821 B2 | 6/2022 | Seidel et al. |
| 11,377,478 B2 | 7/2022 | Seidel et al. |
| 11,380,821 B2 | 7/2022 | Jia et al. |
| 11,479,595 B2 | 10/2022 | Seidel, III et al. |
| 11,505,588 B2 | 11/2022 | Seidel, III et al. |

(Continued)

FOREIGN PATENT DOCUMENTS

| | | |
|---|---|---|
| CN | 101418309 | 4/2009 |
| EP | 2998740 | 3/2016 |

(Continued)

OTHER PUBLICATIONS

Favier, et al.; "Tolerogenic Function of Dimeric Forms of HLA-G Recombinant Proteins: A Comparative Study In Vivo"; PLoS One; vol. 6, No. 7, 26 pages (Jul. 2011).
Ackerman, et al.; "Highly Avid Magnetic Bead Capture: An Efficient Selection Method for de novo Protein Engineering Utilizing yeast Surface Display"; Biotechnol. Prog.; vol. 25, No. 3, pp. 774-783 (2009).
Aina, et al.; "Identification of novel targeting peptides for human ovarian cancer cells using 'one-bead one-compount' combinatorial libraries"; Mol. Cancer Ther.; vol. 4, No. 5, 8 pages (May 2005).
Arduin, et al.; "Highly reduced binding to high and low affinity mouse Fc gamma receptors by L234A/L235A and N297A Fc mutations engineered into mouse IgG2a"; Molecular Immunology; vol. 63, pp. 456-463 (Feb. 2015).

(Continued)

*Primary Examiner* — G. R. Ewoldt
(74) *Attorney, Agent, or Firm* — Bozicevic, Field & Francis LLP; James J. Diehl

(57) ABSTRACT

The present disclosure provides T-cell modulatory multimeric polypeptides (TMMPs) comprising a type 1 diabetes (T1D)-associated peptide epitope, MHC class II polypeptides, and PD-L1 polypeptides. A TMMP of the present disclosure is useful for modulating activity of a T cell. Thus, the present disclosure provides compositions and methods for modulating the activity of T cells, as well as compositions and methods for treating persons who have T1D.

2 Claims, 106 Drawing Sheets

Specification includes a Sequence Listing.

(56) References Cited

U.S. PATENT DOCUMENTS

| | | |
|---|---|---|
| 11,530,248 B2 | 12/2022 | Seidel, III et al. |
| 11,708,400 B2 | 7/2023 | Seidel et al. |
| 11,739,133 B2 | 8/2023 | Seidel, III et al. |
| 11,767,355 B2 | 9/2023 | Seidel, III et al. |
| 11,851,467 B2 | 12/2023 | Seidel, III et al. |
| 11,878,062 B2 | 1/2024 | Cemerski et al. |
| 2002/0006664 A1 | 1/2002 | Sabatini |
| 2002/0031520 A1 | 3/2002 | Economou et al. |
| 2002/0165136 A1 | 11/2002 | Baserga et al. |
| 2003/0235536 A1 | 12/2003 | Blumberg et al. |
| 2004/0038349 A1 | 2/2004 | Hilbert et al. |
| 2004/0132977 A1 | 7/2004 | Gantier et al. |
| 2004/0161817 A1 | 8/2004 | Benton et al. |
| 2004/0209363 A1 | 10/2004 | Watts et al. |
| 2005/0003431 A1 | 1/2005 | Wucherpfennig et al. |
| 2005/0009012 A1 | 1/2005 | Holzberg et al. |
| 2005/0100926 A1 | 5/2005 | Hedley et al. |
| 2005/0142142 A1 | 6/2005 | Burrows et al. |
| 2006/0034865 A1 | 2/2006 | Hildebrand et al. |
| 2006/0269515 A1 | 11/2006 | Deniz-Mize et al. |
| 2007/0036752 A1 | 2/2007 | Gillies et al. |
| 2007/0148162 A1 | 6/2007 | Bhardwaj et al. |
| 2007/0286843 A1 | 12/2007 | Pfizenmaier et al. |
| 2008/0199485 A1 | 8/2008 | Kundig et al. |
| 2008/0219947 A1 | 9/2008 | Linette et al. |
| 2008/0269070 A1 | 10/2008 | Ramseier et al. |
| 2010/0159594 A1 | 6/2010 | Hansen et al. |
| 2010/0190720 A1 | 7/2010 | Hollingsworth et al. |
| 2010/0226854 A1 | 9/2010 | Schøller et al. |
| 2011/0002956 A1 | 1/2011 | Weiner et al. |
| 2011/0268737 A1 | 11/2011 | Favier et al. |
| 2011/0318380 A1 | 12/2011 | Brix et al. |
| 2012/0003220 A1 | 1/2012 | Chen |
| 2012/0121577 A1 | 5/2012 | Weidanz et al. |
| 2012/0177595 A1 | 7/2012 | Wong et al. |
| 2012/0264161 A1 | 10/2012 | Scholler et al. |
| 2013/0017199 A1 | 1/2013 | Langermann |
| 2013/0149305 A1 | 6/2013 | Ostrand-Rosenberg |
| 2014/0046026 A1 | 2/2014 | Garcia et al. |
| 2014/0162293 A1 | 6/2014 | Springer et al. |
| 2014/0242077 A1 | 8/2014 | Choi et al. |
| 2015/0071987 A1 | 3/2015 | Selvaraj |
| 2015/0224186 A1 | 8/2015 | Nakagawa |
| 2015/0232532 A1 | 8/2015 | Ostrand-Rosenberg |
| 2015/0352201 A1 | 12/2015 | David et al. |
| 2015/0374788 A1 | 12/2015 | Paulsen et al. |
| 2016/0011204 A1 | 1/2016 | Almo et al. |
| 2016/0083477 A1 | 3/2016 | Klein et al. |
| 2016/0090407 A1 | 3/2016 | Hosse et al. |
| 2016/0114019 A1 | 4/2016 | Li et al. |
| 2016/0152725 A1 | 6/2016 | Cheung et al. |
| 2016/0175397 A1 | 6/2016 | Umana et al. |
| 2016/0304580 A1 | 10/2016 | Ellmark et al. |
| 2016/0362465 A1 | 12/2016 | Nishimura et al. |
| 2017/0044229 A1 | 2/2017 | Garcia et al. |
| 2017/0058015 A1 | 3/2017 | Seidel, III et al. |
| 2017/0334951 A1 | 11/2017 | O'Reilly et al. |
| 2018/0044404 A1 | 2/2018 | Oda et al. |
| 2018/0064795 A1 | 3/2018 | Sugiyama |
| 2018/0086832 A1 | 3/2018 | Vogelstein et al. |
| 2018/0127481 A1 | 5/2018 | Santamaria |
| 2018/0208626 A1 | 7/2018 | Scheinberg et al. |
| 2018/0282392 A1 | 10/2018 | Seidel, III et al. |
| 2018/0339030 A1 | 11/2018 | Scheinberg |
| 2019/0046648 A1* | 2/2019 | Seidel, III .............. A61K 47/65 |
| 2019/0119377 A1 | 4/2019 | Spirig et al. |
| 2020/0317747 A1 | 10/2020 | Seidel, III et al. |
| 2020/0369745 A1 | 11/2020 | Seidel, III et al. |
| 2021/0284709 A1 | 9/2021 | Brandt et al. |
| 2021/0393693 A1 | 12/2021 | Seidel, III et al. |
| 2022/0008467 A1 | 1/2022 | Seidel, III et al. |
| 2022/0079985 A1 | 3/2022 | Seidel, III et al. |
| 2022/0143063 A1 | 5/2022 | Seidel, III et al. |
| 2022/0162314 A1 | 5/2022 | Yeung et al. |
| 2022/0251202 A1 | 8/2022 | Djuretic et al. |
| 2022/0409732 A1 | 12/2022 | MacDonald et al. |
| 2023/0117521 A1 | 4/2023 | Seidel, III et al. |
| 2023/0126199 A1 | 4/2023 | Hanayama et al. |
| 2023/0139456 A1 | 5/2023 | Cemerski et al. |
| 2024/0025964 A1 | 1/2024 | Seidel, III et al. |
| 2024/0067700 A1 | 2/2024 | Seidel, III et al. |

FOREIGN PATENT DOCUMENTS

| | | | |
|---|---|---|---|
| EP | 3596118 | 1/2020 | |
| JP | 2012516854 | 7/2012 | |
| WO | WO 1997/028191 | 8/1997 | |
| WO | WO 2001/090747 | 11/2001 | |
| WO | WO 2002/072631 | 9/2002 | |
| WO | WO 2002/087613 | 11/2002 | |
| WO | WO 2002/093129 | 11/2002 | |
| WO | WO 2002/102299 | 12/2002 | |
| WO | WO 2003/048334 | 6/2003 | |
| WO | WO 2004/029197 | 4/2004 | |
| WO | WO 2004/111190 | 12/2004 | |
| WO | WO 2007/136778 | 11/2007 | |
| WO | WO 2008/019888 | 2/2008 | |
| WO | WO 2008/113970 | 9/2008 | |
| WO | WO 2008/116468 | 10/2008 | |
| WO | WO 2008/134461 | 11/2008 | |
| WO | WO 2009/023270 | 2/2009 | |
| WO | WO 2010/037395 | 4/2010 | |
| WO | WO 2010/085495 | 7/2010 | |
| WO | WO 2010/091122 | 8/2010 | |
| WO | WO 2011/066342 | 6/2011 | |
| WO | WO 2011/066389 | 6/2011 | |
| WO | WO 2012/007951 | 1/2012 | |
| WO | WO 2012/107417 | 2/2012 | |
| WO | WO 2012/146628 | 4/2012 | |
| WO | WO 2012/127464 | 9/2012 | |
| WO | WO 2012/175508 | 12/2012 | |
| WO | WO 2013/003761 | 1/2013 | |
| WO | WO 2013/079174 | 6/2013 | |
| WO | WO 2014/083004 | 6/2014 | |
| WO | WO 2014/093118 | 6/2014 | |
| WO | WO 2014/145806 | 9/2014 | |
| WO | WO 2015/007903 | 1/2015 | |
| WO | WO 2015/112541 | 7/2015 | |
| WO | WO 2015/164815 | 10/2015 | |
| WO | WO 2015/195531 | 12/2015 | |
| WO | WO 2016/000619 | 1/2016 | |
| WO | WO 2016/014428 | 1/2016 | |
| WO | WO 2016/025642 | 2/2016 | |
| WO | WO 2016/029043 | 2/2016 | |
| WO | WO 2016/030350 | 3/2016 | |
| WO | WO 2016/141357 | 9/2016 | |
| WO | WO 2016/164937 | 10/2016 | |
| WO | WO 2016/168771 | 10/2016 | |
| WO | WO 2016/198932 | 12/2016 | |
| WO | WO 2017/008844 | 1/2017 | |
| WO | WO 2017/023779 | 2/2017 | |
| WO | WO 2017/059819 | 4/2017 | |
| WO | WO 2017/120222 | 7/2017 | |
| WO | WO 2017/151818 | 9/2017 | |
| WO | WO 2017/151940 | 9/2017 | |
| WO | WO 2017/201131 | 11/2017 | |
| WO | WO 2017/201210 | 11/2017 | |
| WO | WO 2018/119114 | 6/2018 | |
| WO | WO 2018/165631 | 9/2018 | |
| WO | WO 2018/170168 | 9/2018 | |
| WO | WO 2018/170475 | 9/2018 | |
| WO | WO 2019/038230 | 2/2019 | |
| WO | WO 2019/051091 | 3/2019 | |
| WO | WO 2019/051126 | 3/2019 | |
| WO | WO 2019/051127 | 3/2019 | |
| WO | WO-2019051094 A1 * | 3/2019 | ............ A61K 35/17 |
| WO | WO 2019/139896 | 7/2019 | |
| WO | WO 2019/162937 | 8/2019 | |
| WO | WO 2020/243315 | 12/2020 | |
| WO | WO 2020/247843 | 12/2020 | |
| WO | WO 2020/257191 | 12/2020 | |
| WO | WO 2021/055594 | 3/2021 | |
| WO | WO 2021/081232 | 4/2021 | |
| WO | WO 2021/081239 | 4/2021 | |

(56) References Cited

FOREIGN PATENT DOCUMENTS

| WO | WO 2021/127495 | 6/2021 | | |
|---|---|---|---|---|
| WO | WO 2021/172596 | 9/2021 | | |
| WO | WO 2021/209759 | 10/2021 | | |
| WO | WO 2022/015880 | 1/2022 | | |
| WO | WO 2022/087458 | 4/2022 | | |
| WO | WO-2022099156 A2 * | 5/2022 | ........... | A61K 31/519 |
| WO | WO 2022/125694 | 6/2022 | | |
| WO | WO 2022/125711 | 6/2022 | | |

OTHER PUBLICATIONS

Azuma, et al.; "B7-H1 is a ubiquitous antiapoptotic receptor on cancer cells"; Immunobiology; vol. 111, No. 7, pp. 3635-3643 (Apr. 1, 2008).

Baldi, et al.; "Recombinant protein production by large-scale transient gene expression in mammalian cells: state of the art and future perspectives"; Biotechnol. Lett.; vol. 29, pp. 677-684 (2007).

Bowers, et al.; "Coupling mammalian cell surface display with somatic hypermutation for the discovery and maturation of human antibodies"; PNAS; vol. 108, No. 51, pp. 20455-20460 (Dec. 20, 2011).

Bresson, et al; "Anti-CD3 and nasal proinsulin combination therapy enhances remission from recent-onset autoimmune diabetes by inducing Tregs"; The Journal of Clinical Investigation; vol. 116, No. 5, pp. 1371-1381 (May 2006).

Brophy, et al.; "A yeast display system for engineering functional peptide-MHC complexes"; Journal of Immunological Methods; vol. 272, pp. 235-246 (2003).

Buonaguro, et al.; "Translating Tumor Antigens into Cancer Vaccines"; Clinical and Vaccine Immunology; vol. 18, No. 1, pp. 23-24 (Jan. 2011).

Büttner; "Cell-based assays for high-throughput screening"; Expert Opin. Drug Discov..; vol. 1, No. 4, pp. 301-306 (Sep. 2006).

Card, et al.; "A soluble single-chain T-cell receptor IL-2 fusion protein retains MHC-restricted peptide specificity and IL-2 bioactivity"; Cancer Immunol Immunother; vol. 53, pp. 345-357 (Nov. 11, 2003).

Cafri, et al.; "Development of novel genetic cancer vaccines based on membrane-attached β2 microglobulin"; Ann. N.Y. Acad. Sci.; vol. 1283, pp. 87-90 (2013).

Carey, et al.; "A soluble divalent class I MHC/IgG1 fusion protein activates CD8+ T cells in vivo"; Clinical Immunology; vol. 116, pp. 65-76 (2005).

Casares, et al.; "A Peptide-Major Histocompatibility Complex II Chimera Favors Survival of Pancreatic β-Islets Grafted in Type 1 Diabetic Mice"; Transplantation; vol. 85, No. 12, pp. 1717-1725 (Jun. 27, 2008).

Cebecauer, et al.; "Soluble MHC-Peptide Complexes Induce Rapid Death of CD8+ CTL"; The Journal of Immunology; vol. 174, pp. 6809-6819 (2005).

Celis, et al.; "Identification of Potential CTL Epitopes of Tumor-Associated Antigen Mage-1 for Five Common HLA-A Alleles"; Molecular Immunology; vol. 31, No. 18, pp. 1423-1430 (1994).

Center for Disease Control and Prevention; "How Many Cancers are Linked with HPV Each Year?"; 4 pages (2016).

Chames, et al.; "Bispecific antibodies for cancer therapy; The light at the end of the tunnel?" mAbs; vol. 1, No. 6, pp. 539-547 (Nov.-Dec. 2009).

Cheever, et al.; "The Prioritization of Cancer Antigens: A National Cancer Institute Pilot Project for the Acceleration of Translational Research"; Clinical Cancer Research; vol. 15, No. 17, pp. 5324-5337 (Sep. 1, 2009).

Crawford, et al.; "Use of baculovirus MHC/ peptide display libraries to characterize T-cell receptor ligands"; Immunological Reviews; vol. 210, pp. 156-170 (2006).

Crisci, et al.; "Virus-like particles: The new frontier of vaccines for animal viral infections"; Veterinary Immunology and Immunopathology; vol. 148, pp. 211-225 (2012).

Czajkowsky, et al.; "Fc-fusion proteins: new developments and future perspectives"; EMBO Mol. Med.; vol. 4, pp. 1015-1028 (2012).

Das, et al.; "Generation of murine tumor cell lines deficient in MHC molecule surface expression using the CRISPR/Cas9 system"; PLoS One; vol. 12, No. 3, 19 pages (Mar. 16, 2017).

De Charette, et al.; "Turning tumour cells into antigen presenting cells: The next step to improve cancer immunotherapy?"; European Journal of Cancer; vol. 68, pp. 134-147 (Oct. 2016).

Desmond, et al.; "A systematic review of T-cell epitopes in hepatitis B virus: identification, genotypic variation and relevance to antiviral therapeutics"; Antiviral Therapy; vol. 13, pp. 161-175 (2008).

Dimasi, et al.; "The design and characterization of oligospecific antibodies for simultaneous targeting of multiple disease mediators"; Journal of Molecular Biology; 393(3): p. 672-692 (2009).

Doussal, et al.; "Phage display of peptide /major histocompatibility complex"; Journal of Immunological Methods; vol. 241, pp. 147-158 (2000).

Dulberger, et al.; "Human leukocyte antigen F (HLA-F) presents peptides and regulates immunity through interactions with NK-cell receptors"; Immunity; vol. 46, No. 6, pp. 1018-1027 (Jun. 20, 2017).

Durinovic-Bello, et al.; "DRB1*0401-restricted human T cell clone specific for the major proinsulin73-90 epitope expresses a down-regulatory T helper 2 phenotype"; PNAS; vol. 103, No. 31, pp. 11683-11688 (Aug. 1, 2006).

Emboss Needle; 2 pages (Feb. 10, 2022).

Edwards, et al.; "The Remarkable Flexibility of the Human Antibody Repertoire; Isolation of Over One Thousand Different Antibodies to a Single Protein, BLyS"; J. Mol. Biol.; vol. 334, pp. 103-118 (2003).

Engelhard; "Structure of peptides associated with MHC class I molecules"; Current Opinion in Immunology; vol. 6, pp. 13-23 (1994).

Engler, et al.; "Peptide vaccines against hepatitis B virus: from animal model to human studies"; Molecular Immunology; vol. 38, pp. 457-465 (Dec. 2001).

Genbank:NP_001300958.1; "programmed cell death 1 ligand 1 isoform c precursor [Homo sapiens]"; 3 pages (Jun. 9, 2021).

Goel, et al.; "Plasticity within the Antigen-Combining Site May Manifest as Molecufar Mimicry in the Humoral Immune Response"; The Journal of Immunology; vol. 173, pp. 7358-7367 (2004).

Gojanovich, et al.; "The Use of Peptide-Major-Histocompatibility-Complex Multimers in Type 1 Diabetes Mellitus"; Journal of Diabetes Science and Technology; vol. 6, No. 3, pp. 515-524 (May 2012).

Gough, et al.; "The HLA Region and Autoimmune Disease: Associations and Mechanisms of Action"; Current Genomics; vol. 8, pp. 453-465 (2007).

Greten, et al.; "Peptide-β2-microglobulin-MHC fusion molecules bind antigen-specific T cells and can be used for multivalent MHC-Ig complexes"; Journal of Immunological Methods; vol. 271, pp. 125-135 (2002).

Grupp, et al.; "Adoptive Cellular Therapy"; Curr Top Microbiol Immunol.; 344: p. 149-172 (2011).

Guo, et al.; "Different length peptides bind to HLA-Aw68 similarly at their ends but bulge out in the middle"; Nature; vol. 360, pp. 364-366 (Nov. 26, 1992).

Hansen, et al.; "Phage display of peptide/major histocompatibility class I complexes"; Eur. J. Immunol.; vol. 31, pp. 32-38 (2001).

Huang, et al.; "Bone regeneration in a rat cranial defect with delivery of PEI-condensed plasmid DNA encoding for bone morphogenetic protein-4 (BMP-4)"; Gene Therapy; vol. 12, No. 5, p. 418 (2005).

Huang, et al.; "Cancer immunotherapy using a DNA vaccine encoding a single-chain trimer of MHC class I linked to an HPV-16 E6 immunodominant CTL epitope"; Gene Ther.; vol. 12, No. 15, pp. 1180-1186 (Aug. 2005).

Hug, et al.; "T-cadherin is a receptor for hexameric and high-molecular-weight forms of Acrp30/adiponectin"; PNAS; vol. 101, No. 28, pp. 10308-10313 (Jul. 13, 2004).

Hugues, et al.; "Generation and use of alternative multimers of peptide/MHC complexes"; Journal of Immunological Methods; vol. 268, pp. 83-92 (2002).

(56) References Cited

OTHER PUBLICATIONS

Judkowski, et al.; "Identification of MHC Class II-Restricted Peptide Ligands, Including a Glutamic Acid Decarboxylase 65 Sequence, that Stimulate Diabetogenic T Cells from Transgenic BDC2.5 Nonobese Diabetic Mice"; The Journal of Immunology; vol. 166, pp. 908-917 (2001).

Karaki, et al.; "Is There Still Room for Cancer Vaccines at the Era of Checkpoint Inhibitors"; Vaccines; vol. 4, No. 37, 24 pages (2016).

Karin, et al.; "Reversal of Experimental Autoimmune Encephalomyelitis by a Soluble Peptide Variant of a Myelin Basic Protein Epitope: T Cell Receptor Antagonism and Reduction of Interferon $\gamma$ and Tumor Necrosis Factor $\alpha$ Production"; J. Exp. Med.; vol. 180, pp. 2227-2237 (Dec. 1994).

Khan, et al.; "Adjustable Locks and Flexible Keys: Plasticity of Epitope-Paratope Interactions in Germline Antibodies"; The Journal of Immunology; vol. 192, pp. 5398-5405 (2014).

Kim, et al.; "Single chain MHC I trimer-based DNA vaccines for protection against *Listeria monocytogenes* infection"; Vaccine; vol. 30, pp. 2178-2186 (2012).

Krautwurst, et al.; "Identification of Ligands for Olfactory Receptors by Functional Expression of a Receptor Library"; Cell; vol. 95, pp. 917-926 (Dec. 23, 1998).

Kreiter, et al.; "Increased Antigen Presentation Efficiency by Coupling Antigens to MHC Class I Trafficking Signals"; The Journal of Immunology; vol. 180, No. 1, pp. 309-318 (Jan. 1, 2008).

Kushnir, et al.; "Virus-like particles as a highly efficient vaccine platform: Diversity of targets and production systems and advances in clinical development"; Vaccine; vol. 31, pp. 58-83 (2012).

Lazar-Molnar, et al.; "Crystal structure of the complex between programmed death-1 (PD-1) and its ligand PD-L2"; PNAS; vol. 105, No. 30, pp. 10483-10488 (Jul. 29, 2008).

Lazar-Molnar, et al.; "The PD-1/PD-L costimulatory pathway critically affects host resistance to the pathogenic fungus *Histoplasma capsulatum*"; PNAS; vol. 105, No. 7, pp. 2658-2663 (Feb. 19, 2008).

Lenormand, et al.; "HLA-DQA2 and HLA-DQB2 Genes are Specifically Expressed in Human Langerhans Cells and Encode a New HLA Class II Molecule"; The Journal of Immunology; vol. 199, No. 8, pp. 3903-3911 (Apr. 15, 2012).

Li, et al.; "Chain A, anti-connexin26 scFv,Ig heavy chain,Linker,anti-connexin26 scFv,Ig light chain"; Accession 5WYM_A, Front Mol Neurosci 10, 298, 3 pages (Jan. 13, 2017).

Li, et al.; "Suppression of Ongoing T Cell-Mediated Autoimmunity by Peptide-MHC Class II Dimer Vaccination"; The Journal of Immunology; vol. 183, pp. 4809-4816 (Sep. 14, 2009).

Liao, et al.; "Interleukin-2 at the Crossroads of Effector Responses, Tolerance, and Immunotherapy"; Immunity; vol. 38, No. 1, pp. 13-25 (Jan. 1, 2013).

Lin, et al.; "Reversal of type 1 diabetes by a new MHC II-peptide chimera: "Single-epitope-mediated suppression" to stabilize a polyclonal autoimmune T-cell process"; Eur. J. Immunol.; vol. 40, pp. 2277-2288 (2010).

Lin, et al.; "The PD-1/PD-L1 complex resembles the antigen-binding Fv domains of antibodies and T cell receptors"; PNAS; vol. 105, No. 8, pp. 3011-3016 (Feb. 26, 2008).

Liu, et al.; "Attaining High Transient Titers in CHO Cells"; Genetic Engineering & Biotechnology News; vol. 35, No. 17, 3 pages (Oct. 1, 2015).

Liu, et al.; "Major Histocompatibility Complex: Interaction with Peptides"; eLS; 12 pages (Aug. 15, 2011).

Lloyd, et al.; "Modelling the human immune response: performance of a 1011 human antibody repertoire against a broad panel of therapeutically relevant antigens"; Protein Engineering, Design & Selection; vol. 22, No. 3, pp. 159-168 (2009).

Mallone, et al.; "T Cell Recognition of Autoantigens in Human Type 1 Diabetes: Clinical Perspectives"; Clinical and Developmental Immunology; vol. 2011, 16 pages (2011).

Margalit, et al.; "Induction of Antitumor Immunity by CTL Epitopes Genetically Linked to Membrane-Anchored $\beta$2-Microglobulin"; The Journal of Immunology; vol. 176, pp. 217-224 (2006).

Martin-Orozco, et al.; "Melanoma Cells Express ICOS Ligand to Promote the Activation and Expansion of T-Regulatory Cells"; Cancer Research; vol. 70, No. 23, pp. 9581-9590 (2010).

McAllister, et al.; "Adaptation of Recombinant HEK-293 Cells to Growth in Serum Free Suspension"; Animal Cell Technology: Products from Cells, Cells as Products; 3 pages (1999).

McNally, et al.; "$CD4^+CD25^+$ regulatory T cells control $CD8^+$ T-cell effector differentiation by modulating IL-2 homeostasis"; PNAS; vol. 108, No. 18, pp. 7529-7534 (May 3, 2011).

Medina, et al.; "PD-1 Pathway Inhibitors: Immuno-Onology Agents for Restoring Anititumor Immune Responses"; Pharmacotherapy; vol. 36, No. 3, pp. 317-334 (Mar. 2016).

Miao, et al.; "Transient expression of fluorescent fusion proteins in protoplasts of suspension cultured cells"; Nature Protocols; vol. 2, No. 10, pp. 2348-2353 (2007).

Michels, et al.; "Islet-Derived CD4 T Cells Targeting Proinsulin in Human Autoimmune Diabetes"; Diabetes; vol. 66, pp. 722-734 (Mar. 2017).

Mizukoshi, et al.; "Identification of $\alpha$-fetoprotein-derived peptides recognized by cytotoxic T lymphocytes in HLA-A24+ patients with hepatocellular carcinoma"; Int. J. Cancer; vol. 118, pp. 1194-1204 (2006).

Mott, et al.; "The Solution Structure of the F42A Mutant of Human Interleukin 2"; J. Mol. Biol.; vol. 247, pp. 979-994 (1995).

Mottez, et al.; "Cells Expressing a Major Histocompatibility Complex Class I Molecule with a Single Covalently Bound Peptide are Highly Immunogenic"; J. Exp. Med.; vol. 181, pp. 493-502 (Feb. 1995).

Motz, et al.; "Tumor Endothelium FasL Establishes a Selective Immune Barrier Promoting Tolerance in Tumors"; Nat. Med.; vol. 20, No. 6, pp. 607-615 (Jun. 2014).

Muller, et al.; "Random peptide libraries displayed on adeno-associated virus to select for targeted gene therapy vectors"; Nature Biotechnology; vol. 21, No. 9, pp. 1040-1046 (Sep. 2003).

Naidoo, et al.; "Toxicities of the anti-PD-1 and anti-PD-L1 immune checkpoint antibodies"; Annals of Oncology; vol. 26, pp. 2375-2391 (Sep. 2015).

Nielsen, et al.; "MHC Class II epitope predictive algorithms"; Immunology; vol. 130, pp. 319-328 (2010).

Oates, et al.; "ImmTACs: Novel bi-specific agents for targeted cancer therapy"; OncoImmunology; vol. 2, No. 2, 3 pages (Feb. 2013).

Obermann, et al.; "Peptide-$\beta$2-microglobulin-major histocompatibility complex expressing cells are potent antigen-presenting cells that can generate specific T cells"; Immunology; vol. 122, pp. 90-97 (2007).

Ochoa-Garay, et al.; "The Ability of Peptides to Induce Cytotoxic T Cells In Vitro Does Not Strongly Correlate with Their Affinity for the $H-2L^d$ Molecule: Implications for Vaccine Design and Immunotherapy"; Molecular Immunology; vol. 34, No. 3, pp. 273-281 (1997).

Oka, et al.; "Induction of WT1 (Wilms' tumor gene)-specific cytotoxic T lymphocytes by WT1 peptide vaccine and the resultant cancer regression"; PNAS; vol. 101, No. 38, pp. 13885-13890 (Sep. 21, 2004).

Oliveira, et al.; "Design, Immune Responses and Anti-Tumor Potential of an HPV16 E6E7 Multi-Epitope Vaccine"; PLoS One; vol. 10, No. 9, 13 pages (Sep. 21, 2015).

PDB:1I8L_A; "Chain A, T Lymphocyte Activation Antigen Cd80" 2 pages (Dec. 27, 2012).

Peach, et al.; "Both Extracellular Immunoglobin-like Domains of CD80 Contain Residues Critical for Binding T Cell Surface Receptors CTLA-4 and CD28*"; The Journal of Biological Chemistry; vol. 270, No. 36, pp. 21181-21187 (1995).

Ponstingl, et al.; "The Rule of Antibody Structure: The Primary Structure of a Monoclonal IgG1 Immunoglobulin (Myeloma Protein Nie)"; Hoppe Seylers Z Physiol Chem.; vol. 357, No. 11, pp. 1571-1604 (Nov. 1976). [English translation of Abstract Only].

(56) References Cited

OTHER PUBLICATIONS

Poosarla, et al.; "Computational De Novo Design of Antibodies Binding to a Peptide With High Affinity"; Biotechnology & Bioengineering; vol. 114, No. 6, pp. 1331-1342 (Jun. 2017).

Preda, et al.; "Soluble, dimeric HLA DR4-peptide chimeras: An approach for detection and immunoregulation of human type-1 diabetes"; Eur. J. Immunol.; vol. 35, pp. 2763-2776 (Aug. 16, 2005).

Quayle, et al.; "CUE-101, a Novel HPV16 E7-pHLA-IL-2-Fc Fusion Protein, Enhances Tumor Antigen Specific T Cell Activation for the Treatment of HPV16-Driven Malignancies"; Clinical Cancer Research; vol. 26, No. 8, pp. 1953-1964 (Jan. 21, 2020).

Quayle, et al.; "Immuno-STAT(TM) (Selective Targeting and Alteration of T cells) Platform: Targeting Tumor Heterogeneity and Tumor Escape Mechanisms"; DOI: 10.1158/1078-0432.CCR-19-3354; URL:https://www.cuebiopharma.com/our-appro ch/scien ific-presentatjons-publications/; 1 page (Jan. 21, 2020).

Rabu, et al.; "Production of recombinant human trimeric CD137L (4-1BBL). Cross-linking is essential to its T cell co-stimulation activity"; The Journal of Biological Chemistry; vol. 280, No. 50, pp. 41472-41481 (Dec. 16, 2005).

Ramani, et al.; "A secreted protein microarray platform for extracellular protein interaction discovery"; Analytical Biochemistry; vol. 420, pp. 127-138 (2012).

Reche, et al.; "Sequence Variability Analysis of Human Class I and Class II MHC Molecules: Functional and Structural Correlates of Amino Acid Polymorphisms"; Journal of Molecular Biology; vol. 331, No. 3, pp. 623-641 (Aug. 15, 2003).

Repana, et al.; "The Network of Cancer Genes (NCG): a comprehensive catalogue of known and candidate cancer genes from cancer sequencing screens"; Genome Biology; vol. 20, No. 1, 12 pages (2019).

Ressing, et al.; "Human CTL epitopes encoded by human papillomavirus type 16 E6 and E7 identified through in vivo and in vitro immunogenicity studies of HLA-A*0201-binding peptides"; The Journal of Immunology; vol. 154, pp. 5934-5943 (1995).

Rocha-Zavaleta, et al.; "Interleukin-2 (IL-2) receptor-βγ signalling is activated by c-Kit in the absence of IL-2, or by exogenous IL-2 via JAK3/STAT5 in human papillomavirus-associated cervical cancer"; Cellular Signalling; vol. 16, pp. 1239-1247 (2004).

Sang, et al.; "Long-term silencing of autoimmune diabetes and improved life expectancy by a soluble pHLA-DR4 chimera in a newly-humanized NOD-DR4/B7 mouse"; Human Vaccines & Immunotherapeutics; vol. 10, No. 3, pp. 693-699 (Mar. 2014).

Schmittnaegel, et al.; "A New Class of Bifunctional Major Histocompatibility Class I Antibody Fusion Molecules to Redirect CDS T Cells"; Molecular Cancer Therapeutics; vol. 15, No. 9, pp. 2130-2142 (Sep. 2016).

Schumacher, et al.; "Neoantigens in cancer immunotherapy"; Science; vol. 348, No. 6230, pp. 69-74 (Apr. 2, 2015).

Seidel, et al.; "Peptide-HLA-based immunotherapeutics platforms for direct modulation of antigen-specific T cells"; Scientific Reports; vol. 11, No. 19220, 8 pages (Sep. 2021).

Shah, et al.; "Bio-layer Interferometry for Measuring Kinetics of Protein-protein Interactions and Allosteric Ligand Effects"; Journal of Visualized Experiments; vol. 84, 11 pages (2014).

Sharma, et al.; "A synthetic chimeric peptide harboring human papillomavirus 16 cytotoxic T lymphocyte epitopes shows therapeutic potential in a murine model of cervical cancer"; Immunologic Research; 58(1): p. 132-138 (2014).

Solinas, et al.; "The rationale behind targeting the ICOS-ICOS ligand costimulatory pathway in cancer immunotherapy"; ESMO Open; vol. 5, 7 pages (Jan. 2020).

Spang, et al.; "Heterodimeric Barnase-Barstar Vaccine Molecules: Influence of One versus Two Targeting Units Specific for Antigen Presenting Cells"; PLoS One; vol. 7, No. 9, 11 pages (Sep. 2012).

Stadinski, et al.; "Diabetogenic T cells recognize insulin bound to IAg7 in an unexpected, weakly binding register"; PNAS; vol. 107, No. 24, pp. 10978-10983 (Jun. 15, 2010).

Stamper, et al.; "Crystal structure of the B7-1/CTLA-4 complex that inhibits human immune responses"; Nature; vol. 410, pp. 608-611 (Mar. 29, 2001).

Stauber et al.; "Crystal structure of the IL-2 signaling complex: Paradigm for a heterotrimeric cytokine receptor"; Proc. Natl. Acad. Sci.; vol. 103, No. 8, pp. 2788-2793 (Feb. 21, 2006).

Strohl; "Optimization of Fc-mediated effector functions of monoclonal antibodies"; Current Opinion in Biotechnology; vol. 20, pp. 685-691 (2009).

Tafuro, et al.; "Reconstitution of antigen presentation in HLA class I-negative cancer cells with peptide-β2m fusion molecules"; Eur. J. Immunol.; vol. 31, pp. 440-449 (2001).

Tan, et al.; "Type 1 diabetes induction in humanized mice"; PNAS; vol. 114, No. 41, pp. 10954-10959 (Oct. 10, 2017).

Taube, et al.; "Lentivirus Display: Stable Expression of Human Antibodies on the Surface of Human Cells and Virus Particles"; PLoS One; vol. 3, No. 9, 12 pages (Sep. 2008).

Tham, et al.; "Activation of antigen-specific T cells by artificial cell constructs having immobilized multimeric peptide-class I complexes and recombinant B7-Fc proteins"; Journal of Immunological Methods; vol. 249, pp. 111-119 (2001).

Torres, et al.; "The immunoglobulin constant region contributes to affinity and specificity"; Trends in Immunology; vol. 29, No. 2, pp. 91-97 (Jan. 10, 2008).

Toukam, et al.; "Targeting Antibody Responses to the Membrane Proximal External Region of the Envelope Glycoprotein of Human Immunodeficiency Virus"; PLoS One; vol. 7, No. 5, 10 pages (May 2012).

Trolle, et al.; "The length distribution of class I restricted T cell epitopes is determined by both peptide supply and MHC allele specific binding preference"; J Immunol; vol. 196, No. 4, pp. 1480-1487 (Feb. 15, 2016).

Unverdorben, et al.; "Pharmacokinetic properties of IgG and various Fc fusion proteins in mice"; MABS; vol. 8, No. 1, pp. 120-128 (Oct. 29, 2015).

Van Der Burg, et al.; "An HLA Class I Peptide-Binding Assay Based on Competition for Binding to Class I Molecules on Intact Human B Cells Identification of Conserved HIV-1 Polymerase Peptides Binding to HLA-A*0301"; Hum. Immunol.; vol. 44, No. 4, pp. 189-198 (Dec. 1995).

Venkatakrishnan, et al.; "The Structural Biology of Hepatitis B Virus: Form and Function"; Annu. Rev. Virol.; vol. 3, No. 1, pp. 429-451 (Sep. 29, 2016).

Vitello, et al.; "Neoantigen prediction and the need for validation"; Nature Biotechnology; vol. 35, No. 9, pp. 815-817 (Sep. 2017).

Wang, et al.; "Molecular Modeling and Functional Mapping of B7-H1 and B7-DC Uncouple Costimulatory Function from PD-1 Interaction"; J. Exp. Med.; vol. 197, No. 9, pp. 1083-1091 (May 5, 2003).

Wang, et al.; "Using a baculovirus display library to identify MHC class I mimotopes"; PNAS; vol. 102, No. 7, pp. 2476-2481 (Feb. 15, 2005).

Wen, et al.; "Construction and screening of an antigen-derived peptide library displayed on yeast cell surface for CD4+ T cell epitope identification"; Methods Mol. Biol.; vol. 1061, pp. 245-264 (2013).

White, et al.; "Soluble Class I MHC with $β_2$-MicroglobulinCovalently Linked Peptides: Specific Binding to a T Cell Hybridoma"; J Immunol; vol. 162, pp. 2671-2676 (1999).

Whitehead, et al.; "Optimization of affinity, specificity and function of designed influenza inhibitors using deep sequencing"; Nat. Biotechnol.; vol. 30, No. 6, pp. 543-548 (Apr. 29, 2013).

Wieczorek, et al.; "Major Histocompatibility Complex (MHC) Class I and MHC Class II Proteins: Conformational Plasticity in Antigen Presentation"; Frontiers in Immunology; vol. 8, No. 292, pp. 1-16 (Mar. 2017).

Won, et al.; "The structure of the trimer of human 4-1BB ligand is unique among members of the tumor necrosis factor superfamily"; J Biol Chem; vol. 285, No. 12, pp. 9202-9210 (Mar. 19, 2010).

Woodham, et al.; "In vivo detection of antigen-specific CD8T cells by immuno-positron emission tomography"; Nat Methods.; vol. 17, No. 10, pp. 1025-1032 (Oct. 2020).

(56) References Cited

OTHER PUBLICATIONS

Wu, et al.; "Simultaneous targeting of multiple disease mediators by a dual-variable-domain immunoglobulin"; Nature Biotechnology; 25: p. 1290-1297 (2007).

Xu, et al.; "Cytokine release syndrome in cancer immunotherapy with chimeric antigen receptor engineered T cells"; Cancer Letters; 343(2): p. 172-178 (2014).

Zheng, et al.; "B7-CTLA4 interaction enhances both production of antitumor cytotoxic T lymphocytes and resistance to tumor challenge"; PNAS; vol. 95, pp. 6284-6289 (May 1998).

Zhang, et al.; "Monoclonal antibody blocking the recognition of an insulin peptide-MHC complex modulates type 1 diabetes"; PNAS; vol. 111, No. 7, pp. 2656-2661 (Feb. 18, 2014).

Ziauddin, et al.; "Microarrays of cells expressing defined cDNAs"; Nature; vol. 411, pp. 107-110 (May 3, 2011).

Fellner; "Ipilimumab (Yervoy) Prolongs Survival in Advanced Melanoma"; Drug Forecast; vol. 37, No. 9, pp. 503-530 (Sep. 2012).

Zhou, et al.; "Epitopes of MUC1 Tandem Repeats in Cancer as Revealed by Antibody Crystallography: Toward Glycopeptide Signature-Guided Therapy"; Molecules; vol. 23, No. 1326, 27 pages (2018).

Carmenate, et al.; "Human IL-2 Mutein with Higher Antitumor Efficacy Than Wild Type IL-2"; The Journal of Immunology; vol. 190, No. 12, pp. 6230-6238 (Jun. 15, 2013).

Anonymous; "Rationally engineered biologics to harness nature's cues for selective and specific immune modulation", Powerpoint presentation; 24 pages (Feb. 1, 2021).

Johannsen, et al.; "Definition of Key Variables for the Induction of Optimal NY-ESO-1-Specific T Cells in HLA Transgene Mice"; The Journal of Immunology; vol. 185, pp. 3445-3455 (2010).

Linard, et al.; "A ras-Mutated Peptide Targeted by CTL Infiltrating a Human Melanoma Lesion"; The Journal of Immunology; vol. 168, pp. 4802-4808 (2002).

Terashima, et al.; "P53, hTERT, WT-1, and VEGFR2 are the most suitable targets for cancer vaccine therapy in HLA-A24 positive pancreatic adenocarcinoma"; Cancer Immunol Immunother; vol. 63, pp. 479-489 (2014).

Kowalski, et al.; "Delivering the Messenger: Advances in Technologies for Therapeutic mRNA Delivery"; Molecular Therapy; vol. 27, No. 4, pp. 710-728 (Feb. 18, 2019).

Wu, et al.; "Remote control of therapeutic T cells through a small molecule-gated chimeric receptor"; Science; vol. 350, No. 6258, 12 pages (Oct. 16, 2015).

* cited by examiner

FIG. 6

MHC Class II DRA alpha chain

*Homo sapiens*

GenBank NP_061984 MHC Class II DRA(DRA*01:02) alpha chain (SEQ ID NO:130)

```
  1  MAISGVPVLG FFIIAVLMSA QESWAIKEEH VIIQAEFYLN PDQSGEFMFD FDGDEIFHVD
 61  MAKKETVWRL EEFGRFASFE AQGALANIAV DKANLEIMTK RSNYTPITNV PPEVTVLTNS
121  PVELREPNVL ICFIDKFTPP VVNVTWLRNG KPVTTGVSET VFLPREDHLF RKFHYLPFLP
181  STEDVYDCRV EHWGLDEPLL KHWEFDAPSP LPETTENVVC ALGLTVGLVG IIIGTIFIIK
241  GLRKSNAAER RGPL
```

Amino acids 1-25 = signal peptide
Amino acids 26-109 = α1
Amino acids 110-203 = α2
Amino acids 204-216 = connecting peptide
Amino acids 217-239 = TM
‡ DRA*01:01 contains a Val residue at position 242 in place of the Leu in DRA*01:02

FIG. 7A

MHC Class II DRB1 beta chains (*Homo sapiens*)

```
DRB1*03:01  MVCLRLPGGSCMAVLTVTLMVLSSPLALAGDTRPRFLEYSTSECHFFNGTERVRYLDRYF  60
DRB1*04:01  MVCLKFPGGSCMAALTVTLMVLSSPLALAGDTRPRFLEQVKHECHFFNGTERVRFLDRYF  60
DRB1*04:02  MVCLKFPGGSCMAALTVTLMVLSSPLALAGDTRPRFLEQVKHECHFFNGTERVRFLDRYF  60
DRB1*04:05  MVCLKFPGGSCMAALTVTLMVLSSPLALAGDTRPRFLEQVKHECHFFNGTERVRFLDRYF  60
DRB1*08:01  MVCLRLPGGSCMAVLTVTLMVLSSPLALAGDTRPRFLEYSTGECYFFNGTERVRFLDRYF  60
DRB1*09:01  MVCLKLPGGSCMAALTVTLMVLSSPLALAGDTQPRFLKQDKFECHFFNGTERVRYLHRGI  60
DRB1*16:01  MVCLKLPGGSCMTALTVTLMVLSSPLALAGDTRPRFLWQPKRECHFFNGTERVRFLDRYF  60

DRB1*03:01  HNQEENVRFDSDVGEFRAVTELGRPDAEYWNSQKDLLEQKRGRVDNYCRHNYGVVESFTV  120
DRB1*04:01  YHQEEYVRFDSDVGEYRAVTELGRPDAEYWNSQKDLLEQKRAAVDTYCRHNYGVGESFTV  120
DRB1*04:02  YHQEEYVRFDSDVGEYRAVTELGRPDAEYWNSQKDILEDERAAVDTYCRHNYGVVESFTV  120
DRB1*04:05  YHQEEYVRFDSDVGEYRAVTELGRPSAEYWNSQKDLLEQRRAAVDTYCRHNYGVGESFTV  120
DRB1*08:01  YNQEEYVRFDSDVGEYRAVTELGRPSAEYWNSQKDFLEDRRALVDTYCRHNYGVGESFTV  120
DRB1*09:01  YNQEENVRFDSDVGEYRAVTELGRPVAESWNSQKDFLERRAEVDTVCRHNYGVGESFTV  120
DRB1*16:01  YNQEESVRFDSDVGEYRAVTELGRPDAEYWNSQKDFLEDRRAAVDTYCRHNYGVGESFTV  120

DRB1*03:01  QRRVHPKVTVYPSKTQPLQHHNLLVCSVSGFYPGSIEVRWFRNGQEEKTGVVSTGLIHNG  180
DRB1*04:01  QRRVYPEVTVYPAKTQPLQHHNLLVCSVNGFYPGSIEVRWFRNGQEEKTGVVSTGLIQNG  180
DRB1*04:02  QRRVYPEVTVYPAKTQPLQHHNLLVCSVNGFYPGSIEVRWFRNGQEEKTGVVSTGLIQNG  180
DRB1*04:05  QRRVYPEVTVYPAKTQPLQHHNLLVCSVNGFYPGSIEVRWFRNGQEEKTGVVSTGLIQNG  180
DRB1*08:01  QRRVHPKVTVYPSKTQPLQHHNLLVCSVSGFYPGSIEVRWFRNGQEEKTGVVSTGLIHNG  180
DRB1*09:01  QRRVHPEVTVYPAKTQPLQHHNLLVCSVSGFYPGSIEVRWFRNGQEEKAGVVSTGLIQNG  180
DRB1*16:01  QRRVQPKVTVYPSKTQPLQHHNLLVCSVSGFYPGSIEVRWFLNGQEEKAGMVSTGLIQNG  180

DRB1*03:01  DWTFQTLVMLETVPRSGEVYTCQVEHPSVTSPLTVEWRARSESAQSKMLSGVGGFVLGLL  240
DRB1*04:01  DWTFQTLVMLETVPRSGEVYTCQVEHPSLTSPLTVEWRARSESAQSKMLSGVGGFVLGLL  240
DRB1*04:02  DWTFQTLVMLETVPRSGEVYTCQVEHPSLTSPLTVEWRARSESAQSKMLSGVGGFVLGLL  240
DRB1*04:05  DWTFQTLVMLETVPRSGEVYTCQVEHPSLTSPLTVEWRARSESAQSKMLSGVGGFVLGLL  240
DRB1*08:01  DWTFQTLVMLETVPRSGEVYTCQVEHPSVTSPLTVEWSARSESAQSKMLSGVGGFVLGLL  240
DRB1*08:02  DWTFQTLVMLETVPRSGEVYTCQVEHPSVTSPLTVEWSARSESAQSKMLSGVGGFVLGLL  240
DRB1*09:01  DWTFQTLVMLETVPRSGEVYTCQVEHPSVMSPLTVEWRARSESAQSKMLSGVGGFVLGLL  240
DRB1*16:01  DWTFQTLVMLETVPRSGEVYTCQVEHPSVTSPLTVEWRARSESAQSKMLSGVGGFVLGLL  240

DRB1*03:01  FLGAGLFIYFRNQKGHSGLQPRGFLS    266  (SEQ ID NO:131)
DRB1*04:01  FLGAGLFIYFRNQKGHSGLQPTGFLS    266  (SEQ ID NO:132)
DRB1*04:02  FLGAGLFIYFRNQKGHSGLQPTGFLS    266  (SEQ ID NO:133)
DRB1*04:05  FLGAGLFIYFRNQKGHSGLQPTGFLS    266  (SEQ ID NO:134)
DRB1*08:01  FLGAGLFIYFRNQKGHSGLQPTGFLS    266  (SEQ ID NO:135)
DRB1*08:02  (SEQ ID NO:138)
DRB1*09:01  FLGAGLFIYFRNQKGHSGLQPTGFLS    266  (SEQ ID NO:136)
DRB1*16:01  FLGAGLFIYFRNQKGHSGLQPTGFLS    266  (SEQ ID NO:137)
```

Amino acids 1-29 = signal peptide
Amino acids 30-124 = β1
Amino acids 125-227 = β2
Amino acids 228-250 = TM (transmembrane)

FIG. 7B

MHC Class II DRB3 beta chains
*Homo sapiens*

```
DRB3*01:01      MVCLKLPGGSSLAALTVTLMVLSSRLAFAGDTRPRFLELRKSECHFFNGTERVRYLDRYF    60
DRB3-EAX03632   MVCLKLPGGSSLAALTVTLMVLSSRLAFAGDTRPRFLELRKSECHFFNGTERVRYLDRYF    60
DRB3*02:01      MVCLKLPGGSSLAALTVTLMVLSSRLAFAGDTRPRFLELLKSECHFFNGTERVRFLERHF    60
DRB3*03:01      MVCLKLPGGSSLAALTVTLMVLSSRLAFAGDTRPRFLELLKSECHFFNGTERVRFLERYF    60
                ******************************************* **************.*:*:*

DRB3*01:01      HNQEEFLRFDSDVGEYRAVTELGRPVAESWNSQKDLLEQKRGRVDNYCRHNYGVGESFTV   120
DRB3-EAX03632   HNQEEFLRFDSDVGEYRAVTELGRPVAESWNSQKDLLEQKRGQVDNYCRHNYGVVESFTV   120
DRB3*02:01      HNQEEYARFDSDVGEYRAVRELGRPDAEYWNSQKDLLEQKRGQVDNYCRHNYGVVESFTV   120
DRB3*03:01      HNQEEFVRFDSDVGEYRAVTELGRPVAESWNSQKDLLEQKRGQVDNYCRHNYGVVESFTV   120
                *****: *********** ***** ** ****************:************ *****

DRB3*01:01      QRRVHPQVTVYPAKTQPLQHHNLLVCSVSGFYPGSIEVRWFRNGQEEKAGVVSTGLIQNG   180
DRB3-EAX03632   QRRVHPQVTVYPAKTQPLQHHNLLVCSVSGFYPGSIEVRWFRNGQEEKAGVVSTGLIQNG   180
DRB3*02:01      QRRVHPQVTVYPAKTQPLQHHNLLVCSVSGFYPGSIEVRWFRNGQEEKAGVVSTGLIQNG   180
DRB3*03:01      QRRVHPQVTVYPAKTQPLQHHNLLVCSVSGFYPGSIEVRWFRNGQEEKTGVVSTGLIHNG   180
                ************************************************:*******:**

DRB3*01:01      DWTFQTLVMLETVPRSGEVYTCQVEHPSVTSALTVEWRARSESAQSKMLSGVGGFVLGLL   240
DRB3-EAX03632   DWTFQTLVMLETVPRSGEVYTCQVEHPSVTSALTVEWRARSESAQSKMLSGVGGFVLGLL   240
DRB3*02:01      DWTFQTLVMLETFPRSGEVYTCQVEHPSVTSPLTVEWSARSESAQSKMLSGVGGFVLGLL   240
DRB3*03:01      DWTFQTLVMLETVPRSGEVYTCQVEHPSVTSPLTVEWRARSESAQSKMLSGVGGFVLGLL   240
                ************.***************** ***** ****** ********************

DRB3*01:01      FLGAGLFIYFRNQKGHSGLQPTGFLS   266  (SEQ ID NO:139)
DRB3-EAX03632   FLGAGLFIYFRNQKGHSGLQPTGFLS   266  (SEQ ID NO:140)
DRB3*02:01      FLGAGLFIYFRNQKGHSGLQPTGFLS   266  (SEQ ID NO:141)
DRB3*03:01      FLGAGLFIYFRNQKGHSGLQPTGFLS   266  (SEQ ID NO:142)
                **************************
```

Amino acids 1-29 = signal peptide
Amino acids 30-124 = β1
Amino acids 125-227 = β2

FIG. 7C

MHC Class II DRB4 beta chain

*Homo sapiens*

GenBank NP_068818.4 & ImMunoGeneTics ("IMGT")/HLA Acc No: HLA00908 (DRB4*01:03)

```
  1 MVCLKLPGGS CMAALTVTLT VLSSPLALAG DTQPRFLEQA KCECHFLNGT ERVWNLIRYI
 61 YNQEEYARYN SDLGEYQAVT ELGRPDAEYW NSQKDLLERR RAEVDTYCRY NYGVVESFTV
121 QRRVQPKVTV YPSKTQPLQH HNLLVCSVNG FYPGSIEVRW FRNGQEEKAG VVSTGLIQNG
181 DWTFQTLVML ETVPRSGEVY TCQVEHPSMM SPLTVQWSAR SESAQSKMLS GVGGFVLGLL
241 FLGTGLFIYF RNQKGHSGLQ PTGLLS (SEQ ID NO:143)
```

Amino acids 1-29 = signal peptide
Amino acids 30-124 = β1
Amino acids 125-227 = β2

FIG. 7D

MHC Class II DRB5 beta chain

*Homo sapiens*

GenBank NP_002116 and IMGT/HLA Acc No: HLA00915 (DRB5*01:01)

```
  1 MVCLKLPGGS YMAKLTVTLM VLSSPLALAG DTRPRFLQQD KYECHFFNGT ERVRFLHRDI
 61 YNQEEDLRFD SDVGEYRAVT ELGRPDAEYW NSQKDFLEDR RAAVDTYCRH NYGVGESFTV
121 QRRVEPKVTV YPARTQTLQH HNLLVCSVNG FYPGSIEVRW FRNSQEEKAG VVSTGLIQNG
181 DWTFQTLVML ETVPRSGEVY TCQVEHPSVT SPLTVEWRAQ SESAQSKMLS GVGGFVLGLL
241 FLGAGLFIYF KNQKGHSGLH PTGLVS (SEQ ID NO:144)
```

Amino acids 1-29 = signal peptide
Amino acids 30-124 = β1
Amino acids 125-227 = β2

FIG. 8

MHC Class II DPA1 alpha chains (*Homo sapiens*)

GenBank NP_001229453.1 and IMGT/HLA Acc No: HLA00499 MHC Class II DPA1(DPA1*01:03) alpha chain  (SEQ ID NO:145)

```
1   MRPEDRMFHI RAVILRALSL AFLLSLRGAG AIKADHVSTY AAFVQTHRPT GEFMFEFDED
61  EMFYVDLDKK ETVWHLEEFG QAFSFEAQGG LANIAILNNN LNTLIQRSNH TQATNDPPEV
121 TVFPKEPVEL GQPNTLICHI DKFFPPVLNV TWLCNGELVT EGVAESLFLP RTDYSFHKFH
181 YLTFVPSAED FYDCRVEHWG LDQPLLKHWE AQEPIQMPET TETVLCALGL VLGLVGIIVG
241 TVLIIKSLRS GHDPRAQGTL
```

IMGT/HLA Acc No: HLA00504 MHC Class II DPA1:02(DPA1*02:01) alpha chain (SEQ ID NO:25)

```
1   MRPEDRMFHI RAVILRALSL AFLLSLRGAG AIKADHVSTY AAFVQTHRPT GEFMFEFDED
61  EQFYVDLDKK ETVWHLEEFG RAFSFEAQGG LANIAILNNN LNTLIQRSNH TQAANDPPEV
121 TVFPKEPVEL GQPNTLICHI DRFFPPVLNV TWLCNGEPVT EGVAESLFLP RTDYSFHKFH
181 YLTFVPSAED VYDCRVEHWG LDQPLLKHWE AQEPIQMPET TETVLCALGL VLGLVGIIVG
241 TVLIIKSLRS GHDPRAQGPL
```

Amino acids 1-28 = signal peptide
Amino acids 29-115 = α1
Amino acids 116-209 = α2

FIG. 9

MHC Class II DPB1 beta chain (*Homo sapiens*)

```
DPB1*02:02   MMVLQVSAAPRTVALTALLMVLLTSVVQGRATPENYLFQGRQECYAFNGTQRFLERYIYN  60
DPB1*03:01   MMVLQVSAAPRTVALTALLMVLLTSVVQGRATPENYVYQLRQECYAFNGTQRFLERYIYN  60

DPB1*02:02   REELVRFDSDVGEFRAVTELGRPEAEYWNSQKDILEEERAVPDRMCRHNYELGGPMTLQR  120
DPB1*03:01   REEFVRFDSDVGEFRAVTELGRPDEDYWNSQKDLLEEKRAVPDRVCRHNYELDEAVTLQR  120

DPB1*02:02   RVQPRVNVSPSKKGPLQHHNLLVCHVTDFYPGSIQVRWFLNGQEETAGVVSTNLIRNGDW  180
DPB1*03:01   RVQPKVNVSPSKKGPLQHHNLLVCHVTDFYPGSIQVRWFLNGQEETAGVVSTNLIRNGDW  180

DPB1*02:02   TFQILVMLEMTPQQGDVYTCQVEHTSLDSPVTVEWKAQSDSARSKTLTGAGGFVLGLIIC  240
DPB1*03:01   TFQILVMLEMTPQQGDVYICQVEHTSLDSPVTVEWKAQSDSARSKTLTGAGGFVLGLIIC  240

DPB1*02:02   GVGIFMHRRSKKVQRGSA   258  (SEQ ID NO:146)
DPB1*03:01   GVGIFMHRRSKKVQRGSA   258  (SEQ ID NO:147)
```

Amino acids 1-29 = signal peptide
Amino acids 30-121 = β1
Amino acids 122-215 = β2

FIG. 10

**MHC Class II DQA1 alpha chain (*Homo sapiens*)**

```
DQA1*01:01   MILNKALLLGALALTTVMSPCGGEDIVADHVASCGVNLYQFYGPSGQYTHEFDGDEEFYV 60
DQA1*03:01   MILNKALMLGALALTTVMSPCGGEDIVADHVASYGVNLYQSYGPSGQYSHEFDGDEEFYV 60
DQA1*04:01   MILNKALLLGALALTTVMSPCGGEDIVADHVASYGVNLYQSYGPSGQYTHEFDGDEQFYV 60
DQA1*05:01   MILNKALMLGALALTTVMSPCGGEDIVADHVASYGVNLYQSYGPSGQYTHEFDGDEQFYV 60

DQA1*01:01   SPVTLGQPNTLICLVDNIFPPVVNITWLSNGQSVTEGVSETSFLSKSDHSFFKISYLTFL 180
DQA1*03:01   SPVTLGQPNTLICLVDNIFPPVVNITWLSNGHSVTEGVS-TSFLSKSDHSFFKISYLTFL 179
DQA1*04:01   SPVTLGQPNTLICLVDNIFPPVVNITWLSNGHSVTEGVSETSFLSKSDHSFFKISYLTFL 179
DQA1*05:01   SPVTLGQPNILICLVDNIFPPVVNITWLSNGHSVTEGVSETSFLSKSDHSFFKISYLTLL 179

DQA1*01:01   QGLRSVGASRHQGPL 255  (SEQ ID NO:148)
DQA1*03:01   RGLRSVGASRHQGPL 254  (SEQ ID NO:149)
DQA1*04:01   RGLRSVGASRHQGPL 254  (SEQ ID NO:150)
DQA1*05:01   RGLRSVGASRHQGPL 254  (SEQ ID NO:151)
```

Amino acids 1-23 = signal peptide
Amino acids 24-110 = α1
Amino acids 111-204 = α2

FIG. 11A

MHC Class II DQB1 beta chains (*Homo sapiens*) (SEQ ID NOs:152-158)

```
DQB1*02:01    MSWKKALRIPGGLRAATVTLMLSMLSTPVAEGRDSPEDFVYQFKGMCYFTNGTERVRLVS  60
DQB1*03:02    MSWKKALRIPGGLRVATVTLMLAMLSTPVAEGRDSPEDFVYQFKGMCYFTNGTERVRLVT  60
DQB1*03:03    MSWKKALRIPGGLRVATVTLMLAMLSTPVAEGRDSPEDFVYQFKGMCYFTNGTERVRLVT  60
DQB1*04:01    MSWKKALRIPGGLRVATVTLMLAMLSTPVAEGRDSPEDFVFQFKGMCYFTNGTELVRGVT  60
DQB1*04:02    MSWKKALRIPGGLRVATVTLMLAMLSTPVAEGRDSPEDFVFQFKGMCYFTNGTERVRGVT  60
DQB1*05:01    MSWKKSLRIPGDLRVATVTLMLAILSSSLAEGRDSPEDFVYQFKGLCYFTNGTERVRGVT  60

DQB1*02:01    RSIYNREEIVRFDSDVGEFRAVTLLGLPAAEYWNSQKDILERKRAAVDRVCRHNYQLELR  120
DQB1*03:02    RYIYNREEYARFDSDVGVYRAVTPLGPPAAEYWNSQKEVLERTRAELDTVCRHNYQLELR  120
DQB1*03:03    RYIYNREEYARFDSDVGVYRAVTPLGPPDAEYWNSQKEVLERTRAELDTVCRHNYQLELR  120
DQB1*04:01    RYIYNREEYARFDSDVGVYRAVTPLGRLDAEYWNSQKDILEEDRASVDTVCRHNYQLELR  120
DQB1*04:02    RYIYNREEYARFDSDVGVYRAVTPLGRLDAEYWNSQKDILEEDRASVDTVCRHNYQLELR  120
DQB1*05:01    RHIYNREEYVRFDSDVGVYRAVTPQGRPVAEYWNSQKEVLEGARASVDRVCRHNYEVAYR  120

DQB1*02:01    TTLQRRVEPTVTISPSRTEALNHHNLLVCSVTDFYPAQIKVRWFRNDQEETAGVVSTPLI  180
DQB1*03:02    TTLQRRVEPTVTISPSRTEALNHHNLLVCSVTDFYPAQIKVRWFRNDQEETTGVVSTPLI  180
DQB1*03:03    TTLQRRVEPTVTISPSRTEALNHHNLLVCSVTDFYPAQIKVRWFRNDQEETTGVVSTPLI  180
DQB1*04:01    TTLQRRVEPTVTISPSRTEALNHHNLLVCSVTDFYPAQIKVRWFRNDQEETTGVVSTPLI  180
DQB1*04:02    TTLQRRVEPTVTISPSRTEALNHHNLLVCSVTDFYPAQIKVRWFRNDQEETTGVVSTPLI  180
DQB1*05:01    GILQRRVEPTVTISPSRTEALNHHNLLICSVTDFYPSQIKVRWFRNDQEETAGVVSTPLI  180

DQB1*02:01    RNGDWTFQILVMLEMTPQRGDVYTCHVEHPSLQSPITVEWRAQSESAQSKMLSGIGGFVL  240
DQB1*03:02    RNGDWTFQILVMLEMTPQRGDVYTCHVEHPSLQNPIIVEWRAQSESAQSKMLSGIGGFVL  240
DQB1*03:03    RNGDWTFQILVMLEMTPQRGDVYTCHVEHPSLQNPIIVEWRAQSESAQSKMLSGIGGFVL  240
DQB1*04:01    RNGDWTFQILVMLEMTPQRGDVYTCHVEHPSLQNPIIVEWRAQSESAQSKMLSGIGGFVL  240
DQB1*04:02    RNGDWTFQILVMLEMTPQRGDVYTCHVEHPSLQNPIIVEWRAQSESAQSKMLSGIGGFVL  240
DQB1*05:01    RNGDWTFQILVMLEMTPQRGDVYTCHVEHPSLQSPITVEWRAQSESAQSKMLSGVGGFVL  240
```

FIG. 11B

```
DQB1*02:01  GLIFLGLGLIIHHRSQKGLLH--------- 261 (SEQ ID NO:152)
DQB1*03:02  GLIFLGLGLIIHHRSQKGLLH--------- 261 (SEQ ID NO:153)
DQB1*03:03  GLIFLGLGLIIHHRSQKGLLH--------- 261 (SEQ ID NO:154)
DQB1*04:01  GLIFLGLGLIIHHRSQKGLLH--------- 261 (SEQ ID NO:155)
DQB1*04:02  GLIFLGLGLIIHHRSQKGLLH--------- 261 (SEQ ID NO:156)
DQB1*05:01  GLIFLGLGLIIRQRSRKGLLH--------- 261 (SEQ ID NO:157)
DQB1*05:03  GLIFLGLGLIIRQRSRKGPQGPPPAGLLH 269 (SEQ ID NO:158)
```

Amino acids 1-32 = signal peptide
Amino acids 33-126 = β1
Amino acids 127-220 = β2

FIG. 12A

GenBank 3S7G_A
*Homo sapiens* IgG1 Fc (SEQ ID NO:159)
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqgg nvfscsvmhe alhnhytqks lslspgk
```

GenBank AAN76044
*Homo sapiens* IgG2 Fc (amino acids 99-325) (SEQ ID NO:160)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947
*Homo sapiens* IgG3 Fc (amino acids 19-246) (SEQ ID NO:161)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

FIG. 12B

GenBank AAA52770
*Homo sapiens* IgD Fc (amino acids 162-383) (SEQ ID NO:162)
222 aa

```
  1 ptkapdvfpi isgcrhpkdn spvvlaclit gyhptsvtvt wymgtqsqpq rtfpeiqrrd
 61 syymtssqls tplqqwrqge ykcvvqhtas kskkeifrwp espkaqassv ptaqpqaegs
121 lakattapat trntgrggee kkkekekeeq eeretktpec pshtqplgvy lltpavqdlw
181 lrdkatftcf vvgsdlkdah ltwevagkvp tggveeglle rhsngsqsqh srltlprslw
241 nagtsvtctl nhpslppqrl malrepaaqa pvklslnlla ssdppeaasw llcevsgfsp
301 pnillmwled qrevntsqfa parpppqprs ttfwawsvlr vpappspqpa tytcvvshed
361 srtllnasrs levsyvtdhg pmk
```

GenBank 0308221A
*Homo sapiens* IgM Fc (SEQ ID NO:163)
276 aa

```
  1 vtstltikzs dwlgesmftc rvdhrgltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

FIG. 12C

GenBank P01876

*Homo sapiens* IgA Fc (amino acids 120-353) (SEQ ID NO:164)

234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg seanltctlt glrdasgvtf twtpssgksa vqgppperdlc
181 gcysvssvlp gcaepwnhgk tftctaaype sktpltatls ksgntfrpev hllpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B

*Homo sapiens* IgE Fc (amino acids 6-222) (SEQ ID NO:165)

212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861

*Homo sapiens* IgG4 Fc (amino acids 100-327) (SEQ ID NO:166)

228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 12D

WT Human IgG1 Fc Sequence: (SEQ ID NO:167)
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK

FIG. 12E

Human IgG1 Fc Mutant: L234F/L235E/P331S (Triple Mutant "TM") (SEQ ID NO:168)
DKTHTCPPCPAPEFEGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPASIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK

FIG. 12F

Human IgG1 Fc Mutant: N297A (SEQ ID NO:169)
DKTHTCPPCPAPELLGGPSVFLFPPKPKDTLMISRTPEVTCVVVDVSHEDPEVKFNWYVDGVEVHNAKTKPREEQYASTY
RVVSVLTVLHQDWLNGKEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK

FIG. 12G

Human IgG1 Fc Mutant: L234A/L235A ("LALA") (SEQ ID NO:170)
DKTHTCPPCPAPEAAGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK Residue numbered according to EU index (Kabat Numbering)

FIG. 13A

DRA*0101 (wild-type)

IKEEHVIIQAEFYLNPDQSGEFMFDFDGDEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:9)

FIG. 13B

DRA*0101 (E3C)

IKCEHVIIQAEFYLNPDQSGEFMFDFDGDEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:171)

FIG. 13C

DRA*0101 (E4C)

IKECHVIIQAEFYLNPDQSGEFMFDFDGDEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:172)

FIG. 13D

DRA*0101 (F12C)

IKEEHVIIQAECYLNPDQSGEFMFDFDGDEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:173)

FIG. 13E

DRA*0101 (G28C)

IKEEHVIIQAEFYLNPDQSGEFMFDFD[C]DEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:174)

FIG. 13F

DRA*0101 (D29C)

IKEEHVIIQAEFYLNPDQSGEFMFDFDG[C]EIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:10)

FIG. 13G

DRA*0101 (I72C)

IKEEHVIIQAEFYLNPDQSGEFMFDFDGDEIFHVDMAKKETVWRLEEFGRFASFE
AQGALANIAVDKANLE[C]MTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:11)

FIG. 13H

DRA*0101 (K75C)

IKEEHVIIQAEFYLNPDQSGEFMFDFDGDEIFHVDMAKKETVWRLEEFGRFASFE
AQGALANIAVDKANLEIMT[C]RSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:12)

FIG. 13I

DRA*0101 (T80C)

IKEEHVIIQAEFYLNPDQSGEFMFDFDGDEIFHVDMAKKETVWRLEEFGRFASFE
AQGALANIAVDKANLEIMTKRSNY[C]PITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:175)

FIG. 13J

DRA*0101 (P81C)

IKEEHVIIQAEFYLNPDQSGEFMFDFDGDEIFHVDMAKKETVWRLEEFGRFASFE
AQGALANIAVDKANLEIMTKRSNYT[C]TNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:13)

FIG. 13K

DRA*0101 (I82C)

IKEEHVIIQAEFYLNPDQSGEFMFDFDGDEIFHVDMAKKETVWRLEEFGRFASFE
AQGALANIAVDKANLEIMTKRSNYTP[C]NVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:14)

FIG. 13L

DRA*0101 (T93C)

IKEEHVIIQAEFYLNPDQSGEFMFDFDGDEIFHVDMAKKETVWRLEEFGRFASFE
AQGALANIAVDKANLEIMTKRSNYTPITNVPPEVTVL[C]NSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:176)

FIG. 13M

DRA*0101 (N94C)

IKEEHVIIQAEFYLNPDQSGEFMFDFDGDEIFHVDMAKKETVWRLEEFGRFASFE
AQGALANIAVDKANLEIMTKRSNYTPITNVPPEVTVLT[C]SPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:177)

FIG. 13N

DRA*0101 (S95C)

IKEEHVIIQAEFYLNPDQSGEFMFDFDGDEIFHVDMAKKETVWRLEEFGRFASFE
AQGALANIAVDKANLEIMTKRSNYTPITNVPPEVTVLTN[C]PVELREPNVLICFIDK
FTPPVVNVTWLRNGKPVTTGVSETVFLPREDHLFRKFHYLPFLPSTEDVYDCRVE
HWGLDEPLLKHWEFDAPSPLPET (SEQ ID NO:178)

FTVTVPKDLYVVEYGSNMTIECKFPVEKQLDLAALIVYWEMEDKNIIQFVHGEE
DLKVQHSSYRQRARLLKDQLSLGNAALQITDVKLQDAGVYRCMISYGGADYKR
ITVKVNAPYNKINQRILVVDPVTSEHELTCQAEGYPKAEVIWTSSDHQVLSGKTT
TTNSKREEKLFNVTSTLRINTTTNEIFYCTFRRLDPEENHTAELVIPELPLAHPPNE
R (SEQ ID NO:99)

FIG. 14A

DRB1*0401 (wild-type)

GDTRPRFLEQVKHECHFFNGTERVRFLDRYFYHQEEYVRFDSDVGEYRAVTELG
RPDAEYWNSQKDLLEQKRAAVDTYCRHNYGVGESFTVQRRVYPEVTVYPAKT
QPLQHHNLLVCSVNGFYPASIEVRWFRNGQEEKTGVVSTGLIQNGDWTFQTLVM
LETVPRSGEVYTCQVEHPSLTSPLTVEWRARSESAQSKM (SEQ ID NO:30)

FIG. 14B

DRB1*0401 (P5C)

GDTR[C]RFLEQVKHECHFFNGTERVRFLDRYFYHQEEYVRFDSDVGEYRAVTELG
RPDAEYWNSQKDLLEQKRAAVDTYCRHNYGVGESFTVQRRVYPEVTVYPAKT
QPLQHHNLLVCSVNGFYPASIEVRWFRNGQEEKTGVVSTGLIQNGDWTFQTLVM
LETVPRSGEVYTCQVEHPSLTSPLTVEWRARSESAQSKM (SEQ ID NO:35)

FIG. 14C

DRB1*0401 (F7C)

GDTRPR[C]LEQVKHECHFFNGTERVRFLDRYFYHQEEYVRFDSDVGEYRAVTELG
RPDAEYWNSQKDLLEQKRAAVDTYCRHNYGVGESFTVQRRVYPEVTVYPAKT
QPLQHHNLLVCSVNGFYPASIEVRWFRNGQEEKTGVVSTGLIQNGDWTFQTLVM
LETVPRSGEVYTCQVEHPSLTSPLTVEWRARSESAQSKM (SEQ ID NO:179)

FIG. 14D

DRB1*0401 (Q10C)

GDTRPRFLE[C]VKHECHFFNGTERVRFLDRYFYHQEEYVRFDSDVGEYRAVTELG
RPDAEYWNSQKDLLEQKRAAVDTYCRHNYGVGESFTVQRRVYPEVTVYPAKT
QPLQHHNLLVCSVNGFYPASIEVRWFRNGQEEKTGVVSTGLIQNGDWTFQTLVM
LETVPRSGEVYTCQVEHPSLTSPLTVEWRARSESAQSKM (SEQ ID NO:180)

FIG. 14E

DRB1*0401 (N19C)
GDTRPRFLEQVKHECHFF[C]GTERVRFLDRYFYHQEEYVRFDSDVGEYRAVTELG
RPDAEYWNSQKDLLEQKRAAVDTYCRHNYGVGESFTVQRRVYPEVTVYPAKT
QPLQHHNLLVCSVNGFYPASIEVRWFRNGQEEKTGVVSTGLIQNGDWTFQTLVM
LETVPRSGEVYTCQVEHPSLTSPLTVEWRARSESAQSKM (SEQ ID NO:181)

FIG. 14F

DRB1*0401 (G20C)
GDTRPRFLEQVKHECHFFN[C]TERVRFLDRYFYHQEEYVRFDSDVGEYRAVTELG
RPDAEYWNSQKDLLEQKRAAVDTYCRHNYGVGESFTVQRRVYPEVTVYPAKT
QPLQHHNLLVCSVNGFYPASIEVRWFRNGQEEKTGVVSTGLIQNGDWTFQTLVM
LETVPRSGEVYTCQVEHPSLTSPLTVEWRARSESAQSKM (SEQ ID NO:182)

FIG. 14G

DRB1*0401 (H33C)
GDTRPRFLEQVKHECHFFNGTERVRFLDRYFY[C]QEEYVRFDSDVGEYRAVTELG
RPDAEYWNSQKDLLEQKRAAVDTYCRHNYGVGESFTVQRRVYPEVTVYPAKT
QPLQHHNLLVCSVNGFYPASIEVRWFRNGQEEKTGVVSTGLIQNGDWTFQTLVM
LETVPRSGEVYTCQVEHPSLTSPLTVEWRARSESAQSKM (SEQ ID NO:183)

FIG. 14H

DRB1*0401 (G151C)
GDTRPRFLEQVKHECHFFNGTERVRFLDRYFYHQEEYVRFDSDVGEYRAVTELG
RPDAEYWNSQKDLLEQKRAAVDTYCRHNYGVGESFTVQRRVYPEVTVYPAKT
QPLQHHNLLVCSVNGFYPASIEVRWFRNGQEEKTGVVSTGLIQN[C]DWTFQTLVM
LETVPRSGEVYTCQVEHPSLTSPLTVEWRARSESAQSKM (SEQ ID NO:36)

FIG. 14I

DRB1*0401 (D152C)
GDTRPRFLEQVKHECHFFNGTERVRFLDRYFYHQEEYVRFDSDVGEYRAVTELG
RPDAEYWNSQKDLLEQKRAAVDTYCRHNYGVGESFTVQRRVYPEVTVYPAKT
QPLQHHNLLVCSVNGFYPASIEVRWFRNGQEEKTGVVSTGLIQNGCWTFQTLVM
LETVPRSGEVYTCQVEHPSLTSPLTVEWRARSESAQSKM (SEQ ID NO:184)

FIG. 14J

DRB1*0401 (W153C)
GDTRPRFLEQVKHECHFFNGTERVRFLDRYFYHQEEYVRFDSDVGEYRAVTELG
RPDAEYWNSQKDLLEQKRAAVDTYCRHNYGVGESFTVQRRVYPEVTVYPAKT
QPLQHHNLLVCSVNGFYPASIEVRWFRNGQEEKTGVVSTGLIQNGDCTFQTLVM
LETVPRSGEVYTCQVEHPSLTSPLTVEWRARSESAQSKM (SEQ ID NO:37)

SLQPLALEGSLQSRGGGCGSGGGGSGGGGSGDTRPRFLEQVKHECHFFNGTER
VRFLDRYFYHQEEYVRFDSDVGEYRAVTELGRPDAEYWNSQKDLLEQKRAAVD
TYCRHNYGVGESFTVQRRVYPEVTVYPAKTQPLQHHNLLVCSVNGFYPASIEVR
WFRNGQEEKTGVVSTGLIQNGDWTFQTLVMLETVPRSGEVYTCQVEHPSLTSPL
TVEWRARSESAQSKM (SEQ ID NO:185)

Pro-insulin epitope: SLQPLALEGSLQSRG (SEQ ID NO:90)
GGCGSGGGGSGGGGS (SEQ ID NO:128) linker – bold
DRB1*0401 – underlined

<u>FTVTVPKDLYVVEYGSNMTIECKFPVEKQLDLAALIVYWEMEDKNIIQFVHGEE
DLKVQHSSYRQRARLLKDQLSLGNAALQITDVKLQDAGVYRCMISYGGADYKR
ITVKVNAPYNKINQRILVVDPVTSEHELTCQAEGYPKAEVIWTSSDHQVLSGKTT
TTNSKREEKLFNVTSTLRINTTTNEIFYCTFRRLDPEENHTAELVIPELPLAHPPNE
R</u>GGGGSGGGGSGGGGSGGGGS<u>IKEEHVIIQAEFYLNPDQSGEFMFDFDGDEI
FHVDMAKKETVWRLEEFGRFASFEAQGALANIAVDKANLEIMTCRSNYTPI
TNVPPEVTVLTNSPVELREPNVLICFIDKFTPPVVNVTWLRNGKPVTTGVSET
VFLPREDHLFRKFHYLPFLPSTEDVYDCRVEHWGLDEPLLKHWEFDAPSPL
PET</u><u>*GGSAAAGG*</u>*DKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQ
KSLSLSPG* (SEQ ID NO:186)

PDL1 – underlined
(G4S)4 linker (SEQ ID NO:75) – bold
DRA*0101 (K75C) – bold and underlined
GGSAAAGG (SEQ ID NO:83) linker – underlined and italicized
IgG1 Fc (L234A; L235A) – italicized

FIG. 15C

<u>2639</u> (proIns (78-90; K88S);
SLQPLALEGSLQSRGGGGGSGGGGSGGGGSGDTRPRFLEQVKHECHFFNGTER
VRFLDRYFYHQEEYVRFDSDVGEYRAVTELGRPDAEYWNSQKDLLEQKRAAVD
TYCRHNYGVGESFTVQRRVYPEVTVYPAKTQPLQHHNLLVCSVNGFYPASIEVR
WFRNGQEEKTGVVSTGLIQNGDWTFQTLVMLETVPRSGEVYTCQVEHPSLTSPL
TVEWRARSESAQSKM (SEQ ID NO:187)

Epitope: proinsulin 78-90; K88S; SLQPLALEGSLQSRG (SEQ ID NO:90)
(G4S)3 (SEQ ID NO:74)– bold and underlined
hDRB1-β1/β2 (DRB1*0401) – underlined

FIG. 15D

<u>3005</u>
IKEEHVIIQAEFYLNPDQSGEFMFDFDGDEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPETGGSAAAGG*DKTHTCPPCPAPEAAGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRW
QQGNVFSCSVMHEALHNHYTQKSLSLSP*GGGGSGGGGSGGGGSGGGGSFTVT
VPKDLYVVEYGSNMTIECKFPVEKQLDLAALIVYWEMEDKNIIQFVHGEEDLKV
QHSSYRQRARLLKDQLSLGNAALQITDVKLQDAGVYRCMISYGGADYKRITVK
VNAPYNKINQRILVVDPVTSEHELTCQAEGYPKAEVIWTSSDHQVLSGKTTTTNS
KREEKLFNVTSTLRINTTTNEIFYCTFRRLDPEENHTAELVIPELPLAHPPNER
(SEQ ID NO:188)

hDRA*0101-α1/α2 – underlined
(G4S)4 (SEQ ID NO:75)– bold and underlined
hIgG1 (LALA) -- italicized
PD-L1 – double underlined

NFFRMVISNPAATGGGGSGGGGSGGGGS<u>GDTRPRFLEQVKHECHFFNGTERVR FLDRYFYHQEEYVRFDSDVGEYRAVTELGRPDAEYWNSQKDLLEQKRAAVDTY CRHNYGVGESFTVQRRVYPEVTVYPAKTQPLQHHNLLVCSVNGFYPASIEVRWF RNGQEEKTGVVSTGLIQNGDWTFQTLVMLETVPRSGEVYTCQVEHPSLTSPLTV EWRARSESAQSKM</u> (SEQ ID NO:189)

Peptide epitope: NFFRMVISNPAAT (GAD65 (555-567); SEQ ID NO:87)
(G4S)n (SEQ ID NO:74) – bold
hDRB1*0401 -- underlined

FIG. 15F

Construct 3003

<u>FTVTVPKDLYVVEYGSNMTIECKFPVEKQLDLAALIVYWEMEDKNIIQFVHGEE DLKVQHSSYRQRARLLKDQLSLGNAALQITDVKLQDAGVYRCMISYGGADYKR ITVKVNAPYNKINQRILVVDPVTSEHELTCQAEGYPKAEVIWTSSDHQVLSGKTT TTNSKREEKLFNVTSTLRINTTTNEIFYCTFRRLDPEENHTAELVIPELPLAHPPNE R</u>GGGGSGGGGSGGGGSGGGGS<u>IKEEHVIIQAEFYLNPDQSGEFMFDFDGDEIFH VDMAKKETVWRLEEFGRFASFEAQGALANIAVDKANLEIMTKRSNYTPITNVPP EVTVLTNSPVELREPNVLICFIDKFTPPVVNVTWLRNGKPVTTGVSETVFLPREDH LFRKFHYLPFLPSTEDVYDCRVEHWGLDEPLLKHWEFDAPSPLPET</u>GGSAAAGG *DKTHTCPPCPAPEAAGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIEKT ISKAKGQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPG*
(SEQ ID NO:190)

PD-L1 – double underlined
(G4S)4 (SEQ ID NO:75)– bold and underlined
hDRA*0101-α1/α2 – underlined
hIgG1 (LALA) -- italicized

<u>NFIRMVISNPAAT</u>GGGGSGGGGSGGGGS<u>GDTRPRFLEQVKHECHFFNGTERVRFLDRY
FYHQEEYVRFDSDVGEYRAVTELGRPDAEYWNSQKDLLEQKRAAVDTYCRHNYGVGE
SFTVQRRVYPEVTVYPAKTQPLQHHNLLVCSVNGFYPASIEVRWFRNGQEEKTGVVSTG
LIQNGDWTFQTLVMLETVPRSGEVYTCQVEHPSLTSPLTVEWRARSESAQSKM</u>
(SEQ ID NO:191)

Peptide: NFIRMVISNPAAT (SEQ ID NO:88; GAD65 555-567; F557I)
(G4S)$_3$ (SEQ ID NO:74) -- bold
DRB1*0401 class II β chain – underlined

<u>IKEEHVIIQAEFYLNPDQSGEFMFDFDGDEIFHVDMAKKETVWRLEEFGRFASFE
AQGALANIAVDKANLEIMTKRSNYTC TNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET</u>GGSAAAGG*DKTHTCPPCPAPEAAGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRW
QQGNVFSCSVMHEALHNHYTQKSLSLSPG* (SEQ ID NO:192)

DRA1 MHC class II α chain (P81C)
GGSAAGG linker (SEQ ID NO:193) – bold
hIgG1 Fc (LALA) – italicized

GSLQPLALEGSLQSRGIVGGGGSGGGGSGGGGS<u>GDTRPRC</u>LEQVKHECHFFNG
TERVRFLDRYFYHQEEYVRFDSDVGEYRAVTELGRPDAEYWNSQKDLLEQKRA
AVDTYCRHNYGVGESFTVQRRVYPEVTVYPAKTQPLQHHNLLVCSVNGFYPASI
EVRWFRNGQEEKTGVVSTGLIQNGDWTFQTLVMLETVPRSGEVYTCQVEHPSLT
SPLTVEWRARSESAQSKM (SEQ ID NO:194)

Peptide epitope: GSLQPLALEGSLQSRGIV (SEQ ID NO:91; proIns 75-92 (K88S))
(G4S)n linker (SEQ ID NO:74)– bold
hDRB1*0401 (F7C) – underlined

GSLQPLALEGSLQSRGIVGGGGSGGGGSGGGGS<u>GDTRCR</u>FLEQVKHECHFFNG
TERVRFLDRYFYHQEEYVRFDSDVGEYRAVTELGRPDAEYWNSQKDLLEQKRA
AVDTYCRHNYGVGESFTVQRRVYPEVTVYPAKTQPLQHHNLLVCSVNGFYPASI
EVRWFRNGQEEKTGVVSTGLIQNGDWTFQTLVMLETVPRSGEVYTCQVEHPSLT
SPLTVEWRARSESAQSKM (SEQ ID NO:195)

Peptide epitope: GSLQPLALEGSLQSRGIV (SEQ ID NO:91; proIns 75-92 (K88S))
(G4S)n linker (SEQ ID NO:74)– bold
DRB1*0401 (P5C) -- underlined

GSLQPLALEGSLQSRGIVGGGGSGGGGSGGGGS<u>GDTRPRFLEQVKHECHFFNG
TERVRFLDRYFY</u>[<u>C</u>]<u>QEEYVRFDSDVGEYRAVTELGRPDAEYWNSQKDLLEQKRA
AVDTYCRHNYGVGESFTVQRRVYPEVTVYPAKTQPLQHHNLLVCSVNGFYPASI
EVRWFRNGQEEKTGVVSTGLIQNGDWTFQTLVMLETVPRSGEVYTCQVEHPSLT
SPLTVEWRARSESAQSKM</u> (SEQ ID NO:196)

Peptide epitope: GSLQPLALEGSLQSRGIV (SEQ ID NO:91; proIns 75-92 (K88S))
(G4S)n linker (SEQ ID NO:74) – bold
DRB1*0401 (H33C) -- underlined

<u>IKE</u>[<u>C</u>]<u>HVIIQAEFYLNPDQSGEFMFDFDGDEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET</u>GGSAAAGG*DKTHTCPPCPAPEAAGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRW
QQGNVFSCSVMHEALHNHYTQKSLSLSPG* (SEQ ID NO:197)

hDRA1 MHC class II α chain (E4C) – underlined
GGSAAAGG linker (SEQ ID NO:83) – bold
hIgG1 Fc (LALA) -- italicized

GSLQPLALEGSLQSRGIVGGGGSGGGGSGGGGSGDTRPRFLEQVKHECHFF[C]G
TERVRFLDRYFYHQEEYVRFDSDVGEYRAVTELGRPDAEYWNSQKDLLEQKRA
AVDTYCRHNYGVGESFTVQRRVYPEVTVYPAKTQPLQHHNLLVCSVNGFYPASI
EVRWFRNGQEEKTGVVSTGLIQNGDWTFQTLVMLETVPRSGEVYTCQVEHPSLT
SPLTVEWRARSESAQSKM (SEQ ID NO:198)

Peptide epitope: GSLQPLALEGSLQSRGIV (SEQ ID NO:91; proIns 75-92 (K88S))
(G4S)n linker (SEQ ID NO:74)– bold
hDRB1*0401 MHC class II β chain (N19C) – underlined

GSLQPLALEGSLQSRGIVGGGGSGGGGSGGGGSGDTRPRFLEQVKHECHFFN[C]
TERVRFLDRYFYHQEEYVRFDSDVGEYRAVTELGRPDAEYWNSQKDLLEQKRA
AVDTYCRHNYGVGESFTVQRRVYPEVTVYPAKTQPLQHHNLLVCSVNGFYPASI
EVRWFRNGQEEKTGVVSTGLIQNGDWTFQTLVMLETVPRSGEVYTCQVEHPSLT
SPLTVEWRARSESAQSKM (SEQ ID NO:199)

Peptide epitope: GSLQPLALEGSLQSRGIV (SEQ ID NO:91; proIns 75-92 (K88S))
(G4S)n linker (SEQ ID NO:74)– bold
hDRB1*0401 MHC class II β chain (G20C) – underlined

IKEEHVIIQAEFYLNPDQSGEFMFDFDGDEIFHVDMAKKETVWRLEEFGRFASFE
AQGALANIAVDKANLEIMTKRSNYTPITNVPPEVTVL[C]NSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPETGGSAAAGG_DKTHTCPPCPAPEAAGGPSVFLFP_
_PKPKDTLMISRTPEVTCVVVDVSHEDPEVKFNWYVDGVEVHNAKTKPREEQYNSTYR_
_VVSVLTVLHQDWLNGKEYKCKVSNKALPAPIEKTISKAKGQPREPQVYTLPPSREEMT_
_KNQVSLTCLVKGFYPSDIAVEWESNGQPENNYKTTPPVLDSDGSFFLYSKLTVDKSRW_
_QQGNVFSCSVMHEALHNHYTQKSLSLSPG_ (SEQ ID NO:200)

GGSAAAGG linker (SEQ ID NO:83) – bold
hDRA1 MHC class II α chain (T93C) – underlined
IgG1 Fc (LALA) – italicized

GSLQPLALEGSLQSRGIVGGGGSGGGGSGGGGSGDTRPRFLEQVKHECHFFNG
TERVRFLDRYFYHQEEYVRFDSDVGEYRAVTELGRPDAEYWNSQKDLLEQKRA
AVDTYCRHNYGVGESFTVQRRVYPEVTVYPAKTQPLQHHNLLVCSVNGFYPASI
EVRWFRNGQEEKTGVVSTGLIQNGDWTF[C]TLVMLETVPRSGEVYTCQVEHPSLT
SPLTVEWRARSESAQSKM (SEQ ID NO:201)

Peptide epitope: GSLQPLALEGSLQSRGIV (SEQ ID NO:91; proIns 75-92 (K88S))
(G4S)n linker (SEQ ID NO:74) – bold
hDRB1*0401 MHC class II β chain (Q156C) – underlined

GSLQPLALEGSLQSRGIVGGGGSGGGGSGGGGS<u>GDTRPRFLEQVKHECHFFNG</u>
<u>TERVRFLDRYFYHQEEYVRFDSDVGEYRAVTELGRPDAEYWNSQKDLLEQKRA</u>
<u>AVDTYCRHNYGVGESFTVQRRVYPEVTVYPAKTQPLQHHNLLVCSVNGFYPASI</u>
<u>EVRWFRNGQEEKTGVVSTGLIQNGD[C]TFQTLVMLETVPRSGEVYTCQVEHPSLT</u>
<u>SPLTVEWRARSESAQSKM</u> (SEQ ID NO:202)

Peptide epitope: GSLQPLALEGSLQSRGIV (SEQ ID NO:91; proIns 75-92 (K88S))
(G4S)n linker (SEQ ID NO:74)– bold
hDRB1*0401 MHC class II β chain (W153C) – underlined

<u>IKEEHVIIQAE[C]YLNPDQSGEFMFDFDGDEIFHVDMAKKETVWRLEEFGRFASFE</u>
<u>AQGALANIAVDKANLEIMTKRSNYTPITNVPPEVTVLTNSPVELREPNVLICFIDK</u>
<u>FTPPVVNVTWLRNGKPVTTGVSETVFLPREDHLFRKFHYLPFLPSTEDVYDCRVE</u>
<u>HWGLDEPLLKHWEFDAPSPLPET</u>GGSAAAGG*DKTHTCPPCPAPEAAGGPSVFLFP*
*PKPKDTLMISRTPEVTCVVVDVSHEDPEVKFNWYVDGVEVHNAKTKPREEQYNSTYR*
*VVSVLTVLHQDWLNGKEYKCKVSNKALPAPIEKTISKAKGQPREPQVYTLPPSREEMT*
*KNQVSLTCLVKGFYPSDIAVEWESNGQPENNYKTTPPVLDSDGSFFLYSKLTVDKSRW*
*QQGNVFSCSVMHEALHNHYTQKSLSLSPG* (SEQ ID NO:203)

GGSAAAGG linker (SEQ ID NO:83)– bold
hDRA1 MHC class II α chain (F12C) – underlined
IgG1 Fc (LALA) – italicized

GSLQPLALEGSLQSRGIVGGGGSGGGGSGGGGS<u>GDTRPRFLE</u>[C]<u>VKHECHFFNG TERVRFLDRYFYHQEEYVRFDSDVGEYRAVTELGRPDAEYWNSQKDLLEQKRA AVDTYCRHNYGVGESFTVQRRVYPEVTVYPAKTQPLQHHNLLVCSVNGFYPASI EVRWFRNGQEEKTGVVSTGLIQNGDWTFQTLVMLETVPRSGEVYTCQVEHPSLT SPLTVEWRARSESAQSKM</u> (SEQ ID NO:204)

Peptide epitope: GSLQPLALEGSLQSRGIV (SEQ ID NO:91; proIns 75-92 (K88S))
(G4S)n linker (SEQ ID NO:74)– bold
hDRB1*0401 MHC class II β chain (Q10C) – underlined

<u>IKEEHVIIQAEFYLNPDQSGEFMFDFDGDEIFHVDMAKKETVWRLEEFGRFASFE AQGALANIAVDKANLEIMTKRSNY</u>[C]<u>PITNVPPEVTVLTNSPVELREPNVLICFIDK FTPPVVNVTWLRNGKPVTTGVSETVFLPREDHLFRKFHYLPFLPSTEDVYDCRVE HWGLDEPLLKHWEFDAPSPLPET</u>GGSAAAGG*DKTHTCPPCPAPEAAGGPSVFLFP PKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSREEMT KNQVSLTCLVKGFYPSDIAVEWESNGQPENNYKTTPPVLDSDGSFFLYSKLTVDKSRW QQGNVFSCSVMHEALHNHYTQKSLSLSPG* (SEQ ID NO:205)

hDRA1 MHC class II α chain (T80C) – underlined
GGSAAAGG linker (SEQ ID NO:83)– bold
hIgG1 Fc (LALA) italicized

<u>IKEEHVIIQAEFYLNPDQSGEFMFDFDGDEIFHVDMAKKETVWRLEEFGRFASFE
AQGALANIAVDKANLEIMTKRSNYTP[C]TNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET</u>GGSAAAGG*DKTHTCPPCPAPEAAGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRW
QQGNVFSCSVMHEALHNHYTQKSLSLSPG* (SEQ ID NO:206)

hDRA1 MHC class II α chain (I82C) – underlined
GGSAAAGG linker (SEQ ID NO:83) – bold
hIgG1 Fc (LALA) italicized

GSLQPLALEGSLQSRGIVGGGGSGGGGSGGGGS<u>GDTRPRFLEQVKHECHFFNG
TERVRFLDRYFY[C]QEEYVRFDSDVGEYRAVTELGRPDAEYWNSQKDLLEQKRA
AVDTYCRHNYGVGESFTVQRRVYPEVTVYPAKTQPLQHHNLLVCSVNGFYPASI
EVRWFRNGQEEKTGVVSTGLIQNGDWTFQTLVMLETVPRSGEVYTCQVEHPSLT
SPLTVEWRARSESAQSKM</u> (SEQ ID NO:196)

Peptide epitope: GSLQPLALEGSLQSRGIV (SEQ ID NO:91; proIns 75-92 (K88S))
(G4S)n linker (SEQ ID NO:74) – bold
hDRB1*0401 MHC class II β chain (H33C) – underlined

IKEEHVIIQAEFYLNPDQSGEFMFDFD[C]DEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPETGGSAAAGG_DKTHTCPPCPAPEAAGGPSVFLFP_
_PKPKDTLMISRTPEVTCVVVDVSHEDPEVKFNWYVDGVEVHNAKTKPREEQYNSTYR_
_VVSVLTVLHQDWLNGKEYKCKVSNKALPAPIEKTISKAKGQPREPQVYTLPPSREEMT_
_KNQVSLTCLVKGFYPSDIAVEWESNGQPENNYKTTPPVLDSDGSFFLYSKLTVDKSRW_
_QQGNVFSCSVMHEALHNHYTQKSLSLSPG_ (SEQ ID NO:207)

hDRA1 MHC class II α chain (G28C) – underlined
GGSAAAGG linker (SEQ ID NO:83) – bold
hIgG1 Fc (LALA) italicized

GSLQPLALEGSLQSRGIVGGGGSGGGGSGGGGSGDTRPRFLEQVKHECHFFNG
TERVRFLDRYFYHQEEYVRFDSDVGEYRAVTELGRPDAEYWNSQKDLLEQKRA
AVDTYCRHNYGVGESFTVQRRVYPEVTVYPAKTQPLQHHNLLVCSVNGFYPASI
EVRWFRNGQEEKTGVVSTGLIQN[C]DWTFQTLVMLETVPRSGEVYTCQVEHPSLT
SPLTVEWRARSESAQSKM (SEQ ID NO:208)

Peptide epitope: GSLQPLALEGSLQSRGIV (SEQ ID NO:91; proIns 75-92 (K88S))
(G4S)n linker (SEQ ID NO:74) – bold
hDRB1*0401 MHC class II β chain (G151C) – underlined

GSLQPLALEGSLQSRGIVGGGGSGGGGSGGGGS<u>GDTRPRFLEQVKHECHFFNG</u>
<u>TERVRFLDRYFYHQEEYVRFDSDVGEYRAVTELGRPDAEYWNSQKDLLEQKRA</u>
<u>AVDTYCRHNYGVGESFTVQRRVYPEVTVYPAKTQPLQHHNLLVCSVNGFYPASI</u>
<u>EVRWFRNGQEEKTGVVSTGLIQNG[C]WTFQTLVMLETVPRSGEVYTCQVEHPSLT</u>
<u>SPLTVEWRARSESAQSKM</u> (SEQ ID NO:209)

Peptide epitope: GSLQPLALEGSLQSRGIV (SEQ ID NO:91; proIns 75-92 (K88S))
(G4S)n linker (SEQ ID NO:74)– bold
hDRB1*0401 MHC class II β chain (D152C) – underlined

<u>IKEEHVIIQAEFYLNPDQSGEFMFDFDGDEIFHVDMAKKETVWRLEEFGRFASFE</u>
<u>AQGALANIAVDKANLEIMTKRSNYTPITNVPPEVTVLTNSPVELREPNVLICFIDK</u>
<u>FTPPVVNVTWLRNGKPVTTGVSETVFLPREDHLFRKFHYLPFLPSTEDVYDCRVE</u>
<u>HWGLDEPLLKHWEFDAPSPLPET</u>GGSAAAGG*DKTHTCPPCPAPEAAGGPSVFLFP*
*PKPKDTLMISRTPEVTCVVVDVSHEDPEVKFNWYVDGVEVHNAKTKPREEQYNSTYR*
*VVSVLTVLHQDWLNGKEYKCKVSNKALPAPIEKTISKAKGQPREPQVYTLPPSREEMT*
*KNQVSLTCLVKGFYPSDIAVEWESNGQPENNYKTTPPVLDSDGSFFLYSKLTVDKSRW*
*QQGNVFSCSVMHEALHNHYTQKSLSLSPG* (SEQ ID NO:210)

hDRA1 MHC class II α chain – underlined
GGSAAAGG linker (SEQ ID NO:83)– bold
hIgG1 Fc (LALA) italicized

GSLQPLALEGSLQSRGIVGGGGSGGGGSGGGGS<u>GDTRPRFLEQVKHECHFFNG
TERVRFLDRYFYHQEEYVRFDSDVGEYRAVTELGRPDAEYWNSQKDLLEQKRA
AVDTYCRHNYGVGESFTVQRRVYPEVTVYPAKTQPLQHHNLLVCSVNGFYPASI
EVRWFRNGQEEKTGVVSTGLIQNGDWTFQTLVMLETVPRSGEVYTCQVEHPSLT
SPLTVEWRARSESAQSKM</u> (SEQ ID NO:211)

Peptide epitope: GSLQPLALEGSLQSRGIV (SEQ ID NO:91; proIns 75-92 (K88S))
(G4S)n linker (SEQ ID NO:74)– bold
hDRB1*0401 MHC class II β chain – underlined

<u>IKEEHVIIQAEFYLNPDQSGEFMFDFDGCEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET</u>GGSAAAGG*DKTHTCPPCPAPEAAGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRW
QQGNVFSCSVMHEALHNHYTQKSLSLSPG* (SEQ ID NO:212)

hDRA1 MHC class II α chain (D29C) – underlined
GGSAAAGG linker (SEQ ID NO:83)– bold
hIgG1 Fc (LALA) italicized

IKEEHVIIQAEFYLNPDQSGEFMFDFDGDEIFHVDMAKKETVWRLEEFGRFASFE
AQGALANIAVDKANLEIMTKRSNYTPITNVPPEVTVLTCSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPETGGSAAAGG*DKTHTCPPCPAPEAAGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRW
QQGNVFSCSVMHEALHNHYTQKSLSLSPG* (SEQ ID NO:213)

hDRA1 MHC class II α chain (N94C) – underlined
GGSAAAGG linker (SEQ ID NO:83) – bold
hIgG1 Fc (LALA) italicized

GSLQPLALEGSLQSRGIVGGGGSGGGGSGGGGS<u>GDTRPRFLEQVKHECHFFNG</u>
<u>TERVRFLDRYFYHQEEYVRFDSDVGEYRAVTELGRPDAEYWNSQKDLLEQKRA</u>
<u>AVDTYCRHNYGVGESFTVQRRVYPEVTVYPAKTQPLQHHNLLVCSV</u>[C]<u>GFYPASI</u>
<u>EVRWFRNGQEEKTGVVSTGLIQNGDWTFQTLVMLETVPRSGEVYTCQVEHPSLT</u>
<u>SPLTVEWRARSESAQSKM</u> (SEQ ID NO:214)

Peptide epitope: GSLQPLALEGSLQSRGIV (SEQ ID NO:91; proIns 75-92 (K88S))
(G4S)n linker (SEQ ID NO:74)– bold
hDRB1*0401 MHC class II β chain (N120C) – underlined

<u>IKEEHVIIQAEFYLNPDQSGEFMFDFDGDEIFHVDMAKKETVWRLEEFGRFASFE</u>
<u>AQGALANIAVDKANLEIMTKRSNYTPITNVPPEVTVLTN</u>[C]<u>PVELREPNVLICFIDK</u>
<u>FTPPVVNVTWLRNGKPVTTGVSETVFLPREDHLFRKFHYLPFLPSTEDVYDCRVE</u>
<u>HWGLDEPLLKHWEFDAPSPLPET</u>GGSAAAGG*DKTHTCPPCPAPEAAGGPSVFLFP*
*PKPKDTLMISRTPEVTCVVVDVSHEDPEVKFNWYVDGVEVHNAKTKPREEQYNSTYR*
*VVSVLTVLHQDWLNGKEYKCKVSNKALPAPIEKTISKAKGQPREPQVYTLPPSREEMT*
*KNQVSLTCLVKGFYPSDIAVEWESNGQPENNYKTTPPVLDSDGSFFLYSKLTVDKSRW*
*QQGNVFSCSVMHEALHNHYTQKSLSLSPG* (SEQ ID NO:215)

hDRA1 MHC class II α chain (S95C) – underlined
GGSAAAGG linker (SEQ ID NO:83)– bold
hIgG1 Fc (LALA) italicized

<u>IKCEHVIIQAEFYLNPDQSGEFMFDFDGDEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET</u>GGSAAAGG_DKTHTCPPCPAPEAAGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRW
QQGNVFSCSVMHEALHNHYTQKSLSLSPG_ (SEQ ID NO:216)

hDRA1 MHC class II α chain (E3C) – underlined
GGSAAAGG linker (SEQ ID NO:83) – bold
hIgG1 Fc (LALA) italicized

<u>IKEEHVIIQAEFYLNPDQSGEFMFDFDGDEIFHVDMAKKETVWRLEEFGRFASFE
AQGALANIAVDKANLECMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET</u>GGSAAAGG_DKTHTCPPCPAPEAAGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRW
QQGNVFSCSVMHEALHNHYTQKSLSLSPG_ (SEQ ID NO:217)

hDRA1 MHC class II α chain (I72C) – underlined
GGSAAAGG linker (SEQ ID NO:83) – bold
hIgG1 Fc (LALA) italicized

IKEEHVIIQAEFYLNPDQSGEFMFDFDGDEIFHVDMAKKETVWRLEEFGRFASFE
AQGALANIAVDKANLEIMTCRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPETGGSAAAGG*DKTHTCPPCPAPEAAGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRW
QQGNVFSCSVMHEALHNHYTQKSLSLSPG* (SEQ ID NO:218)

hDRA1 MHC class II α chain (K75C) – underlined
GGSAAAGG linker (SEQ ID NO:83) – bold
hIgG1 Fc (LALA) italicized

SLQPLALEGSLQSRGCGGGSGGGGSGGGGSGDTRPRFLEQVKHECHFFNGTER
VRFLDRYFYHQEEYVRFDSDVGEYRAVTELGRPDAEYWNSQKDLLEQKRAAVD
TYCRHNYGVGESFTVQRRVYPEVTVYPAKTQPLQHHNLLVCSVNGFYPASIEVR
WFRNGQEEKTGVVSTGLIQNGDWTFQTLVMLETVPRSGEVYTCQVEHPSLTSPL
TVEWRARSESAQSKM (SEQ ID NO:219)

Peptide epitope: SLQPLALEGSLQSRG (SEQ ID NO:90; proinsulin 76-90 (K88S))
(CGGGS)(GGGGS)2 linker (SEQ ID NO:220) – bold
hDRB1*0401 – underlined

SLQPLALEGSLQSRGGCGGSGGGGSGGGGS<u>GDTRPRFLEQVKHECHFFNGTER
VRFLDRYFYHQEEYVRFDSDVGEYRAVTELGRPDAEYWNSQKDLLEQKRAAVD
TYCRHNYGVGESFTVQRRVYPEVTVYPAKTQPLQHHNLLVCSVNGFYPASIEVR
WFRNGQEEKTGVVSTGLIQNGDWTFQTLVMLETVPRSGEVYTCQVEHPSLTSPL
TVEWRARSESAQSKM</u> (SEQ ID NO:221)

Peptide epitope: SLQPLALEGSLQSRG (SEQ ID NO:90; proinsulin 76-90 (K88S))
(GCGGS)(GGGGS)2 linker (SEQ ID NO:222)– bold
hDRB1*0401 – underlined

SLQPLALEGSLQSRGGGCGSGGGGSGGGGS<u>GDTRPRFLEQVKHECHFFNGTER
VRFLDRYFYHQEEYVRFDSDVGEYRAVTELGRPDAEYWNSQKDLLEQKRAAVD
TYCRHNYGVGESFTVQRRVYPEVTVYPAKTQPLQHHNLLVCSVNGFYPASIEVR
WFRNGQEEKTGVVSTGLIQNGDWTFQTLVMLETVPRSGEVYTCQVEHPSLTSPL
TVEWRARSESAQSKM</u> (SEQ ID NO:185)

Peptide epitope: SLQPLALEGSLQSRG (SEQ ID NO:90; proinsulin 76-90 (K88S))
(GGCGS)(GGGGS)2 linker (SEQ ID NO:128)– bold
hDRB1*0401 – underlined

SLQPLALEGSLQSRGGGGGCGGGGSGGGGSGDTRPRFLEQVKHECHFFNGTER
VRFLDRYFYHQEEYVRFDSDVGEYRAVTELGRPDAEYWNSQKDLLEQKRAAVD
TYCRHNYGVGESFTVQRRVYPEVTVYPAKTQPLQHHNLLVCSVNGFYPASIEVR
WFRNGQEEKTGVVSTGLIQNGDWTFQTLVMLETVPRSGEVYTCQVEHPSLTSPL
TVEWRARSESAQSKM (SEQ ID NO:223)

Peptide epitope: SLQPLALEGSLQSRG (SEQ ID NO:90; proinsulin 76-90 (K88S))
(GGGGC)(GGGGS)2 linker (SEQ ID NO:224)– bold
hDRB1*0401 – underlined

SLQPLALEGSLQSRGGGGCSGGGGSGGGGSGDTRPRFLEQVKHECHFFNGTER
VRFLDRYFYHQEEYVRFDSDVGEYRAVTELGRPDAEYWNSQKDLLEQKRAAVD
TYCRHNYGVGESFTVQRRVYPEVTVYPAKTQPLQHHNLLVCSVNGFYPASIEVR
WFRNGQEEKTGVVSTGLIQNGDWTFQTLVMLETVPRSGEVYTCQVEHPSLTSPL
TVEWRARSESAQSKM (SEQ ID NO:225)

Peptide epitope: SLQPLALEGSLQSRG (SEQ ID NO:90; proinsulin 76-90 (K88S))
(GGGCS)(GGGGS)2 linker (SEQ ID NO:226)– bold
hDRB1*0401 – underlined

<u>IKEEHVIIQAEFYLNPDQSGEFMFDFDGDEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET</u>GGSAAAGG*DKTHTCPPCPAPEAAGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRW
QQGNVFSCSVMHEALHNHYTQKSLSLSPG***GGGGSGGGGSGGGGSGGGGS*<ins>FTVT
VPKDLYVVEYGSNMTIECKFPVEKQLDLAALIVYWEMEDKNIIQFVHGEEDLKV
QHSSYRQRARLLKDQLSLGNAALQITDVKLQDAGVYRCMISYGGADYKRITVK
VNAPC̲NKINQRILVVDPVTSEHELTCQAEC̲YPKAEVIWTSSDHQVLSGKTTTTNS
KREEKLFNVTSTLRINTTTNEIFYCTFRRLDPEENHTAELVIPELPLAHPPNER</ins>

(SEQ ID NO:227)

hDRA1 MHC class II α chain – underlined
GGSAAAGG linker (SEQ ID NO:83) – bold
(G4S)n linker (SEQ ID NO:75) – bold
PD-L1 (IgV domain 19-131; Y134C; G159C) – double underlined

QAVHAAHAEINGGGGSGGGGSGGGGS<u>LEQPNVAISLSRTEALNHHNTLVCSVT DFYPAKIKVRWFRNGQEETVGVSSTQLIRNGDWTFQVLVMLEMTPHQGEVYTC HVEHPSLKSPITVEWRAQSESARSK</u>GGGGSGGGGSGGGGSGGGGSGGGGSGG GGS*DKTHTCPPCPAPEAAGGPSVFLFPPKPKDTLMISRTPEVTCVVVDVSHEDPEVK FNWYVDGVEVHNAKTKPREEQYNSTYRVVSVLTVLHQDWLNGKEYKCKVSNKALPAP IEKTISKAKGQPREPQVYTLPPSREEMTKNQVSLTCLVKGFYPSDIAVEWESNGQPEN NYKTTPPVLDSDGSFFLYSKLTVDKSRWQQGNVFSCSVMHEALHNHYTQKSLSLSPG* (SEQ ID NO:228)

Peptide epitope: QAVHAAHAEIN (SEQ ID NO:229)
IAg7 MHC class II β chain – underlined
(G4S)n linker (SEQ ID NO:71)– bold
IgG1 Fc (LALA) – italicized

<u>FTVTVPKDLYVVEYGSNMTIECKFPVEKQLDLAALIVYWEMEDKNIIQFVHGEE
DLKVQHSSYRQRARLLKDQLSLGNAALQITDVKLQDAGVYRCMISYGGADYKR
ITVKVNAPYNKINQRILVVDPVTSEHELTCQAEGYPKAEVIWTSSDHQVLSGKTT
TTNSKREEKLFNVTSTLRINTTTNEIFYCTFRRLDPEENHTAELVIPELPLAHPPNE
R</u>GGGGSGGGGSGGGGSGGGGS<u>IKEEHVIIQAEFYLNPDQSGEFMFDFDGDEIFH
VDMAKKETVWRLEEFGRFASFEAQGALANIAVDKANLEC̲MTKRSNYTPITNVPP
EVTVLTNSPVELREPNVLICFIDKFTPPVVNVTWLRNGKPVTTGVSETVFLPREDH
LFRKFHYLPFLPSTEDVYDCRVEHWGLDEPLLKHWEFDAPSPLPET</u>GGSAAAGG
*DKTHTCPPCPAPEAAGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPG* (SEQ
ID NO:230)

PD-L1 – double underlined
(G4S)n linker (SEQ ID NO:75) – bold
hDRA1 MHC class II α chain (I82C) – underlined
GGSAAAGG linker (SEQ ID NO:83) – bold
hIgG1 Fc (LALA) italicized

<u>IKEEHVIIQAEFYLNPDQSGEFMFDFDGDEIFHVDMAKKETVWRLEEFGRFASFE
AQGALANIAVDKANLEIMTKRSNYTPITNVPPEVTVLTNSPVELREPNVLICFIDK
FTPPVVNVTWLRNGKPVTTGVSETVFLPREDHLFRKFHYLPFLPSTEDVYDCRVE
HWGLDEPLLKHWEFDAPSPLPET</u>GGGGSGGGGSGGGGSGGGGS<u>FTVTVPKDL
YVVEYGSNMTIECKFPVEKQLDLAALIVYWEMEDKNIIQFVHGEEDLKVQHSSY
RQRARLLKDQLSLGNAALQITDVKLQDAGVYRCMISYGGADYKRITVKVNAPY
NKINQRILVVDPVTSEHELTCQAEGYPKAEVIWTSSDHQVLSGKTTTTNSKREEK
LFNVTSTLRINTTTNEIFYCTFRRLDPEENHTAELVIPELPLAHPPNER</u>**GGGGSGG
GGSGGGGSGGGGS***DKTHTCPPCPAPEAAGGPSVFLFPPKPKDTLMISRTPEVTCVV
VDVSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHN
HYTQKSLSLSPG* (SEQ ID NO:231)

hDRA*0101 α chain – underlined
(G4S)n linker (SEQ ID NO:74)– bold
PD-L1 – double underlined
IgG1 Fc (LALA) – italicized

<u><u>FTVTVPKDLYVVEYGSNMTIECKFPVEKQLDLAALIVYWEMEDKNIIQFVHGEE</u></u>
<u><u>DLKVQHSSYRQRARLLKDQLSLGNAALQITDVKLQDAGVYRCMISYGGADYKR</u></u>
<u><u>ITVKVNAPYNKINQRILVVDPVTSEHELTCQAEGYPKAEVIWTSSDHQVLSGKTT</u></u>
<u><u>TTNSKREEKLFNVTSTLRINTTTNEIFYCTFRRLDPEENHTAELVIPELPLAHPPNE</u></u>
<u><u>R</u></u>GGGGSGGGGSGGGGSNFFRMVISNPAATGGGGSGGGGSGGGGS<u>GDTRPRF</u>
<u>LEQVKHECHFFNGTERVRFLDRYFYHQEEYVRFDSDVGEYRAVTELGRPDAEY</u>
<u>WNSQKDLLEQKRAAVDTYCRHNYGVGESFTVQRRVYPEVTVYPAKTQPLQHH</u>
<u>NLLVCSVNGFYPASIEVRWFRNGQEEKTGVVSTGLIQNGDWTFQTLVMLETVPR</u>
<u>SGEVYTCQVEHPSLTSPLTVEWRARSESAQSKM</u> (SEQ ID NO:232)

PD-L1 – double underlined
Peptide epitope – NFFRMVISNPAAT (SEQ ID NO:87; GAD65 555-567)
(G4S)n linker (SEQ ID NO:74)– bold
hDRB1*0401 β chain – underlined

NFFRMVISNPAATGGGGSGGGGSGGGGS<u>GDTRPRFLEQVKHECHFFNGTERVR FLDRYFYHQEEYVRFDSDVGEYRAVTELGRPDAEYWNSQKDLLEQKRAAVDTY CRHNYGVGESFTVQRRVYPEVTVYPAKTQPLQHHNLLVCSVNGFYPASIEVRWF RNGQEEKTGVVSTGLIQNGDWTFQTLVMLETVPRSGEVYTCQVEHPSLTSPLTV EWRARSESAQSKM</u>GGGGSGGGGSGGGGS<u>FTVTVPKDLYVVEYGSNMTIECKF PVEKQLDLAALIVYWEMEDKNIIQFVHGEEDLKVQHSSYRQRARLLKDQLSLGN AALQITDVKLQDAGVYRCMISYGGADYKRITVKVNAPYNKINQRILVVDPVTSE HELTCQAEGYPKAEVIWTSSDHQVLSGKTTTTNSKREEKLFNVTSTLRINTTTNEI FYCTFRRLDPEENHTAELVIPELPLAHPPNER</u> (SEQ ID NO:233)

Peptide epitope – NFFRMVISNPAAT (SEQ ID NO:87; GAD65 555-567)
(G4S)n linker (SEQ ID NO:74) – bold
hDRB1*0401 β chain – underlined
PD-L1 – double underlined

FIG. 17A

| Syn | Mutation | ProA Yield mg/L | % mono |
|---|---|---|---|
| 2932-2639 | No DS | 80 | 80 |
| 2983-2987 | P81C, P5C | 67 | 81 |
| 2983-3027 | P81C, N33C | 67 | 72 |
| 3020-3027 | I82C, N33C | 53 | 78 |
| 3022-3028 | D29C, G151C | 44 | 78 |
| 3022-3030 | D29C, W153C | 40 | 69 |
| 2933-2935 | I72C, (P)R89C | 44 | 81 |
| 2933-2936 | I72C, (P)G90C | 98 | 86 |
| 2934-2937 | I72C, G1C | 98 | 86 |
| 2933-2640 | I72C, G2C | 98 | 86 |
| 2933-2938 | I72C, G3C | 76 | 86 |
| 2933-2940 | I72C, S5C | 27 | 84 |
| 2934-2937 | K75C, G1C | 71 | 86 |
| 2934-2640 | K75C, G2C | 107 | 81 |
| 2934-2938 | K75C, G3C | 89 | 85 |
| 2934-2939 | K75C, G4C | 76 | 86 |
| 2934-2940 | K75C, S5C | 53 | 88 |

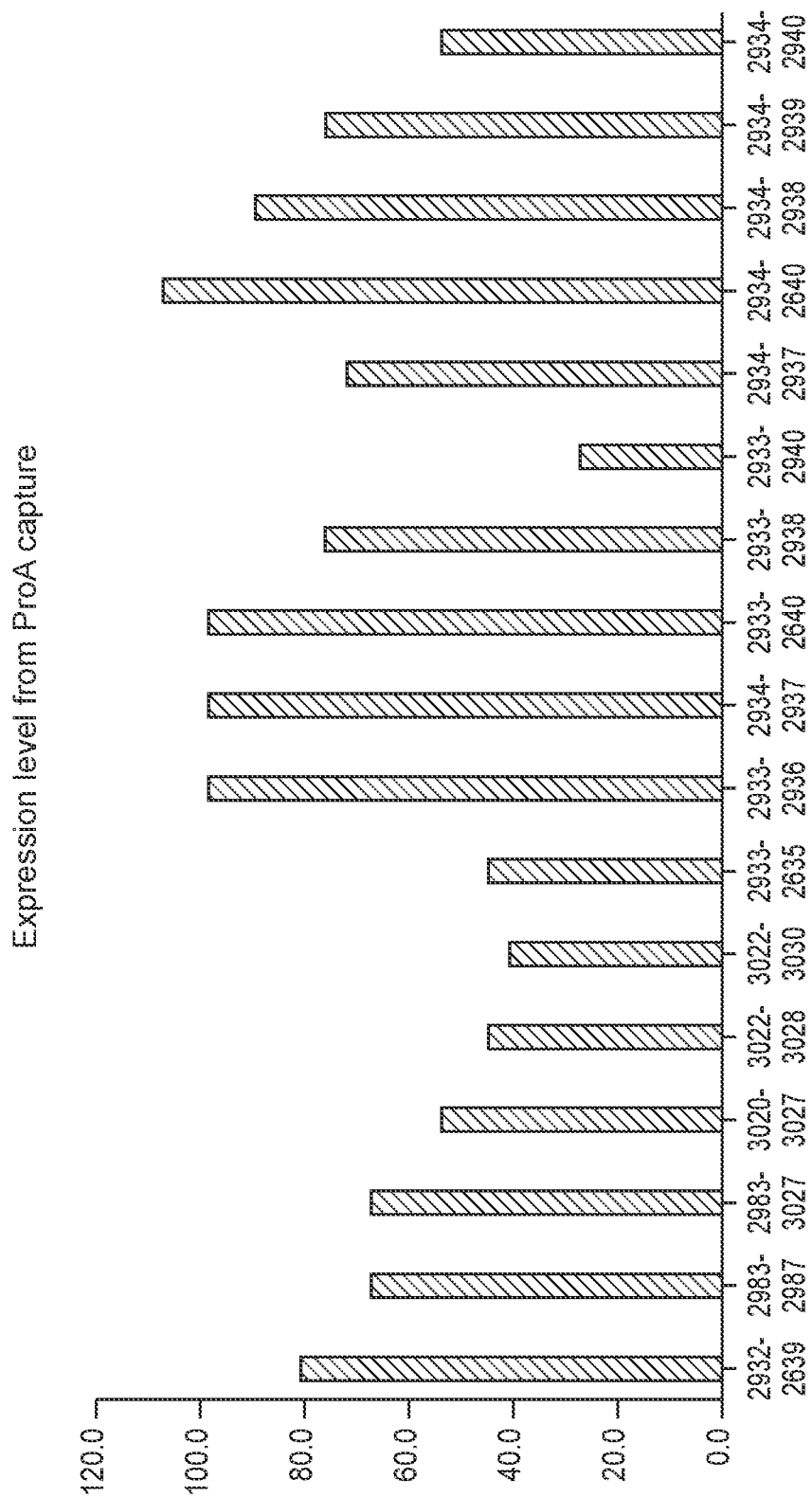

FIG. 18A

| Plasmid | Heavy | Light | Ratio | MW (H/L) | Gel Lane |
|---|---|---|---|---|---|
| 2983-2986 | hDRA1*0101-alpha1-2(P81C)-GGSAAAGG-hIgG1(LALA) | Proins(75-92;K88S)-(G4S)3-hDRB1*0401-beta1-2(F7C) | 1:1 | 48/26 | 1 |
| 2983-2987 | hDRA1*0101-alpha1-2(P81C)-GGSAAAGG-hIgG1(LALA) | Proins(75-92;K88S)-(G4S)3-hDRB1*0401-beta1-2(P5C) | 1:1 | 48/26 | 2 |
| 2983-3027 | hDRA1*0101-alpha1-2(P81C)-GGSAAAGG-hIgG1(LALA) | Proins(75-92;K88S)-(G4S)3-hDRB1*0401-beta1-2(N33C) | 1:1 | 48/26 | 3 |
| 2984-2988 | hDRA1*0101-alpha1-2(E4C)-GGSAAAGG-hIgG1(LALA) | Proins(75-92;K88S)-(G4S)3-hDRB1*0401-beta1-2(N19C) | 1:1 | 48/26 | 4 |
| 2984-3032 | hDRA1*0101-alpha1-2(E4C)-GGSAAAGG-hIgG1(LALA) | Proins(75-92;K88S)-(G4S)3-hDRB1*0401-beta1-2(G20C) | 1:1 | 48/26 | 5 |
| 2985-2989 | hDRA1*0101-alpha1-2(T93C)-GGSAAAGG-hIgG1(LALA) | Proins(75-92;K88S)-(G4S)3-hDRB1*0401-beta1-2(Q156C) | 1:1 | 48/26 | 6 |
| 2985-3030 | hDRA1*0101-alpha1-2(T93C)-GGSAAAGG-hIgG1(LALA) | Proins(75-92;K88S)-(G4S)3-hDRB1*0401-beta1-2(W153C) | 1:1 | 48/26 | 7 |
| 3018-2986 | hDRA1*0101-alpha1-2(F12C)-GGSAAAGG-hIgG1(LALA) | Proins(75-92;K88S)-(G4S)3-hDRB1*0401-beta1-2(F7C) | 1:1 | 48/26 | 8 |
| 3018-3026 | hDRA1*0101-alpha1-2(F12C)-GGSAAAGG-hIgG1(LALA) | Proins(75-92;K88S)-(G4S)3-hDRB1*0401-beta1-2(Q10C) | 1:1 | 48/26 | 9 |
| 3019-2986 | hDRA1*0101-alpha1-2(T80C)-GGSAAAGG-hIgG1(LALA) | Proins(75-92;K88S)-(G4S)3-hDRB1*0401-beta1-2(F7C) | 1:1 | 48/26 | 10 |

FIG. 18B

| Plasmid | Heavy | Light | Ratio | MW (H/L) | Gel Lane |
|---|---|---|---|---|---|
| 3019-2987 | hDRA1*0101-alpha1-2(T80C)-GGSAAAGG-hIgG1(LALA) | Proins(75-92;K88S)-(G4S)3-hDRB1*0401-beta1-2(P5C) | 1:1 | 48/26 | 11 |
| 3019-3027 | hDRA1*0101-alpha1-2(T80C)-GGSAAAGG-hIgG1(LALA) | Proins(75-92;K88S)-(G4S)3-hDRB1*0401-beta1-2(N33C) | 1:1 | 48/26 | 12 |
| 3020-2986 | hDRA1*0101-alpha1-2(I82C)-GGSAAAGG-hIgG1(LALA) | Proins(75-92;K88S)-(G4S)3-hDRB1*0401-beta1-2(F7C) | 1:1 | 48/26 | 13 |
| 3020-2987 | hDRA1*0101-alpha1-2(I82C)-GGSAAAGG-hIgG1(LALA) | Proins(75-92;K88S)-(G4S)3-hDRB1*0401-beta1-2(P5C) | 1:1 | 48/26 | 14 |
| 3020-3027 | hDRA1*0101-alpha1-2(I82C)-GGSAAAGG-hIgG1(LALA) | Proins(75-92;K88S)-(G4S)3-hDRB1*0401-beta1-2(N33C) | 1:1 | 48/26 | 15 |
| 3021-3028 | hDRA1*0101-alpha1-2(G28C)-GGSAAAGG-hIgG1(LALA) | Proins(75-92;K88S)-(G4S)3-hDRB1*0401-beta1-2(G151C) | 1:1 | 48/26 | 16 |
| 3021-3029 | hDRA1*0101-alpha1-2(G28C)-GGSAAAGG-hIgG1(LALA) | Proins(75-92;K88S)-(G4S)3-hDRB1*0401-beta1-2(D152C) | 1:1 | 48/26 | 17 |
| 3021-3030 | hDRA1*0101-alpha1-2(G28C)-GGSAAAGG-hIgG1(LALA) | Proins(75-92;K88S)-(G4S)3-hDRB1*0401-beta1-2(W153C) | 1:1 | 48/26 | 18 |
| 2932-2744 | Native leader-hDRA1*0101-alpha1-2-GGSAAAGG-hIgG1(LALA) | Proins(75-92;K88S)-(G4S)3-hDRB1*0401-beta1-2 | 1:1 | 48/26 | 19 |
| 2932-2639 | Native leader-hDRA1*0101-alpha1-2-GGSAAAGG-hIgG1(LALA) | Proins(75-92;K88S)-(G4S)3-hDRB1*0401-beta1-2 | 1:1 | 48/26 | 20 |

FIG. 18C
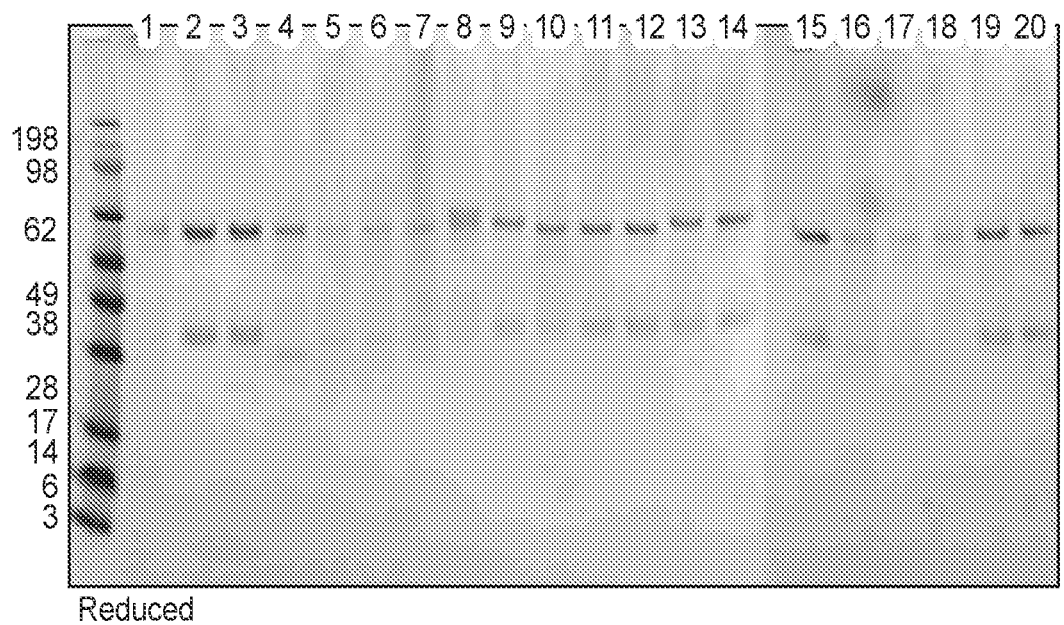
Reduced
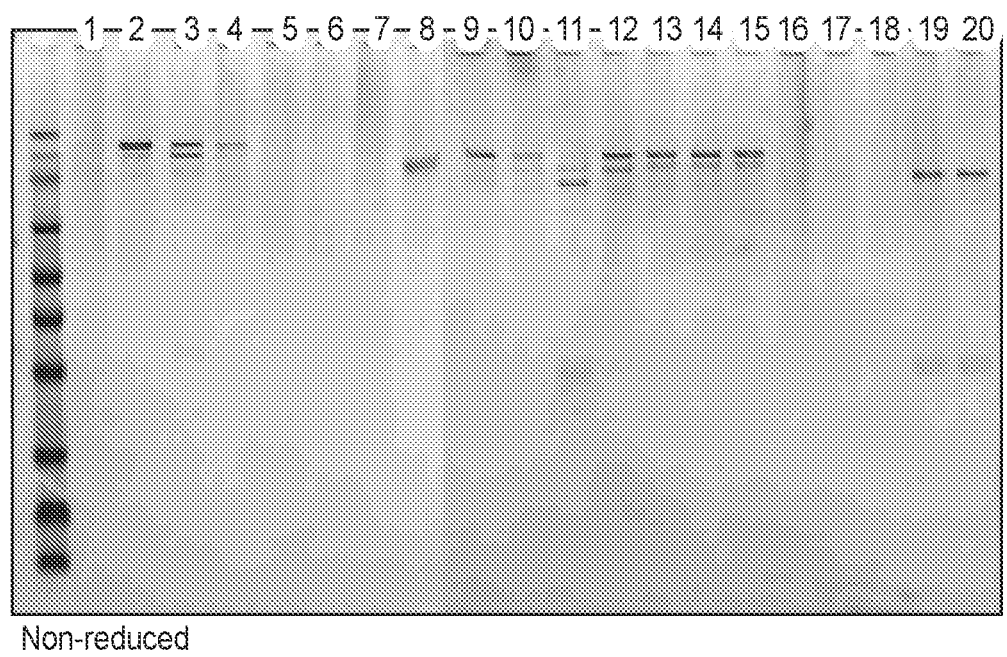
Non-reduced

% monomer

| Sample ID | Peptide | Mod | Expression mg/L | Mw H/L | 0x | 1x | 3x |
|---|---|---|---|---|---|---|---|
| ST-3003, 2579 | | PDL1 (pos. 1) | 8 | 74 / 26 | 95 | 95 | 95 |
| ST-3004, 2579 | | PDL1 (pos. 2) | 21.5 | 75 / 26 | 95 | 95 | 96 |
| ST-3005, 2579 | Gad65 (WT) | PDL1 (pos. 3) | 29.5 | 74 / 26 | 97 | 97 | 97 |
| ST-2932-3006 | | PDL1 (pos. 4) | 125 | 48 / 52 | 99 | 99 | 96 |
| ST-2932-3007 | | PDL1 (pos. 5) | 24 | 48 / 52 | 58 | 56 | 56 |

FIG. 20A

| Plasmid | Heavy | Light | MW (H/L) | Gel Lane |
|---|---|---|---|---|
| 2567-2580 | IL2(H16T,F42A)-(G4S)6-hDRA1*0101-alpha1-2-GGSAAAGG-hIgG1(LALA) | GAD65(555-567;F557I)-(G4S)3-hDRB1*0401-beta1-2 | 65/26 | 1 |
| 2568-2580 | hDRA1*0101-alpha1-2-(G4S)4-IL2(H16T,F42A)-(G4S)4-hIgG1(LALA) | GAD65(555-567;F557I)-(G4S)3-hDRB1*0401-beta1-2 | 65/26 | 2 |
| 2569-2580 | hDRA1*0101-alpha1-2-GGSAAAGG-hIgG1(LALA)-(G4S)4-IL2(H16T,F42A) | GAD65(555-567;F557I)-(G4S)3-hDRB1*0401-beta1-2 | 64/28 | 3 |
| 1977-3001 | hDRA1*0101-alpha1-2-GGSAAAGG-hIgG1(LALA) | IL2(H16T,F42A)-(G4S)3-GAD65(555-567)-(G4S)3-hDRB1*0401-beta1-2 | 48/42 | 4 |
| 1977-3002 | hDRA1*0101-alpha1-2-GGSAAAGG-hIgG1(LALA) | GAD65(555-567;F557I)-(G4S)3-hDRB1*0401-beta1-2-(G4S)3-IL2(H16T,F42A) | 48/42 | 5 |
| 3003-2580 | hPDL1ecto(wt)-(G4S)4-hDRA1*0101-alpha1-2-GGSAAAGG-hIgG1(LALA) | GAD65(555-567;F557I)-(G4S)3-hDRB1*0401-beta1-2 | 74/26 | 6 |
| 3005-2580 | hDRA1*0101-alpha1-2-GGSAAAGG-hIgG1(LALA)-(G4S)4-hPDL1ecto(wt) | GAD65(555-567;F557I)-(G4S)3-hDRB1*0401-beta1-2 | 74/26 | 7 |
| 2932-3006 | Native leader-hDRA1*0101-alpha1-2-GGSAAAGG-hIgG1(LALA) | hPDL1ecto(wt)-(G4S)3-GAD65(555-567)-(G4S)3-hDRB1*0401-beta1-2 | 48/52 | 8 |
| 2932-3007 | Native leader-hDRA1*0101-alpha1-2-GGSAAAGG-hIgG1(LALA) | GAD65(555-567;F557I)-(G4S)3-hDRB1*0401-beta1-2-(G4S)3-hPDL1ecto(wt) | 48/52 | 9 |

FIG. 20B

| Plasmid | Heavy | Light | MW (H/L) | Gel Lane |
|---|---|---|---|---|
| 3003-3002 | hPDL1ecto(wt)-(G4S)4-hDRA1*0101-alpha1-2-GGSAAAGG-hIgG1(LALA) | GAD65(555-567)-(G4S)3-hDRB1*0401-beta1-2-(G4S)3-IL2(H16T,F42A) | 74 / 42 | 10 |
| 3005-3002 | hDRA1*0101-alpha1-2-GGSAAAGG-hIgG1(LALA)-(G4S)4-hPDL1ecto(wt) | GAD65(555-567)-(G4S)3-hDRB1*0401-beta1-2-(G4S)3-IL2(H16T,F42A) | 74 / 42 | 11 |
| 3003-2639 | hPDL1ecto(wt)-(G4S)4-hDRA1*0101-alpha1-2-GGSAAAGG-hIgG1(LALA) | ProIns(75-90:K88S)-(G4S)3-hDRB1*0401-beta1-2 | 74 / 26 | 12 |
| 3005-2639 | hDRA1*0101-alpha1-2-GGSAAAGG-hIgG1(LALA)-(G4S)4-hPDL1ecto(wt) | ProIns(76-90:K88S)-(G4S)3-hDRB1*0401-beta1-2 | 74 / 26 | 13 |
| 3005-2571 | hDRA1*0101-alpha1-2-GGSAAAGG-hIgG1(LALA)-(G4S)4-hPDL1ecto(wt) | ProIns(73-90)-(G4S)3-hDRB1*0401-beta1-2-(G4S)3-IL2(H16T,F42A) | 74 / 42 | 14 |
| 3013-2580 | Betagly can-(G4S)4-hDRA1*0101-alpha1-2-GGSAAAGG-hIgG1(LALA) | GAD65(555-567,F557I)-(G4S)3-hDRB1*0401-beta1-2 | 133 / 26 | 15 |
| 3015-2580 | hDRA1*0101-alpha1-2-GGSAAAGG-hIgG1(LALA)-(G4S)4-betagly can | GAD65(555-567,F557I)-(G4S)3-hDRB1*0401-beta1-2 | 133 / 26 | 16 |
| 2932-3016 | Native leader-hDRA1*0101-alpha1-2-GGSAAAGG-hIgG1(LALA) | Betagly can-(G4S)3-GAD65(555-567)-(G4S)3-hDRB1*0401-beta1-2 | 48 / 111 | 17 |
| 2932-3017 | Native leader-hDRA1*0101-alpha1-2-GGSAAAGG-hIgG1(LALA) | GAD65(555-567)-(G4S)3-hDRB1*0401-beta1-2-(G4S)3-betagly can | 48 / 111 | 18 |

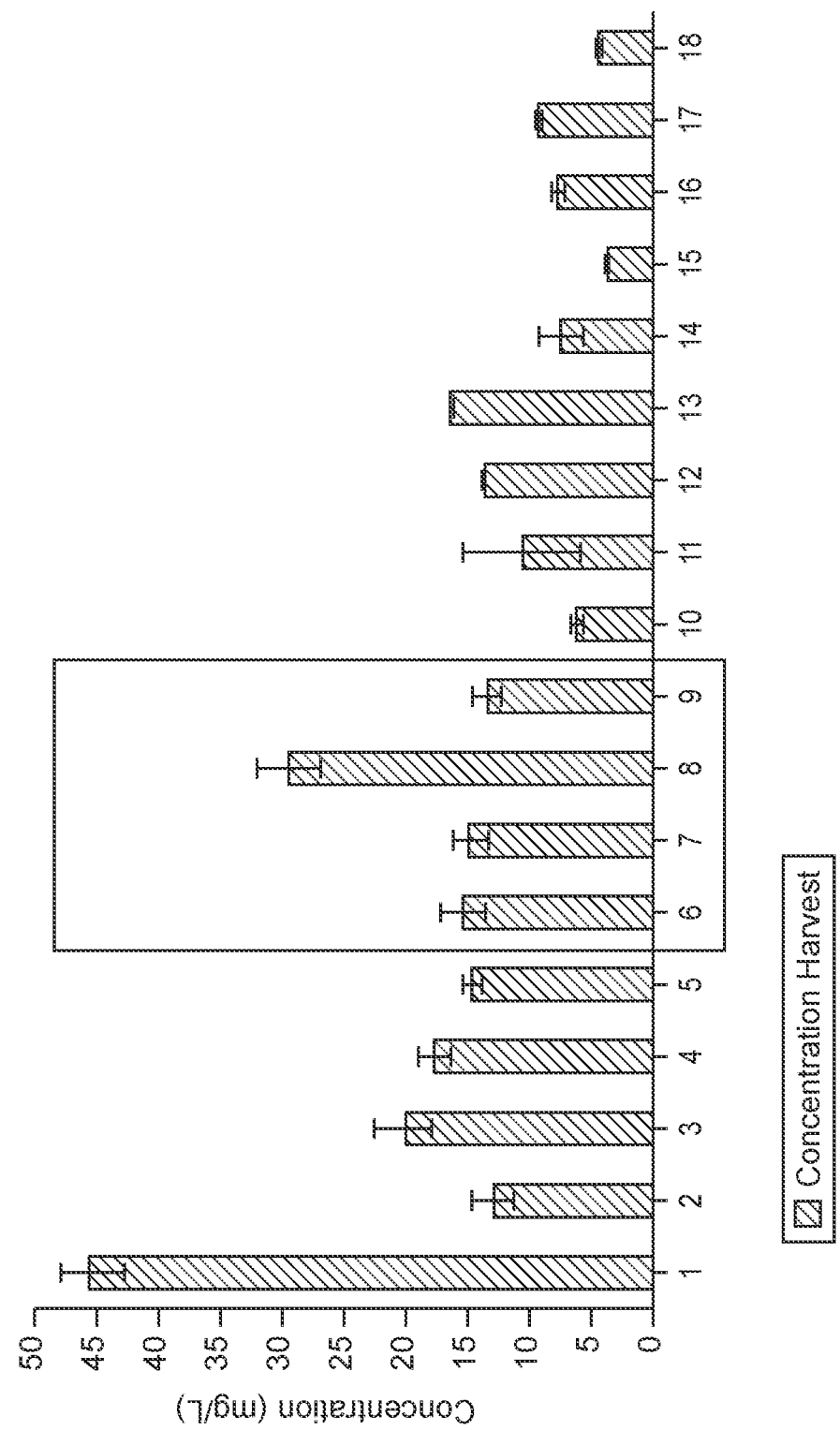

FIG. 21E

IST-3005-2639-005 Dose Stability
% Monomer Recovery

|  | 4C | 25C | 37C | 42C |
|---|---|---|---|---|
| 10mg/mL | 99% | 83% | 25% | 6% |
| 1mg/mL | 100% | 98% | 42% | 13% |
| 0.1mg/mL | 100% | 97% | 59% | 24% |

FIG. 23

| | Position 3 | | Position 1 | | Position 1 | | Position 1 | |
|---|---|---|---|---|---|---|---|---|
| | IST-3005-2639-006 (Study Control) | | IST-3892-2640-001 (I72C G2C) | | IST-3893-2938-001 (K75C G3C) | | IST-3893-2640-001 (K75C G2C) | |
| | Day 3 | Day 5 | Day 3 | Day 5 | Day 3 | Day 5 | Day 3 | Day 5 |
| 37C | 43.69% | 36.02% | 87.32% | 84.19% | 91.62% | 89.21% | 89.13% | 86.52% |
| 42C | 6.35% | 6.08% | 66.47% | 61.20% | 72.98% | 68.01% | 71.33% | 66.59% |

FIG. 24

Table 6

| | α chain | FIG. | β chain | FIG. | S-S | MOD; position | peptide | Expression level |
|---|---|---|---|---|---|---|---|---|
| 3893-2938 | 3893 (K75C) | 15B | 2938 (GGCGS) | 15A | Y | PD-L1; Pos. 1 | proIns 76-90 (K88S) | 48 mg/mL |
| 3003-2639 | 3003 | 15F | 2639 | 15C | N | PD-L1; Pos. 1 | proIns 76-90 (K88S) | ~15 mg/mL |
| 3005-2639 | 3005 | 15D | 2639 | 15C | N | PD-L1; Pos. 3 | proIns 76-90 (K88S) | 12.8 mg/mL |
| 3003-2579 | 3003 | 15F | 2579 | 15E | N | PD-L1; Pos. 1 | GAD65 555-567 | 8 mg/mL |
| 3005-2580 | 3005 | 15D | 2580 | 15G | N | PD-L1; Pos. 3 | GAD65 555-567 (F557I) | ~15 mg/mL |
| 3732-2639 | 3732 | 15NN | 2639 | 15C | N | PD-L1; Pos. 3 | proIns 76-90 (K88S) | |
| 2792-2639 | 2792 | 15OO | 2639 | 15C | N | PD-L1; Pos. 3 | proIns 76-90 (K88S) | |
| 3892-2640 | 3892 (I82C) | 15PP | 2640 (GCGGS) | 15JJ | Y | PD-L1; Pos. 1 | proIns 76-90 (K88S) | |
| 3893-2640 | 3893 (K75C) | 15BB | 2640 (GCGGS) | 15JJ | Y | PD-L1; Pos. 1 | proIns 76-90 (K88S) | |
| 3004-2579 | 3004 | 15QQ | 2579 | 15E | N | PD-L1; Pos.2 | GAD65 | 21.5 |
| 2932-3006 | 2932 | 15Z | 3006 | 15RR | N | PD-L1; Pos. 4 | GAD65 | 125 |
| 2932-3007 | 2932 | 15Z | 3007 | 15SS | N | PD-L1; Pos. 5 | GAD65 | 24 |
| 3005-2579 | 3005 | 15D | 2579 | 15E | N | PD-L1; Pos. 3 | GAD65 | 29.5 |

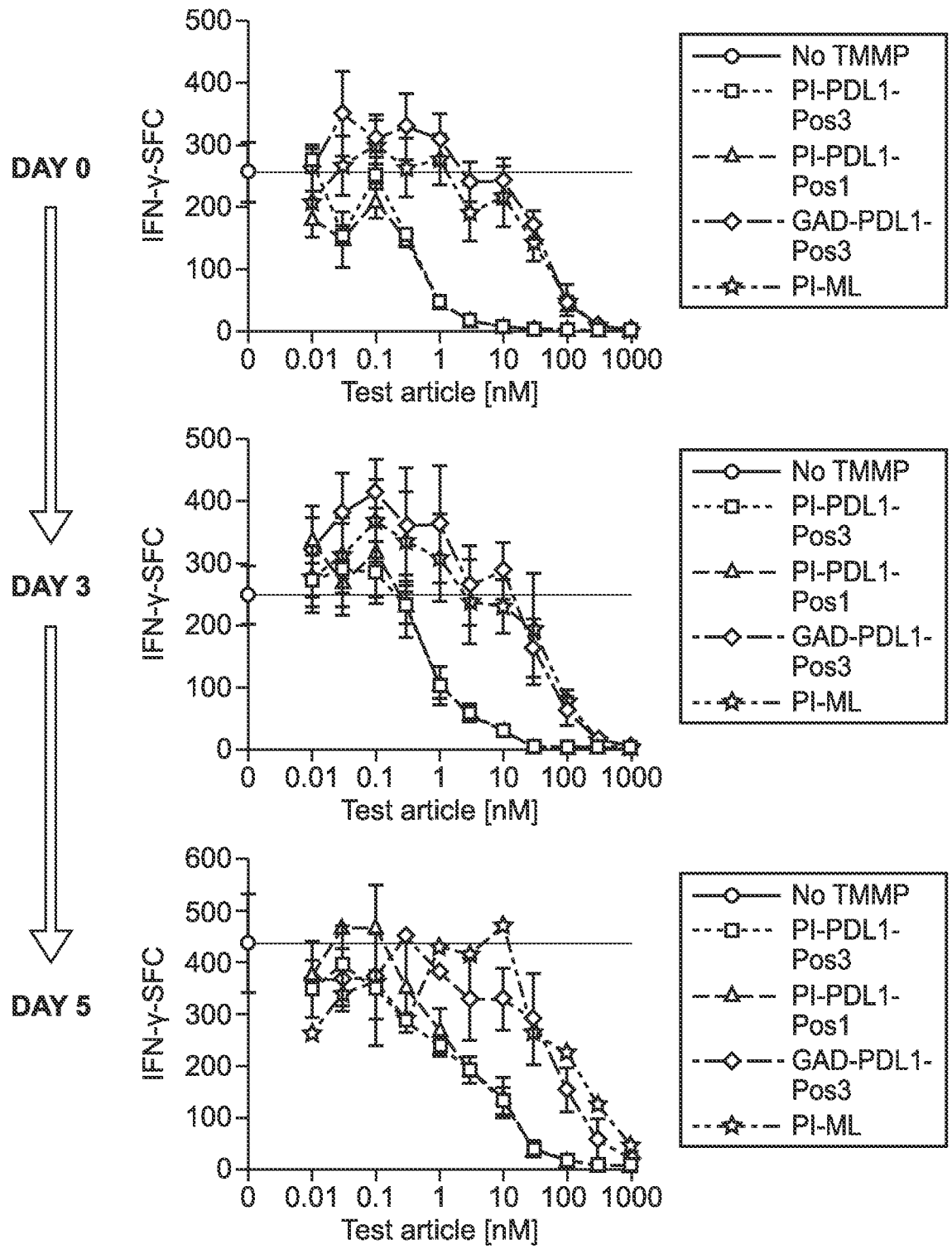
FIG. 26 (Cont.) T1D donors: Donor 555173

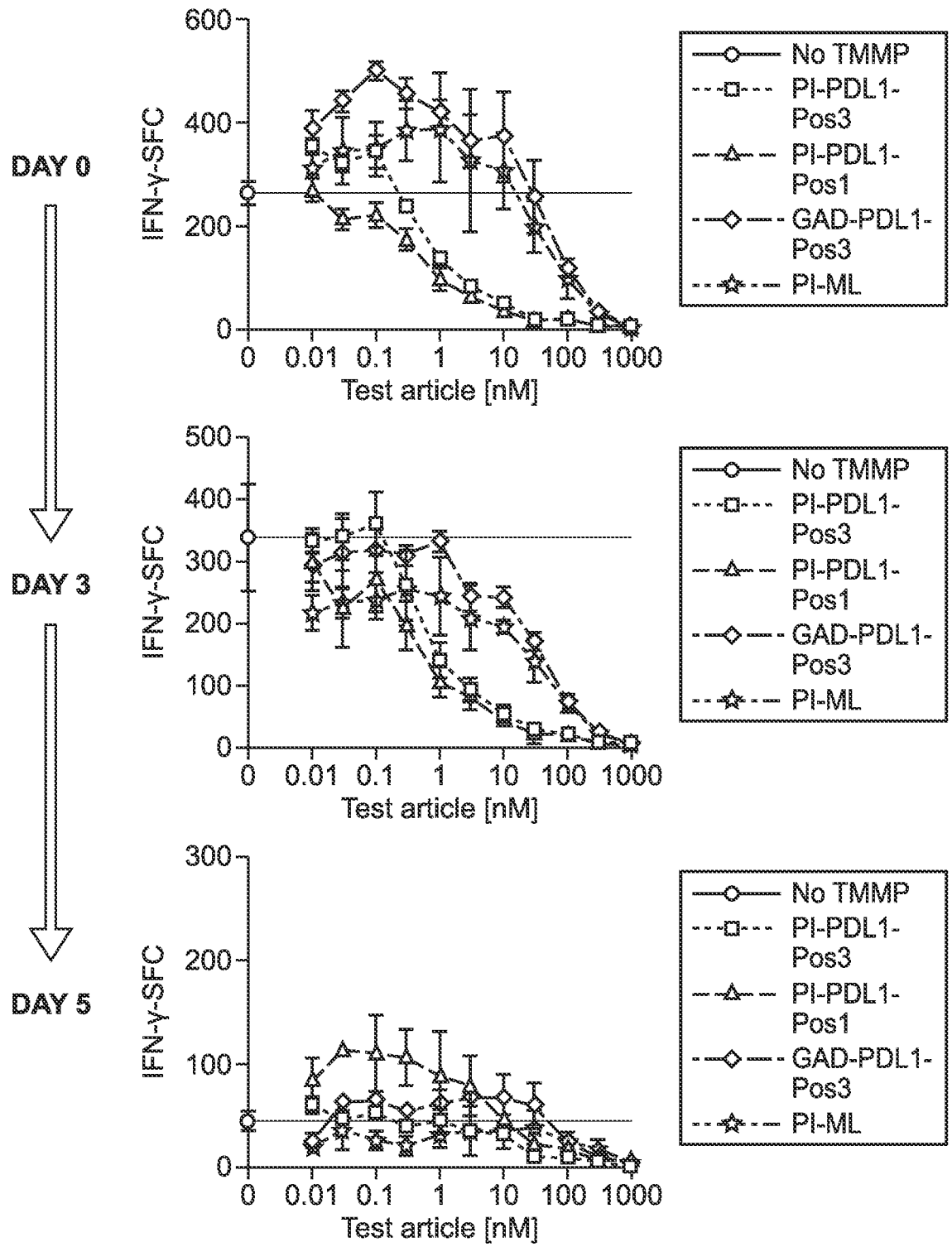
FIG. 28 (Cont.) T1D donors: Donor 555115

FIG. 29
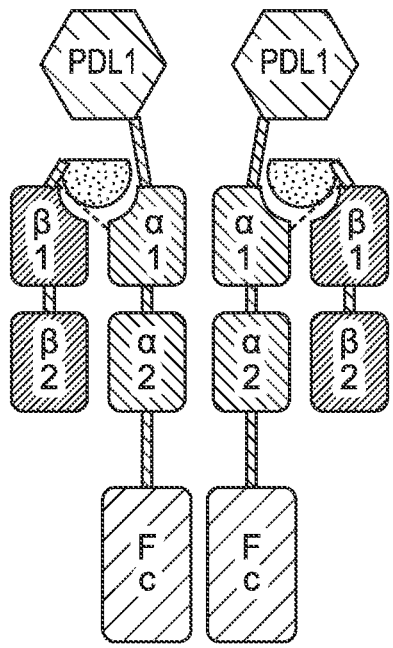
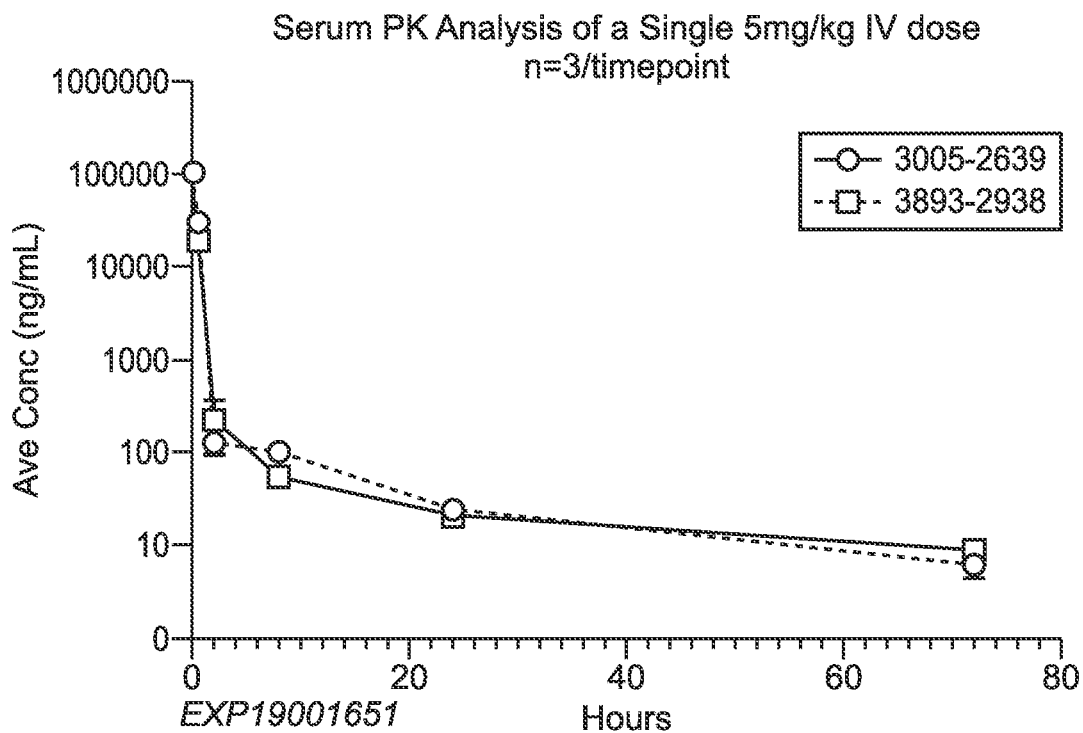

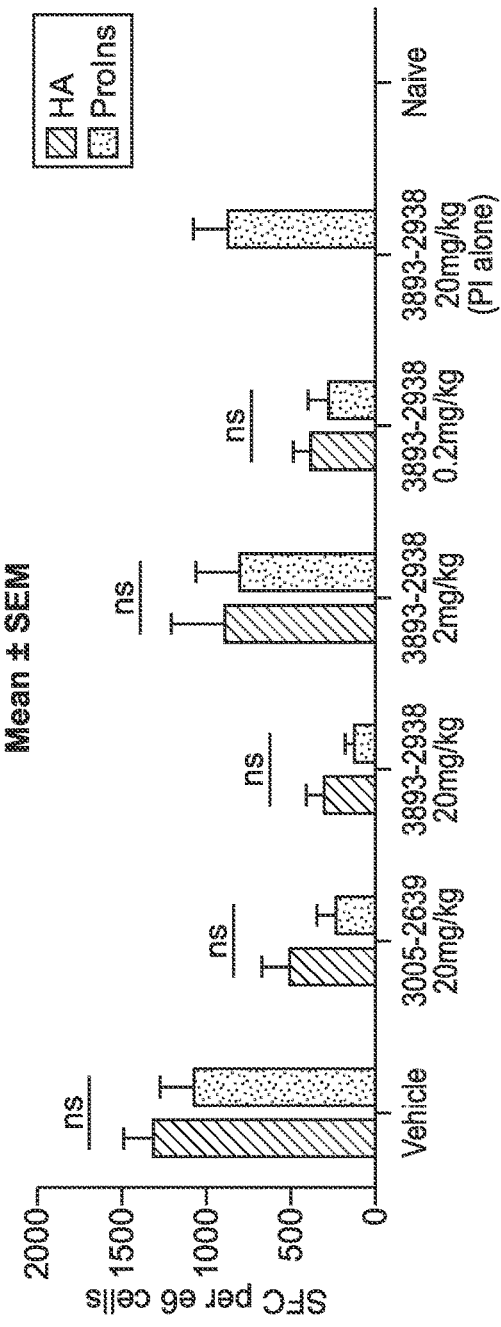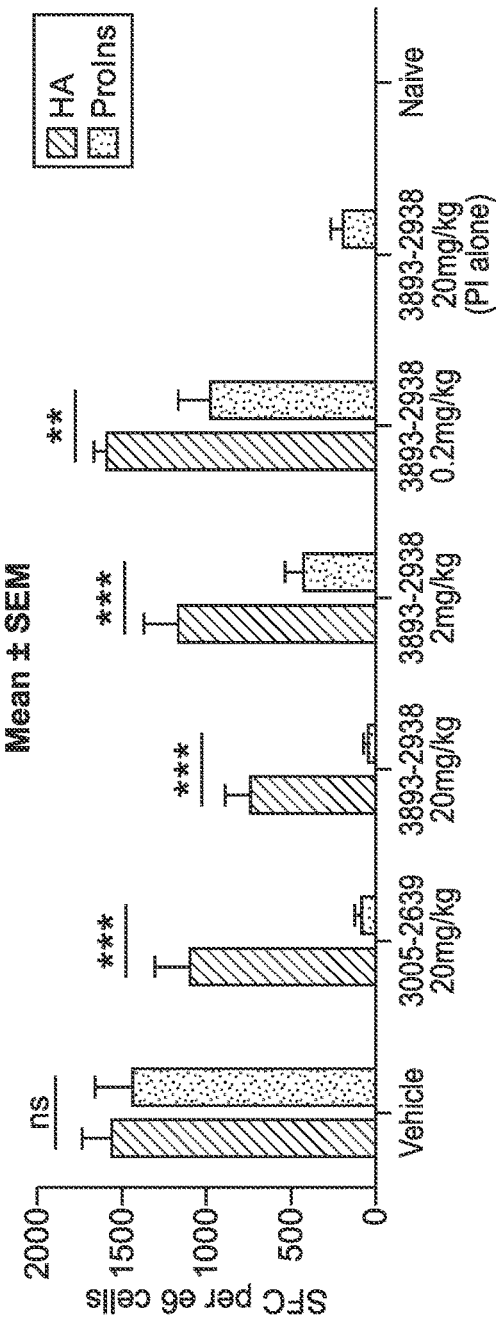

FIG. 34
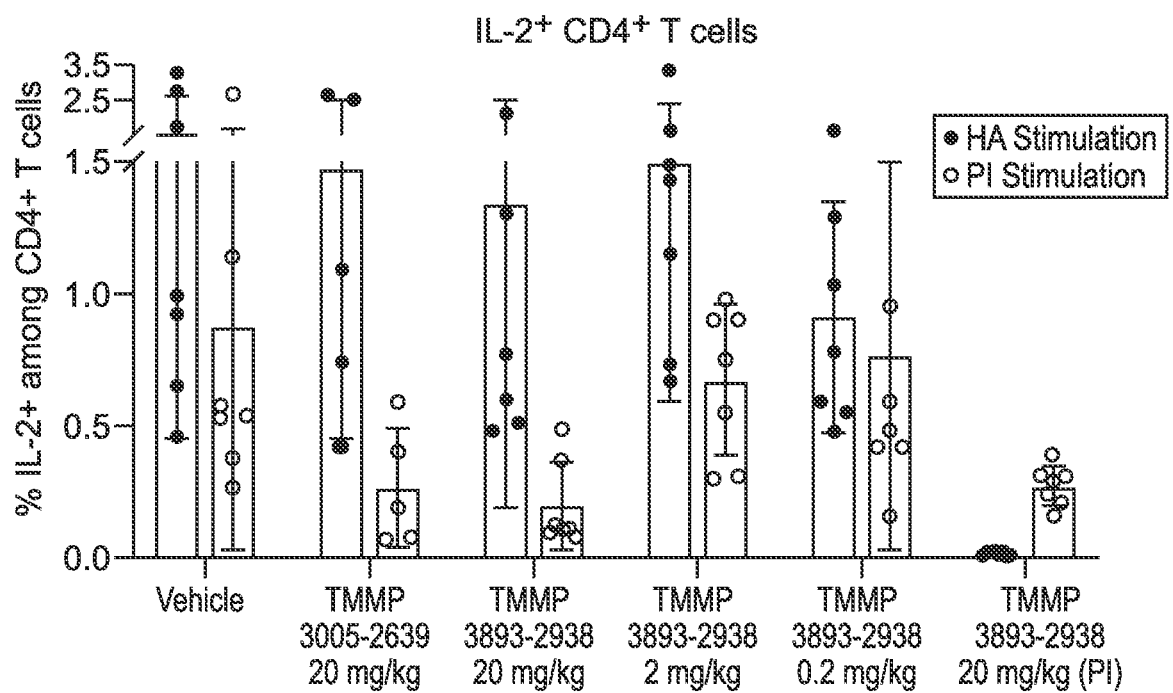
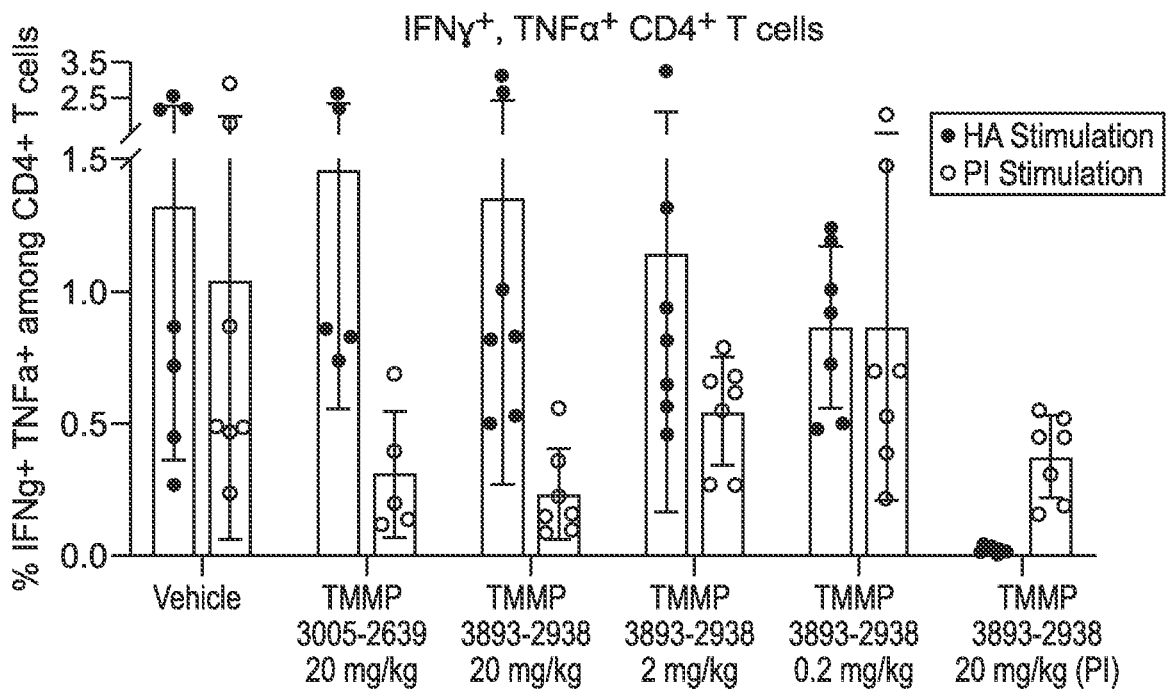

MHC CLASS II T-CELL MODULATORY MULTIMERIC POLYPEPTIDES FOR TREATING TYPE 1 DIABETES MELLITUS (T1D) AND METHODS OF USE THEREOF

CROSS-REFERENCE

This application claims the benefit of U.S. Provisional Patent Application No. 63/076,310, filed Sep. 9, 2020, which application is incorporated herein by reference in its entirety.

INCORPORATION BY REFERENCE OF SEQUENCE LISTING XML

A Sequence Listing is provided herewith as a Sequence Listing XML, "CUEB-134CON_SEQ_LIST" created on Jun. 2, 2023, and having a size of 266,063 bytes. The contents of the Sequence Listing XML are incorporated by reference herein in their entirety.

INTRODUCTION

Central to the proper functioning of the mammalian immune system are the coordinated activities and communications between two specialized cell types, antigen-presenting cells ("APCs") and T cells. APCs serve to capture and break the proteins from foreign organisms, or abnormal proteins (e.g., from genetic mutation in cancer cells), into smaller fragments suitable as signals for scrutiny by the larger immune system, including T cells. In particular, APCs break down proteins into small peptide fragments, which are then paired with proteins of the major histocompatibility complex ("MHC") and displayed on the cell surface. Cell surface display of an MHC together with a peptide fragment, also known as a T cell epitope, provides the underlying scaffold surveilled by T cells, allowing for specific recognition. The peptide fragments can be pathogen-derived, tumor-derived, or derived from natural host proteins (self-proteins). Moreover, APCs can recognize other foreign components, such as bacterial toxins, viral proteins, viral DNA, viral RNA, etc., whose presence denotes an escalated threat level. The APCs relay this information to T cells through additional costimulatory signals in order to generate a more effective response.

T cells recognize peptide-major histocompatibility complex ("pMHC") complexes through a specialized cell surface receptor, the T cell receptor ("TCR"). The TCR is unique to each T cell; as a consequence, each T cell is highly specific for a particular pMHC target. In order to adequately address the universe of potential threats, a very large number (~10,000,000) of distinct T cells with distinct TCRs exist in the human body. Further, any given T cell, specific for a particular T cell peptide, is initially a very small fraction of the total T cell population. Although normally dormant and in limited numbers, T cells bearing specific TCRs can be readily activated and amplified by APCs to generate highly potent T cell responses that involve many millions of T cells. Such activated T cell responses are capable of attacking and clearing viral infections, bacterial infections, and other cellular threats including tumors, as illustrated below. Conversely, the broad, non-specific activation of overly active T cell responses against self or shared antigens can give rise to T cells inappropriately attacking and destroying healthy tissues or cells.

MHC proteins are referred to as human leukocyte antigens (HLA) in humans. HLA class II gene loci include HLA-DM (HLA-DMA and HLA-DMB that encode HLA-DM α chain and HLA-DM β chain, respectively), HLA-DO (HLA-DOA and HLA-DOB that encode HLA-DO α chain and HLA-DO β chain, respectively), HLA-DP (HLA-DPA and HLA-DPB that encode HLA-DP α chain and HLA-DP β chain, respectively), HLA-DQ (HLA-DQA and HLA-DQB that encode HLA-DQ α chain and HLA-DQ β chain, respectively), and HLA-DR (HLA-DRA and HLA-DRB that encode HLA-DR α chain and HLA-DR β chain, respectively).

SUMMARY

The present disclosure provides T-cell modulatory multimeric polypeptides (TMMPs) comprising a type 1 diabetes (T1D)-associated peptide epitope, MHC class II polypeptides, and one or more immunomodulatory polypeptides. A TMMP of the present disclosure is useful for modulating activity of a T cell. Thus, the present disclosure provides compositions and methods for modulating the activity of T cells, as well as compositions and methods for treating persons who have T1D.

BRIEF DESCRIPTION OF THE DRAWINGS

FIG. 6 provides amino acid sequence of an HLA Class II DRA α chain (SEQ ID NO:130).

FIG. 7A-7D provide amino acid sequences of HLA Class II DRB1β chains (FIG. 7A), HLA Class II DRB3β chains (FIG. 7B), an HLA Class II DRB4β chain (FIG. 7C), and an HLA Class II DRB5β chain (FIG. 7D).

FIG. 8 provides amino acid sequences of HLA Class II DPA1α chains.

FIG. 9 provides amino acid sequences of HLA Class II DPB 1β chains.

FIG. 10 provides amino acid sequences of HLA Class II DQA1α chains.

FIG. 11A-11B provide amino acid sequences of HLA Class II DQB1β chains.

FIG. 12A-12G provide amino acid sequences of immunoglobulin Fc polypeptides.

FIG. 13A-13N provide amino acid sequences of wild-type (FIG. 13A) and variant (FIG. 13B-3N) DRA*0101α chains.

FIG. 13O provides an amino acid sequence of a PD-L1 polypeptide.

FIG. 14A-14J provide amino acid sequences of wild-type (FIG. 14A) and variant (FIG. 14B-4J) DRB1*0401β chains.

FIGS. 15A-15Z and 15AA-15SS provide amino acid sequences of first and second polypeptide chains of TMMPs and APPs of the present disclosure.

FIG. 17A-17C depict various disulfide-linked heterodimers and their characterization. These disulfide-linked heterodimers do not include immunomodulatory polypeptides.

FIG. 18A-18C depict various disulfide-linked heterodimers and their characterization. These disulfide-linked heterodimers include immunomodulatory polypeptides. Linkers: GGSAAAGG (SEQ ID NO:83) and (G4S)3 (SEQ ID NO:74)

FIG. 20A-20D depict production and monomer formation of exemplary TMMPs. Linkers: (G4S)6 (SEQ ID NO:77), (G4S)3 (SEQ ID NO:74), (G4S)4 (SEQ ID NO:75), GGSAAAGG (SEQ ID NO:83).

FIG. 21A-21E depict the results of stability analysis of TMMP 3005-2639.

FIG. 23 depict the results of stability analysis of disulfide-stabilized TMMPs with the MOD at Position 1.

FIG. 24 presents a table (Table 6) that provides the expression level (in mg/mL) of various TMMPs. Linkers: GGCGS (SEQ ID NO:234) and GCGGS (SEQ ID NO:235)

FIG. 29 depicts serum pharmacokinetics (PK) analysis of a single 5 mg/kg intravenous dose of TMMP 3893-2938.

FIG. 31 depicts frequencies of Proins- and HA-reactive T cells following administration of proinsulin (Proins) or hemagglutinin (HA) peptides.

FIG. 32 depicts frequencies of Proins- and HA-reactive T cells following administration of the TMMPs indicated.

FIG. 34 depicts the effect of treatment with TMMPs on cytokine production.

DEFINITIONS

Figure 1A:
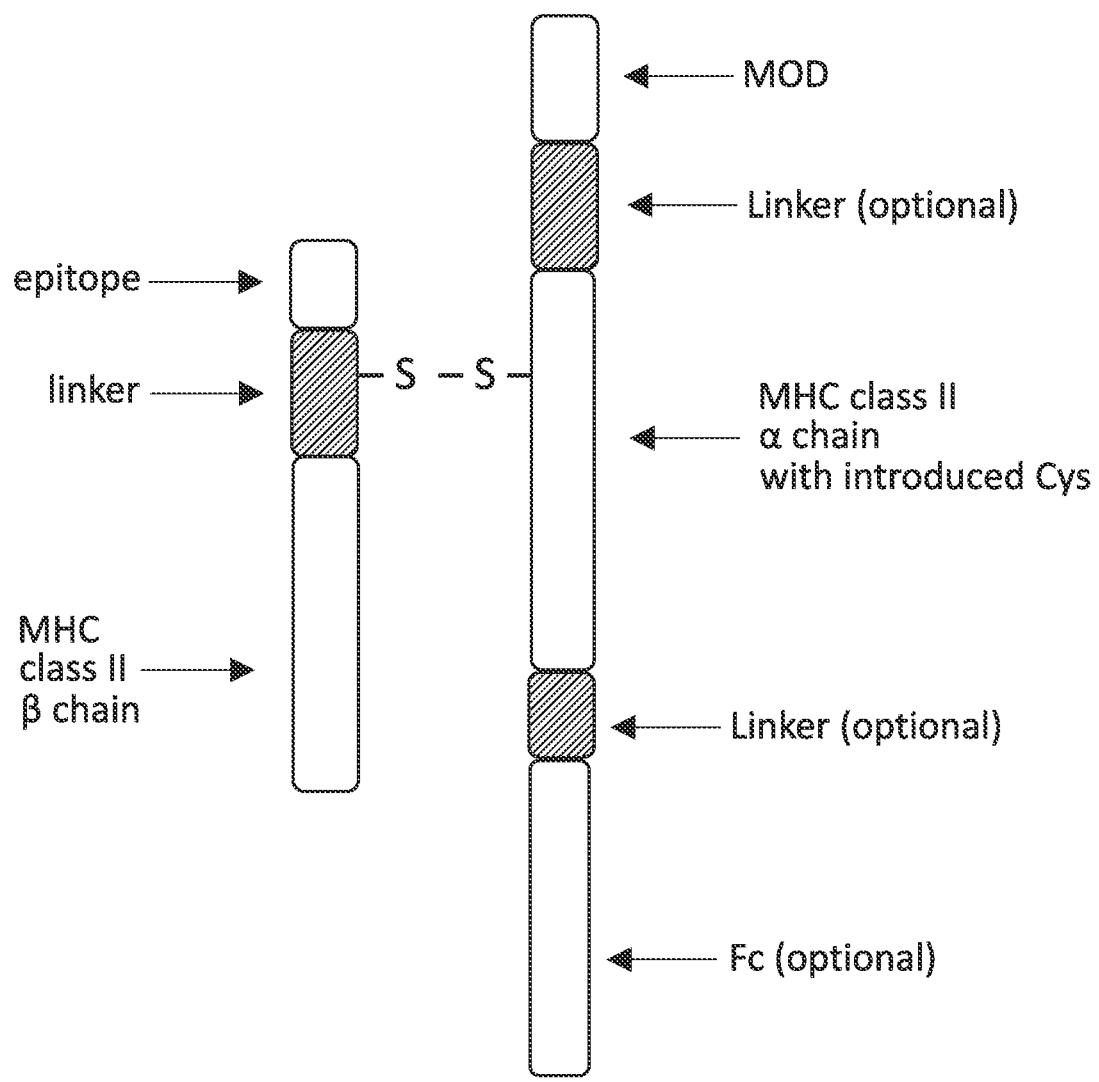
FIG. 1A-1E present schematic depictions of TMMPs of the present disclosure, in which the immunomodulatory polypeptide is in Position 1.
Figure 1B:
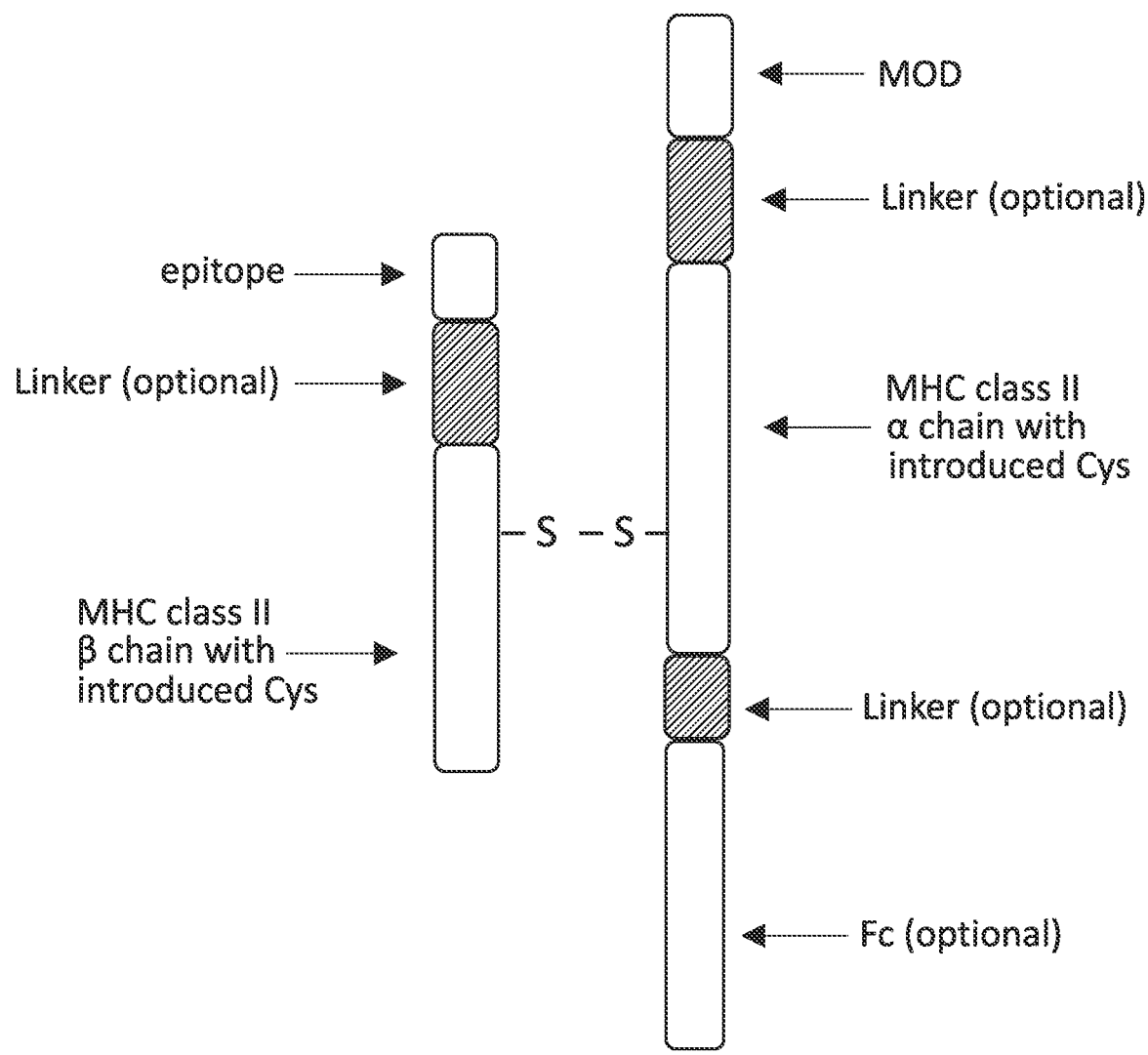
Figure 1C:
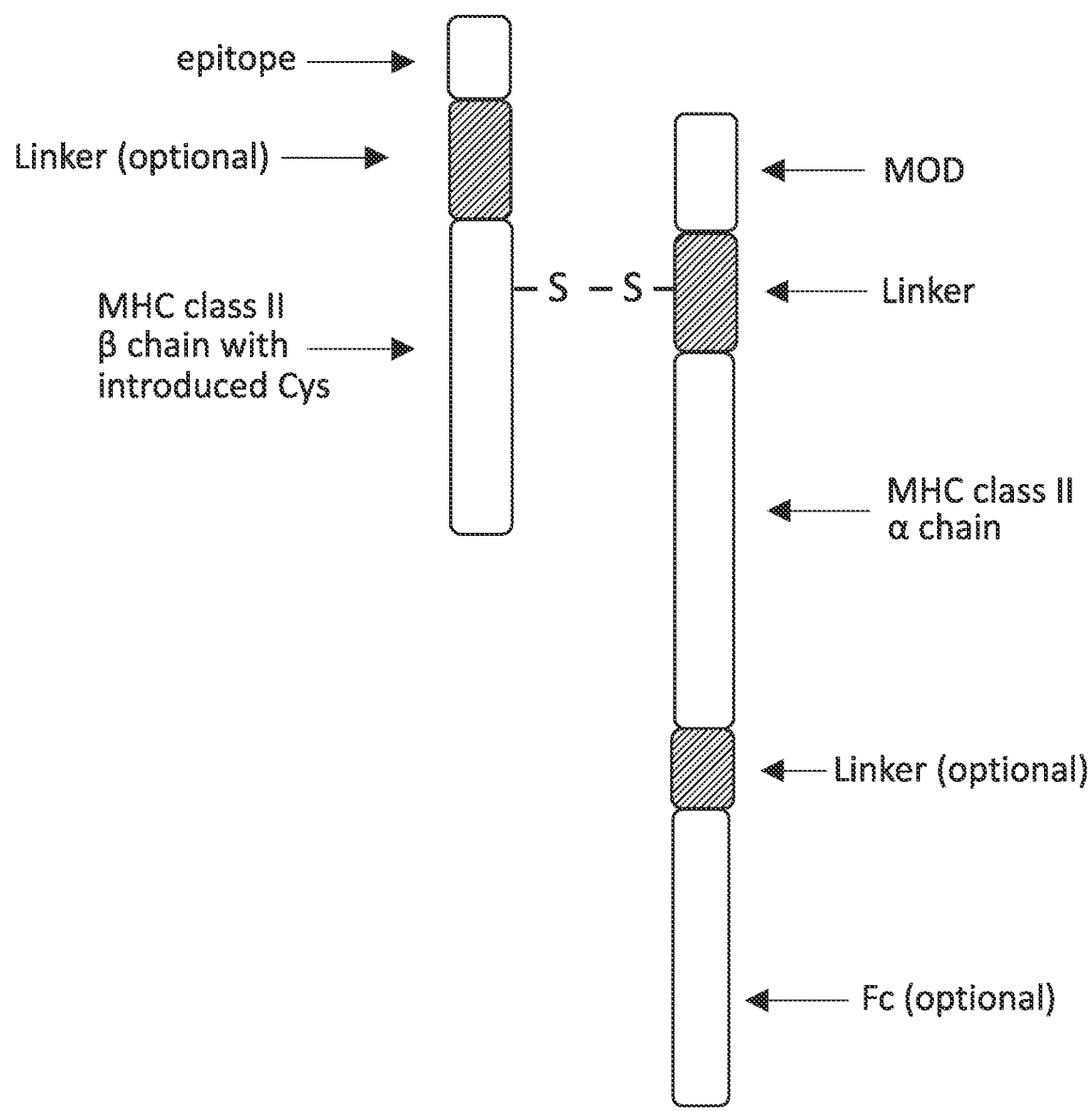
Figure 1D:
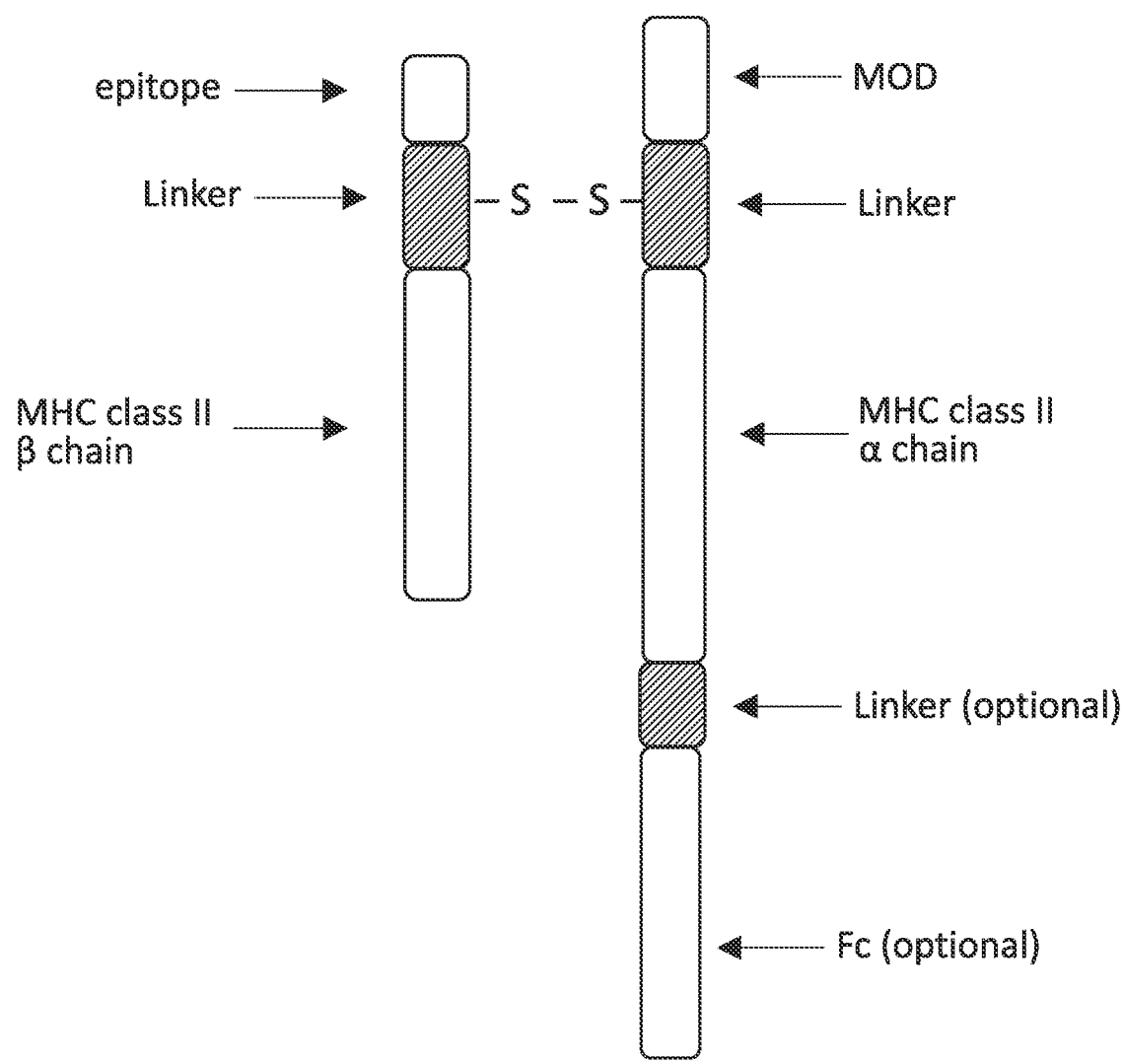

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to polymerase chain reaction (PCR) amplification or other recombinant DNA methods. References herein to a specific residue or residue number in a known polypeptide, e.g., position 72 or 75 of human DRA MHC class II polypeptide, are understood to refer to the amino acid at that position in the wild-type polypeptide (i.e. I72 or K75). To the extent that the sequence of the wild-type polypeptide is altered, either by addition or deletion of one or more amino acids, one of ordinary skill will understand that a reference to the specific residue or residue number will be correspondingly altered so as to refer to the same specific amino acid in the altered polypeptide, which would be understood to reside at an altered position number. For example, if a human DRA MHC class II polypeptide is altered by the addition of one amino acid at the N-terminus, then a reference to position 72 or 75, or to residue I72 or K75, will be understood to indicate the amino acids that are at positions 73 or 76, or to residues I73 and K76. Likewise, a reference herein to substitution of a specific amino acid as a specific position, e.g., I72C, is understood to refer to a substitution of a cysteine ("Cys") for the amino acid at position 72 in the wild-type polypeptide, i.e., isoleucine. If, e.g., the wild-type polypeptide is altered to change the amino acid at position 72 from isoleucine to an alternate amino acid, then the reference to I72C will be understood to refer to the substitution of a cysteine for the alternate amino acid. If in such case the polypeptide is also altered by the addition or deletion of one or more amino acids, then the reference to I72C will be understood to refer to the substitution of a cysteine for the alternate amino acid at the altered position number. A reference to a "non-naturally occurring Cys residue" in a polypeptide, e.g., a DRA MHC class II polypeptide, means that the polypeptide comprises a Cys residue in a location where there is no Cys in the corresponding wild-type polypeptide. This can be accomplished through routine protein engineering in which a cysteine is substituted for the amino acid that occurs in the wild-type sequence, e.g., at position 72 or 75 of the DRA*0101 polypeptide (see FIG. 13G and FIG. 13H) instead of the isoleucine (I) or lysine (K) residues that are present in the wild-type DRA*0101 polypeptide (see FIG. 13A).

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/,ebi.ac.uk/Tools/msa/muscle/, mafft.cbrc.jp/alignment/software/. See, e.g., Altschul et al. (1990) *J. Mol. Biol.* 215:403-10. Unless otherwise stated, "sequence identity" as referred to herein is determined by BLAST (Basic Local Alignment Search Tool), as described in Altschul et al. (1990) *J. Mol. Biol.* 215:403.

As used herein the term "in vivo" refers to any process or procedure occurring inside of the body, e.g., of a T1D patient.

As used herein, "in vitro" refers to any process or procedure occurring outside of the body.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

The term "binding," as used herein (e.g. with reference to binding of a T-cell modulatory antigen-presenting polypeptide to a polypeptide (e.g., a T-cell receptor) on a T cell), refers to a non-covalent interaction between two molecules. Non-covalent binding refers to a direct association between two molecules, due to, for example, electrostatic, hydrophobic, ionic, and/or hydrogen-bond interactions, including interactions such as salt bridges and water bridges. "Covalent binding" or "covalent bond," as used herein, refers to the formation of one or more covalent chemical bonds between two different molecules.

"T cell" includes all types of immune cells expressing CD3, including T-helper cells ($CD4^+$ cells), cytotoxic T-cells ($CD8^+$ cells), T-regulatory cells (Treg), and NK-T cells.

The term "immunomodulatory polypeptide" (also referred to as a "co-stimulatory polypeptide"), as used herein, includes a polypeptide on an antigen presenting cell (APC) (e.g., a dendritic cell, a B cell, and the like), or a portion of the polypeptide on an APC, that specifically binds a cognate co-immunomodulatory polypeptide on a T cell, thereby providing a signal which, in addition to the primary signal provided by, for instance, binding of a TCR/CD3 complex with a major histocompatibility complex (MHC) polypeptide loaded with peptide, mediates a T cell response, including, but not limited to, proliferation, activation, differentiation, and the like. An immunomodulatory polypeptide can include, but is not limited to, a cytokine (e.g., IL-2; TGFβ), CD7, B7-1 (CD80), B7-2 (CD86), PD-L1, PD-L2, 4-1BBL, OX40L, Fas ligand (FasL), inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, and HVEM.

As noted above, an "immunomodulatory polypeptide" (also referred to herein as a "MOD") specifically binds a cognate co-immunomodulatory polypeptide on a T cell (e.g., a target T cell).

"Phosphate buffer saline" or "PBS", as used herein, means a water-based buffer solution, typically available as a concentrated solution. Unless stated otherwise, the PBS solution used in this disclosure contains sodium chloride (500 mM), sodium phosphate dibasic (10 mM), potassium phosphate monobasic (2 mM), potassium chloride (2.7 mM), and the rest water. The pH of the PBS is 7.5±0.15. The buffer can be prepared in 18.2 megohms DNase, and RNase free water and filtered through 0.22 micron filter.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system.

The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

As used herein, the term "affinity" refers to the equilibrium constant for the reversible binding of two agents (e.g., an antibody and an antigen) and is expressed as a dissociation constant ($K_D$). As used herein, the term "avidity" refers to the resistance of a complex of two or more agents to dissociation after dilution.

The term "binding" refers to a direct association between two molecules, due to, for example, covalent, electrostatic, hydrophobic, and ionic and/or hydrogen-bond interactions, including interactions such as salt bridges and water bridges.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; and/or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pigs, horses, goats, and the like), etc.

Unless indicated otherwise, the term "substantially" is intended to encompass both "wholly" and "largely but not wholly". For example, an Ig Fc that "substantially does not induce cell lysis" means an Ig Fc that induces no cell lysis at all or that largely but not wholly induces no cell lysis.

As used herein, the term "about" used in connection with an amount indicates that the amount can vary by 10%. For example, "about 100" means an amount of from 90-110. Where about is used in the context of a range, the "about" used in reference to the lower amount of the range means that the lower amount includes an amount that is 10% lower than the lower amount of the range, and "about" used in reference to the higher amount of the range means that the higher amount includes an amount 10% higher than the higher amount of the range. For example, from about 100 to about 1000 means that the range extends from 90 to 1100.

It is to be understood that this disclosure is not limited to particular embodiments described, as such may, of course, vary. It is also to be understood that the terminology used herein is for the purpose of describing particular embodiments only, and is not intended to be limiting, since the scope of the inventions described in the appended claims will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an immunomodulatory polypeptide" includes a plurality of such immunomodulatory polypeptides and reference to "the Treg" includes reference to one or more Tregs and equivalents thereof known to those skilled in the art, and so forth. It is further noted that the claims may be drafted to exclude any optional element or any element that is included in a list or other recitation of elements that share a common generic or specific feature, property, or activity. As such, this statement is intended to serve as antecedent basis for use of such exclusive terminology as "solely," "only" and the like in connection with the recitation of claim elements, or use of a "negative" limitation.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

DETAILED DESCRIPTION

The present disclosure provides T-cell modulatory multimeric polypeptides (TMMPs) comprising a type 1 diabetes (T1D)-associated peptide, MHC class II polypeptides, and one or more immunomodulatory polypeptides. A TMMP of the present disclosure is useful for modulating activity of a T cell. Thus, the present disclosure provides compositions and methods for modulating the activity of T cells, as well as compositions and methods for treating individuals who have T1D.

T-Cell Modulatory Multimeric Polypeptides

Figure 1E:
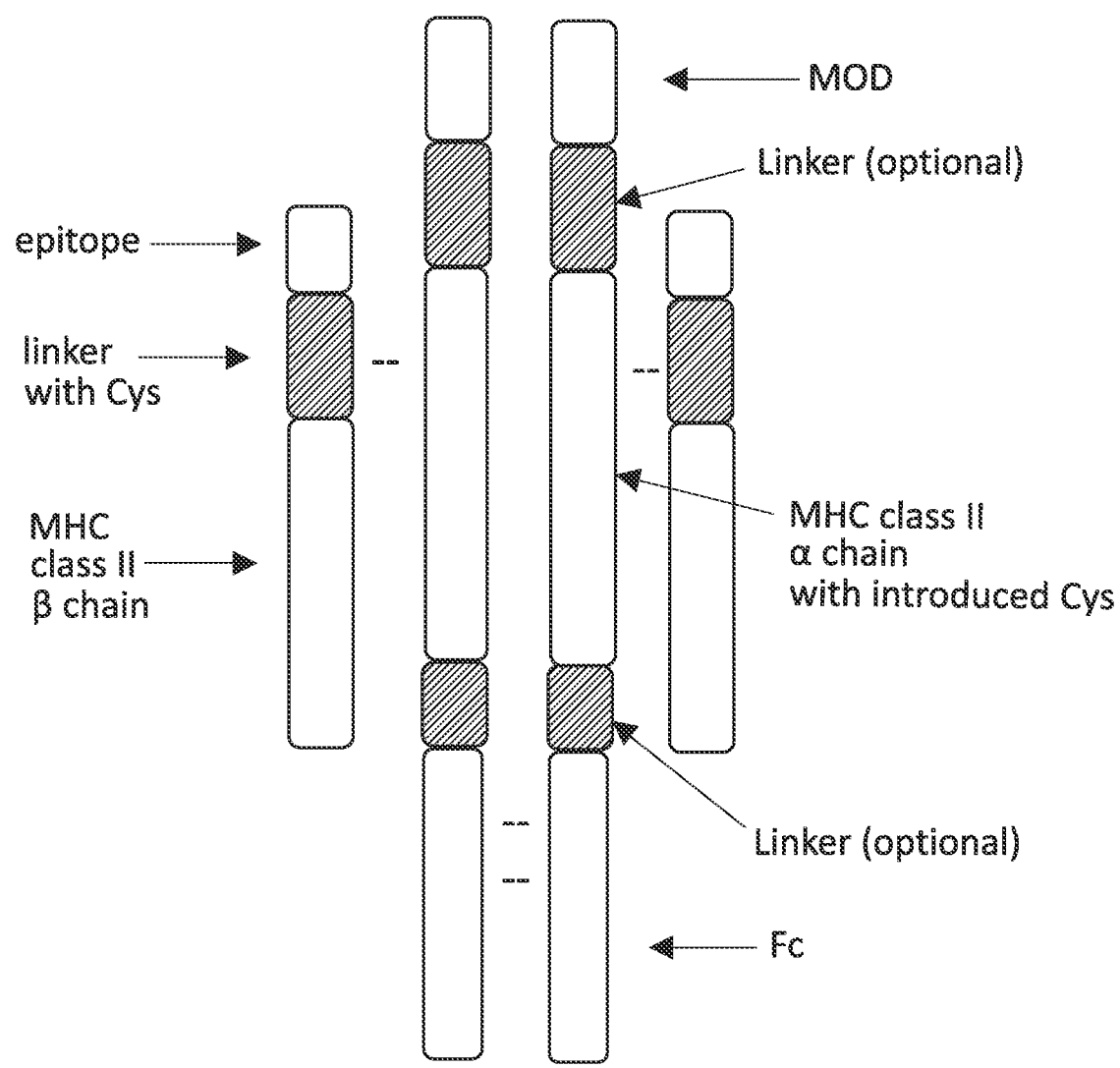

The present disclosure provides TMMPs that comprise a disulfide-linked heterodimer comprising: a) a first polypeptide comprising: i) a peptide that, when present in a TMMP of this disclosure, presents a T1D-associated epitope capable of being bound by a T-cell receptor (TCR) on the surface of a T cell (hereinafter a "T1D peptide"); and ii) a first major histocompatibility complex (MHC) class II polypeptide; and b) a second polypeptide comprising a second MHC class II polypeptide. One or both polypeptides of the heterodimer comprise one or more immunomodulatory polypeptides. The first and the second polypeptides of the heterodimer are covalently linked to one another via at least one disulfide bond. One of the polypeptides of the heterodimer optionally comprises an immunoglobulin (Ig) Fc polypeptide or a non-Ig scaffold. A TMMP of the present disclosure can comprise two disulfide-linked heterodimers. When both heterodimers include Ig Fc polypeptides, disulfide bonds will spontaneously form between the respective Ig Fc polypeptides to covalently link the two heterodimers to one another (depicted schematically in FIG. 1E).

As noted above, the first polypeptide and the second polypeptide of a heterodimer of a TMMP of the present disclosure are covalently linked to one another via at least one disulfide bond. For example, the at least one disulfide bond is present between: i) a Cys present in the first MHC class II polypeptide and a Cys present in the second MHC class II polypeptide; or ii) a Cys present in a peptide linker in the first polypeptide and a Cys present in an MHC class II polypeptide present in the second polypeptide; or iii) a Cys present in a peptide linker in the second polypeptide and a Cys present in an MHC class II polypeptide present in the first polypeptide. These various embodiments are depicted schematically in FIG. 1A-1E, FIG. 2A-2D, FIG. 3A-3D, and FIG. 4A-4D.

The at least one disulfide bond formed between the first polypeptide and the second polypeptide of a heterodimer of a TMMP of the present disclosure provides for increased stability and/or expression of the TMMP, compared to a control TMMP lacking the at least one disulfide bond. For example, in some cases, a TMMP of the present disclosure is at least 10%, at least 20%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 20-fold, at least 50-fold, at least 100-fold, or more than 100-fold, more stable than a control TMMP lacking the at least one disulfide bond. Stability can be determined by measuring the amount of intact TMMP monomer remaining after incubation of the TMMP for a specific period of time at a specific temperature (e.g., for 1 hour at 37° C.; 1 day at 37° C.; 5 days at 37° C.; 1 hour at 42° C.; 1 day at 42° C.; 5 days at 42° C.; and the like). A disulfide-bonded TMMP of the present disclosure will in some cases exhibit a stability after 3 days at 37° C. at TMMP concentrations of 9.5 mg/mL, 1 mg/mL, or 0.1 mg/mL in the PBS buffer solution containing 500 mM NaCl (described above), as measured by the percent monomer remaining, that is greater than 50%, greater than 60%, greater than 70%, greater than 80%, or greater than 90%. A disulfide-bonded TMMP of the present disclosure will in some cases exhibit a stability after 5 days at 37° C. at TMMP concentrations of 9.5 mg/mL, 1 mg/mL, or 0.1 mg/mL in the PBS buffer solution containing 500 mM NaCl (described above), as measured by the percent monomer remaining, that is greater than 50%, greater than 60%, greater than 70%, or greater than 80%. A disulfide-bonded TMMP of the present disclosure will in some cases exhibit a stability after 3 days at 42° C. at TMMP concentrations of 9.5 mg/mL, 1 mg/mL, or 0.1 mg/mL in the PBS buffer solution containing 500 mM NaCl (described above), as measured by the percent monomer remaining, that is greater than 30%, greater than 40%, greater than 50%, or greater than 60%. A disulfide-bonded TMMP of the present disclosure will in some cases exhibit a stability after 5 days at 42° C. at TMMP concentrations of 9.5 mg/mL, 1 mg/mL, or 0.1 mg/mL in the PBS buffer solution containing 500 mM NaCl (described above), as measured by the percent monomer remaining, that is greater than 30%, greater than 40%, greater than 50%, or greater than 60%. Whether a protein is present in solution as a monomer can be determined using size exclusion chromatography (SEC). Analytical SEC can be performed using a Superdex 200 Increase (3.2×300 mm) column (e.g., from GE Healthcare). For example, for analytical SEC, the running buffer can be PBS containing 500 mM NaCl (described above) and the flow rate can be 0.15 ml/minute.

As another example, in some cases, a TMMP of the present disclosure is expressed (produced) in a Chinese hamster ovary (CHO) cell in vitro at a level that is at least 10%, at least 20%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 20-fold, at least 50-fold, at least 100-fold, or more than 100-fold, higher than the expression level of a control TMMP lacking the at least one disulfide bond when expressed under the same conditions and in the same CHO cells. Expression levels can be determined by: i) producing the TMMP in a mammalian cell in vitro in a CHO cell in vitro; and ii) determining the amount of TMMP produced by the mammalian cell. For example, where a TMMP comprises an Ig Fc polypeptide, the TMMP can be isolated from the mammalian cells and/or from culture medium in which the mammalian cells are cultured, where isolation of the TMMP can be carried out by affinity chromatography, e.g., on a Protein A column, a Protein G column, or the like. An example of a suitable mammalian cell is a CHO cell; e.g., an Expi-CHO-S™ cell (e.g., ThermoFisher Scientific, Catalog #A29127).

A protein consisting of the desired TMMP is referred to herein as a "monomer." For example, "monomer" can refer to a single heterodimer that is the desired TMMP when the heterodimer is not covalently bonded to another heterodimer, e.g., when the heterodimer does not include an optional Ig Fc polypeptide. Likewise, a homodimeric TMMP protein comprising 2 heterodimers, each comprising 2 polypeptide chains (for a total of 4 polypeptide chains), where 2 of the four polypeptide chains comprise Ig Fc polypeptides, wherein the Ig Fc polypeptides spontaneously form disulfide bonds that covalently link the heterodimers to each other, also is referred to herein as a "monomer." The term "monomer" does not include aggregates of monomers. Whether a protein is present in solution as a monomer can be determined using size exclusion chromatography (SEC). Analytical SEC can be performed using a Superdex 200 Increase (3.2×300 mm) column (e.g., from GE Healthcare). For example, for analytical SEC, the running buffer can be PBS containing 500 mM NaCl (described above) and the flow rate can be 0.15 ml/minute.

In some cases, a TMMP of the present disclosure exhibits at least 10%, at least 20%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 20-fold, at least 50-fold, at least 100-fold, or more than 100-fold, greater stability in the PBS buffer solution containing 500 mM NaCl (described above) in vitro over a specified period of time and at a specified temperature (e.g., in a solution at a temperature of 37° C. to 42° C. for a period of time of from 1 hour to 28 days; e.g., for 1 hour at 37° C.; 1 day at 37° C.; 5 days at 37° C.; 1 hour at 42° C.; 1 day at 42° C.; 5 days at 42° C.; 5 days at 37° C.; 10 days at 37° C.; 14 days at 37° C.; 28 days at 37° C.; and the like), compared to a control TMMP lacking the at least one disulfide bond between the first polypeptide and the second polypeptide of the heterodimer. The TMMP can be present in the PBS buffer solution in a concentration of from 0.1 mg/mL to 10 mg/mL, and the buffer solution can be kept at 37° C. or 42° C. for 1 hour, 5 days, 10 days, 14 days, 21 days, or 28 days. As discussed herein, stability is determined by measuring the percent of monomer (as defined above) remaining in the solution after a specified time in the solution at a specified temperature. Loss of monomer often is characterized by the formation of aggregates, or alternatively by the breakdown of the monomer into one or more separate polypeptide chains or fragments thereof. Thus, for example, "at least 10% greater stability" means that at least 10% more TMMP monomer is present in a test sample than in a control sample comprising the same polypeptide chains but lacking the at least one disulfide bond between the first polypeptide and the second polypeptide of the heterodimer. The percent more monomer in the test sample is calculated based on the amount of monomer in the control sample. Thus, e.g., after a specified period of time at a specified temperature, at least at least 10%, at least 20%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 20-fold, at least 50-fold, at least 100-fold, or more than 100-fold, more monomer remains of a TMMP of the present disclosure (comprising a disulfide bond between the first and second polypeptide chains) compared to the amount of monomer remaining of a control TMMP lacking a disulfide bond between the first and second polypeptide chains.

For example, in some cases, a TMMP of the present disclosure exhibits at least at least 10%, at least 20%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 20-fold, at least 50-fold, at least 100-fold, or more than 100-fold, greater stability in a buffered solution such as the PBS containing 500 mM NaCl (described above) in vitro than the TMMP 3003-2579 (FIG. 15F and FIG. 15E) or than the TMMP 3003-2639 (FIG. 15F and FIG. 15C) when kept for 1 hour, 5 days, or 10 days at 37° C. or at 42° C. As another example, in some cases, a TMMP of the present disclosure exhibits at least at least 10%, at least 20%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 20-fold, at least 50-fold, at least 100-fold, or more than 100-fold, greater stability in the PBS solution containing 500 mM NaCl (described above) in vitro than the TMMP 3005-2639 (FIG. 15D and FIG. 15C) when kept for 1 hour, 5 days, or 10 days at 37° C. or at 42° C.

As noted above, the presence of the at least one disulfide bond between the first polypeptide and the second polypeptide of the heterodimer can lead to greater expression of the TMMP as compared to a TMMP lacking the at least one disulfide bond. In some cases, a TMMP of the present disclosure is expressed (produced) at a level that is at least 10%, at least 20%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 20-fold, at least 50-fold, at least 100-fold, or more than 100-fold, higher than the expression level of the TMMP 3003-2579 (FIG. 15F and FIG. 15E) or of the TMMP 3003-2639 (FIG. 15F and FIG. 15C). In some cases, a TMMP of the present disclosure is expressed (produced) at a level that is at least 10%, at least 20%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 20-fold, at least 50-fold, at least 100-fold, or more than 100-fold, higher than the expression level of the TMMP 3005-2639 (FIG. 15D and FIG. 15C).

As discussed herein and set out in the Examples, stability can be expressed as the "% monomer" (as defined above) remaining after incubation of a TMMP of the present disclosure in the PBS buffer described above at a certain temperature for a certain amount of time. In some cases, the % monomers remaining after incubation of a TMMP of the present disclosure in the PBS buffer for a given time at a given temperature (e.g., 37° C. for 1 hour; 37° C. for 1 day; 37° C. for 5 days; 37° C. for 10 days; 37° C. for 14 days, 37° C. for 28 days; 42° C. for 1 hour; 42° C. for 1 day; 42° C. for 5 days; 42° C. for 10 days; or the like) is at least 10%, at least 20%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 20-fold, at least 50-fold, at least 100-fold, or more than 100-fold, higher than the % monomers of a control TMMP lacking at least one disulfide bond between the two polypeptides of the heterodimers.

A TMMP of the present disclosure can comprise two heterodimers. In some cases, the two heterodimers each include an Ig Fc polypeptide. In some cases, the TMMP comprises two heterodimers that are disulfide linked to one another via Cys residues present in the Ig Fc polypeptides. See, e.g., FIG. 1 for a schematic depiction of an example of such a TMMP.

Immunomodulatory Polypeptides

A TMMP of the present disclosure comprises one or more immunomodulatory polypeptides. In some cases, a TMMP of the present disclosure comprises a single immunomodulatory polypeptide. In some cases, where a TMMP of the present disclosure comprises a single immunomodulatory polypeptide, the single immunomodulatory polypeptide is on the first polypeptide. In some cases, where a TMMP of the present disclosure comprises a single immunomodulatory polypeptide, the single immunomodulatory polypeptide is on the second polypeptide. In some cases, where a TMMP of the present disclosure comprises a single immunomodulatory polypeptide, the single immunomodulatory polypeptide is on the second polypeptide, and the second polypeptide comprises an MHC class II alpha polypeptide.

In some cases, a TMMP of the present disclosure comprises two or more immunomodulatory polypeptides (e.g., 2, 3, 4, or 5 immunomodulatory polypeptides). As noted above, a TMMP of the present disclosure comprises a disulfide-linked heterodimer comprising a first polypeptide and a second polypeptide. In some cases, the two or more immunomodulatory polypeptides are present in the first polypeptide chain only. In some cases, the two or more immunomodulatory polypeptides are present in the second polypeptide chain only. In some cases, where a TMPP of the present disclosure comprises a first polypeptide and a second polypeptide, at least one of the two or more immunomodulatory polypeptides are present in the first polypeptide chain; and at least one of the two or more immunomodulatory polypeptides are present in the second polypeptide chain. In some cases, where a TMMP of the present disclosure comprises two or more immunomodulatory polypeptides, the immunomodulatory polypeptides are on the second polypeptide, and the second polypeptide comprises an MHC class II alpha polypeptide. Where a TMPP of the present disclosure comprises 2 or 3 copies of an immunomodulatory polypeptide, in some cases, the 2 or 3 copies are in tandem. Where a TMPP of the present disclosure comprises 2 or 3 copies of an immunomodulatory polypeptide, in some cases, the 2 or 3 copies are separated from one another by a linker.

In some cases, where a TMPP of the present disclosure comprises two immunomodulatory polypeptides, the two immunomodulatory polypeptides have the same amino acid sequence, i.e., the TMPP comprises two copies of an immunomodulatory polypeptide. In some cases, where a TMPP of the present disclosure comprises two immunomodulatory polypeptides, the two immunomodulatory polypeptides do not have the same amino acid sequence; e.g., one of the two immunomodulatory polypeptides comprises a first amino acid sequence and the second of the two immunomodulatory polypeptides comprises a second amino acid sequence, where the first and the second amino acid sequences are not identical. In some cases, the first and the second amino acid sequences differ from one another in amino acid sequence by from 1 amino acid to 10 amino acids, from 10 amino acids to 25 amino acids, or more than 25 amino acids. In some cases, the first and the second amino acid sequences share less than 98%, less than 95%, less than 90%, less than 85%, less than 80%, less than 75%, or less than 70%, amino acid sequence identity with one another.

A TMMP of the present disclosure modulates activity of a T cell. In some cases, a TMMP of the present disclosure reduces activity of an autoreactive T cell and/or an autoreactive B cell, e.g., a T cell reactive with a T1D-associated epitope or a B cell reactive with a T1D-associated epitope (e.g., a B cell that produces antibodies that bind to a T1D-associated epitope). In some cases, a TMMP of the present disclosure increases the number and/or activity of a regulatory T cell (Treg), resulting in reduced activity of an autoreactive T cell and/or an autoreactive B cell. Thus, a TMMP of the present disclosure is useful for treating T1D in an individual.

Immunomodulatory polypeptides that are suitable for inclusion in a TMPP of the present disclosure include, but are not limited to, IL-2, transforming growth factor-beta (TGFβ), JAG1, CD7, B7-1 (CD80), B7-2 (CD86), PD-L1, PD-L2, 4-1BBL, OX40L, Fas ligand (FasL), inducible costimulatory ligand (ICOS-L), intercellular adhesion molecule (ICAM), CD30L, CD40, CD70, CD83, HLA-G, MICA, MICB, lymphotoxin beta receptor, 3/TR6, ILT3, ILT4, and HVEM. In some cases, a TMMP of the present disclosure comprises one or more immunomodulatory polypeptides selected from the group consisting of an IL-2 polypeptide, a PD-L1 polypeptide, a FasL polypeptide, a TGF-β polypeptide, and combinations thereof. In some cases, a TMMP of the present disclosure comprises one or more immunomodulatory polypeptides, where at least one of the one or more immunomodulatory polypeptides is a PD-L1 polypeptide. In some cases, a TMMP of the present disclosure comprises one or more immunomodulatory polypeptides, where at least one of the one or more immunomodulatory polypeptides is an IL-2 polypeptide. In some cases, a TMMP of the present disclosure comprises one or more immunomodulatory polypeptides, where at least one of the one or more immunomodulatory polypeptides is a TGF-β polypeptide. In some cases, a TMMP of the present disclosure comprises one or more immunomodulatory polypeptides, where at least one of the one or more immunomodulatory polypeptides is a FasL polypeptide.

In some cases, an immunomodulatory polypeptide suitable for inclusion in a TMPP of the present disclosure comprises a wild-type amino acid sequence. In some cases, an immunomodulatory polypeptide suitable for inclusion in a TMPP of the present disclosure is a variant, e.g., comprising from 1 to 10 amino acid substitutions relative to a wild-type or naturally-occurring immunomodulatory polypeptide. In some cases, an immunomodulatory polypeptide suitable for inclusion in a TMPP of the present disclosure is a variant that exhibits reduced affinity to its cognate co-immunomodulatory polypeptide (e.g., a co-immunomodulatory polypeptide present on the surface of a T cell), compared to the affinity of the wild-type or naturally-occurring immunomodulatory polypeptide for the cognate co-immunomodulatory polypeptide.

Arrangement of TMMP Components

A TMMP of the present disclosure comprises two disulfide-linked heterodimeric polypeptides comprising the following components: a) a T1D peptide; b) an MHC class II α polypeptide; c) an MHC class II β polypeptide; and d) one or more immunomodulatory polypeptides; and may also one or more peptide linkers; and may also include Ig Fc polypeptide(s). Although the T1D peptide can be on same polypeptide with either the MHC class II α polypeptide or MHC class II β polypeptide, the T1D peptide typically will be on the same polypeptide chain as the MHC class II β polypeptide. These components can be present in a TMMP of the present disclosure in various arrangements. Examples of such arrangements are depicted schematically in FIG. 1A-1E, FIG. 2A-2D, FIG. 3A-3D, and FIG. 4A-4D. In some cases, a TMMP of the present disclosure comprises a heterodimer comprising: a) a first polypeptide comprising, in order from N-terminus to C-terminus: i) a T1D peptide; and ii) an MHC class II β polypeptide, optionally joined by a linker; and b) a second polypeptide comprising: i) an immunomodulatory polypeptide; and ii) an MHC class II α polypeptide, optionally joined by a linker, where the first polypeptide and the second polypeptide are covalently linked to one another via a disulfide bond. In some cases, a TMPP of the present disclosure comprises: a) a first polypeptide comprising, in order from N-terminus to C-terminus: i) a T1D peptide; and ii) an MHC class II β polypeptide, optionally joined by a linker; and b) a second polypeptide comprising: i) one or more immunomodulatory polypeptides (where two or more immunomodulatory polypeptides are present, they optionally may be joined by one or more linkers); ii) an MHC class II α polypeptide, optionally joined by a linker to the immunomodulatory polypeptide(s); and iii) an Ig Fc polypeptide, optionally joined by a linker to the MHC class II α polypeptide; where the first polypeptide and the second polypeptide are covalently linked to one another via a disulfide bond. The arrangement (N-terminus to C-terminus order) of the immunomodulatory polypeptide, the MHC class II α polypeptide, and the Ig Fc polypeptide, can vary.

Figure 5:
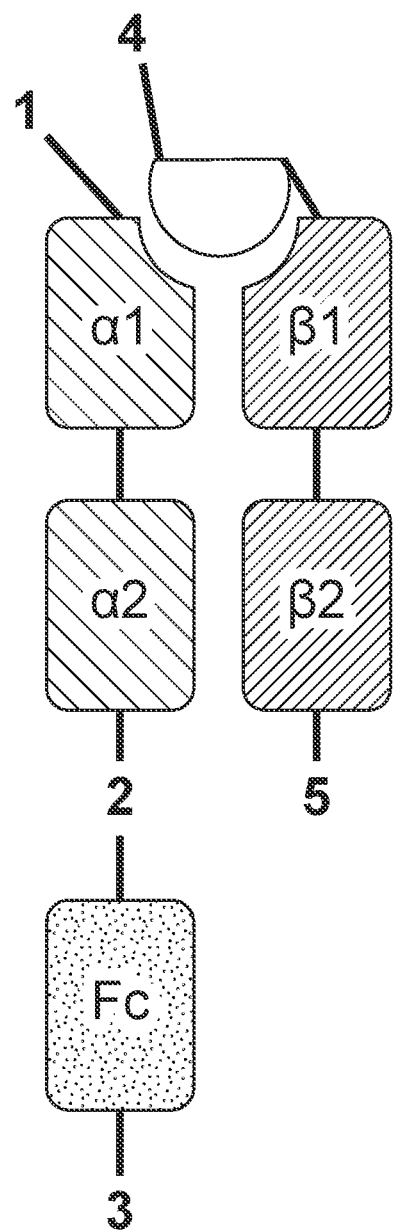
FIG. 5 is a schematic depiction of various possible positions of an immunomodulatory polypeptide in a TMMP of the present disclosure.

As one example of a possible arrangement, in some cases, a TMPP of the present disclosure comprises a heterodimer comprising two disulfide-linked polypeptides, wherein the heterodimer comprises: a) a first polypeptide comprising, in order from N-terminus to C-terminus (optionally including linkers): i) a T1D peptide; and ii) an MHC class II β polypeptide; and b) a second polypeptide comprising, in order from N-terminus to C-terminus (optionally including linkers): i) an immunomodulatory polypeptide; ii) an MHC class II α polypeptide; and iii) an Ig Fc polypeptide. (See FIG. 5, MOD position 1.) As another example of a possible arrangement, in some cases, a TMPP of the present disclosure comprises: a) a first polypeptide comprising, in order from N-terminus to C-terminus (optionally including linkers): i) a T1D peptide; and ii) an MHC class II β polypeptide; and b) a second polypeptide comprising, in order from N-terminus to C-terminus (optionally including one or more linkers that do not comprise a Cys): i) an MHC class II α polypeptide; ii) one or more immunomodulatory polypeptides; and iii) an Ig Fc polypeptide. (See FIG. 5, MOD position 2.) As another example of a possible arrangement, in some cases, a TMPP of the present disclosure comprises: a) a first polypeptide comprising, in order from N-terminus to C-terminus (optionally including linkers): i) a T1D peptide; and ii) an MHC class II β polypeptide; and b) a second polypeptide comprising, in order from N-terminus to C-terminus (optionally including linkers): i) an MHC class II α polypeptide; ii) an Ig Fc polypeptide; and iii) one or more immunomodulatory polypeptides. (See FIG. 5, MOD position 3.). As another example of a possible arrangement, in some cases, a TMPP of the present disclosure comprises: a) a first polypeptide comprising, in order from N-terminus to C-terminus (optionally including linkers): i) one or more immunomodulatory polypeptides; ii) a T1D peptide; and iii) an MHC class II β polypeptide; and b) a second polypeptide comprising, in order from N-terminus to C-terminus (optionally including linkers): i) an MHC class II α polypeptide; and ii) an Ig Fc polypeptide. (See FIG. 5, MOD position 4.). As another example of a possible arrangement, in some cases, a TMMP of the present disclosure comprises: a) a first polypeptide comprising, in order from N-terminus to C-terminus (optionally including linkers): i) a T1D peptide; ii) an MHC class II β polypeptide; and iii) one or more immunomodulatory polypeptides; and b) a second polypeptide comprising, in order from N-terminus to C-terminus (optionally including linkers): i) an MHC class II α polypeptide; and ii) an Ig Fc polypeptide. (See FIG. 5, MOD position 5.) The immunomodulatory polypeptide(s) can be on the same polypeptide chain as the MHC class II α polypeptides.

Generally speaking, potential locations in the heterodimer for disulfide bonds are where residues in the first and second polypeptides of the heterodimer are separated by a distance of 5 angstroms or less. Such locations represent potential locations where Cys residues, if not naturally present, can be substituted for the residues that exist in the polypeptides. A first polypeptide and a second polypeptide thus can be linked via a disulfide bond between two Cys residues that are generally no more than about 5 angstroms apart from one another in the heterodimer. In some cases, one or both of the Cys residues are non-naturally-occurring. An amino acid in the alpha chain and an amino acid in the beta chain of MHC class II polypeptides that are no more than 5 angstroms from one another in an MHC class II heterodimer, represent amino acids that, when substituted with a Cys, can form a disulfide bond in a TMMP of the present disclosure. Similarly, a disulfide bond can be formed i) between a Cys residue in a linker and a Cys residue in an MHC class II polypeptide, or ii) between a Cys residue in a linker in one polypeptide of the heterodimer and a Cys residue in a linker in the other polypeptide of the heterodimer, where the two Cys residues are no more than about 5 angstroms apart from each other in the heterodimer. Notably, however, not all pairs of residues separated by about 5 angstroms or less will be suitable for formation of a disulfide bond or provide a disulfide bond that stabilizes the resulting heterodimer.

Disulfide Bond Between a Peptide Linker and an MHC class II Polypeptide

In any of the above embodiments, in some cases the TMMP comprises a peptide linker between the T1D peptide and the MHC class II polypeptide. Where desired, the linker can comprise a Cys that can be used to form a disulfide bond between the two polypeptides in the heterodimer.

Position 1 MOD(s)

In some cases, a TMMP of the present disclosure comprises: a) a first polypeptide comprising, in order from N-terminus to C-terminus: i) a T1D peptide; ii) a peptide linker comprising a Cys; and iii) an MHC class II β polypeptide; and b) a second polypeptide comprising, in order from N-terminus to C-terminus (optionally including one or more linkers that do not comprise a Cys): i) one or more immunomodulatory polypeptides; ii) an MHC class II α chain; and (optionally) iii) an Ig Fc polypeptide. (See FIG. 5, MOD position 1.) The peptide linker comprising a Cys can comprise an amino acid sequence selected from (CGGGS)(GGGGS)n (SEQ ID NO: 1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10). In any of the above embodiments, in some cases the immunomodulatory polypeptide is a PD-L1 polypeptide or variant thereof, in some cases the immunomodulatory polypeptide is a TGF-β polypeptide or variant thereof, in some cases the immunomodulatory polypeptide is an IL-2 polypeptide or variant thereof, and in some cases the immunomodulatory polypeptide is a FasL polypeptide or variant thereof. In some cases, the T1D peptide is a proinsulin peptide. In some cases, the T1D peptide is a GAD peptide. In any of the above embodiments, in some cases, the MHC class II α chain comprises an amino acid substitution of an amino acid (other than a Cys) with a Cys, such that the Cys in the MHC class II α chain forms a disulfide bond with the Cys in the first polypeptide linker.

Position 2 MOD(s)

In some cases, a TMMP of the present disclosure comprises: a) a first polypeptide comprising, in order from N-terminus to C-terminus: i) a T1D peptide; ii) a peptide linker comprising a Cys; and iii) an MHC class II β polypeptide; and b) a second polypeptide comprising, in order from N-terminus to C-terminus (optionally including one or more linkers that do not comprise a Cys): i) an MHC class II α chain; ii) one or more immunomodulatory polypeptides; and iii) an Ig Fc polypeptide. (See FIG. 5, MOD position 2.) The peptide linker comprising a Cys can comprise, e.g., an amino acid sequence selected from (CGGGS)(GGGGS)n (SEQ ID NO: 1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10). Other peptide linkers comprising a Cys may be used. In any of the above embodiments, in some cases the immunomodulatory polypeptide is a PD-L1 polypeptide or variant thereof, in some cases the immunomodulatory polypeptide is a TGF-β polypeptide or variant thereof, in some cases the immunomodulatory polypeptide is an IL-2 polypeptide or variant thereof, and in some cases, the immunomodulatory polypeptide is a FasL polypeptide or variant thereof. In some cases, the T1D peptide is a proinsulin peptide. In some cases, the T1D peptide is a GAD peptide. In any of the above embodiments, in some cases, the MHC class II α chain comprises an amino acid substitution of an amino acid (other than a Cys) with a Cys, such that the Cys in the MHC class II α chain forms a disulfide bond with the Cys in the linker.

Position 3 MOD(s)

In some cases, a TMMP of the present disclosure comprises: a) a first polypeptide comprising, in order from N-terminus to C-terminus: i) a T1D peptide; ii) a peptide linker comprising a Cys; and iii) an MHC class II β polypeptide; and b) a second polypeptide comprising, in order from N-terminus to C-terminus (optionally including one or more linkers that do not comprise a Cys): i) an MHC class II α chain; ii) an Ig Fc polypeptide; and iii) one or more immunomodulatory polypeptides. (See FIG. 5, MOD position 3.) The peptide linker comprising a Cys can comprise, e.g., an amino acid sequence selected from (CGGGS)(GGGGS)n (SEQ ID NO:1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10). Other peptide linkers comprising a Cys may be used. In any of the above embodiments, in some cases, the immunomodulatory polypeptide is a PD-L1 polypeptide or variant thereof. In any of the above embodiments, in some cases the immunomodulatory polypeptide is a TGF-β polypeptide or variant thereof. In any of the above embodiments, in some cases, the immunomodulatory polypeptide is an IL-2 polypeptide or variant thereof. In any of the above embodiments, in some cases, the immunomodulatory polypeptide is a FasL polypeptide or variant thereof. In some cases, the T1D peptide is a proinsulin peptide. In some cases, the T1D peptide is a GAD peptide. In any of the above embodiments, in some cases, the MHC class II α chain comprises an amino acid substitution of an amino acid (other than a Cys) with a Cys, such that the Cys in the MHC class II α chain forms a disulfide bond with the Cys in the linker.

Position 4 MOD(s)

In some cases, a TMMP of the present disclosure comprises: a) a first polypeptide comprising, in order from N-terminus to C-terminus: i) one or more immunomodulatory polypeptides; ii) a T1D peptide; ii) a peptide linker comprising a Cys; and iii) an MHC class II β polypeptide; and b) a second polypeptide comprising, in order from N-terminus to C-terminus: i) an MHC class II α chain; and (optionally) ii) an Ig Fc polypeptide, optionally joined by a linker that does not comprise a Cys. (See FIG. 5, MOD position 4.) The peptide linker comprising a Cys can comprise, e.g., an amino acid sequence selected from (CGGGS)(GGGGS)n (SEQ ID NO: 1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10). Other peptide linkers comprising a Cys may be used. In any of the above embodiments, in some cases the immunomodulatory polypeptide is a PD-L1 polypeptide or variant thereof, in some cases the immunomodulatory polypeptide is a TGF-β polypeptide or variant thereof, in some cases the immunomodulatory polypeptide is an IL-2 polypeptide or variant thereof, and in some cases the immunomodulatory polypeptide is a FasL polypeptide or variant thereof. In some cases, the T1D peptide is a proinsulin peptide. In some cases, the T1D peptide is a GAD peptide. In any of the above embodiments, in some cases, the MHC class II α chain comprises an amino acid substitution of an amino acid (other than a Cys) with a Cys, such that the Cys in the MHC class II α chain forms a disulfide bond with the Cys in the linker.

Position 5 MOD(s)

In some cases, a TMMP of the present disclosure comprises: a) a first polypeptide comprising, in order from N-terminus to C-terminus: i) a T1D peptide; ii) a peptide linker comprising a Cys; iii) an MHC class II β polypeptide; and iv) one or more immunomodulatory polypeptides; and b) a second polypeptide comprising, in order from N-terminus to C-terminus: i) an MHC class II α chain; and (optionally) ii) an Ig Fc polypeptide, optionally joined by a linker that does not comprise a Cys. (See FIG. 5, MOD position 4.) The peptide linker comprising a Cys can comprise, e.g., an amino acid sequence selected from (CGGGS)(GGGGS)n (SEQ ID NO: 1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10). Other peptide linkers comprising a Cys may be used. In any of the above embodiments, in some cases the immunomodulatory polypeptide is a PD-L1 polypeptide or variant thereof, in some cases the immunomodulatory polypeptide is a TGF-β polypeptide or variant thereof, in some cases the immunomodulatory polypeptide is an IL-2 polypeptide or variant thereof, and in some cases the immunomodulatory polypeptide is a FasL polypeptide or variant thereof. In some cases, the T1D peptide is a proinsulin peptide. In some cases, the T1D peptide is a GAD peptide. In any of the above embodiments, in some cases, the MHC class II α chain comprises an amino acid substitution of an amino acid (other than a Cys) with a Cys, such that the Cys in the MHC class II α chain forms a disulfide bond with the Cys in the linker.

Disulfide Bond Between Peptide Linkers in the First and Second Polypeptides

In some cases, the TMMP comprises a first Cys-containing peptide linker between the T1D peptide and the MHC class II polypeptide in the first polypeptide, and a second Cys-containing peptide linker between two of the components in the second polypeptide. In such cases, the Cys residues in the first and second Cys-containing linkers can be used to form a disulfide bond between the two polypeptides in the heterodimer.

Position 1 MOD(s)

In some cases, a TMMP of the present disclosure comprises: a) a first polypeptide comprising, in order from N-terminus to C-terminus: i) a T1D peptide; ii) a first peptide linker comprising a Cys; and iii) an MHC class II β polypeptide (e.g., a DRB MHC class II polypeptide comprising an amino acid sequence having at least 80%, at least 85%, at least 90%, at least 95%, at least 98%, at least 99%, or 100% amino acid sequence identity to the amino acid sequence depicted in FIG. 14A); and b) a second polypeptide comprising, in order from N-terminus to C-terminus: i) one or more immunomodulatory polypeptides; ii) an MHC class II α chain (e.g., a DRA MHC class II polypeptide comprising an amino acid sequence having at least 80%, at least 85%, at least 90%, at least 95%, at least 98%, at least 99%, or 100% amino acid sequence identity to the amino acid sequence depicted in FIG. 13A); and (optionally) iii) an Ig Fc polypeptide. (See FIG. 5, MOD position 1.) The second polypeptide comprises a second peptide linker that comprises a Cys, where the second peptide linker is positioned either between the immunomodulatory polypeptides and the MHC class II α chain or between the MHC class II α chain and the Ig Fc, if present. The second polypeptide optionally may include one or more linkers that do not comprise a Cys. The peptide linkers comprising a Cys can comprise an amino acid sequence selected from (CGGGS)(GGGGS)n (SEQ ID NO: 1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10). In any of the above embodiments, in some cases the immunomodulatory polypeptide is a PD-L1 polypeptide or variant thereof, in some cases the immunomodulatory polypeptide is a TGF-β polypeptide or variant thereof, in some cases the immunomodulatory polypeptide is an IL-2 polypeptide or variant thereof, and in some cases the immunomodulatory polypeptide is a FasL polypeptide or variant thereof. In some cases, the T1D peptide is a proinsulin peptide. In some cases, the T1D peptide is a GAD peptide.

Position 3 MOD(s)

In some cases, a TMMP of the present disclosure comprises: a) a first polypeptide comprising, in order from N-terminus to C-terminus: i) a T1D peptide; ii) a first peptide linker comprising a Cys; and iii) an MHC class II β polypeptide (e.g., a DRB MHC class II polypeptide comprising an amino acid sequence having at least 80%, at least 85%, at least 90%, at least 95%, at least 98%, at least 99%, or 100% amino acid sequence identity to the amino acid sequence depicted in FIG. 14A); and b) a second polypeptide comprising, in order from N-terminus to C-terminus: i) an MHC class II α chain (e.g., a DRA MHC class II polypeptide comprising an amino acid sequence having at least 80%, at least 85%, at least 90%, at least 95%, at least 98%, at least 99%, or 100% amino acid sequence identity to the amino acid sequence depicted in FIG. 13A); ii) an Ig Fc polypeptide; and iii) one or more immunomodulatory polypeptides. (See FIG. 5, MOD position 3.) The second polypeptide comprises a second peptide linker that comprises a Cys, where the second peptide linker is positioned either between the MHC class II α chain and the Ig Fc or between the IG Fc and the one or more immunomodulatory polypeptides. The second polypeptide optionally may include one or more linkers that do not comprise a Cys. The peptide linkers comprising a Cys can comprise an amino acid sequence selected from (CGGGS)(GGGGS)n (SEQ ID NO:1), (GCGGS)(GGGGS)n (SEQ ID NO:2), (GGCGS) (GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10). In any of the above embodiments, in some cases the immunomodulatory polypeptide is a PD-L1 polypeptide or variant thereof, in some cases the immunomodulatory polypeptide is a TGF-β polypeptide or variant thereof, in some cases the immunomodulatory polypeptide is an IL-2 polypeptide or variant thereof, and in some cases the immunomodulatory polypeptide is a FasL polypeptide or variant thereof. In some cases, the T1D peptide is a proinsulin peptide. In some cases, the T1D peptide is a GAD peptide. The peptide linkers comprising a Cys can comprise, e.g., an amino acid sequence selected from (CGGGS)(GGGGS)n (SEQ ID NO: 1), (GCGGS)(GGGGS)n (SEQ ID NO:2), (GGCGS)(GGGGS)n (SEQ ID NO:3), (GGGCS) (GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10). Other peptide linkers comprising a Cys may be used. In any of the above embodiments, in some cases, the immunomodulatory polypeptide is a PD-L1 polypeptide or variant thereof. In any of the above embodiments, in some cases the immunomodulatory polypeptide is a TGF-β polypeptide or variant thereof. In any of the above embodiments, in some cases, the immunomodulatory polypeptide is an IL-2 polypeptide or variant thereof. In any of the above embodiments, in some cases, the immunomodulatory polypeptide is a FasL polypeptide or variant thereof. In some cases, the T1D peptide is a proinsulin peptide. In some cases, the T1D peptide is a GAD peptide.

Alternatively, following the same design of including a Cys-containing linker in the first polypeptide between the T1D peptide and the MHC class II β polypeptide, and a Cys-containing linker between two of the components in the second polypeptide, a disulfide-linked TMMP can be constructed in which the one or more immunomodulatory polypeptides are at Position 2, 4 or 5 as those positions are described above and depicted schematically in FIG. 5.

Disulfide Bond Between the Two MHC Class II Polypeptides

As noted above, in some cases, the first polypeptide of a heterodimer of a TMMP of the present disclosure comprises a first MHC class II polypeptide comprising an amino acid substitution that results in a Cys (a "first Cys"); and the second polypeptide comprises a second MHC class II polypeptide comprising an amino acid substitution that results in a Cys (a "second Cys"); where the heterodimer comprises a disulfide bond formed between the first Cys and the second Cys. For example, in some cases, the first polypeptide comprises an MHC class II β polypeptide comprising an amino acid substitution that results in a Cys (a "first Cys"); and the second polypeptide comprises an MHC class II α polypeptide comprising an amino acid substitution that results in a Cys (a "second Cys"); where the heterodimer comprises a disulfide bond formed between the first Cys and the second Cys.

Position 1 MOD(s)

In some cases, for example, a TMMP of the present disclosure comprises: a) a first polypeptide comprising, in order from N-terminus to C-terminus: i) a T1D peptide; and ii) a first MHC class II polypeptide comprising a substitution of an amino acid (other than a Cys) with a Cys (a "first Cys"), the components of the first polypeptide optionally being joined by a linker that does not comprise a Cys; and b) a second polypeptide comprising, in order from N-terminus to C-terminus: i) one or more immunomodulatory polypeptides; ii) a second MHC class II polypeptide comprising a substitution of an amino acid (other than a Cys) with a Cys (a "second Cys"); and iii) optionally an Ig Fc polypeptide, the components of the second polypeptide optionally being joined by one or more linkers that do not comprise a Cys; where the first polypeptide and the second polypeptide are linked via a disulfide bond between the first Cys and the second Cys. (See FIG. 5, MOD position 1.) In any of the above embodiments, in some cases, the one or more immunomodulatory polypeptides is a PD-L1 polypeptide or variant thereof, in some cases the one or more immunomodulatory polypeptides is a TGF-β polypeptide or variant thereof, in some cases the one or more immunomodulatory polypeptides is an IL-2 polypeptide or variant thereof, and in some cases the one or more immunomodulatory polypeptides is a FasL polypeptide or variant thereof. In some cases, the T1D peptide is a proinsulin peptide. In some cases, the T1D peptide is a GAD peptide. In any of the above embodiments, in some cases, the first MHC class II polypeptide is an MHC class II β chain polypeptide and the second MHC class II polypeptide is an MHC class II α chain polypeptide.

Position 2 MOD(s)

As another example, in some cases, a TMMP of the present disclosure comprises: a) a first polypeptide comprising, in order from N-terminus to C-terminus: i) a T1D peptide; and ii) a first MHC class II polypeptide comprising a substitution of an amino acid (other than a Cys) with a Cys (a "first Cys"), the components of the first polypeptide optionally being joined by a linker that does not comprise a Cys; and b) a second polypeptide comprising, in order from N-terminus to C-terminus: i) a second MHC class II polypeptide comprising a substitution of an amino acid (other than a Cys) with a Cys (a "second Cys"); ii) one or more immunomodulatory polypeptides; and iii) optionally an Ig Fc polypeptide, the components of the second polypeptide optionally being joined by one or more linkers that do not comprise a Cys; where the first polypeptide and the second polypeptide are linked via a disulfide bond between the first Cys and the second Cys. (See FIG. 5, MOD position 2.) In any of the above embodiments, in some cases the one or more immunomodulatory polypeptides is a PD-L1 polypeptide or variant thereof, in some cases the one or more immunomodulatory polypeptides is a TGF-β polypeptide or variant thereof, in some cases the one or more immunomodulatory polypeptides is an IL-2 polypeptide or variant thereof, and in some cases the one or more immunomodulatory polypeptides is a FasL polypeptide or variant thereof. In some cases, the T1D peptide is a proinsulin peptide. In some cases, the T1D peptide is a GAD peptide. In any of the above embodiments, in some cases, the first MHC class II polypeptide is an MHC class II β chain polypeptide and the second MHC class II polypeptide is an MHC class II α chain polypeptide.

Position 3 MOD(s)

As another example, in some cases, a TMMP of the present disclosure comprises: a) a first polypeptide comprising, in order from N-terminus to C-terminus: i) a T1D peptide; and ii) a first MHC class II polypeptide comprising a substitution of an amino acid (other than a Cys) with a Cys (a "first Cys"), the components of the first polypeptide optionally being joined by a linker that does not comprise a Cys; and b) a second polypeptide comprising, in order from N-terminus to C-terminus: i) a second MHC class II polypeptide comprising a substitution of an amino acid (other than a Cys) with a Cys (a "second Cys"); ii) an Ig Fc polypeptide; and iii) one or more immunomodulatory polypeptides, the components of the second polypeptide optionally being joined by a linker that does not comprise a Cys; where the first polypeptide and the second polypeptide are linked via a disulfide bond between the first Cys and the second Cys. (See FIG. 5, MOD position 3.) In any of the above embodiments, in some cases the one or more immunomodulatory polypeptides is a PD-L1 polypeptide or variant thereof, in some cases the one or more immunomodulatory polypeptides is a TGF-β polypeptide or variant thereof, in some cases the one or more immunomodulatory polypeptides is an IL-2 polypeptide or variant thereof, and in some cases the one or more immunomodulatory polypeptides is a FasL polypeptide or variant thereof. In some cases, the T1D peptide is a proinsulin peptide. In some cases, the T1D peptide is a GAD peptide. In any of the above embodiments, in some cases, the first MHC class II polypeptide is an MHC class II β chain polypeptide and the second MHC class II polypeptide is an MHC class II α chain polypeptide.

Position 4 MOD(s)

As another example, in some cases, a TMMP of the present disclosure comprises: a) a first polypeptide comprising, in order from N-terminus to C-terminus: i) one or more immunomodulatory polypeptides; ii) a T1D peptide; and iii) a first MHC class II polypeptide comprising a substitution of an amino acid (other than a Cys) with a Cys (a "first Cys"), the components of the first polypeptide optionally being joined by one or more linkers that do not comprise a Cys; and b) a second polypeptide comprising, in order from N-terminus to C-terminus: i) a second MHC class II polypeptide comprising a substitution of an amino acid (other than a Cys) with a Cys (a "second Cys"); and ii) optionally an Ig Fc polypeptide, where when the optional Ig Fc is present, the components of the second polypeptide are optionally joined by a linker that does not comprise a Cys; where the first polypeptide and the second polypeptide are linked via a disulfide bond between the first Cys and the second Cys. (See FIG. 5, MOD position 4.) In any of the above embodiments, in some cases the one or more immunomodulatory polypeptides is a PD-L1 polypeptide or variant thereof, in some cases the one or more immunomodulatory polypeptides is a TGF-β polypeptide or variant thereof, in some cases the one or more immunomodulatory polypeptides is an IL-2 polypeptide or variant thereof, and in some cases the one or more immunomodulatory polypeptides is a FasL polypeptide or variant thereof. In some cases, the T1D peptide is a proinsulin peptide. In some cases, the T1D peptide is a GAD peptide. In any of the above embodiments, in some cases, the first MHC class II polypeptide is an MHC class II β chain polypeptide and the second MHC class II polypeptide is an MHC class II α chain polypeptide.

Position 5 MOD(s)

As another example, in some cases, a TMMP of the present disclosure comprises: a) a first polypeptide comprising, in order from N-terminus to C-terminus: i) a T1D peptide; ii) a first MHC class II polypeptide comprising a substitution of an amino acid (other than a Cys) with a Cys (a "first Cys"); and iii) one or more immunomodulatory polypeptides, the components of the first polypeptide optionally being joined by one or more linkers that do not comprise a Cys; and b) a second polypeptide comprising, in order from N-terminus to C-terminus: i) a second MHC class II polypeptide comprising a substitution of an amino acid (other than a Cys) with a Cys (a "second Cys"); and ii) optionally an Ig Fc polypeptide, where when the optional Ig Fc is present, the components of the second polypeptide are optionally joined by a linker that does not comprise a Cys; where the first polypeptide and the second polypeptide are linked via a disulfide bond between the first Cys and the second Cys. (See FIG. 5, MOD position 5.) In any of the above embodiments, in some cases, the one or more immunomodulatory polypeptides is a PD-L1 polypeptide or variant thereof, in some cases the one or more immunomodulatory polypeptides is a TGF-β polypeptide or variant thereof, in some cases the one or more immunomodulatory polypeptides is an IL-2 polypeptide or variant thereof, and in some cases the one or more immunomodulatory polypeptides is a FasL polypeptide or variant thereof. In some cases, the T1D peptide is a proinsulin peptide. In some cases, the T1D peptide is a GAD peptide. In any of the above embodiments, in some cases, the first MHC class II polypeptide is an MHC class II β chain polypeptide and the second MHC class II polypeptide is an MHC class II α chain polypeptide.

MHC Class II Polypeptides

As noted above, a TMMP of the present disclosure comprises MHC class II polypeptides.

Naturally occurring MHC class II polypeptides comprise an α chain and a β chain. As used herein, the term "MHC class II polypeptides" include human leukocyte antigen (HLA) α- and β -chains. MHC class II polypeptides include MHC class II DP α and β polypeptides, DM α and β polypeptides, DOA α and β polypeptides, DOB α and β polypeptides, DQ α and β polypeptides, and DR α and β polypeptides. As used herein, a "MHC class II polypeptide" can comprise a MHC class II α chain polypeptide, a MHC class II β chain polypeptide, or only a portion of a MHC class II α or β chain polypeptide. For example, a "MHC class II polypeptide" can be a polypeptide that includes: i) only the α1 domain of a MHC class II α chain polypeptide; ii) only the α2 domain of a MHC class II α chain; iii) only the α1 domain and an α2 domain of a MHC class II α chain; iv) only the β1 domain of a MHC class II β chain; v) only the β2 domain of a MHC class II β chain; vi) only the β1 domain and the β2 domain of a MHC class II β chain; vii) the α1 domain of a MHC class II α chain, the β1 domain of a MHC class II β chain, and the β2 domain of a MHC class II; and the like.

MHC class II polypeptides include allelic forms. The HLA locus is highly polymorphic in nature. As disclosed in the Nomenclature for Factors of the HLA System 2000 (Hum. Immunol.; 62(4):419-68, 2001) there are 221 HLA-DRB1 alleles, 19 DRB3 alleles, 89 DRB4 alleles, 14 DRB5 alleles, 19 DQA1 alleles and 39 DQB 1 alleles, with new alleles being discovered continuously. A 2007 update by the WHO nomenclature Committee for Factors of the HLA System (www.anthonynolan.com/HIG/) showed there are 3 DRA alleles, 494 DRB 1 alleles, 1 DRB2 alleles, 44 DRB3 alleles, 13 DRB4 alleles, 18 DRB5 alleles, 3 DRB6 alleles, 2 DRB7 alleles, 10 DRB8 alleles, 1 DRB9 alleles, 34 DQA1 alleles, 83 DQB1 alleles, 23 DPA1, 126 DPB1 alleles, 4 DMA alleles, 7 DMB alleles, 12 DOA alleles and 9 DOB alleles. As used herein, the term "MHC class II polypeptide" includes allelic forms of any known MHC class II polypeptide.

In some cases, a TMMP of the present disclosure comprises an MHC class II α chain (e.g., a DPA1, DRA1, or DQA1α chain), without the leader, transmembrane, and intracellular portions (e.g., cytoplasmic tails) that may be present in a naturally-occurring MHC class II α chain. Thus, in some cases, a TMMP of the present disclosure comprises only the α1 and α2 portions of an MHC class II α chain (e.g., only the α1 and α2 portions of a DPA1, DRA1, or DQA1α chain); and does not include the leader, transmembrane, and intracellular portions (e.g., cytoplasmic tails) that may be present in a naturally-occurring MHC class II α chain.

In some cases, a TMMP of the present disclosure comprises an MHC class II β chain (e.g., a DPB 1, DRB 1, or DQB 1β chain), without the leader, transmembrane, and intracellular portions (e.g., cytoplasmic tails) that may be present in a naturally-occurring MHC class II β chain. Thus, in some cases, a TMMP of the present disclosure comprises only the 01 and 02 portions of an MHC class II β chain (e.g., only the 01 and 02 portions of a DPB1, DRB1, or DQB1β chain); and does not include the leader, transmembrane, and intracellular portions (e.g., cytoplasmic tails) that may be present in a naturally-occurring MHC class II β chain.

MHC Class II Alpha Chains

MHC class II alpha chains comprise an α1 domain and an α2 domain. In some cases, the α1 domain and the α2 domain present in an antigen-presenting cell are from the same MHC class II α chain polypeptide. In some cases, the α1 domain and the α2 domain present in an antigen-presenting cell are from two different MHC class II α chain polypeptides.

MHC class II alpha chains suitable for inclusion in a TMMP of the present disclosure lack a signal peptide. An MHC class II alpha chain suitable for inclusion in a multimeric polypeptide of the present disclosure can have a length of from about 60 amino acids to about 190 amino acids; for example, an MHC class II alpha chain suitable for inclusion in a TMMP of the present disclosure can have a length of from about 60 amino acids to about 80 amino acids, from about 80 amino acids to about 100 amino acids, from about 100 amino acids to about 120 amino acids, from about 120 amino acids to about 140 amino acids, from about 140 amino acids to about 160 amino acids, from about 160 amino acids to about 180 amino acids, or from about 180 amino acids to about 200 amino acids. An MHC class II α1 domain suitable for inclusion in a TMMP of the present disclosure can have a length of from about 30 amino acids to about 95 amino acids; for example, an MHC class II α1 domain suitable for inclusion in a TMMP of the present disclosure can have a length of from about 30 amino acids to about 40 amino acids, from about 40 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, or from about 90 amino acids to about 95 amino acids. An MHC class II α2 domain suitable for inclusion in a TMMP of the present disclosure can have a length of from about 30 amino acids to about 95 amino acids; for example, an MHC class II α2 domain suitable for inclusion in a TMMP of the present disclosure can have a length of from about 30 amino acids to about 40 amino acids, from about 40 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, or from about 90 amino acids to about 95 amino acids.

In some cases, an MHC class II α chain polypeptide present in a TMMP of the present disclosure comprises an amino acid substitution, relative to a wild-type MHC class II α chain polypeptide, where the amino acid substitution replaces an amino acid (other than a Cys) with a Cys. Such an amino acid substitution can occur between amino acid 55 and 110 of the MHC class II α chain polypeptide. For example, an amino acid substitution that replaces an amino acid other than a Cys with a Cys can be present between amino acids 55 and 60, between amino acids 60 and 65, between amino acids 65 and 70, between amino acids 70 and 75, between amino acids 75 and 80, between amino acids 80 and 85, between amino acids 85 and 90, between amino acids 90 and 95, between amino acids 95 and 100, between amino acids 100 and 105, or between amino acids 105 and 110.

DRA Polypeptides

In some cases, a suitable MHC class II α chain polypeptide is a DRA polypeptide, more specifically a DRA1 polypeptide. A DRA polypeptide can have at least 60%, at least 70%, at least 80%, at least 90%, at least 95%, at least 98%, at least 99%, or 100%, amino acid sequence identity with amino acids 26-203 of the DRA amino acid sequence depicted in FIG. 6. In some cases, the DRA polypeptide has a length of about 178 amino acids (e.g., 175, 176, 177, 178, 179, or 180 amino acids).

A "DRA polypeptide" includes allelic variants, e.g., naturally occurring allelic variants. Thus, in some cases, a suitable DRA polypeptide comprises the following amino acid sequence: IKEEH VIIQAEFYLN PDQSGEFMFD FDGDEIFHVD MAKKETVWRL EEFGRFASFE AQGALANIAV DKANLEIMTK RSNYTPITNV PPEVTVLTNSPVELREPNVL ICFIDKFTPP VVNVTWLRNG KPVTTGVSET VFLPREDHLF RKFHYLPFLPSTEDVYDCRV EHWGLDEPLL KHW (SEQ ID NO:6, amino acids 26-203 of DRA*01:02, see FIG. 6), or an allelic variant thereof. In some cases, the allelic variant is the DRA*01:01:01:01 allelic variant that differs from DRA*01:02:01 by having a valine in place of the leucine at position 242 of the sequence in FIG. 6. In some cases, a DRA polypeptide suitable for inclusion in a TMMP of the present disclosure comprises an amino acid substitution, relative to a wild-type DRA polypeptide, where the amino acid substitution replaces an amino acid (other than a Cys) with a Cys.

In some cases, a TMMP of the present disclosure comprises a variant DRA polypeptide that comprises a non-naturally occurring Cys residue. For example, in some cases, a TMMP of the present disclosure comprises a variant DRA polypeptide that comprises an amino acid substitution selected from E3C, E4C, F12C, G28C, D29C, I72C, K75C, T80C, P81C, I82C, T93C, N94C, and S95C.

In some cases, a suitable DRA polypeptide comprises the following amino acid sequence: IKEEH VIIQAEFYLN PDQSGEFMFD FDGDEIFHVD MAKKETVWRL EEFGRFASFE AQGALANIAV DKANLECMTK RSNYTPITNV PPEVTVLTNSPVELREPNVL ICFIDKFTPP VVNVTWLRNG KPVTTGVSET VFLPREDHLF RKFHYLPFLPSTEDVYDCRV EHWGLDEPLL KHW (SEQ ID NO:7), where amino acid I72 is substituted with a Cys (shown in bold text). In some cases, a suitable DRA polypeptide comprises the following amino acid sequence: IKEEH VIIQAEFYLN PDQSGEFMFD FDGDEIFHVD MAKKETVWRL EEFGRFASFE AQGALANIAV DKANLEIMTC RSNYTPITNV PPEVTVLTNSPVELREPNVL ICFIDKFTPP VVNVTWLRNG KPVTTGVSET VFLPREDHLF RKFHYLPFLPSTEDVYDCRV EHWGLDEPLL KHW (SEQ ID NO:8), where amino acid K75 is substituted with a Cys (shown in bold text).

In some cases, a suitable DRA polypeptide comprises the following amino acid sequence: IKEEHVIIQAEFYLNPDQSGEFMFDFDGDEIFHVD-MAKKETV WRLEEFGRFASFEAQGALANIAV DKAN-LEIMTKRSNYTPITNVPPEVTVLTNSPVELREPNVLIC-FIDKFTPPV VNVTW LRNGKPVTT GVSETVFLPREDHLFRKFHYLPFLPST- EDVYDCRVEHWGLDEPLLKHWEFDAPSPLPET (SEQ ID NO:9). In some cases, an amino acid between amino acids 55 and 110 is substituted with a Cys. In some cases, an amino acid between amino acids 70 and 85 is substituted with a Cys. In some cases, a suitable DRA polypeptide comprises the following amino acid sequence: IKEEHVIIQAEFYLNPDQSGEFMFDFDGCEIFHVD-MAKKETV WRLEEFGRFASFEAQGALANIAV DKAN-LEIMTKRSNYTPITNVPPEVTVLTNSPVELREPNVLIC-FIDKFTPPV VNVTW LRNGKPVTT GVSETVFLPREDHLFRKFHYLPFLPST-EDVYDCRVEHWGLDEPLLKHWEFDAPSPLPET (SEQ ID NO: 10), where D29 is substituted with a Cys (shown in bold text). In some cases, a suitable DRA polypeptide comprises the following amino acid sequence: IKEEHVIIQAEFYLNPDQSGEFMFDFDGDEIFHVD-MAKKETV WRLEEFGRFASFEAQGALANIAV DKAN-LECMTKRSNYTPITNVPPEVTVLTNSPVEL-REPNVLICFIDKFTPPV VNVTW LRNGKPVTT GVSETVFLPREDHLFRKFHYLPFLPST-EDVYDCRVEHWGLDEPLLKHWEFDAPSPLPET (SEQ ID NO: 11), where I72 is substituted with a Cys (shown in bold text). In some cases, a suitable DRA polypeptide comprises the following amino acid sequence: IKEEHVIIQAEFYLNPDQSGEFMFDFDGDEIFHVD-MAKKETV WRLEEFGRFASFEAQGALANIAV DKAN-LEIMTCRSNYTPITNVPPEVTVLTNSPVELREPNVLIC-FIDKFTPPV V NVTWLRNGKPVTT GVSETVFLPREDHLFRKFHYLPFLPST-EDVYDCRVEHWGLDEPLLKHWEFDAPSPLPET (SEQ ID NO: 12), where K75 is substituted with a Cys (shown in bold text). In some cases, a suitable DRA polypeptide comprises the following amino acid sequence: IKEEHVIIQAEFYLNPDQSGEFMFDFDGDEIFHVD-MAKKETV WRLEEFGRFASFEAQGALANIAV DKAN-LEIMTKRSNYTCITNVPPEVTVLTNSPVEL-REPNVLICFIDKFTPPV V NVTWLRNGKPVTT GVSETVFLPREDHLFRKFHYLPFLPST-EDVYDCRVEHWGLDEPLLKHWEFDAPSPLPET (SEQ ID NO:13), where P81 is substituted with a Cys (shown in bold text). In some cases, a suitable DRA polypeptide comprises the following amino acid sequence: IKEEHVIIQAEFYLNPDQSGEFMFDFDGDEIFHVD-MAKKETV WRLEEFGRFASFEAQGALANIAV DKAN-LEIMTKRSNYTPCTNVPPEVTVLTNSPVEL-REPNVLICFIDKFTPPV VNVTW LRNGKPVTT GVSETVFLPREDHLFRKFHYLPFLPST-EDVYDCRVEHWGLDEPLLKHWEFDAPSPLPET (SEQ ID NO: 14), where I82 is substituted with a Cys (shown in bold text).

A suitable DRA α1 domain comprises an amino acid sequence having at least 60%, at least 70%, at least 80%, at least 90%, at least 95%, at least 98%, at least 99%, or 100%, amino acid sequence identity to the following amino acid sequence: VIIQAEFYLN PDQSGEFMFD FDGDEIFHVD MAKKETVWRL EEFGRFASFE AQGALANIAV DKAN-LEIMTK RSNYTPITN (SEQ ID NO:15); and can have a length of about 84 amino acids (e.g., 80, 81, 82, 83, 84, 85, or 86 amino acids). A suitable DRA α1 domain can comprise the following amino acid sequence: VIIQAEFYLN PDQSGEFMFD FDGDEIFHVD MAKKETVWRL EEFGRFASFE AQGALANIAV DKANLEIMTK RSNYT-PITN (SEQ ID NO: 15), or a naturally-occurring allelic variant. A suitable DRA α1 domain can comprise the following amino acid sequence: IKEEH VIIQAEFYLN PDQSGEFMFD FDGCEIFHVD MAKKETVWRL EEFGRFASFE AQGALANIAV DKANLEIMTK RSNYT-PITN (SEQ ID NO:16), where amino acid D29C is substituted with a Cys (shown in bold text). A suitable DRA α1 domain can comprise the following amino acid sequence: IKEEH VIIQAEFYLN PDQSGEFMFD FDGDEIFHVD MAKKETVWRL EEFGRFASFE AQGALANIAV DKAN-LECMTK RSNYTPITN (SEQ ID NO: 17), where amino acid I72 is substituted with a Cys (shown in bold text). A suitable DRA α1 domain can comprise the following amino acid sequence: IKEEH VIIQAEFYLN PDQSGEFMFD FDGDEIFHVD MAKKETVWRL EEFGRFASFE AQGALANIAV DKANLEIMTC RSNYTPITN (SEQ ID NO:18), where amino acid K75 is substituted with a Cys (shown in bold text). A suitable DRA α1 domain can comprise the following amino acid sequence: IKEEH VIIQAEFYLN PDQSGEFMFD FDGDEIFHVD MAKKETVWRL EEFGRFASFE AQGALANIAV DKAN-LEIMTK RSNYTCITN (SEQ ID NO:19), where amino acid P81 is substituted with a Cys (shown in bold text). A suitable DRA α1 domain can comprise the following amino acid sequence: IKEEH VIIQAEFYLN PDQSGEFMFD FDG-DEIFHVD MAKKETVWRL EEFGRFASFE AQGALA-NIAV DKANLEIMTK RSNYTPCTN (SEQ ID NO:20), where amino acid I82 is substituted with a Cys (shown in bold text).

A suitable DRA α2 domain comprises an amino acid sequence having at least 60%, at least 70%, at least 80%, at least 90%, at least 95%, at least 98%, at least 99%, or 100%, amino acid sequence identity to the following amino acid sequence: V PPEVTVLTNSPVELREPNVL ICFIDKFTPP VVNVTWLRNG KPVTTGVSET VFLPREDHLF RKFHYLPFLPSTEDVYDCRV EHWGLDEPLL KHW (SEQ ID NO:21); and can have a length of about 94 amino acids (e.g., 90, 91, 92, 93, 94, 95, 96, 97, or 98 amino acids).

DPA1 Polypeptides

In some cases, a suitable MHC class II α chain polypeptide is a DPA1 polypeptide. A DPA1 polypeptide can have at least 60%, at least 70%, at least 80%, at least 90%, at least 95%, at least 98%, at least 99%, or 100%, amino acid sequence identity with amino acids 29-209 of the DPA1 amino acid sequence depicted in FIG. 8. In some cases, the DPA1 polypeptide has a length of about 181 amino acids (e.g., 178, 179, 180, 181, 182, 183, or 184 amino acids). In some cases, a DPA polypeptide suitable for inclusion in a TMMP of the present disclosure comprises an amino acid substitution, relative to a wild-type DPA polypeptide, where the amino acid substitution replaces an amino acid (other than a Cys) with a Cys.

A "DPA1 polypeptide" includes allelic variants, e.g., naturally occurring allelic variants. Thus, in some cases, a suitable DPA1 polypeptide comprises the following amino acid sequence: AG AIKADHVSTY AAFVQTHRPT GEFMFEFDED EMFYVDLDKK ETVWHLEEFG QAFS-FEAQGG LANIAILNNN LNTLIQRSNH TQATNDPPEV TVFPKEPVEL GQPNTLICHI DKFFPPVLNV TWLCN-GELVT EGVAESLFLP RTDYSFHKFH YLTFVPSAED FYDCRVEHWG LDQPLLKHW (SEQ ID NO:22; amino acids 29-209 of DPA1*01:03:01:01, see FIG. 8), or an allelic variant thereof (e.g., DPA1*02:01; see FIG. 8). In some cases, a DPA polypeptide suitable for inclusion in a TMMP of the present disclosure comprises an amino acid substitution, relative to a wild-type DPA polypeptide, where the amino acid substitution replaces an amino acid (other than a Cys) with a Cys.

A suitable DPA1α1 domain may comprise an amino acid sequence having at least 60%, at least 70%, at least 80%, at least 90%, at least 95%, at least 98%, at least 99%, or 100%, amino acid sequence identity to the following amino acid sequence: AIKADHVSTY AAFVQTHRPT GEFMFEFDED EMFYVDLDKK ETVWHLEEFG QAFSFEAQGG LANIAILNNN LNTLIQRSNH TQATN (SEQ ID NO:23); and can have a length of about 87 amino acids (e.g., 84, 85, 86, 87, 88, or 89 amino acids). A suitable DPA1α1 domain can comprise the following amino acid sequence: AIKADHVSTY AAFVQTHRPT GEFMFEFDED EMFYVDLDKK ETVWHLEEFG QAFSFEAQGG LANIAILNNN LNTLIQRSNH TQATN (SEQ ID NO:23), or a naturally-occurring allelic variant.

A suitable DPA1α2 domain may comprise an amino acid sequence having at least 60%, at least 70%, at least 80%, at least 90%, at least 95%, at least 98%, at least 99%, or 100%, amino acid sequence identity to the following amino acid sequence: DPPEV TVFPKEPVEL GQPNTLICHI DKFFPPVLNV TWLCNGELVT EGVAESLFLP RTDYSFHKFH YLTFVPSAED FYDCRVEHWG LDQPLLKHW (SEQ ID NO:24); and can have a length of about 97 amino acids (e.g., 91, 92, 93, 94, 95, 96, or 97 amino acids). A suitable DPA1α2 domain can comprise the following amino acid sequence: DPPEV TVFPKEPVEL GQPNTLICHI DKFFPPVLNV TWLCNGELVT EGVAESLFLP RTDYSFHKFH YLTFVPSAED FYDCRVEHWG LDQPLLKHW (SEQ ID NO:24), or a naturally-occurring allelic variant thereof.

Other DPA1 polypeptides comprise the sequence: MRPEDRMFHIRAVILRALSLAFLLSLRGAGAIKADHV STYAAFV QTHRPTGEFMFEFDEDEQFY VDLDKKETV WHLEEFGRAFSFEAQGGLANIAILNNNLNTLIQRSNHTQAANDPPEVTVFPKEPV ELGQPNTLICHIDRFFPPVLNVTW LCNGEPVTEGVAESLFLPRTDYSFHKFHYLTFVPSAEDVYD CRVEHWGLDQPLLKHW EAQEPIQMPETTETVLCALGLVLGLVGIIVGTV LIIKSLRSGHDPRAQ GPL (SEQ ID NO:25; amino acids 29-209 of DPA1*02:01:01:01, see FIG. 8), or variant thereof having at least 60%, at least 70%, at least 80%, at least 90%, at least 95%, at least 98%, at least 99%, or 100%, amino acid sequence identity.

A suitable DPA1α1 domain may comprise an amino acid sequence having at least 60%, at least 70%, at least 80%, at least 90%, at least 95%, at least 98%, at least 99%, or 100%, amino acid sequence identity to the amino acids 29-115 of DPA1*02:01:01:01, SEQ ID NO:25; and can have a length of about 87 amino acids (e.g., 84, 85, 86, 87, 88, or 89 amino acids). A suitable DPA1α2 domain may comprise an amino acid sequence having at least 60%, at least 70%, at least 80%, at least 90%, at least 95%, at least 98%, at least 99%, or 100%, amino acid sequence identity to amino acids 116 to 209 of DPA1*02:01:01:01, SEQ ID NO:25; and can have a length of about 97 amino acids (e.g., 91, 92, 93, 94, 95, 96, or 97 amino acids).

DQA1 Polypeptides

In some cases, a suitable MHC class II α chain polypeptide is a DQA1 polypeptide. A DQA1 polypeptide can have at least 60%, at least 70%, at least 80%, at least 90%, at least 95%, at least 98%, at least 99%, or 100%, amino acid sequence identity with amino acids 24-204 of any of the DQA1 amino acid sequences depicted in FIG. 10. In some cases, the DQA1 polypeptide has a length of about 181 amino acids (e.g., 177, 178, 179, 180, 181, 182, or 183 amino acids). In an embodiment, a DQA1α chain polypeptide can have at least 60%, at least 70%, at least 80%, at least 90%, at least 95%, at least 98%, at least 99%, or 100%, amino acid sequence identity with amino acids 30-227 of the DQA1*01:01α chain amino acid in FIG. 10, ImMunoGeneTics ("IMGT")/HLA Acc No:HLA00601. In an embodiment, a DQA1α chain polypeptide can have at least 60%, at least 70%, at least 80%, at least 90%, at least 95%, at least 98%, at least 99%, or 100%, amino acid sequence identity with amino acids 30-227 of the DQA1*03:01: α chain amino acid in FIG. 10, IMGT/HLA Acc No:HLA00609. In an embodiment, a DQA1α chain polypeptide can have at least 60%, at least 70%, at least 80%, at least 90%, at least 95%, at least 98%, at least 99%, or 100%, amino acid sequence identity with amino acids 30-227 of the DQA1*04:01α chain amino acid in FIG. 10, IMGT/HLA Acc No:HLA00612. In an embodiment, a DQA1α chain polypeptide can have at least 60%, at least 70%, at least 80%, at least 90%, at least 95%, at least 98%, at least 99%, or 100%, amino acid sequence identity with amino acids 30-227 of the DQA1*05:01α chain amino acid in FIG. 10, IMGT/HLA Acc No:HLA00613. In some cases, a DQA polypeptide suitable for inclusion in a TMMP of the present disclosure comprises an amino acid substitution, relative to a wild-type DQA polypeptide, where the amino acid substitution replaces an amino acid (other than a Cys) with a Cys.

A "DQA1 polypeptide" includes allelic variants, e.g., naturally occurring allelic variants. Thus, in some cases, a suitable DQA1 polypeptide comprises the following amino acid sequence: EDIVADH VASCGVNLYQ FYGPSGQYTH EFDGDEQFYV DLERKETAWR WPEFSKFGGF DPQGALRNMA VAKHNLNIMI KRYNSTAATN EVPEVTVFSK SPVTLGQPNT LICLVDNIFP PVVNITWLSN GQSVTEGVSE TSFLSKSDHS FFKISYLTFL PSADEIYDCK VEHWGLDQPL LKHW (SEQ ID NO:26), or an allelic variant thereof. In some cases, a DQA polypeptide suitable for inclusion in a TMMP of the present disclosure comprises an amino acid substitution, relative to a wild-type DQA polypeptide, where the amino acid substitution replaces an amino acid (other than a Cys) with a Cys.

A suitable DQA1α1 domain comprises an amino acid sequence having at least 60%, at least 70%, at least 80%, at least 90%, at least 95%, at least 98%, at least 99%, or 100%, amino acid sequence identity to the following amino acid sequence: EDIVADH VASCGVNLYQ FYGPSGQYTH EFDGDEQFYV DLERKETAWR WPEFSKFGGF DPQGALRNMA VAKHNLNIMI KRYNSTAATN (SEQ ID NO:27); and can have a length of about 87 amino acids (e.g., 84, 85, 86, 87, 88, or 89 amino acids). A suitable DQA1α1 domain can comprise the following amino acid sequence: EDIVADH VASCGVNLYQ FYGPSGQYTH EFDGDEQFYV DLERKETAWR WPEFSKFGGF DPQGALRNMA VAKHNLNIMI KRYNSTAATN (SEQ ID NO:28), or a naturally-occurring allelic variant.

A suitable DQA1α2 domain comprises an amino acid sequence having at least 60%, at least 70%, at least 80%, at least 90%, at least 95%, at least 98%, at least 99%, or 100%, amino acid sequence identity to the following amino acid sequence: EVPEVTVFSK SPVTLGQPNT LICLVDNIFP PVVNITWLSN GQSVTEGVSE TSFLSKSDHS FFKISYLTFL PSADEIYDCK VEHWGLDQPL LKHW (SEQ ID NO:29); and can have a length of about 94 amino acids (e.g., 91, 92, 93, 94, 95, 96, or 97 amino acids). A suitable DQA1α2 domain can comprise the following amino acid sequence: EVPEVTVFSK SPVTLGQPNT LICLVDNIFP PVVNITWLSN GQSVTEGVSE TSFLSKSDHS FFKISYLTFL PSADEIYDCK VEHWGLDQPL LKHW (SEQ ID NO:29), or a naturally-occurring allelic variant thereof.

MHC Class II Beta Chains

MHC class II beta chains comprise a β1 domain and a β2 domain. In some cases, the β1 domain and the β2 domain present in an antigen-presenting cell are from the same MHC class II β chain polypeptide. In some cases, the β1 domain and the β2 domain present in an antigen-presenting cell are from two different MHC class II β chain polypeptides. In some cases, MHC class II β chain polypeptide suitable for inclusion in a TMMP of the present disclosure comprises an amino acid substitution, relative to a wild-type MHC class II β chain polypeptide, where the amino acid substitution replaces an amino acid (other than a Cys) with a Cys.

MHC class II beta chains suitable for inclusion in a TMMP of the present disclosure lack a signal peptide. An MHC class II beta chain suitable for inclusion in a TMMP of the present disclosure can have a length of from about 60 amino acids to about 210 amino acids; for example, an MHC class II beta chain suitable for inclusion in a TMMP of the present disclosure can have a length of from about 60 amino acids to about 80 amino acids, from about 80 amino acids to about 100 amino acids, from about 100 amino acids to about 120 amino acids, from about 120 amino acids to about 140 amino acids, from about 140 amino acids to about 160 amino acids, from about 160 amino acids to about 180 amino acids, from about 180 amino acids to about 200 amino acids, or from about 200 amino acids to about 210 amino acids. An MHC class II β1 domain suitable for inclusion in a TMMP of the present disclosure can have a length of from about 30 amino acids to about 105 amino acids; for example, an MHC class II β1 domain suitable for inclusion in a TMMP of the present disclosure can have a length of from about 30 amino acids to about 40 amino acids, from about 40 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, from about 90 amino acids to about 95 amino acids, from about 95 amino acids to about 100 amino acids, or from about 100 amino acids to about 105 amino acids. An MHC class II β2 domain suitable for inclusion in a TMMP of the present disclosure can have a length of from about 30 amino acids to about 105 amino acids; for example, an MHC class II β2 domain suitable for inclusion in a TMMP of the present disclosure can have a length of from about 30 amino acids to about 40 amino acids, from about 40 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, from about 90 amino acids to about 95 amino acids, from about 95 amino acids to about 100 amino acids, or from about 100 amino acids to about 105 amino acids.

In some cases, the MHC class IIβ chain polypeptide is a variant DRB MHC class II polypeptide that comprises a non-naturally occurring Cys residue. For example, in some cases, the MHC class II β chain polypeptide is a variant DRB1 MHC class II polypeptide that comprises an amino acid substitution selected from the group consisting of P5C, F7C, Q10C, N19C, G20C, H33C, G151C, D152C, and W153C. In some cases, the MHC class II β chain polypeptide is a variant DRB1 polypeptide comprising an amino acid sequence having at least 60%, at least 70%, at least 80%, at least 90%, at least 95%, at least 98%, or at least 99%, amino acid sequence identity to the following DRB1 amino acid sequence: GDTRPRFLEQVKHECHFFNGTERVRFLDRYFYHQEEYVRFDSDVGEYRAVTELGRPDAEYWNSQKDLLEQKRAAVDTYCRHNYGVGESFTVQRRVYPEVTVYPAKTQPLQHHNLLVCSVNGFYPASIEVRWFRNGQEEKTGVVSTGLIQNGDWTFQTLVMLETVPRSGEVYTCQVEHPSLTSPLTVEWR ARSESAQSKM (SEQ ID NO:30), and comprising an amino acid substitution selected from the group consisting of P5C, F7C, Q10C, N19C, G20C, H33C, G151C, D152C, and W153C. In some cases, the MHC class II β chain polypeptide is a variant DRB3 polypeptide, a variant DRB4 polypeptide, or a variant DRB5 polypeptide comprising an amino acid substitution corresponding to any of the foregoing amino acid substitutions in a variant DRB 1 polypeptide. For example, as depicted in FIG. 7B: i) an amino acid corresponding to P5 of DRB 1 would be P5 of a mature DRB3 polypeptide (lacking the N-terminal signal peptide MVCLKLPGGSSLAALTVTLMVLSSRLAFA (SEQ ID NO:31)); ii) an amino acid corresponding to F7 of DRB 1 would be F7 of a mature DRB 3 polypeptide; iii) an amino acid corresponding to Q10 of DRB 1 would be L10 of a mature DRB3 polypeptide; iv) an amino acid corresponding to N19 of DRB 1 would be N19 of a mature DRB3 polypeptide; v) an amino acid corresponding to G20 of DRB 1 would be G20 of a mature DRB3 polypeptide; vi) an amino acid corresponding to H33 of DRB 1 would be N33 of a mature DRB3 polypeptide; vii) an amino acid corresponding to G151 of DRB 1 would be G151 of a mature DRB3 polypeptide; viii) an amino acid corresponding to D152 of DRB 1 would be D152 of a mature DRB3 polypeptide; and ix) an amino acid corresponding to W153 of DRB 1 would be W153 of a mature DRB3 polypeptide. As another example, as depicted in FIG. 7C, i) an amino acid corresponding to P5 of DRB1 would be P15 of a mature DRB4 polypeptide (lacking the N-terminal signal peptide MVCLKLPGGSCMAALTVTL (SEQ ID NO:32)); ii) an amino acid corresponding to F7 of DRB 1 would be F17 of a mature DRB4 polypeptide; iii) an amino acid corresponding to Q10 of DRB 1 would be Q20 of a mature DRB4 polypeptide; iv) an amino acid corresponding to N19 of DRB 1 would be N29 of a mature DRB4 polypeptide; v) an amino acid corresponding to G20 of DRB 1 would be G30 of a mature DRB4 polypeptide; vi) an amino acid corresponding to H33 of DRB 1 would be N43 of a mature DRB4 polypeptide; vii) an amino acid corresponding to G151 of DRB 1 would be G161 of a mature DRB4 polypeptide; viii) an amino acid corresponding to D152 of DRB 1 would be D162 of a mature DRB4 polypeptide; and ix) an amino acid corresponding to W153 of DRB 1 would be W153 of a mature DRB4 polypeptide. As another example, as depicted in FIG. 7D, i) an amino acid corresponding to P5 of DRB 1 would be P15 of a mature DRB5 polypeptide (lacking the N-terminal signal peptide MVCLKLPGGSYMAKLTVTL (SEQ ID NO:33)); ii) an amino acid corresponding to F7 of DRB 1 would be F17 of a mature DRB5 polypeptide; iii) an amino acid corresponding to Q10 of DRB 1 would be Q20 of a mature DRB5 polypeptide; iv) an amino acid corresponding to N19 of DRB 1 would be N29 of a mature DRB5 polypeptide; v) an amino acid corresponding to G20 of DRB 1 would be G30 of a mature DRB5 polypeptide; vi) an amino acid corresponding to H33 of DRB 1 would be N43 of a mature DRB5 polypeptide; vii) an amino acid corresponding to G151 of DRB 1 would be G161 of a mature DRB5 polypeptide; viii) an amino acid corresponding to D152 of DRB 1 would be D162 of a mature DRB5 polypeptide; and ix) an amino acid corresponding to W153 of DRB 1 would be W163 of a mature DRB5 polypeptide.

DRB1 Polypeptides

In some cases, a suitable MHC class II β chain polypeptide is a DRB1 polypeptide. In an embodiment, a DRB1 polypeptide can have at least 60%, at least 70%, at least 80%, at least 90%, at least 95%, at least 98%, at least 99%, or 100%, amino acid sequence identity with amino acids 30-227 of any DRB 1 amino acid sequence depicted in FIG. 7, which displays the DRB 1 precursor proteins in which amino acids 1-29 are the signal sequence, 30-124 form the 131 region, 125-227 form the 132 region, and 228-250 form the transmembrane region. In some cases, a DRB 1 polypeptide suitable for inclusion in a TMMP of the present disclosure comprises an amino acid substitution, relative to a wild-type DRB 1 polypeptide, where the amino acid substitution replaces an amino acid (other than a Cys) with a Cys.

In an embodiment, a DRB 1β chain polypeptide can have at least 60%, at least 70%, at least 80%, at least 90%, at least 95%, at least 98%, at least 99%, or 100%, amino acid sequence identity with amino acids 30-227 of the DRB1-3 (DRB1*03:01) beta chain amino acid sequence sp P01912.2 in FIG. 7. In an embodiment, a DRB 1β chain polypeptide can have at least 60%, at least 70%, at least 80%, at least 90%, at least 95%, at least 98%, at least 99%, or 100%, amino acid sequence identity with amino acids 30-227 of the DRB 1-4 (DRB 1*04:01) beta chain amino acid sequence sp P13760.1 in FIG. 7. In an embodiment, a DRB 1β chain polypeptide can have at least 60%, at least 70%, at least 80%, at least 90%, at least 95%, at least 98%, at least 99%, or 100%, amino acid sequence identity with amino acids 30-227 of the DRB1-8 (DRB1*08:01) beta chain amino acid sequence sp Q30134.2 in FIG. 7. In an embodiment, a DRB 1β chain polypeptide can have at least 60%, at least 70%, at least 80%, at least 90%, at least 95%, at least 98%, at least 99%, or 100%, amino acid sequence identity with amino acids 30-227 of the DRB 1-9 (DRB 1*09:01) beta chain amino acid sequence sp Q9TQE0.1 in FIG. 7. In an embodiment, a DRB1β chain polypeptide can have at least 60%, at least 70%, at least 80%, at least 90%, at least 95%, at least 98%, at least 99%, or 100%, amino acid sequence identity with amino acids 30-227 of the DRB1-16 (DRB1*16:01) beta chain amino acid sequence sp Q29974.1 (also HLA00876) in FIG. 7. In some cases, the DRB1β chain polypeptide has a length of about 198 amino acids (e.g., 195, 196, 197, 198, 199, 200, 201, or 202 amino acids).

A "DRB 1 polypeptide" includes allelic variants, e.g., naturally occurring allelic variants. Thus, in some cases, a suitable DRB 1 polypeptide comprises the following amino acid sequence: DTRPRFLEQVKHECHFFNGTERVRFLD-RYFYHQEEYVRFDSDVGEYRAVTELGRP-DAEYWNSQ KDLLEQKRAAVDTYCRHNYGVGESFTV QRRVYPE-VTVYPAKTQPLQHHNLLVCS VNGFYPGSI EVRWFRNGQEEKTGVVSTGLIQNGDWTFQTLVM-LETVPRSGEVYTCQVEHPSLTSPLTVEWRA RSESAQSK (SEQ ID NO:34) (amino acids 31-227 of DRB1-4, see FIG. 7), or an allelic variant thereof.

A suitable DRB 1 polypeptide can comprise an amino acid sequence having at least 60%, at least 70%, at least 80%, at least 90%, at least 95%, at least 98%, at least 99%, or 100%, amino acid sequence identity to the following amino acid sequence: GDTR-PRFLEQVKHECHFFNGTERVRFLD-RYFYHQEEYVRFDSDVGEYRAVTELGRPDAEYWNS QKDLLEQKRAAVDTYCRHNYGVGESFTVQRRVYPE-VTVYPAKTQPLQHHNLLVCSVNGFYPA SIEVRWFRNGQEEKTGVVSTGLIQNGDWTFQTLVM-LETVPRSGEVYTCQVEHPSLTSPLTVEWR ARS-ESAQSKM (SEQ ID NO:30); and can have a length of from 195 to 205 amino acids, e.g., 199 amino acids.

A suitable DRB 1 polypeptide can comprise the following amino acid sequence: GDTR-CRFLEQVKHECHFFNGTERVRFLD-RYFYHQEEYVRFDSDVGEYRAVTELGRPDAEYWNS QKDLLEQKRAAVDTYCRHNYGVGESFTVQRRVYPE-VTVYPAKTQPLQHHNLLVCSVNGFYPA SIEVRWFRNGQEEKTGVVSTGLIQNGDWTFQTLVM-LETVPRSGEVYTCQVEHPSLTSPLTVEWR ARS-ESAQSKM (SEQ ID NO:35), where P5 is substituted with a Cys (shown in bold text).

A suitable DRB 1 polypeptide can comprise the following amino acid sequence: GDTR-PRFLEQVKHECHFFNGTERVRFLD-RYFYHQEEYVRFDSDVGEYRAVTELGRPDAEYWNS QKDLLEQKRAAVDTYCRHNYGVGESFTVQRRVYPE-VTVYPAKTQPLQHHNLLVCSVNGFYPA SIEVRWFRNGQEEKTGVVSTGLIQNCDWTFQTLVM-LETVPRSGEVYTCQVEHPSLTSPLTVEWR ARS-ESAQSKM (SEQ ID NO:36), where G151 is substituted with a Cys (shown in bold text).

A suitable DRB 1 polypeptide can comprise the following amino acid sequence: GDTR-PRFLEQVKHECHFFNGTERVRFLD-RYFYHQEEYVRFDSDVGEYRAVTELGRPDAEYWNS QKDLLEQKRAAVDTYCRHNYGVGESFTVQRRVYPE-VTVYPAKTQPLQHHNLLVCSVNGFYPA SIEVRWFRNGQEEKTGV VSTGLIQNGDCTFQTLVM-LETVPRSGEVYTCQVEHPSLTSPLTVEWR ARS-ESAQSKM (SEQ ID NO:37), where W153 is substituted with a Cys (shown in bold text).

A suitable DRB 1β1 domain comprises an amino acid sequence having at least 60%, at least 70%, at least 80%, at least 90%, at least 95%, at least 98%, at least 99%, or 100%, amino acid sequence identity to the following amino acid sequence: DTRPRFLEQVKHECHFFNGTERVRFLD-RYFYHQEEYVRFDSDVGEYRAVTELGRP-DAEYWNSQ KDLLEQKRAAVDTYCRHNYGVGESFTVQRRV (SEQ ID NO:38); and can have a length of about 95 amino acids (e.g., 92, 93, 94, 95, 96, 97, or 98 amino acids). A suitable DRB1β1 domain can comprise the following amino acid sequence: DTRPRFLEQVKHECHFFNGTERVRFLD-RYFYHQEEYVRFDSDVGEYRAVTELGRP-DAEYWNSQ KDLLEQKRAAVDTYCRHNYGVGESFTVQRRV (SEQ ID NO:38), or a naturally-occurring allelic variant. A suitable DRB1β1 domain can comprise the following amino acid sequence: GDTRC RFLEQVKHECHFFNGTERVRFL-DRYFYHQEEYVRFDSDVGEYRAVTELGRP-DAEYWNS QKDLLEQKRAAVDTYCRHNYGVGESFTVQRRV (SEQ ID NO:39), where P5 is substituted with a Cys (shown in bold text).

A suitable DRB 1β2 domain comprises an amino acid sequence having at least 60%, at least 70%, at least 80%, at least 90%, at least 95%, at least 98%, at least 99%, or 100%, amino acid sequence identity to the following amino acid sequence: YPEVTVYPAKTQPLQHHNLL-VCSVNGFYPGSIEVRWFRNGQEEKTGVVSTGLIQNG DWTFQTL VMLETVPRSGEVYTCQVEHPSLTSPLTVE-WRARSESAQSK (SEQ ID NO:40); and can have a length of about 103 amino acids (e.g., 100, 101, 102, 103, 104, 105, or 106 amino acids). A suitable DRB 1β2 domain can comprise the following amino acid sequence: YPE-VTVYPAKTQPLQHHNLL-VCSVNGFYPGSIEVRWFRNGQEEKTGVVSTGLIQNG DWTFQTL VMLETVPRSGEVYTCQVEHPSLTSPLTVE-WRARSESAQSK (SEQ ID NO:40), or a naturally-occurring allelic variant thereof. A suitable DRB 1β2 domain can comprise the following amino acid sequence: YPE-VTVYPAKTQPLQHHNLL-VCSVNGFYPASIEVRWFRNGQEEKTGVVSTGLIQNCDWTFQTL VMLETVPRSGEVYTCQVEHPSLTSPLTVE-WRARSESAQSKM (SEQ ID NO:41), where G151 is substituted with a Cys (shown in bold text). A suitable DRB 1β2 domain can comprise the following amino acid sequence: YPEVTVYPAKTQPLQHHNLL-VCSVNGFYPASIEVRWFRNGQEEKTGV VSTGLIQNGDCTFQTLV MLETVPRS-GEVYTCQVEHPSLTSPLTVEWRARSESAQSKM (SEQ ID NO:42), where W153 is substituted with a Cys (shown in bold text).

DRB3 Polypeptides

In some cases, a suitable MHC class II β chain polypeptide is a DRB3 polypeptide. In an embodiment, a DRB3 polypeptide can have at least 60%, at least 70%, at least 80%, at least 90%, at least 95%, at least 98%, at least 99%, or 100%, amino acid sequence identity with amino acids 30-227 of any DRB3 amino acid sequence depicted in FIG. 7B, which displays the DRB3 precursor proteins in which amino acids 1-29 are the signal sequence (underlined), 30-124 form the β1 region (shown bolded), 125-227 for the β2 region, and 228-250 the transmembrane region. In an embodiment, a DRB3β chain polypeptide can have at least 60%, at least 70%, at least 80%, at least 90%, at least 95%, at least 98%, at least 99%, or 100%, amino acid sequence identity with amino acids 30-227 of the DRB1-3 (DRB3*01:01) beta chain amino acid sequence GenBank NP_072049.1 in FIG. 7B. In an embodiment, a DRB3β chain polypeptide can have at least 60%, at least 70%, at least 80%, at least 90%, at least 95%, at least 98%, at least 99%, or 100%, amino acid sequence identity with amino acids 30-227 of the DRB1-3 beta chain amino acid sequence in GenBank accession EAX03632.1 in FIG. 7B. In an embodiment, a DRB3β chain polypeptide can have at least 60%, at least 70%, at least 80%, at least 90%, at least 95%, at least 98%, at least 99%, or 100%, amino acid sequence identity with amino acids 30-227 of the DRB1-3 (DRB3*02:01) beta chain amino acid sequence GenBank CAA23781.1 in FIG. 7B. In an embodiment, a DRB3β chain polypeptide can have at least 60%, at least 70%, at least 80%, at least 90%, at least 95%, at least 98%, at least 99%, or 100%, amino acid sequence identity with amino acids 30-227 of the DRB1-3 (DRB3*03:01) beta chain amino acid sequence GenBank AAN15205.1 in FIG. 7B. In some cases, a DRB3 polypeptide suitable for inclusion in a TMMP of the present disclosure comprises an amino acid substitution, relative to a wild-type DRB3 polypeptide, where the amino acid substitution replaces an amino acid (other than a Cys) with a Cys.

A "DRB3 polypeptide" includes allelic variants, e.g., naturally occurring allelic variants. Thus, in some cases, a suitable DRB3 polypeptide comprises the following amino acid sequence: DTRPRFLELR KSECHFFNGT ERVRYL-DRYF HNQEEFLRFD SDVGEYRAVT ELGRPVAESW NSQKDLLEQK RGRVDNYCRH NYGVGESFTV QRRVHPQVTV YPAKTQPLQH HNLLVCSVSG FYPGSIEVRW FRNGQEEKAG VVSTGLIQNG DWTFQTLVML ETVPRSGEVY TCQVEHPSVT SALTVEWRAR SESAQSK (SEQ ID NO:43), or an allelic variant thereof. In some cases, a DRB3 polypeptide suitable for inclusion in a TMMP of the present disclosure comprises an amino acid substitution, relative to a wild-type DRB3 polypeptide, where the amino acid substitution replaces an amino acid (other than a Cys) with a Cys. Thus, e.g., in some cases, the MHC class II β chain polypeptide is a variant DRB3 MHC class II polypeptide that comprises a non-naturally occurring Cys residue; e.g., where the variant DRB3 MHC class II polypeptide comprises an amino acid substitution selected from the group consisting of P5C, F7C, L10C, N19C, G20C, N33C, G151C, D152C, and W153C (of a mature DRB3 polypeptide (lacking the N-terminal signal peptide MVCLKLPGGSSLAALTVTLMVLSSR-LAFA (SEQ ID NO:31) depicted in FIG. 7B).

A suitable DRB3β1 domain comprises an amino acid sequence having at least 60%, at least 70%, at least 80%, at least 90%, at least 95%, at least 98%, at least 99%, or 100%, amino acid sequence identity to the following amino acid sequence: DTRPRFLELR KSECHFFNGT ERVRYLDRYF HNQEEFLRFD SDVGEYRAVT ELGRPVAESW NSQKDLLEQK RGRVDNYCRH NYGVGESFTV QRRV (SEQ ID NO:44); and can have a length of about 95 amino acids (e.g., 93, 94, 95, 96, 97, or 98 amino acids). A suitable DRB3β1 domain can comprise the following amino acid sequence: DTRPRFLELR KSECHFFNGT ERVRYLDRYF HNQEEFLRFD SDVGEYRAVT ELGRPVAESW NSQKDLLEQK RGRVDNYCRH NYGVGESFTV QRRV (SEQ ID NO:44), or a naturally-occurring allelic variant.

A suitable DRB3β2 domain comprises an amino acid sequence having at least 60%, at least 70%, at least 80%, at least 90%, at least 95%, at least 98%, at least 99%, or 100%, amino acid sequence identity to the following amino acid sequence: HPQVTV YPAKTQPLQH HNLLVCSVSG FYPGSIEVRW FRNGQEEKAG VVSTGLIQNG DWTFQTLVML ETVPRSGEVY TCQVEHPSVT SALTVEWRAR SESAQSK (SEQ ID NO:45); and can have a length of about 103 amino acids (e.g., 100, 101, 102, 103, 104, or 105 amino acids). A suitable DRB3β2 domain can comprise the following amino acid sequence: HPQVTV YPAKTQPLQH HNLLVCSVSG FYPGSIEVRW FRNGQEEKAG VVSTGLIQNG DWTFQTLVML ETVPRSGEVY TCQVEHPSVT SALTVEWRAR SES-AQSK (SEQ ID NO:45), or a naturally-occurring allelic variant thereof.

DRB4 Polypeptides

In some cases, a suitable MHC class II β chain polypeptide is a DRB4 polypeptide. A DRB4 polypeptide can have at least 60%, at least 70%, at least 80%, at least 90%, at least 95%, at least 98%, at least 99%, or 100%, amino acid sequence identity with amino acids 30-227 of the DRB4 amino acid sequence depicted in FIG. 7C. In some cases, the DRB4 polypeptide has a length of about 198 amino acids (e.g., 195, 196, 197, 198, 199, 200, 201, or 202 amino acids). In some cases, a DRB4 polypeptide suitable for inclusion in a TMMP of the present disclosure comprises an amino acid substitution, relative to a wild-type DRB4 polypeptide, where the amino acid substitution replaces an amino acid (other than a Cys) with a Cys.

A "DRB4 polypeptide" includes allelic variants, e.g., naturally occurring allelic variants. Thus, in some cases, a suitable DRB4 polypeptide comprises the following amino acid sequence: T VLSSPLALAG DTQPRFLEQA KCECHFLNGT ERVWNLIRYI YNQEEYARYN SDLGEYQAVT ELGRPDAEYW NSQKDLLERR RAEVDTYCRY NYGVVESFTV QRRVQPKVTV YPSKTQPLQH HNLLVCSVNG FYPGSIEVRW FRNGQEEKAG VVSTGLIQNG DWTFQTLVML ETVPRSGEVY TCQVEHPSMM SPLTVQWSAR SES-AQSK (SEQ ID NO:46), or an allelic variant thereof. In some cases, a DRB4 polypeptide suitable for inclusion in a TMMP of the present disclosure comprises an amino acid substitution, relative to a wild-type DRB4 polypeptide, where the amino acid substitution replaces an amino acid (other than a Cys) with a Cys. Thus, e.g., in some cases, the MHC class 110 chain polypeptide is a variant DRB4 MHC class II polypeptide that comprises a non-naturally occurring Cys residue; e.g., where the variant DRB4 MHC class II polypeptide comprises an amino acid substitution selected from the group consisting of P15C, F17C, Q20C, N29C, G30C, N43C, G161C, D162C, and W163C (of a mature DRB4 polypeptide (lacking the N-terminal signal peptide MVCLKLPGGSCMAALTVTL (SEQ ID NO:32) depicted in FIG. 7C).

A suitable DRB4β1 domain comprises an amino acid sequence having at least 60%, at least 70%, at least 80%, at least 90%, at least 95%, at least 98%, at least 99%, or 100%, amino acid sequence identity to the following amino acid sequence: T VLSSPLALAG DTQPRFLEQA KCECHFLNGT ERVWNLIRYI YNQEEYARYN SDLGEYQAVT ELGRPDAEYW NSQKDLLERR RAEVDTYCRY NYGVVESFTV QRRV (SEQ ID NO:47); and can have a length of about 95 amino acids (e.g., 93, 94, 95, 96, 97, or 98 amino acids). A suitable DRB4β1 domain can comprise the following amino acid sequence: T VLSSPLALAG DTQPRFLEQA KCECHFLNGT ERVWNLIRYI YNQEEYARYN SDLGEYQAVT ELGRPDAEYW NSQKDLLERR RAEVDTYCRY NYGVVESFTV QRRV (SEQ ID NO:47), or a naturally-occurring allelic variant.

A suitable DRB4β2 domain comprises an amino acid sequence having at least 60%, at least 70%, at least 80%, at least 90%, at least 95%, at least 98%, at least 99%, or 100%, amino acid sequence identity to the following amino acid sequence: QPKVTV YPSKTQPLQH HNLLVCSVNG FYPGSIEVRW FRNGQEEKAG VVSTGLIQNG DWTFQTLVML ETVPRSGEVY TCQVEHPSMM SPLTVQWSAR SESAQSK (SEQ ID NO:48); and can have a length of about 103 amino acids (e.g., 100, 101, 102, 103, 104, or 105 amino acids). A suitable DRB4β2 domain can comprise the following amino acid sequence: QPKVTV YPSKTQPLQH HNLLVCSVNG FYPGSIEVRW FRNGQEEKAG VVSTGLIQNG DWTFQTLVML ETVPRSGEVY TCQVEHPSMM SPLTVQWSAR SESAQSK (SEQ ID NO:48), or a naturally-occurring allelic variant thereof.

DRB5 Polypeptides

In some cases, a suitable MHC class II β chain polypeptide is a DRB5 polypeptide. A DRB5 polypeptide can have at least 60%, at least 70%, at least 80%, at least 90%, at least 95%, at least 98%, at least 99%, or 100%, amino acid sequence identity with amino acids 30-227 of the DRB5 amino acid sequence depicted in FIG. 7D. In some cases, the DRB5 polypeptide has a length of about 198 amino acids (e.g., 195, 196, 197, 198, 199, 200, 201, or 202 amino acids). In some cases, a DRB5 polypeptide suitable for inclusion in a TMMP of the present disclosure comprises an amino acid substitution, relative to a wild-type DRB5 polypeptide, where the amino acid substitution replaces an amino acid (other than a Cys) with a Cys.

A "DRB5 polypeptide" includes allelic variants, e.g., naturally occurring allelic variants. Thus, in some cases, a suitable DRB5 polypeptide comprises the following amino acid sequence: M VLSSPLALAG DTRPRFLQQD KYECHFFNGT ERVRFLHRDI YNQEEDLRFD SDVGEYRAVT ELGRPDAEYW NSQKDFLEDR RAAVDTYCRH NYGVGESFTV QRRVEPKVTV YPARTQTLQH HNLLVCSVNG FYPGSIEVRW FRNSQEEKAG VVSTGLIQNG DWTFQTLVML ETVPRSGEVY TCQVEHPSVT SPLTVEWRAQ SESAQS (SEQ ID NO:49), or an allelic variant thereof. In some cases, a DRB5 polypeptide suitable for inclusion in a TMMP of the present disclosure comprises an amino acid substitution, relative to a wild-type DRB5 polypeptide, where the amino acid substitution replaces an amino acid (other than a Cys) with a Cys.

Thus, e.g., in some cases, the MHC class II β chain polypeptide is a variant DRB5 MHC class II polypeptide that comprises a non-naturally occurring Cys residue; e.g., where the variant DRB5 MHC class II polypeptide comprises an amino acid substitution selected from the group consisting of P15C, F17C, Q20C, N29C, G30C, N43C, G161C, D162C, and W163C (of a mature DRB5 polypeptide (lacking the N-terminal signal peptide MVCLKLPGGSYMAKLTVTL (SEQ ID NO:33) depicted in FIG. 7D).

A suitable DRB5β1 domain comprises an amino acid sequence having at least 60%, at least 70%, at least 80%, at least 90%, at least 95%, at least 98%, at least 99%, or 100%, amino acid sequence identity to the following amino acid sequence: M VLSSPLALAG DTRPRFLQQD KYECHFFNGT ERVRFLHRDI YNQEEDLRFD SDVGEYRAVT ELGRPDAEYW NSQKDFLEDR RAAVDTYCRH NYGVGESFTV QRRV (SEQ ID NO:50); and can have a length of about 95 amino acids (e.g., 93, 94, 95, 96, 97, or 98 amino acids). A suitable DRB5β1 domain can comprise the following amino acid sequence: M VLSSPLALAG DTRPRFLQQD KYECHFFNGT ERVRFLHRDI YNQEEDLRFD SDVGEYRAVT ELGRPDAEYW NSQKDFLEDR RAAVDTYCRH NYGVGESFTV QRRV (SEQ ID NO:50), or a naturally-occurring allelic variant.

A suitable DRB5β2 domain comprises an amino acid sequence having at least 60%, at least 70%, at least 80%, at least 90%, at least 95%, at least 98%, at least 99%, or 100%, amino acid sequence identity to the following amino acid sequence: EPKVTV YPARTQTLQH HNLLVCSVNG FYPGSIEVRW FRNSQEEKAG VVSTGLIQNG DWTFQTLVML ETVPRSGEVY TCQVEHPSVT SPLTVEWRAQ SESAQS (SEQ ID NO:51); and can have a length of about 103 amino acids (e.g., 100, 101, 102, 103, 104, or 105 amino acids). A suitable DRB5β2 domain can comprise the following amino acid sequence: EPKVTV YPARTQTLQH HNLLVCSVNG FYPGSIEVRW FRNSQEEKAG VVSTGLIQNG DWTFQTLVML ETVPRSGEVY TCQVEHPSVT SPLTVEWRAQ SESAQS (SEQ ID NO:51), or a naturally-occurring allelic variant thereof.

DPB1 Polypeptides

In some cases, a suitable MHC class II β chain polypeptide is a DPB1 polypeptide. A DPB1 polypeptide can have at least 60%, at least 70%, at least 80%, at least 90%, at least 95%, at least 98%, at least 99%, or 100%, amino acid sequence identity with amino acids 30-215 of any of the DPB1 amino acid sequences depicted in FIG. 9. In some cases, the DPB 1 polypeptide has a length of about 186 amino acids (e.g., 184, 185, 186, 187, or 188 amino acids). In an embodiment, a DRB1β chain polypeptide can have at least 60%, at least 70%, at least 80%, at least 90%, at least 95%, at least 98%, at least 99%, or 100%, amino acid sequence identity with amino acids 30-227 of the DPB1*02:02β chain amino acid sequence in FIG. 9, IMGT/HLA Acc No. HLA00519. In an embodiment, a DPB1 DRB3β chain polypeptide can have at least 60%, at least 70%, at least 80%, at least 90%, at least 95%, at least 98%, at least 99%, or 100%, amino acid sequence identity with amino acids 30-227 of the DPB 1*03:01β chain amino acid sequence in FIG. 9, IMGT/HLA Acc No.:HLA00520.

A "DPB 1 polypeptide" includes allelic variants, e.g., naturally occurring allelic variants. Thus, in some cases, a suitable DPB 1 polypeptide comprises the following amino acid sequence: R ATPENYLFQG RQECYAFNGT QRFLE- RYIYN REEFARFDSD VGEFRAVTEL GRPAAEYWNS QKDILEEKRA VPDRMCRHNY ELGGPMTLQR RVQPRVNVSP SKKGPLQHHN LLVCHVTDFY PGSIQVRWFL NGQEETAGVV STNLIRNGDW TFQIL-VMLEM TPQQGDVYTC QVEHTSLDSP VTVEW (SEQ ID NO:52), or an allelic variant thereof. In some cases, a DPB 1 polypeptide suitable for inclusion in a TMMP of the present disclosure comprises an amino acid substitution, relative to a wild-type DPB 1 polypeptide, where the amino acid substitution replaces an amino acid (other than a Cys) with a Cys.

A suitable DPB 1β1 domain comprises an amino acid sequence having at least 60%, at least 70%, at least 80%, at least 90%, at least 95%, at least 98%, at least 99%, or 100%, amino acid sequence identity to the following amino acid sequence: R ATPENYLFQG RQECYAFNGT QRFLE-RYIYN REEFARFDSD VGEFRAVTEL GRPAAEYWNS QKDILEEKRA VPDRMCRHNY ELGGPMTLQR R (SEQ ID NO:53); and can have a length of about 92 amino acids (e.g., 90, 91, 92, 93, or 94 amino acids). A suitable DPB 1β1 domain can comprise the following amino acid sequence: R ATPENYLFQG RQECYAFNGT QRFLERYIYN REEFARFDSD VGEFRAVTEL GRPAAEYWNS QKDILEEKRA VPDRMCRHNY ELGGPMTLQR R (SEQ ID NO:53), or a naturally-occurring allelic variant.

A suitable DPB 1132 domain comprises an amino acid sequence having at least 60%, at least 70%, at least 80%, at least 90%, at least 95%, at least 98%, at least 99%, or 100%, amino acid sequence identity to the following amino acid sequence: VQPRVNVSP SKKGPLQHHN LLVCHVTDFY PGSIQVRWFL NGQEETAGVV STNLIRNGDW TFQIL-VMLEM TPQQGDVYTC QVEHTSLDSP VTVEW (SEQ ID NO:54); and can have a length of about 94 amino acids (e.g., 92, 93, 94, 95, 96, or 97 amino acids). A suitable DPB1β2 domain can comprise the following amino acid sequence: VQPRVNVSP SKKGPLQHHN LLVCHVTDFY PGSIQVRWFL NGQEETAGVV STNLIRNGDW TFQIL-VMLEM TPQQGDVYTC QVEHTSLDSP VTVEW (SEQ ID NO:54), or a naturally-occurring allelic variant thereof.

DQB1 Polypeptides

In some cases, a suitable MHC class II β chain polypeptide is a DQB 1 polypeptide. A DQB1 polypeptide can have at least 60%, at least 70%, at least 80%, at least 90%, at least 95%, at least 98%, at least 99%, or 100%, amino acid sequence identity with amino acids 33-220 of any one of the DQB1 amino acid sequences depicted in FIG. 11A-11B. In some cases, the DQB1 polypeptide has a length of about 188 amino acids (e.g., 186, 187, 188, 190, 191, or 192 amino acids). In some cases, a DQB 1 polypeptide suitable for inclusion in a TMMP of the present disclosure comprises an amino acid substitution, relative to a wild-type DQB 1 polypeptide, where the amino acid substitution replaces an amino acid (other than a Cys) with a Cys.

A "DQB 1 polypeptide" includes allelic variants, e.g., naturally occurring allelic variants. Thus, in some cases, a suitable DQB 1 polypeptide comprises the following amino acid sequence: RDSPEDFV FQFKGMCYFT NGTERVRLVT RYIYNREEYA RFDSDVGVYR AVTPQGRPDA EYWNSQKEVL EGTRAELDTV CRHNYEVAFR GILQRRVEPT VTISPSRTEA LNHHNLLVCS VTDFYPGQIK VRWFRNDQEE TAGVVSTPLI RNGDWTFQIL VMLEMTPQRG DVYTCHVEHP SLQSPITVEW (SEQ ID NO:55), or an allelic variant thereof. In some cases, a DQB 1 polypeptide suitable for inclusion in a TMMP of the present disclosure comprises an amino acid substitution, relative to a wild-type DQB 1 polypeptide, where the amino acid substitution replaces an amino acid (other than a Cys) with a Cys.

A suitable DQB1β1 domain comprises an amino acid sequence having at least 60%, at least 70%, at least 80%, at least 90%, at least 95%, at least 98%, at least 99%, or 100%, amino acid sequence identity to the following amino acid sequence: RDSPEDFV FQFKGMCYFT NGTERVRLVT RYIYNREEYA RFDSDVGVYR AVTPQGRPDA EYWNSQKEVL EGTRAELDTV CRHNYEVAFR GILQRR (SEQ ID NO:56); and can have a length of about 94 amino acids (e.g., 92, 93, 94, 95, or 96 amino acids). A suitable DQB 1β1 domain can comprise the following amino acid sequence: RDSPEDFV FQFKGMCYFT NGTERVRLVT RYIYNREEYA RFDSDVGVYR AVTPQGRPDA EYWNSQKEVL EGTRAELDTV CRHNYEVAFR GILQRR (SEQ ID NO:56), or a naturally-occurring allelic variant.

A suitable DQB1β2 domain comprises an amino acid sequence having at least 60%, at least 70%, at least 80%, at least 90%, at least 95%, at least 98%, at least 99%, or 100%, amino acid sequence identity to the following amino acid sequence: VEPT VTISPSRTEA LNHHNLLVCS VTDFYPGQIK VRWFRNDQEE TAGVVSTPLI RNGDWTFQIL VMLEMTPQRG DVYTCHVEHP SLQSPITVEW (SEQ ID NO:57); and can have a length of about 94 amino acids (e.g., 92, 93, 94, 95, or 96 amino acids). A suitable DQB 1132 domain can comprise the following amino acid sequence: VEPT VTISPSRTEA LNHHNLLVCS VTDFYPGQIK VRWFRNDQEE TAGVVSTPLI RNGDWTFQIL VMLEMTPQRG DVYTCHVEHP SLQSPITVEW (SEQ ID NO:57), or a naturally-occurring allelic variant thereof.

In an embodiment, a DQB β chain polypeptide can have at least 60%, at least 70%, at least 80%, at least 90%, at least 95%, at least 98%, at least 99%, or 100%, amino acid sequence identity with amino acids 30-227 of the DQB1*02:01 beta chain amino acid sequence in FIG. 11A-11B, IMGT/HLA Acc No: HLA00622.

In an embodiment, a DQB β chain polypeptide can have at least 60%, at least 70%, at least 80%, at least 90%, at least 95%, at least 98%, at least 99%, or 100%, amino acid sequence identity with amino acids 30-227 of the DQB1*03:02 beta chain amino acid sequence in FIG. 11A-11B, IMGT/HLA Acc No: HLA00627.

In an embodiment, a DQB β chain polypeptide can have at least 60%, at least 70%, at least 80%, at least 90%, at least 95%, at least 98%, at least 99%, or 100%, amino acid sequence identity with amino acids 30-227 of the DQB1*03:03 beta chain amino acid sequence in FIG. 11A-11B, IMGT/HLA Acc No: HLA00629.

In an embodiment, a DQB β chain polypeptide can have at least 60%, at least 70%, at least 80%, at least 90%, at least 95%, at least 98%, at least 99%, or 100%, amino acid sequence identity with amino acids 30-227 of the DQB1*05:01 beta chain amino acid sequence in FIG. 11A-11B, IMGT/HLA Acc No: HLA00638.

Disease Risk-Associated Alleles and Haplotypes

Certain alleles and haplotypes of MHC class II have been associated with disease, e.g., increased risk of developing a particular disease. See, e.g., Erlich et al. (2008) *Diabetes* 57:1084; Gough and Simmonds (2007) *Curr. Genomics* 8:453; Mitchell et al. (2007) *Robbins Basic Pathology* Philadelphia: Saunders, 8$^{th}$ ed.; Margaritte-Jeannin et al. (2004) *Tissue Antigens* 63:562; and Kurko et al. (2013) *Clin. Rev. Allergy Immunol.* 45:170.

MHC Class II Polypeptides in Type 1 Diabetes Mellitus (T1D)

Alleles/isoforms showing increased association with T1D represent suitable sources of MHC II α1, α2, β1, and β2 polypeptide sequences for incorporation into TMMPs directed to the treatment of T1D. T1D is associated with alleles belonging to the HLA-DR3 and HLA-DR4 haplotypes/serotypes, with the strongest risk associated with the HLA-DQ8, (e.g., HLA-DQB1*03:02) and alleles of the HLA-DQ2 serotype. Some high and moderate risk haplotypes and their association with various DR serotypes are shown in Table 1, below, which is adapted from Kantárova and Buc, *Physiol. Res.* 56: 255-266 (2007).

TABLE 1

| Haplotype | DRB allele | DQ serotype | DQA allele | DQB allele |
|---|---|---|---|---|
| High risk T1D haplotypes | | | | |
| DR3 | DRB1*0301 | DQ 2.5 | DQA1*0501 | DQB1*0201 |
| DR4 | DRB1*0401 | DQ 8.1 | DQA1*0301 | DQB1*0302 |
| DR4 | DRB1*0402 | DQ 8.1 | DQA1*0301 | DQB1*0302 |
| DR4 | DRB1*0405 | DQ 8.1 | DQA1*0301 | DQB1*0302 |
| Moderate risk T1D haplotypes | | | | |
| DR1 | DRB1*01 | DQ 5 | DQA1*0101 | DQB1*0501 |
| DR8 | DRB1*0801 | | DQA1*0401 | DQB1*0402 |
| DR9 | DRB1*0901 | | DQA1*0301 | DQB1*0303 |
| Recognized associations | | | | |
| | DPB allele | | | |
| | DPB1*02:02 | | | |
| | DPB1*03:01 | | | |

The stereotypically defined DR3 and DR4 protein isoforms/haplotypes of the DRB 1 gene are associated with increased risk that an individual expressing such alleles will develop T1D. The DR3 serotype includes the alleles encoding the DRB1*03:01,*03:02,*03:03, and*03:04 proteins, with the HLA-DRB 1*0301 allele often found associated with a predisposition to T1D. The DR4 serotype includes the alleles encoding the DRB 1*04:01,*04:02,*04:03,*04:04, *04:05,*04:06,*04:07,*04:08,*04:09, *04:10,*04:11,*04:12, and*04:13 proteins. Certain HLA-DR4 alleles (e.g., HLA-DRB1*0401, HLA-DRB 1*0402, and HLA-DRB 1*0405) predispose individuals to T1D, whereas HLA-DRB 1*04:03 allele/isoform may afford protection. DRB 1*16:01 also show an increased frequency in diabetic children relative to healthy controls (Deja, et al., *Mediators of Inflammation* 2006:1-7 (2006)).

While T1D is associated with DR3 and DR4 alleles as discussed above, among the strongest associated risk factors for T1D, the presence of alleles belonging to the HLA-DQ8 serotype (e.g., the HLA-DQB 1*03:02 isoform) and the HLA DQ2 serotype (e.g., HLA-DQB 1*0201). HLA-DQ8 T1D susceptible serotypes include the HLA-DQ8.1 serotype (HLA-DQA1*03:01/DQB1*03:02), The HLA-DQ2 serotype (HLA-DQB1*02) associated with T1D include DQB1*02:01). Jones, et al., *Nat. Rev. Immunol.* 2006, 6: 271-282. By contrast, individuals that carry the HLADQB1*0602 allele appear to be protected against type 1 diabetes. Id. DQ2 is most common in Western Europe, North Africa and East Africa, with the highest frequencies observed in parts of Spain and Ireland.

Figures 19A, 19B:
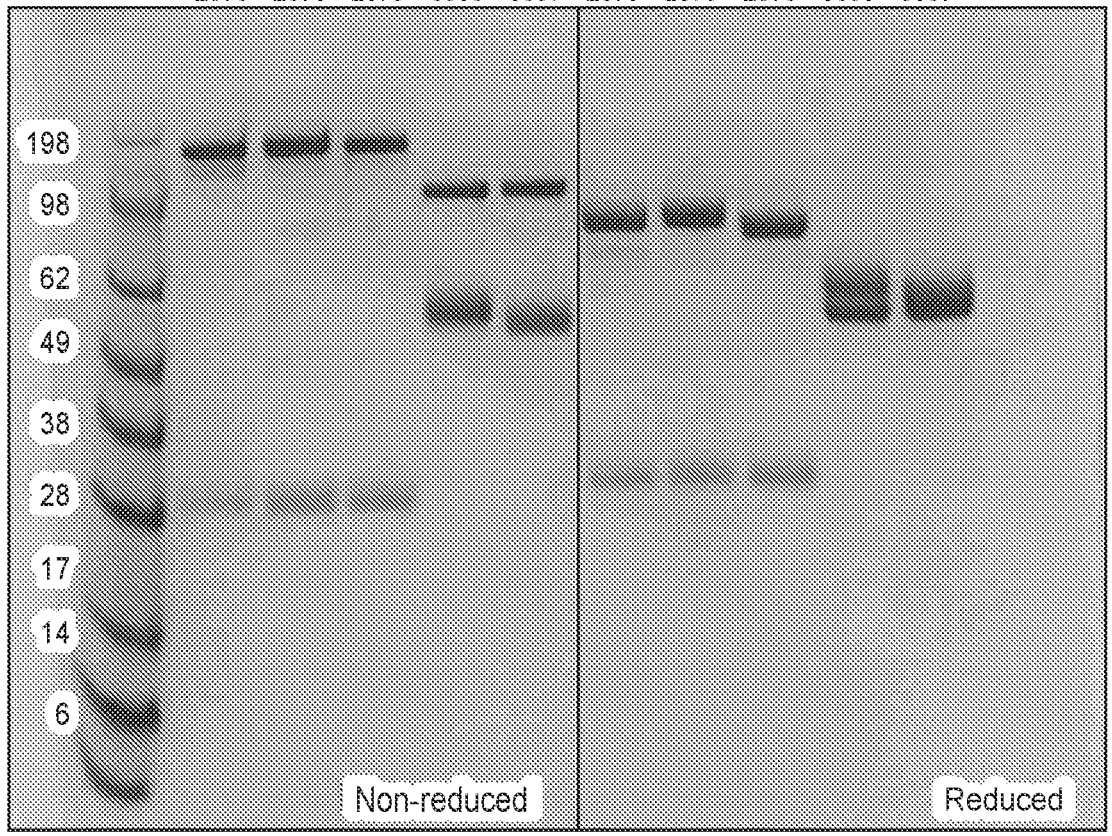
FIG. 19A-19D depict production and monomer formation of exemplary TMMPs.
Figure 19C:
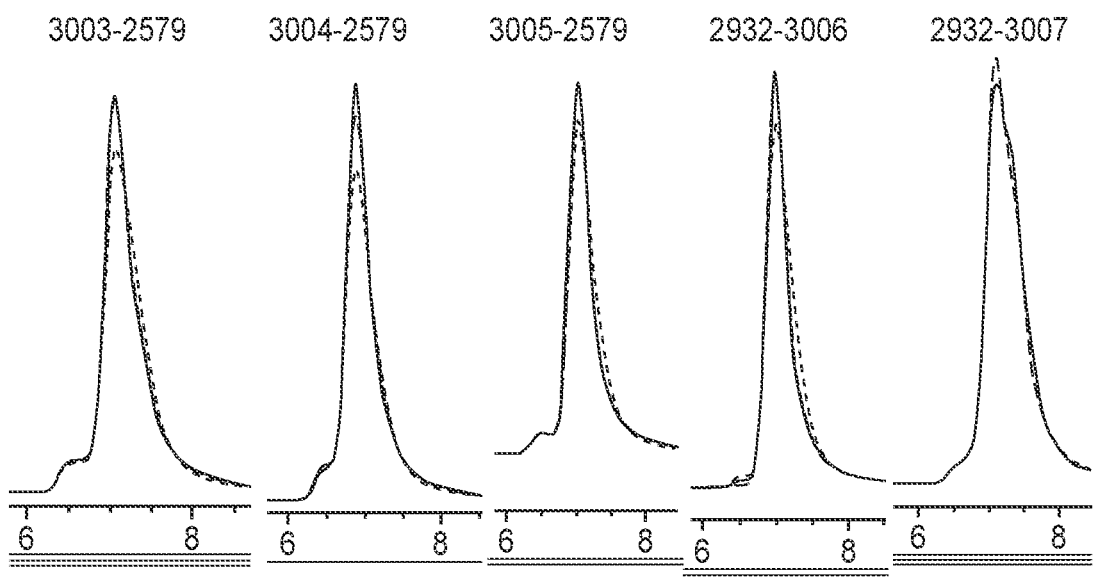

The DQB1 locus alone has also been reported to be associated with T1D when position 057 is a neutral residue such as Ala or Ser. Both the DQ2 and DQ8 serotypes, which are associated with T1D, lack an Asp at the 570 position, and instead have an Ala in its place (see e.g., Ala 89 in FIG. 19B HLA-DQB1*02:01 and FIG. 19C, HLA-DQB1*03:02 respectively) conferred T1D susceptibility. In contrast, DQB1*06:02, which has an Asp) at position 057 of DQB 1 (position 89 in FIG. 11A-11B) was found to be associated with resistance to T1D. Jones et al, Nat. Rev. Immunol. 2006, 6: 271-282. Position 057 of the molecule forms a critical residue in peptide binding pocket nine (P9) of the DQB 1, which is involved in antigen presentation and T cell receptor (TCR) interaction.

Individuals with the HLA haplotype DQA1*03:01-DRB 1*03:02, especially when combined with DQA1*05:01-DRB1*02:01, are highly susceptible (10-20-fold increase) to T1D, see Notkins, A. L., T. *Biol. Chem.*, 2002, 277(46): 43545-48. Among the stereotypically defined groups showing susceptibility to T1D are HLA-DR4.1 (HLA-DRA1*01:01/DRB1*04:01), HLA-DR4.5 (HLA-DRA1*01:01/DRB 1*04:05), HLA-DQ2.5 (HLA-DQA1*05:01/DQB1*02:01), and HLA-DQ8.1 (HLA-DQA1*03:01/DQB1*03:02). (see e.g., Jones et al., *Nat. Rev. Immunol.* 2006, 6: 271-282). The DRβ1*04:05-DQβ1*04:01/DRβ1*08:02-DQβ1*03:02 genotype has shown to be associated with acute-onset and slow progressive T1D. Fulminant diabetes has been associated with DR(31*04:05-DQ131*04:01/DRβ1*04:05-DQβ1*04:01 genotype, in a Japanese population study Kawabata, et al., *Diabetologia* 2009, 52:2513-21.

Although the HLA-DR associations with T1D are not as strong as those of HLA-DQ, insulin-reactive T cells derived from lymph nodes draining the pancreas of patients with T1D appear to be HLA-DR4.1 restricted rather than HLA-DQ8 or HLA-DQ2 restricted (Kent et al., *Nature* 2005 435: 224-228).

The above-mentioned alleles associated with an increased risk of T1D represent suitable candidates from which the α1, α2, β1, and/or 132 polypeptide sequences present in a TMMP of the present disclosure may be taken. In an embodiment, the TMMP is DQ2.5-like with the α1 and α2 polypeptides from DQA1*0501, and the 131 and β2 polypeptides taken from DQB1*0201. In an embodiment, the TMMP is DQ8.1-like with the α1 and α2 polypeptides from DQA1*0301, and the 131 and β2 polypeptides taken from DQB 1*0302.

Scaffold Polypeptides

A TMMP of the present disclosure, whether multimeric or monomeric, can comprise an immunoglobulin or non-immunoglobulin scaffold. A TMMP polypeptide of the present disclosure, whether multimeric or monomeric, can comprise an Fc polypeptide, or can comprise another suitable scaffold polypeptide.

Suitable scaffold polypeptides include antibody-based scaffold polypeptides and non-antibody-based scaffolds. Non-antibody-based scaffolds include, e.g., albumin, an XTEN (extended recombinant) polypeptide, transferrin, an Fc receptor polypeptide, an elastin-like polypeptide (see, e.g., Hassouneh et al. (2012) *Methods Enzymol.* 502:215; e.g., a polypeptide comprising a pentapeptide repeat unit of (Val-Pro-Gly-X-Gly; SEQ ID NO:236), where X is any amino acid other than proline), an albumin-binding polypeptide, a silk-like polypeptide (see, e.g., Valluzzi et al. (2002) *Philos Trans R Soc Lond B Biol Sci.* 357:165), a silk-elastin-like polypeptide (SELP; see, e.g., Megeed et al. (2002) *Adv Drug Deliv Rev.* 54:1075), and the like. Suitable XTEN polypeptides include, e.g., those disclosed in WO 2009/023270, WO 2010/091122, WO 2007/103515, US 2010/0189682, and US 2009/0092582; see also Schellenberger et al. (2009) *Nat Biotechnol.* 27:1186). Suitable albumin polypeptides include, e.g., human serum albumin.

Suitable scaffold polypeptides will in some cases be half-life extending polypeptides. Thus, in some cases, a suitable scaffold polypeptide increases the in vivo half-life (e.g., the serum half-life) of the multimeric polypeptide, compared to a control multimeric polypeptide lacking the scaffold polypeptide. For example, in some cases, a scaffold polypeptide increases the in vivo half-life (e.g., the serum half-life) of the multimeric polypeptide, compared to a control multimeric polypeptide lacking the scaffold polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. As an example, in some cases, an Fc polypeptide increases the in vivo half-life (e.g., the serum half-life) of the multimeric polypeptide, compared to a control multimeric polypeptide lacking the Fc polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold.

Fc Polypeptides

In some cases, the first or the second polypeptide chain of a TMMP of the present disclosure comprises an Fc polypeptide. The Fc polypeptide of a TMMP of the present disclosure can be a human IgG1 Fc, a human IgG2 Fc, a human IgG3 Fc, a human IgG4 Fc, etc. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIG. 12A-12G. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 12A. In some cases, the Fc region comprises an amino acid sequence having at least about 70%, at least about 75%, at least about 80%, at least about 85%, at least about 90%, at least about 95%, at least about 98%, or at least about 99%, amino acid sequence identity to the human IgG1 Fc polypeptide depicted in FIG. 12A, and comprises a substitution of N77; e.g., the Fc polypeptide comprises an N77A substitution.

In some cases, the Ig Fc polypeptide induces cell lysis through activation of complement-dependent cytotoxicity (CDC). In some cases, the Ig Fc polypeptide is a variant that substantially does not induce cell lysis through activation of CDC, e.g., an IgG1 Fc polypeptide comprising L234A and L235A substitutions (L14A and L15A substitution of the amino acid sequence depicted in FIG. 12A). Typically, the TMMPs of this disclosure that employ an Ig Fc polypeptide are meant to engage a target T cell through the MHC-epitope complex and then modulate the activity of a T cell through the immunomodulatory polypeptides, and thus will employ a variant that substantially does not induce cell lysis through activation of CDC.

In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 12A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 12A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 12A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 12A.

Figure 2A:
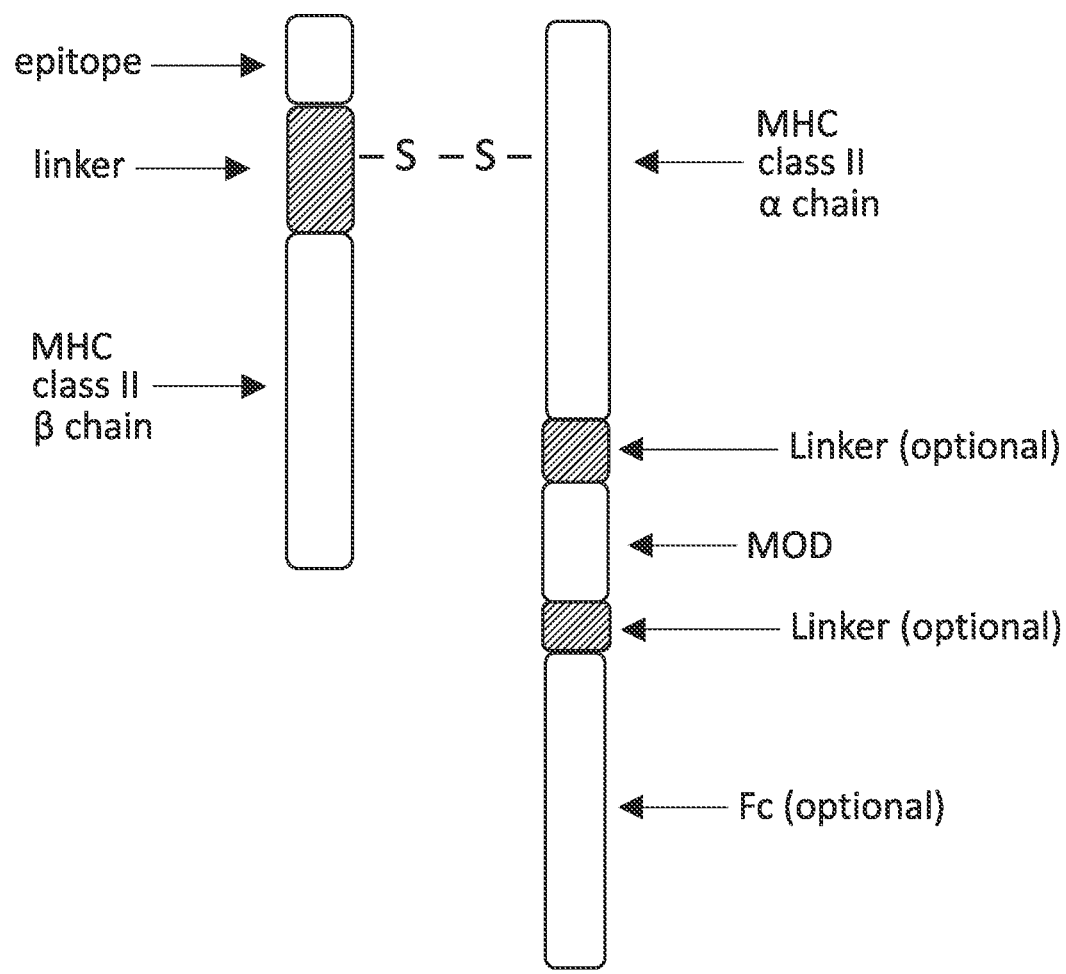
FIG. 2A-2D present schematic depictions of TMMPs of the present disclosure, in which the immunomodulatory polypeptide is in Position 2.
Figure 2B:
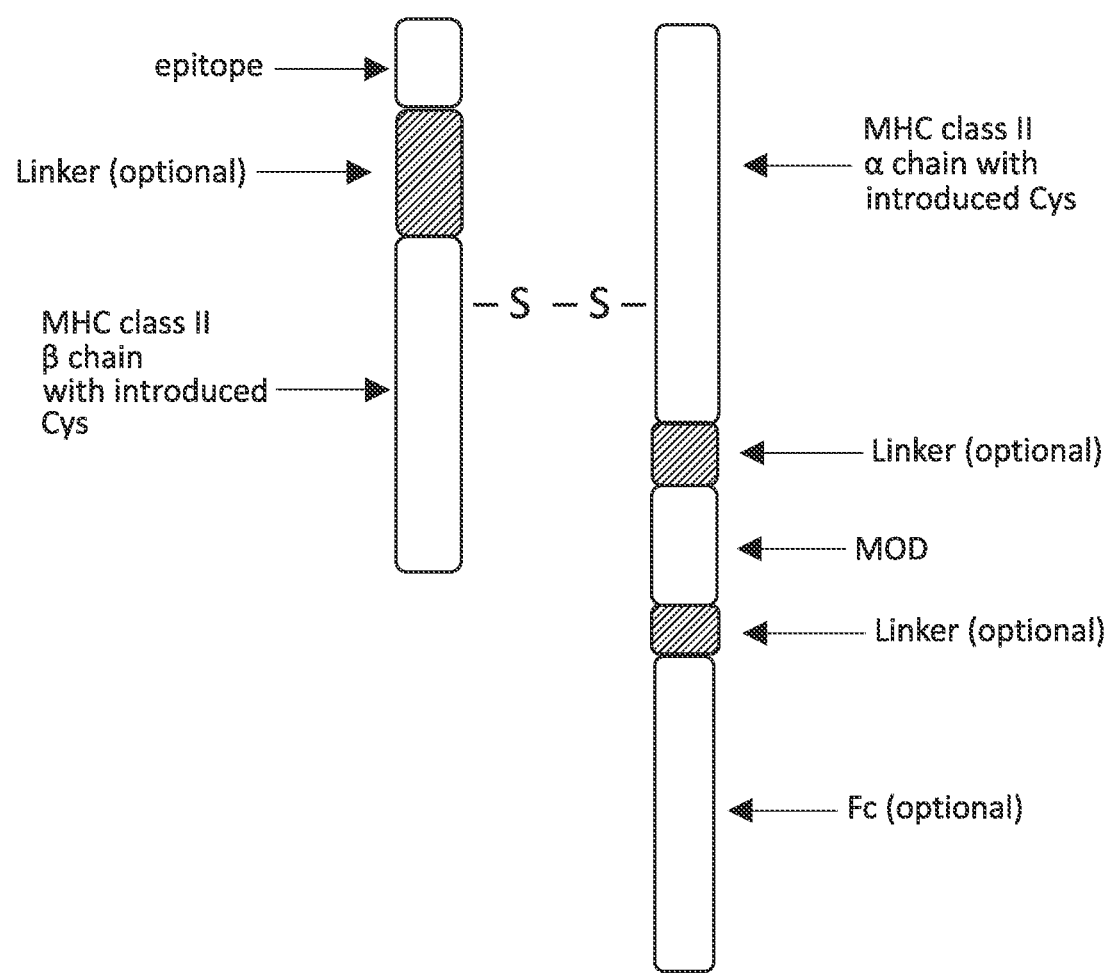
Figure 2C:
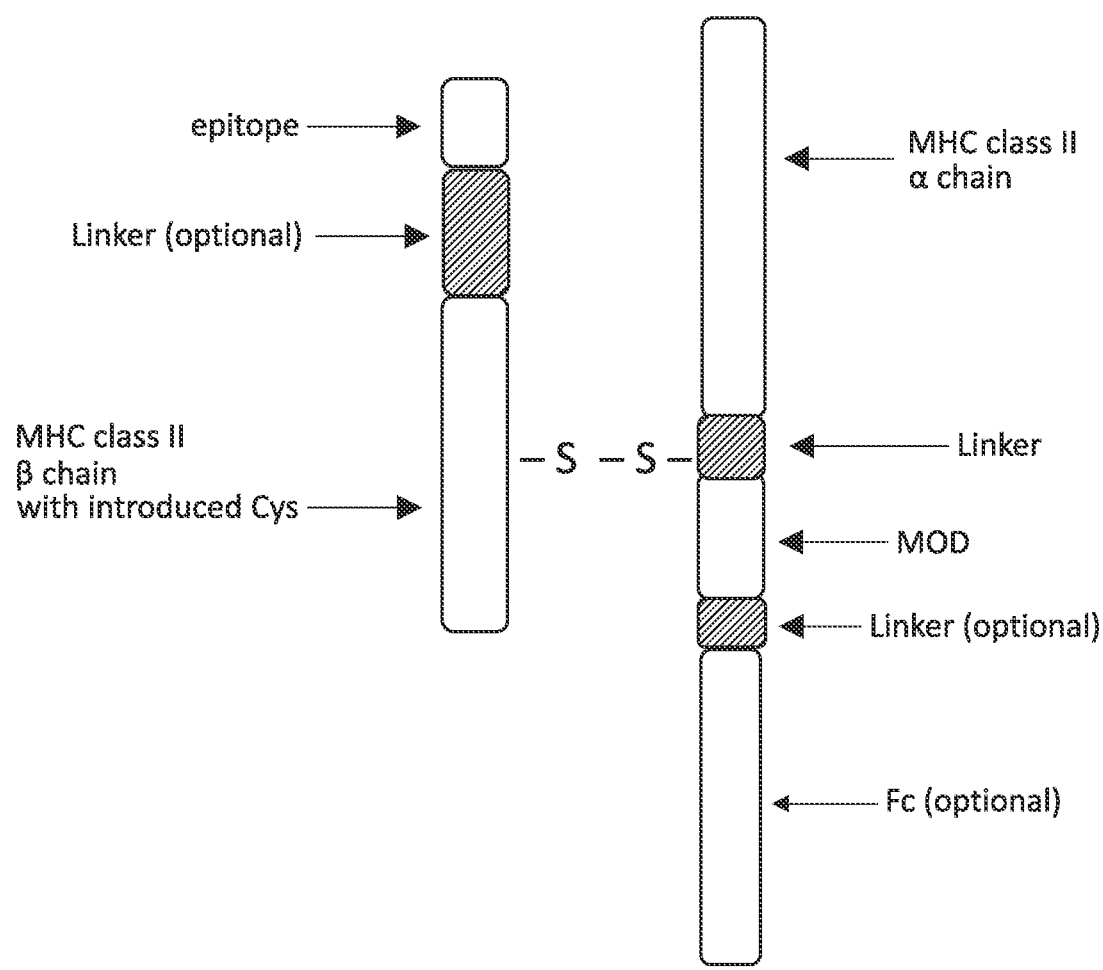
Figure 2D:
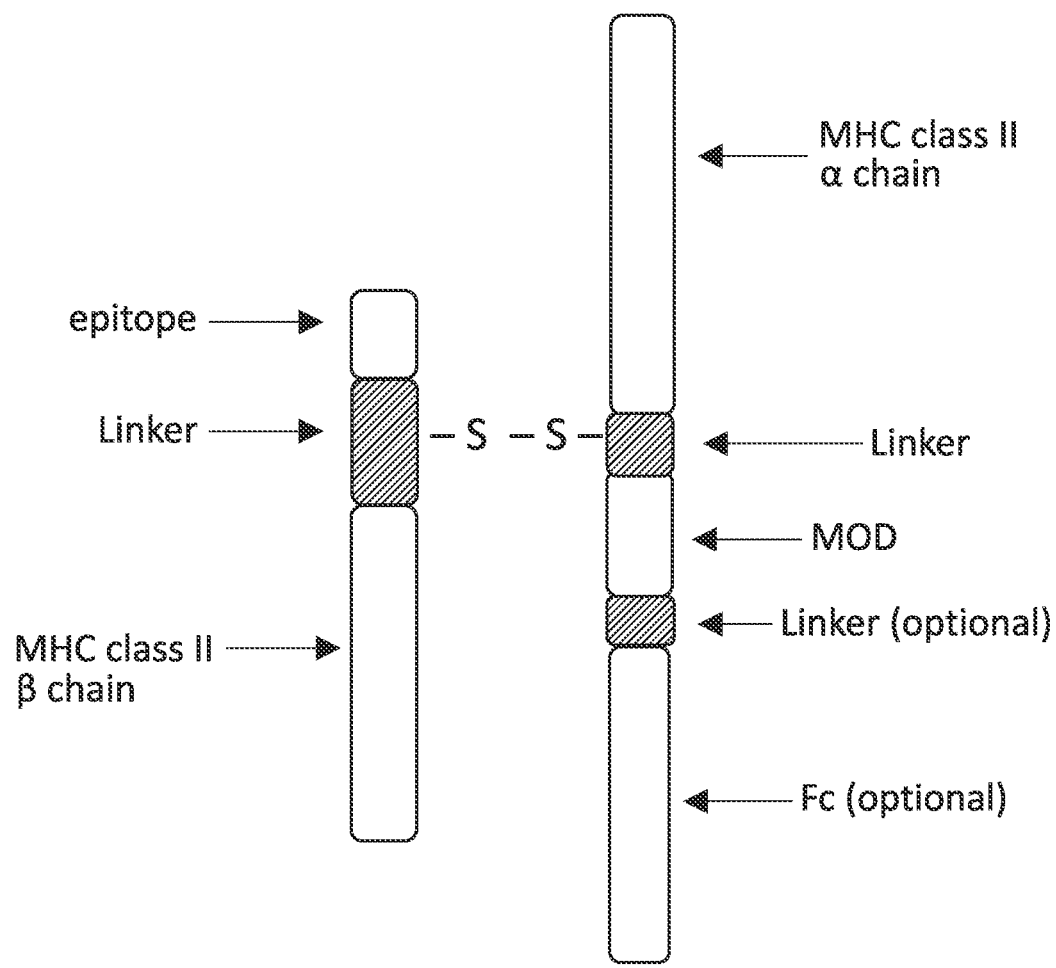
Figure 3A:
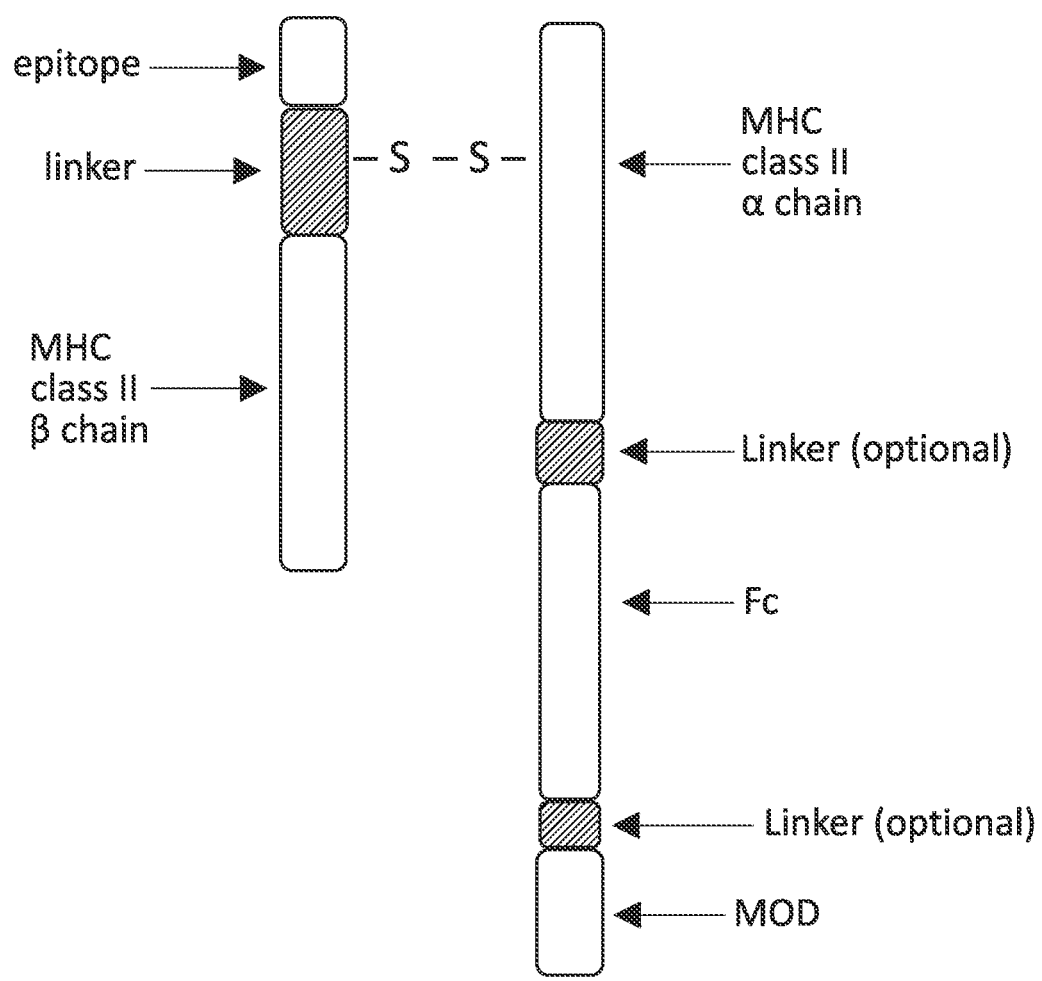
FIG. 3A-3D present schematic depictions of TMMPs of the present disclosure, in which the immunomodulatory polypeptide is in Position 3.
Figure 3B:
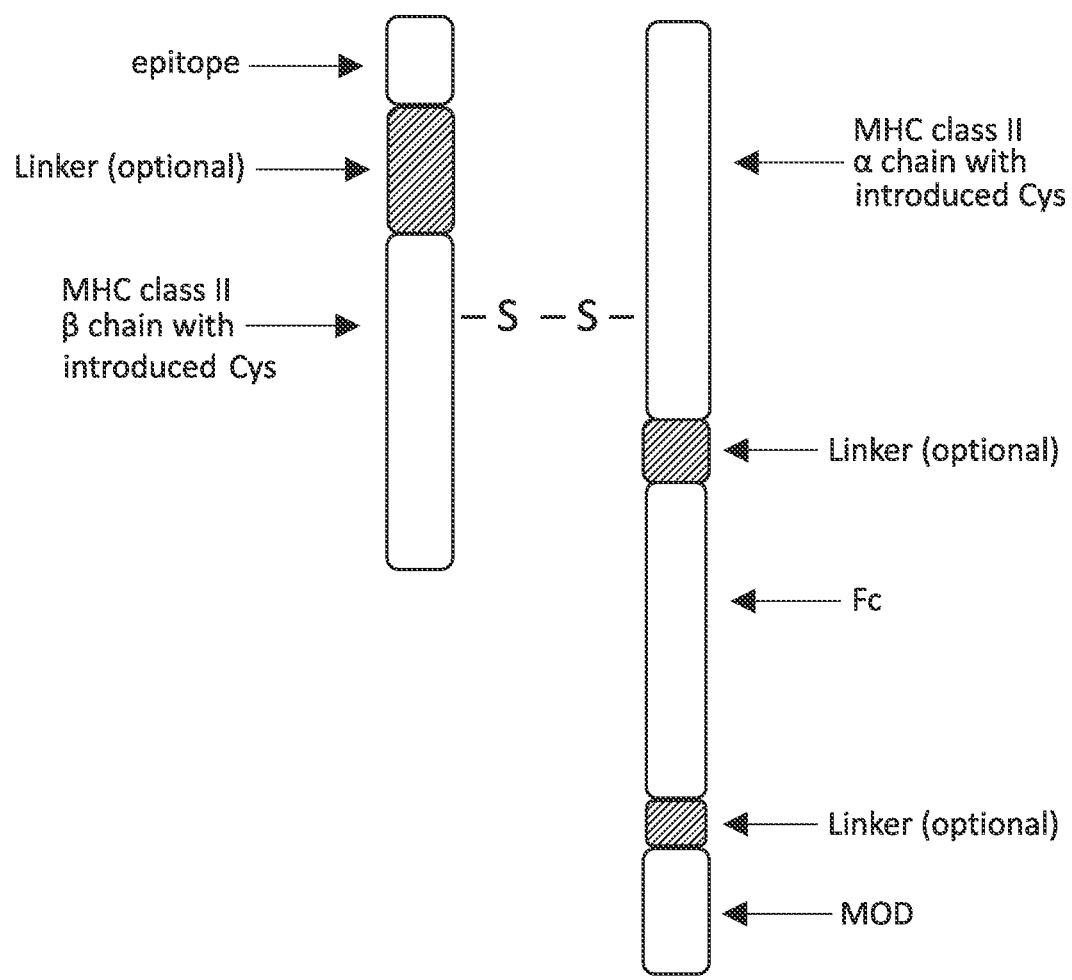
Figure 3C:
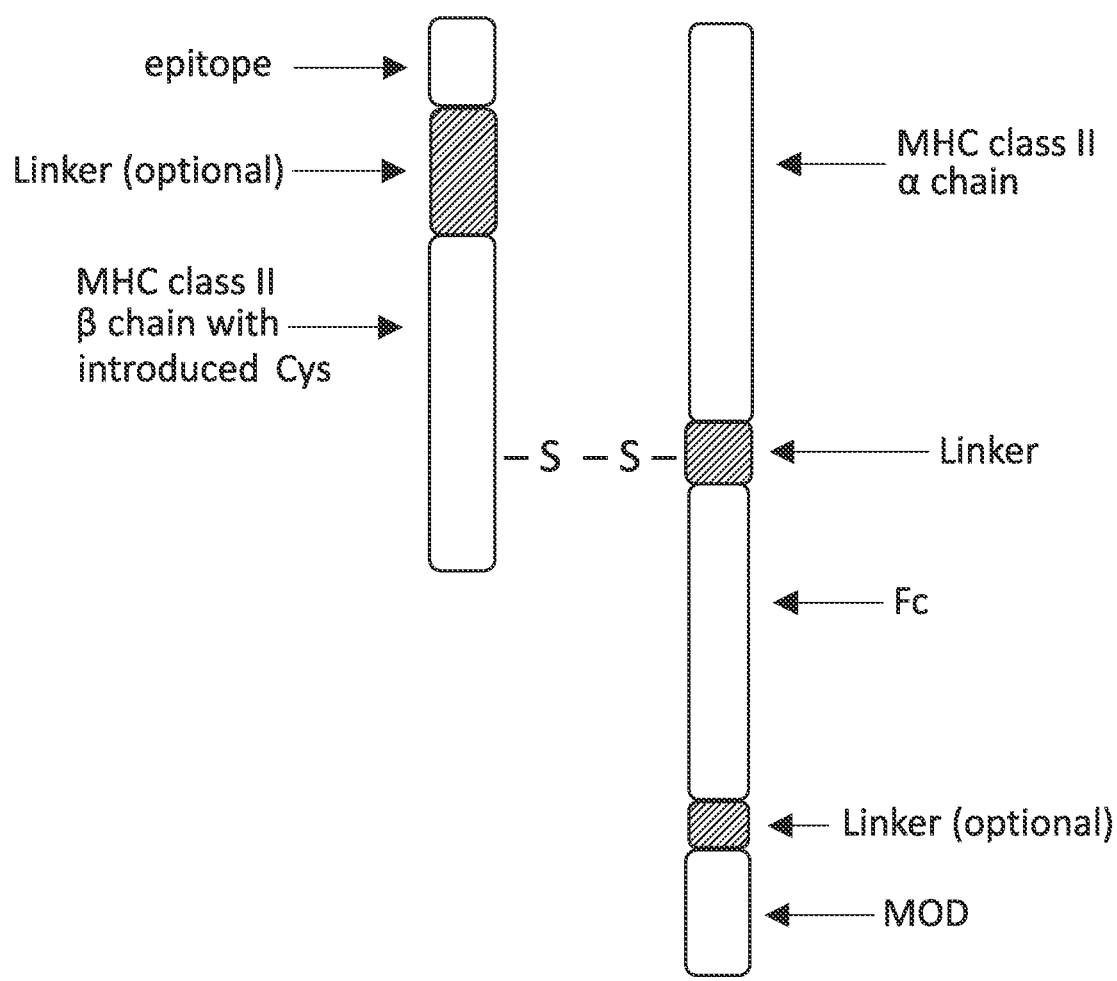
Figure 3D:
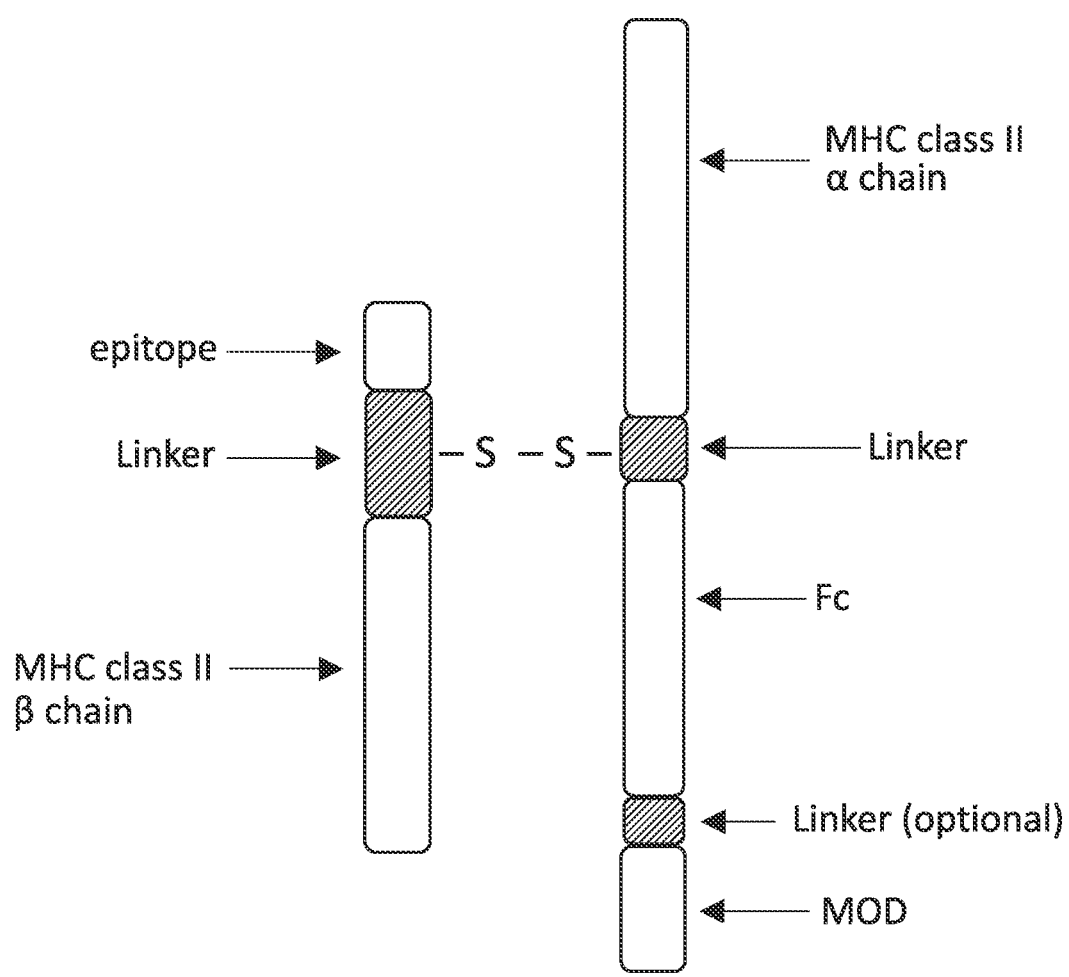
Figure 4A:
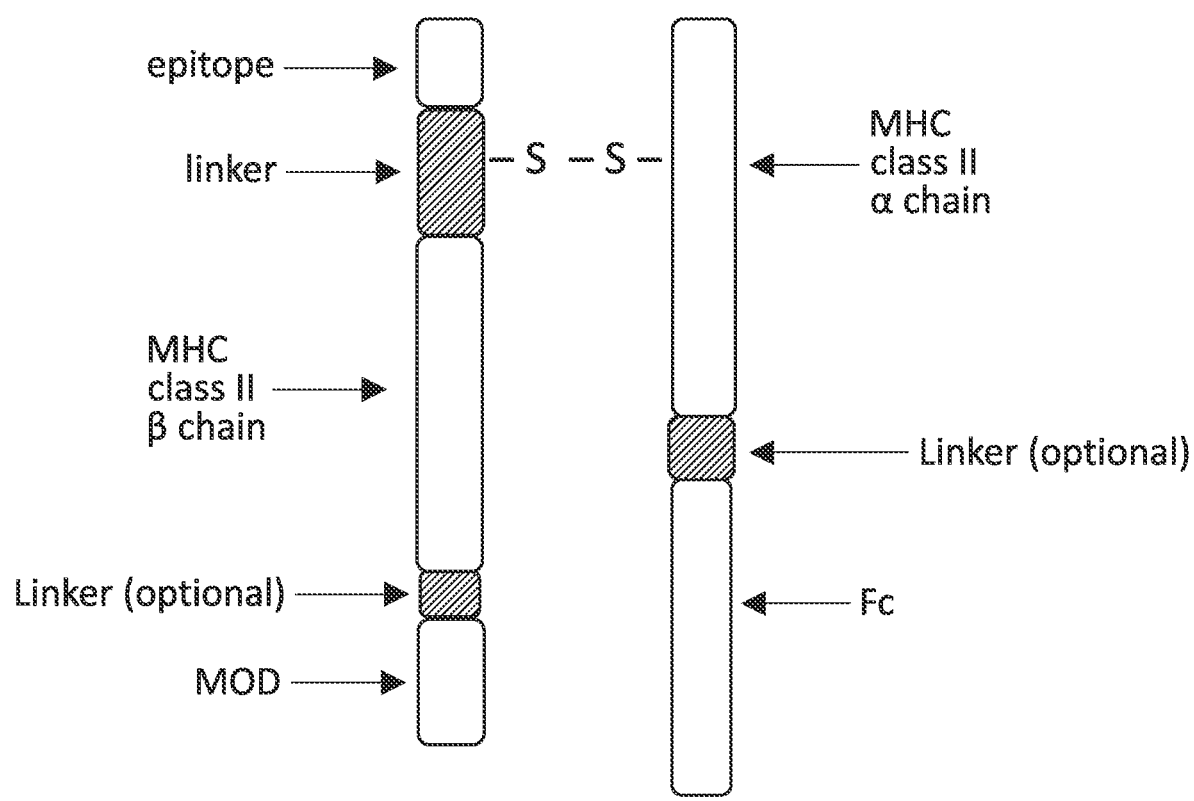
FIG. 4A-4D present schematic depictions of TMMPs of the present disclosure, in which the immunomodulatory polypeptide is in Position 5.
Figure 4B:
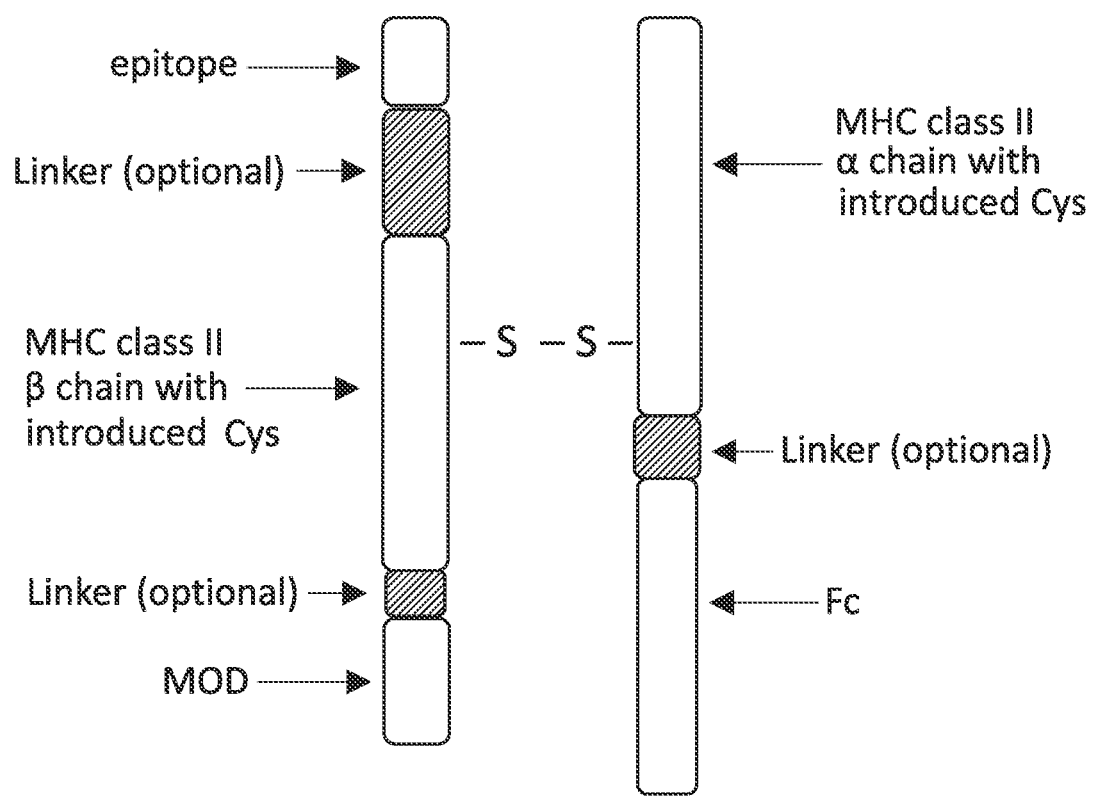
Figure 4C:
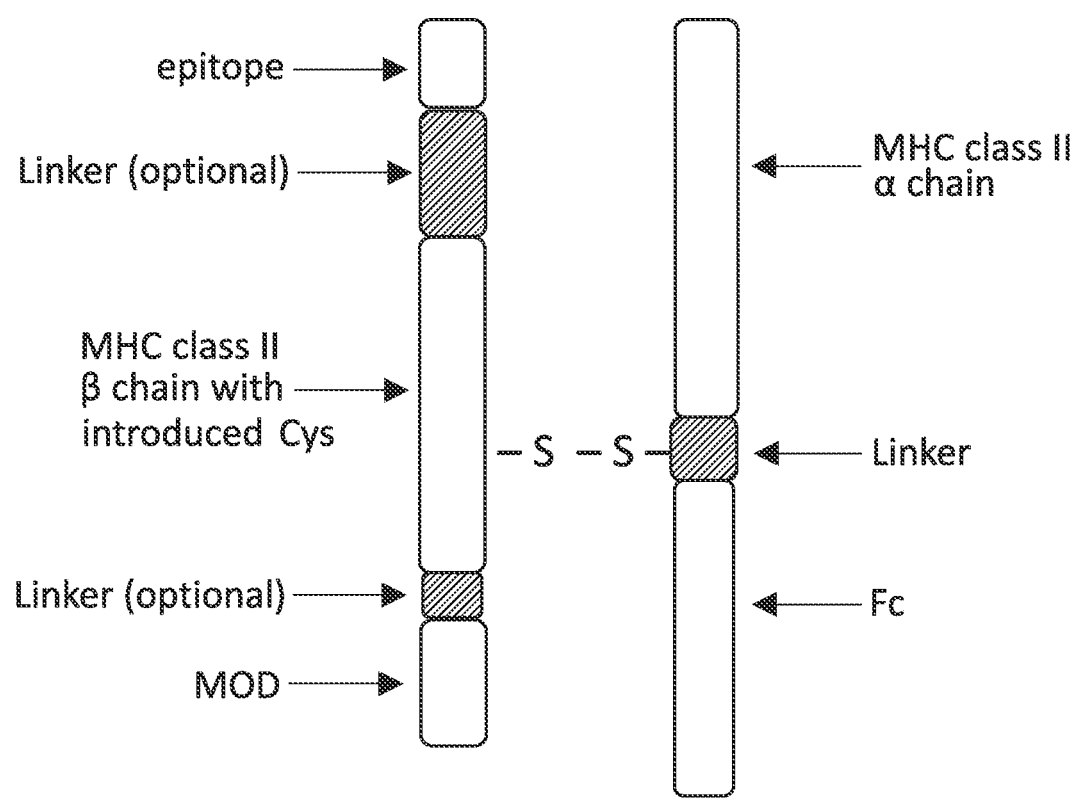
Figure 4D:
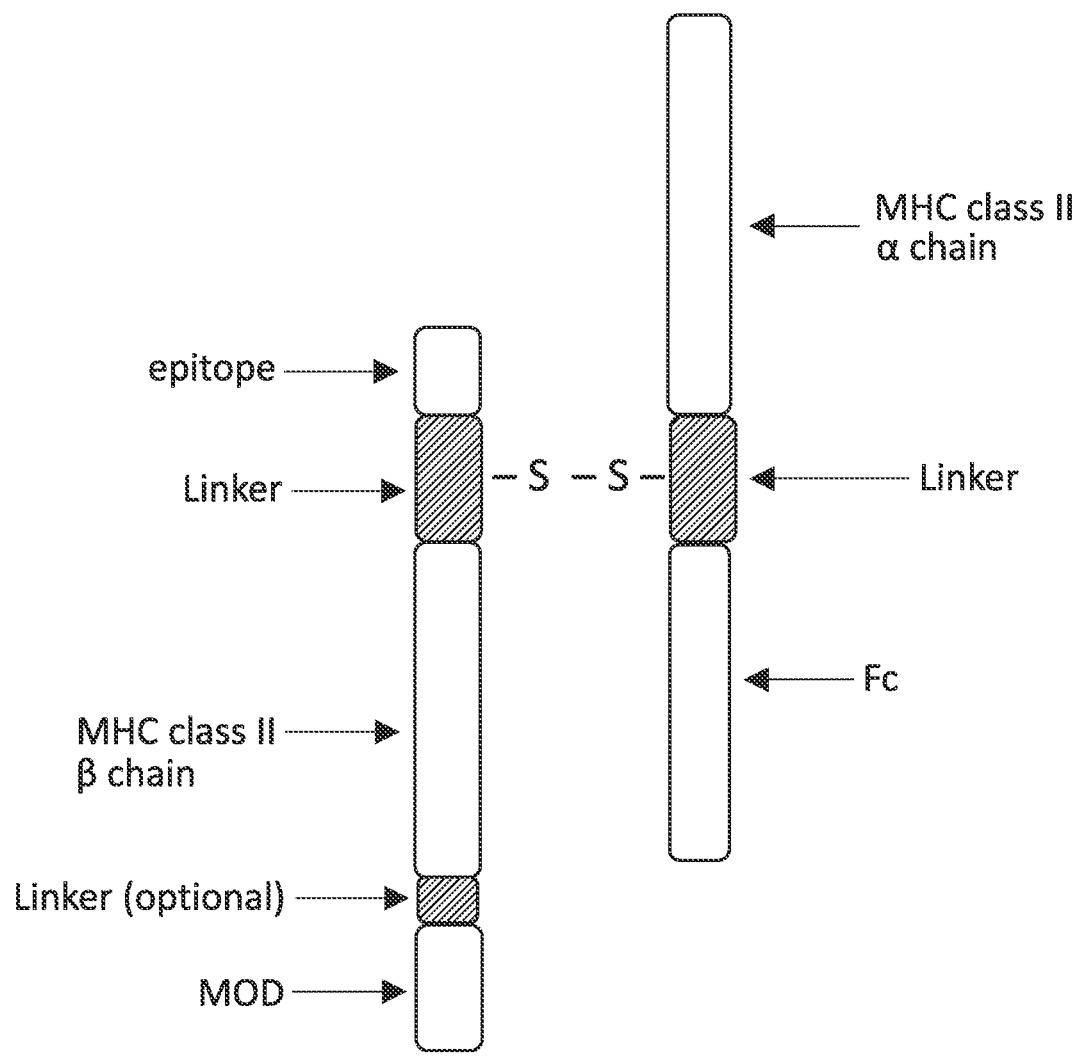

In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgM Fc polypeptide depicted in FIG. 12B; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-276 to the human IgM Fc polypeptide depicted in FIG. 2B.

In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgA Fc polypeptide depicted in FIG. 12C; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-234 to the human IgA Fc polypeptide depicted in FIG. 12C.

In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG4 Fc polypeptide depicted in FIG. 12C. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 100 to 327 of the human IgG4 Fc polypeptide depicted in FIG. 12C.

In some cases, the IgG4 Fc polypeptide comprises the following amino acid sequence:

```
                                        (SEQ ID NO: 58)
PPCPSCPAPEFLGGPSVFLFPPKPKDTLMISRTPEVTCVVVDVSQEDPEV

QFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEGNVF

SCSVMHEALHNHYTQKSLSLSPG.
```

In some cases, the Fc polypeptide present in a TMMP comprises the amino acid sequence depicted in FIG. 12A (human IgG1 Fc). In some cases, the Fc polypeptide present in a TMMP comprises the amino acid sequence depicted in FIG. 12A (human IgG1 Fc), except for a substitution of N297 (N77 of the amino acid sequence depicted in FIG. 12A) with an amino acid other than asparagine. In some cases, the Fc polypeptide present in a TMMP comprises the amino acid sequence depicted in FIG. 12C (human IgG1 Fc comprising an N297A substitution, which is N77 of the amino acid sequence depicted in FIG. 12A). In some cases, the Fc polypeptide present in a TMMP comprises the amino acid sequence depicted in FIG. 12A (human IgG1 Fc), except for a substitution of L234 (L14 of the amino acid sequence depicted in FIG. 12A) with an amino acid other than leucine. In some cases, the Fc polypeptide present in a TMMP comprises the amino acid sequence depicted in FIG. 12A (human IgG1 Fc), except for a substitution of L235 (L15 of the amino acid sequence depicted in FIG. 2A) with an amino acid other than leucine.

In some cases, the Fc polypeptide present in a TMMP comprises the amino acid sequence depicted in FIG. 12E. In some cases, the Fc polypeptide present in a TMMP comprises the amino acid sequence depicted in FIG. 12F. In some cases, the Fc polypeptide present in a TMMP comprises the amino acid sequence depicted in FIG. 12G (human IgG1 Fc comprising an L234A substitution and an L235A substitution, corresponding to positions 14 and 15 of the amino acid sequence depicted in FIG. 12G). In some cases, the Fc polypeptide present in a TMMP comprises the amino acid sequence depicted in FIG. 12A (human IgG1 Fc), except for a substitution of P331 (P111 of the amino acid sequence depicted in FIG. 12A) with an amino acid other than proline; in some cases, the substitution is a P331S substitution. In some cases, the Fc polypeptide present in a TMMP comprises the amino acid sequence depicted in FIG. 12A (human IgG1 Fc), except for substitutions at L234 and L235 (L14 and L15 of the amino acid sequence depicted in FIG. 12A) with amino acids other than leucine. In some cases, the Fc polypeptide present in a TMMP comprises the amino acid sequence depicted in FIG. 12A (human IgG1 Fc), except for substitutions at L234 and L235 (L14 and L15 of the amino acid sequence depicted in FIG. 12A) with amino acids other than leucine, and a substitution of P331 (P111 of the amino acid sequence depicted in FIG. 12A) with an amino acid other than proline. In some cases, the Fc polypeptide present in a TMMP comprises the amino acid sequence depicted in FIG. 12E (human IgG1 Fc comprising L234F, L235E, and P331S substitutions (corresponding to amino acid positions 14, 15, and 111 of the amino acid sequence depicted in FIG. 12E). In some cases, the Fc polypeptide present in a TMMP is an IgG1 Fc polypeptide that comprises L234A and L235A substitutions (substitutions of L14 and L15 of the amino acid sequence depicted in FIG. 12A with Ala), as depicted in FIG. 12G.

In some cases, a TMMP of the present disclosure comprises an Ig Fc polypeptide comprising the following amino acid sequence: DKTHTCPPCPAPEAAGGPS VFLFPPKPKDTLMISRTPEVTC VVVD V SHEDPEV KFNW YVDGVEV HNAKTKPREEQYN-STYRVVSVLTVLHQDWLNGKEYKCKVSNKALPA-PIEKTISKAKGQPREPQ V YTLPPSREEMTKNQV SLT-CLV KGFYPSDIAVE WESNGQPENNYKTTPPVLDSDGSFFLYSKLT VDKSRWQQGNVFSCSVMHEALHNHYTQKSLSLSPG (SEQ ID NO:59), which is an IgG1 Fc polypeptide comprising L234A and L235A substitutions (L14A and L15A in this sequence; shown in bold text).

Linkers

As discussed above, a TMMP of the present disclosure can include one or more linker peptides between components of the first and second polypeptides of the TMMP, e.g., between a T1D peptide and an MHC polypeptide; between an MHC polypeptide and an Ig Fc polypeptide; between a first MHC polypeptide and a second MHC polypeptide; between an immunomodulatory polypeptide and an MHC polypeptide; etc. As also noted above, in some cases, a TMMP of the present disclosure can include a Cys-containing peptide linker between the T1D peptide and an MHC class II polypeptide, e.g., between the T1D peptide and an MHC class II β chain polypeptide. Generally, a Cys-containing peptide linker will be used in either the first or second polypeptide of a TMMP in order to intentionally facilitate formation of a disulfide bond between the linker and a desired site on the other polypeptide. Where a Cys-containing linker is inserted in one polypeptide of a TMMP, the remaining linkers in the TMMP will not include a Cys in order to prevent formation of a disulfide bond at an unwanted site in the TMMP, with the exception that a Cys-containing linker could be used in each of the first and second polypeptides when it is desired to link the first and second polypeptides through a disulfide bond formed between the linkers. A TMMP of the present disclosure thus can include: a) a Cys-containing peptide linker between the T1D peptide and an MHC class II polypeptide, e.g., between the T1D peptide and an MHC class II β chain polypeptide; and b) at least one additional peptide linker, where the at least one additional peptide linker does not include a Cys.

Suitable linkers (also referred to as "spacers") can be readily selected and can be of any of a number of suitable lengths, such as from 1 amino acid to 25 amino acids, from 3 amino acids to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids. A suitable linker can be 1, 2, 3, 4, 5, 6, 7, 8, 9, 10, 11, 12, 13, 14, 15, 16, 17, 18, 19, 20, 21, 22, 23, 24, or 25 amino acids in length. A suitable linker can be from 25 to 35 amino acids in length. A suitable linker can be 25, 26, 27, 28, 29, 30, 31, 32, 33, 34, or 35 amino acids in length. A suitable linker can be from 35 to 45 amino acids in length. A suitable linker can be 35, 36, 37, 38, 39, 40, 41, 42, 43, 44, or 45 amino acids in length. A suitable linker can be from 45 to 50 amino acids in length. A suitable linker can be 45, 46, 47, 48, 49, or 50 amino acids in length.

Linkers Containing a Cys

A peptide linker comprising a Cys can comprise an amino acid sequence selected from (CGGGS)(GGGGS)n (SEQ ID NO:1), (GCGGS)(GGGGS)n (SEQ ID NO:2), (GGCGS) (GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10). In some cases, a TMMP of the present disclosure comprises a heterodimer comprising a first and a second polypeptide, where the first polypeptide comprises a T1D peptide and an MHC class II polypeptide (e.g., an MHC class II β chain polypeptide), and comprises a linker between the T1D peptide and the MHC class II polypeptide (e.g., the MHC class II β chain polypeptide), where the linker comprises an amino acid sequence selected from (CGGGS)(GGGGS)n (SEQ ID NO: 1), (GCGGS) (GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10).

Linkers Not Containing a Cys

Exemplary linkers include glycine polymers (G)n, glycine-serine polymers (including, for example, (GS)$_n$, (GSGGS)$_n$ (SEQ ID NO:60) and (GGGS)$_n$ (SEQ ID NO:61), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, *Rev. Computational Chem.* 11173-142 (1992)). Exemplary linkers can comprise amino acid sequences including, but not limited to, GGSG (SEQ ID NO:62), GGSGG (SEQ ID NO:63), GSGSG (SEQ ID NO:64), GSGGG (SEQ ID NO:65), GGGSG (SEQ ID NO:66), GSSSG (SEQ ID NO:67), and the like. Exemplary linkers can include, e.g., Gly(Ser$_4$)$_n$, (SEQ ID NO:68) where n is 1, 2, 3, 4, 5, 6, 7, 8, 9, or 10. In some cases, a linker comprises the amino acid sequence (GSSSS)$_n$ (SEQ ID NO:69), where n is 4. In some cases, a linker comprises the amino acid sequence (GSSSS)n (SEQ ID NO:70), where n is 5. Exemplary linkers can include, e.g., (GlyGlyGlyGlySer)n (SEQ ID NO:71) (also referred to as "G4S" linkers), where n is 1, 2, 3, 4, 5, 6, 7, 8, 9, or 10. In some cases, a linker comprises the amino acid sequence (GGGGS)n (SEQ ID NO:72), where n is 1. In some cases, a linker comprises the amino acid sequence (GGGGS)n (SEQ ID NO:73), where n is 2. In some cases, a linker comprises the amino acid sequence (GGGGS)n (SEQ ID NO:74), where n is 3. In some cases, a linker comprises the amino acid sequence (GGGGS)n (SEQ ID NO:75), where n is 4. In some cases, a linker comprises the amino acid sequence (GGGGS)n (SEQ ID NO:76), where n is 5. In some cases, a linker comprises the amino acid sequence (GGGGS)n (SEQ ID NO:77), where n is 6. In some cases, a linker comprises the amino acid sequence (GGGGS)n (SEQ ID NO:78), where n is 7. In some cases, a linker comprises the amino acid sequence (GGGGS)n (SEQ ID NO:79), where n is 8. In some cases, a linker comprises the amino acid sequence (GGGGS)n (SEQ ID NO:80), where n is 9. In some cases, a linker comprises the amino acid sequence (GGGGS)n (SEQ ID NO:81), where n is 10. In some cases, a linker comprises the amino acid sequence AAAGG (SEQ ID NO:82). In some cases, a linker comprises the amino acid sequence GGSAAAGG (SEQ ID NO:83). The AAAGG (SEQ ID NO:82) and GGSAAAGG (SEQ ID NO:83) linkers have been found to be useful for linking an MHC class II alpha chain polypeptide (e.g., a DRA class II polypeptide) to an Ig Fc polypeptide (e.g., a human IgG1 Fc polypeptide sequence depicted in FIG. 12G comprising an L234A substitution and an L235A substitution, corresponding to positions 14 and 15 of the amino acid sequence depicted in FIG. 12G).

Peptides Presenting T1D-Associated Epitopes

As used herein, a "T1D peptide" is a peptide that, when present in a TMMP of this disclosure, presents a T1D-associated epitope capable of being bound by a TCR on the surface of a T cell. A T1D peptide can have a length of from about 4 amino acids to about 25 amino acids, e.g., the T1D peptide can have a length of from 4 amino acids (aa) to 10 aa, from 8 aa to 12 aa, from 10 aa to 15 aa, from 12 aa to 20 aa, from 15 aa to 20 aa, from 15 aa to 25 aa, or from 20 aa to 25 aa. For example, a T1D peptide present in a TMPP of the present disclosure can have a length of 4 amino acids (aa), 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, a T1D peptide present in a TMPP of the present disclosure has a length of from 5 amino acids to 10 amino acids, e.g., 5 aa, 6 aa, 7 aa, 8 aa, 9 aa, or 10 aa.

Antigens associated with type 1 diabetes (T1D) include, e.g., preproinsulin, proinsulin, insulin, insulin B chain, insulin A chain, 65 kDa isoform of glutamic acid decarboxylase (GAD65), 67 kDa isoform of glutamic acid decarboxylase (GAD67), tyrosine phosphatase (IA-2), heat-shock protein HSP65, islet-specific glucose6-phosphatase catalytic subunit related protein (IGRP), islet antigen 2 (IA2), and zinc transporter (ZnT8). See, e.g., Mallone et al. (2011) *Clin. Dev. Immunol.* 2011:513210; and U.S. Patent Publication No. 2017/0045529. An antigen "associated with" a particular autoimmune disorder is an antigen that is a target of autoantibodies and/or autoreactive T cells present in individuals with that autoimmune disorder, where such autoantibodies and/or autoreactive T cells mediate a pathological state associated with the autoimmune disorder. A suitable T1D peptide for inclusion in a TMMP of the present disclosure can be an epitope-presenting T1D peptide of from 4 amino acids to about 25 amino acids in length of any one of the aforementioned T1D-associated antigens.

As one non-limiting example, a T1D peptide is proinsulin 73-90 (GAGSLQPLALEGSLQKR; SEQ ID NO:84). As another non-limiting example, a T1D peptide is the following insulin (InsA (1-15) peptide: GIVDQCCTSICSLYQ (SEQ ID NO:85). As another non-limiting example, a T1D peptide is the following insulin (InsA(1-15; D4E) peptide: GIVEQCCTSICSLYQ (SEQ ID NO:86). As another non-limiting example, a T1D peptide is the following GAD65 (555-567) peptide; NFFRMVISNPAAT (SEQ ID NO:87). As another non-limiting example, a T1D peptide is the following GAD65 (555-567; F557I) peptide; NFIRMVISNPAAT (SEQ ID NO: 88). As another non-limiting example, a T1D peptide is the following islet antigen 2 (IA2) peptide: SFYLKNVQTQETRTLTQFHF (SEQ ID NO:89). As another non-limiting example, a T1D peptide is the following proinsulin peptide: SLQPLALEGSLQSRG (SEQ ID NO:90). As another non-limiting example, a T1D peptide is the following proinsulin peptide GSLQPLALEGSLQSR-GIV (SEQ ID NO:91; proIns 75-92(K88S)).

In some cases, a suitable T1D peptide comprises from 4 to 25 contiguous amino acids of an amino acid sequence having at least 90%, at least 95%, at least 98%, at least 99%, or 100% amino acid sequence identity to amino acids 25-110 of the following human preproinsulin amino acid sequence (wherein amino acids 1-24 (underlined) is a signal peptide):

(SEQ ID NO: 92)
MALWMRLLPL LALLALWGPD PAAA

FVNQHL CGSHLVEALY LVCGERGFFY TPKTRREAED LQVGQVELGG

GPGAGSLQPL ALEGSLQKRG IVEQCCTSIC SLYQLENYCN;

where the T1D peptide has a length of 4 amino acids (aa), 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, the T1D peptide has the amino acid sequence: GAGSLQPLALEGSLQKRG (SEQ ID NO:93) (proIns 73-90). In some cases, the T1D peptide has the amino acid sequence: SLQPLALEGSLQKRG (SEQ ID NO:94) (proIns 76-90). In some cases, the T1D peptide has the amino acid sequence: SLQPLALEGSLQSRG (SEQ ID NO:90) (proIns 76-90; K88S). In some cases, the T1D peptide has the amino acid sequence: QPLALEGSLQKRG (SEQ ID NO:95). In some cases, the T1D peptide has the amino acid sequence: QPLALEGSLQSRG (SEQ ID NO:96).

Immunomodulatory Polypeptides ("Mods")

As noted above, immunomodulatory polypeptides ("MODs") that are suitable for inclusion in a TMPP of the present disclosure include, but are not limited to, IL-2, TGFβ, CD7, B7-1 (CD80), B7-2 (CD86), PD-L1, PD-L2, 4-1BBL, OX40L, Fas ligand (FasL), inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, and HVEM. In some cases, the immunomodulatory polypeptide is selected from an IL-2 polypeptide, a 4-1BBL polypeptide, an ICOS-L polypeptide, an OX-40L polypeptide, a CD80 polypeptide, a CD86 polypeptide, a PD-L1 polypeptide, a FasL polypeptide, a TGFβ polypeptide, and a PD-L2 polypeptide.

As also noted above, the immunomodulatory polypeptide can comprise a wild-type amino acid sequence, or can comprise one or more amino acid substitutions relative to a wild-type amino acid sequence. The immunomodulatory polypeptide can comprise only the extracellular portion of a full-length immunomodulatory polypeptide. Thus, for example, the immunomodulatory polypeptide can in some cases exclude one or more of a signal peptide, a transmembrane domain, and an intracellular domain normally found in a naturally-occurring immunomodulatory polypeptide.

In some cases, an immunomodulatory polypeptide suitable for inclusion in a TMPP of the present disclosure comprises all or a portion of (e.g., an extracellular portion of) the amino acid sequence of a naturally-occurring immunomodulatory polypeptide. In other instances, an immunomodulatory polypeptide suitable for inclusion in a TMPP of the present disclosure is a variant immunomodulatory polypeptide that comprises at least one amino acid substitution compared to the amino acid sequence of a naturally-occurring immunomodulatory polypeptide. In some instances, a variant immunomodulatory polypeptide exhibits a binding affinity for a co-immunomodulatory polypeptide that is lower than the affinity of a corresponding naturally-occurring immunomodulatory polypeptide (e.g., an immunomodulatory polypeptide not comprising the amino acid substitution(s) present in the variant) for the co-immunomodulatory polypeptide.

Suitable immunomodulatory domains that exhibit reduced affinity for a co-immunomodulatory domain can have from 1 amino acid (aa) to 20 aa differences from a wild-type immunomodulatory domain. For example, in some cases, a variant immunomodulatory polypeptide present in a TMPP of the present disclosure differs in amino acid sequence by 1 aa, 2 aa, 3 aa, 4 aa, 5 aa, 6 aa, 7 aa, 8 aa, 9 aa, or 10 aa, from a corresponding wild-type immunomodulatory polypeptide. As another example, in some cases, a variant immunomodulatory polypeptide present in a TMPP of the present disclosure differs in amino acid sequence by 11 aa, 12 aa, 13 aa, 14 aa, 15 aa, 16 aa, 17 aa, 18 aa, 19 aa, or 20 aa, from a corresponding wild-type immunomodulatory polypeptide. As an example, in some cases, a variant immunomodulatory polypeptide present in a TMPP of the present disclosure includes 1, 2, 3, 4, 5, 6, 7, 8, 9, or 10 amino acid substitutions, compared to a corresponding reference (e.g., wild-type) immunomodulatory polypeptide.

As discussed above, a variant immunomodulatory polypeptide suitable for inclusion in a TMPP of the present disclosure exhibits reduced affinity for a cognate co-immunomodulatory polypeptide, compared to the affinity of a corresponding wild-type immunomodulatory polypeptide for the cognate co-immunomodulatory polypeptide.

Exemplary pairs of immunomodulatory polypeptide and cognate co-immunomodulatory polypeptide include, but are not limited to those set out in Table 2, below:

TABLE 2

| Immunomodulatory Polypeptide | Cognate Co-Immunomodulatory Polypeptide |
|---|---|
| 4-1BBL | 4-1BB |
| PD-L1 | PD-1 |
| IL-2 | IL-2 receptor |
| CD80 | CD28 |
| CD86 | CD28 |
| OX40L (CD252) | OX40 (CD134) |
| Fas ligand | Fas |
| ICOS-L | ICOS |
| ICAM | LFA-1 |
| CD30L | CD30 |
| CD40 | CD40L |
| CD83 | CD83L |
| HVEM (CD270) | CD160 |
| JAG1 (CD339) | Notch |
| JAG1 | CD46 |
| CD80 | CTLA4 |
| CD86 | CTLA4 |
| CD70 | CD27 |
| TGFβ | TGFβ receptor |

In some cases, a variant immunomodulatory polypeptide present in a TMPP of the present disclosure has a binding affinity for a cognate co-immunomodulatory polypeptide that is from 100 nM to 100 μM. For example, in some cases, a variant immunomodulatory polypeptide present in a TMPP of the present disclosure has a binding affinity for a cognate co-immunomodulatory polypeptide that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

Binding affinity between an immunomodulatory polypeptide and its cognate co-immunomodulatory polypeptide can be determined by bio-layer interferometry (BLI) using purified immunomodulatory polypeptide and purified cognate co-immunomodulatory polypeptide, following the procedure set forth in published PCT Application WO 2020/132138 A1.

Wild-Type PD-L1 and PD-L1 Variants

In some cases, at least one of the one or more immunomodulatory polypeptides present in a TMMP of the present disclosure comprises the amino acid sequence of a wild-type PD-L1 polypeptide. In other instances, at least one of the one or more immunomodulatory polypeptides present in a TMMP of the present disclosure is a variant PD-L1 polypeptide. Wild-type PD-L1 and variant PD-L1 polypeptides bind to PD1.

A wild-type human PD-L1 polypeptide can comprise the following amino acid sequence: MRIFAVFIFM TYWHLLNAFT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKICLT LSPST (SEQ ID NO:97).

A wild-type PD-L1 polypeptide suitable for inclusion in a TMMP of the present disclosure can comprise the following amino acid sequence: FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:98).

A wild-type PD-L1 polypeptide suitable for inclusion in a TMMP of the present disclosure can comprise the following amino acid sequence:

```
                                   (SEQ ID NO: 99)
FTVTVPKDLYVVEYGSNMTIECKFPVEKQLDLAALIVYWEMEDKNIIQFV

HGEEDLKVQHSSYRQRARLLKDQLSLGNAALQITDVKLQDAGVYRCMISY

GGADYKRITVKVNAPYNKINQRILVVDPVTSEHELTCQAEGYPKAEVIWT

SSDHQVLSGKTTTTNSKREEKLFNVTSTLRINTTTNEIFYCTFRRLDPEE

NHTAELVIPELPLAHPPNER.
```

A wild-type PD-1 polypeptide can comprise the following amino acid sequence:

```
                                  (SEQ ID NO: 100)
PGWFLDSPDR PWNPPTFSPA LLVVTEGDNA TFTCSFSNTS

ESFVLNWYRM SPSNQTDKLA AFPEDRSQPG QDCRFRVTQL

PNGRDFHMSV VRARRNDSGT YLCGAISLAP KAQIKESLRA

ELRVTERRAE VPTAHPSPSP RPAGQFQTLV VGVVGGLLGS

LVLLVWVLAV ICSRAARGTI GARRTGQPLK EDPSAVPVFS

VDYGELDFQW REKTPEPPVP CVPEQTEYAT IVFPSGMGTS

SPARRGSADG PRSAQPLRPE DGHCSWPL.
```

In some cases, a variant PD-L1 polypeptide exhibits reduced binding affinity to PD-1 (e.g., a PD-1 polypeptide comprising the amino acid sequence depicted above), compared to the binding affinity of a PD-L1 polypeptide comprising the amino acid sequence: FTVTVPKDLYVVEYGSNMTIECKFPVEKQLDLAALIVYWEMEDKNIIQFVH GEEDLKVQHSSYR QRARLLKDQLSLGNAALQITDVKLQDAGVYRCMISYGGADYKRITVKVNAPYNKINQRILVVD PVTSEHELTCQAEGYPKAEVIWTS SDHQVLSGKTTTTNSKREEKLFNVTSTLRINTTTNEIFYCTF RRLDPEENHTAELVIPELPLAHPPNER (SEQ ID NO:99) or the amino acid sequence: FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:98).

For example, in some cases, a variant PD-L1 polypeptide of the present disclosure binds PD-1 (e.g., a PD-1 polypeptide comprising the PD-1 amino acid sequence depicted above) with a binding affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the binding affinity of a PD-L1 polypeptide comprising the amino acid sequence: FTVTVPKDLYVVEYGSNMTIECKFPVEKQLDLAALIVYWEMEDKNIIQFVHGEEDLKVQHSSYR QRARLLKDQLSLGNAALQITDVKLQDAGVYRCMISYGGADYKRITVKVNAPYNKINQRILVVD PVTSEHELTCQAEGYPKAEVIWTS SDHQVLSGKTTTTNSKREEKLFNVTSTLRINTTTNEIFYCTF RRLDPEENHTAELVIPELPLAHPPNER (SEQ ID NO:99) or the amino acid sequence: FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:98).

In some cases, a variant PD-L1 polypeptide has a binding affinity to PD-1 that is from 1 nM to 1 mM. In some cases, a variant PD-L1 polypeptide of the present disclosure has a binding affinity to PD-1 that is from 100 nM to 100 μM. As another example, in some cases, a variant PD-L1 polypeptide has a binding affinity for PD (e.g., a PD polypeptide comprising the PD-1 amino acid sequence depicted above) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

In some cases, a variant PD-L1 polypeptide has a single amino acid substitution compared to one of the PD-L1 amino acid sequences depicted above. In some cases, a variant PD-L1 polypeptide has from 2 to 10 amino acid substitutions compared to one of the PD-L1 amino acid sequences depicted above.

Wild-Type IL-2 and IL-2 Variants

In some cases, at least one of the one or more immunomodulatory polypeptides present in a TMMP of the present disclosure comprises the amino acid sequence of a wild-type IL-2 polypeptide. In other instances, at least one of the one or more immunomodulatory polypeptides present in a TMMP of the present disclosure is a variant IL-2 polypeptide. Wild-type IL-2 and variant IL-2 polypeptides bind to IL-2 receptor (IL-2R) (e.g., bind to one or more polypeptides of an IL-2R).

A wild-type IL-2 amino acid sequence can be as follows: APTSSSTKKT QLQLEHLLLD LQMILNGINN YKNPKLTRML TFKFYMPKKA TELKHLQCLEEELKPLEEVL NLAQSKNFHL

RPRDLISNIN VIVLELKGSE TTFMCEYADE TATIVE-FLNRWITFCQSIIS TLT (SEQ ID NO:101).

Wild-type IL-2 binds to an IL2 receptor (IL2R) on the surface of a cell. An IL2 receptor is in some cases a heterotrimeric polypeptide comprising an alpha chain (IL-2Ra; also referred to as CD25), a beta chain (IL-2Rβ; also referred to as CD122: and a gamma chain (IL-2Ry; also referred to as CD132). Amino acid sequences of human IL-2Ra, IL2Rβ, and IL-2Ry can be as follows.

```
Human IL-2Rα:
                                        (SEQ ID NO: 102)
ELCDDDPPE IPHATFKAMA YKEGTMLNCE CKRGFRRIKS

GSLYMLCTGN SSHSSWDNQC QCTSSATRNT TKQVTPQPEE

QKERKTTEMQ SPMQPVDQAS LPGHCREPPP WENEATERIY

HFVVGQMVYY QCVQGYRALH RGPAESVCKM THGKTRWTQP

QLICTGEMET SQFPGEEKPQ ASPEGRPESE TSCLVTTTDF

QIQTEMAATM ETSIFTTEYQ VAVAGCVFLL ISVLLLSGLT

WQRRQRKSRR TI.

Human IL-2Rβ:
                                        (SEQ ID NO: 103)
VNG TSQFTCFYNS RANISCVWSQ DGALQDTSCQ

VHAWPDRRRW NQTCELLPVS QASWACNLIL GAPDSQKLTT

VDIVTLRVLC REGVRWRVMA IQDFKPFENL RLMAPISLQV

VHVETHRCNI SWEISQASHY FERHLEFEAR TLSPGHTWEE

APLLTLKQKQ EWICLETLTP DTQYEFQVRV KPLQGEFTTW

SPWSQPLAFR TKPAALGKDT IPWLGHLLVG LSGAFGFIIL

VYLLINCRNT GPWLKKVLKC NTPDPSKFFS QLSSEHGGDV

QKWLSSPFPS SSFSPGGLAP EISPLEVLER DKVTQLLLQQ

DKVPEPASLS SNHSLTSCFT NQGYFFFHLP DALEIEACQV

YFTYDPYSEE DPDEGVAGAP TGSSPQPLQP LSGEDDAYCT

FPSRDDLLLF SPSLLGGPSP PSTAPGGSGA GEERMPPSLQ

ERVPRDWDPQ PLGPPTPGVP DLVDFQPPPE LVLREAGEEV

PDAGPREGVS FPWSRPPGQG EFRALNARLP LNTDAYLSLQ

ELQGQDPTHL V.

Human IL-2Rγ:
                                        (SEQ ID NO: 104)
LNTTILTP NGNEDTTADF FLTTMPTDSL SVSTLPLPEV

QCFVFNVEYM NCTWNSSSEP QPTNLTLHYW YKNSDNDKVQ

KCSHYLFSEE ITSGCQLQKK EIHLYQTFVV QLQDPREPRR

QATQMLKLQN LVIPWAPENL TLHKLSESQL ELNWNNRFLN

HCLEHLVQYR TDWDHSWTEQ SVDYRHKFSL PSVDGQKRYT

FRVRSRFNPL CGSAQHWSEW SHPIHWGSNT SKENPFLFAL

EAVVISVGSM GLIISLLCVY FWLERTMPRI PTLKNLEDLV

TEYHGNFSAW SGVSKGLAES LQPDYSERLC LVSEIPPKGG

ALGEGPGASP CNQHSPYWAP PCYTLKPET.
```

In some cases, where a TMPP of the present disclosure comprises a variant IL-2 polypeptide, a "cognate co-immunomodulatory polypeptide" is an IL-2R comprising polypeptides comprising the amino acid sequences of human IL-2Ra, human IL-2Rβ, and IL-2Ry shown above.

In some cases, a variant IL-2 polypeptide exhibits reduced binding affinity to IL-2R, compared to the binding affinity of an IL-2 polypeptide comprising a wild-type IL-2 polypeptide (e.g., a wild-type IL-2 polypeptide having the amino acid sequence shown above). For example, in some cases, a variant IL-2 polypeptide binds IL-2R with a binding affinity that is at least 10% less, at least 15% less, at least 20% less, at least 25%, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence APTSSSTKKT QLQLEHLLLD LQMILNGINN YKNPKLTRML TFKFYMPKKA TELKHLQCLEEELKPLEEVL NLAQSKNFHL RPRDLISNIN VIVLELKGSE TTFMCEYADE TATIVEFLNRWITFCQSIIS TLT (SEQ ID NO: 101) for an IL-2R (e.g., an IL-2R comprising polypeptides comprising human IL-2Ra, human IL-2Rβ, and IL-2Ry having the amino acid sequences shown above), when assayed under the same conditions.

In some cases, a variant IL-2 polypeptide has a binding affinity to IL-2R that is from 100 nM to 100 μM. As another example, in some cases, a variant IL-2 polypeptide has a binding affinity for IL-2R (e.g., an IL-2R comprising human IL-2Ra, human IL-2Rβ, and IL-2Ry having the amino acid sequences shown above) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

In some cases, a variant IL-2 polypeptide has a single amino acid substitution, or from 2-10 amino acid substitutions compared to the IL-2 amino acid sequence APTSSSTKKT QLQLEHLLLD LQMILNGINN YKNPKLTRML TFKFYMPKKA TELKHLQCLEEELKPLEEVL NLAQSKNFHL RPRDLISNIN VIVLELKGSE TTFMCEYADE TATIVEFLNRWITFCQSIIS TLT (SEQ ID NO: 101).

Suitable IL-2 variants include a polypeptide that comprises an amino acid sequence having at least 60%, at least 70%, at least 80%, at least 90%, at least 95%, at least 98%, at least 99%, or 100%, amino acid sequence identity to any one of the following amino acid sequences:

APTSSSTKKT QLQLEHLLLD LQMILNGINN YKNPKLTRML TXKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:105), where X is any amino acid other than Phe. In some cases, X is Ala;

APTSSSTKKT QLQLEHLLLX LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:106), where X is any amino acid other than Asp. In some cases, X is Ala;

APTSSSTKKT QLQLXHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:107), where X is any amino acid other than Glu. In some cases, X is Ala;

APTSSSTKKT QLQLEXLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:108), where X is any amino acid other than His. In some cases, X is Ala. In some cases, X is Arg. In some cases, X is Asn. In some cases, X is Asp. In some cases, X is Cys. In some cases, X is Glu. In some cases, X is Gln. In some cases, X is Gly. In some cases, X is Ile. In some cases, X is Lys. In some cases, X is Leu. In some cases, X is Met. In some cases, X is Phe. In some cases, X is Pro. In some cases, X is Ser. In some cases, X is Thr. In some cases, X is Tyr. In some cases, X is Trp. In some cases, X is Val;

APTSSSTKKT QLQLEHLLLD LQMILNGINN YKNPKLTRML TFKFXMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:109), where X is any amino acid other than Tyr. In some cases, X is Ala;

APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TAT IVEFLNR WITFCXSI IS TLT (SEQ ID NO:110), where X is any amino acid other than Gln. In some cases, X is Ala;

APTSSSTKKT QLQLEX$_1$LLLD LQMILNGINN YKNPKLTRML TX$_2$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:111), where X$_1$ is any amino acid other than His, and where X$_2$ is any amino acid other than Phe. In some cases, X$_1$ is Ala. In some cases, X$_2$ is Ala. In some cases, X$_1$ is Ala; and X$_2$ is Ala. In some cases, X$_1$ is Thr; and X$_2$ is Ala;

APTSSSTKKT QLQLEHLLLX$_1$LQMILNGINN YKNPKLTRML TX$_2$KFYMPKKA TELKHLQCLE EELKPLEEVL NLAQSKNFHL RPRDLISNIN VIVLELKGSE TTFMCEYADE TAT I VEFLNR WI TFCQS I I S TLT (SEQ ID NO:112), where X$_1$ is any amino acid other than Asp; and where X$_2$ is any amino acid other than Phe. In some cases, X$_1$ is Ala. In some cases, X$_2$ is Ala. In some cases, X$_1$ is Ala; and X$_2$ is Ala;

APTSSSTKKT QLQLX$_1$HLLLX$_2$LQMILNGINN YKNPKLTRML TX$_3$KFYMPKKA TELKHLQCLE EELKPLEEVL NLAQSKNFHL RPRDLISNIN VIVLELKGSE TTFMCEYADE TAT I VEFLNR WI TFCQS I I S TLT (SEQ ID NO:113), where X$_1$ is any amino acid other than Glu; where X$_2$ is any amino acid other than Asp; and where X$_3$ is any amino acid other than Phe. In some cases, X$_1$ is Ala. In some cases, X$_2$ is Ala. In some cases, X$_3$ is Ala. In some cases, X$_1$ is Ala; X$_2$ is Ala; and X$_3$ is Ala;

APTSSSTKKT QLQLEX$_1$LLLX$_2$LQMILNGINN YKNPKLTRML TX$_3$KFYMPKKA TELKHLQCLE EELKPLEEVL NLAQSKNFHL RPRDLISNIN VIVLELKGSE TTFMCEYADE TAT I VEFLNR WI TFCQS I I S TLT (SEQ ID NO:114), where X$_1$ is any amino acid other than His; where X$_2$ is any amino acid other than Asp; and where X$_3$ is any amino acid other than Phe. In some cases, X$_1$ is Ala. In some cases, X$_2$ is Ala. In some cases, X$_3$ is Ala. In some cases, X$_1$ is Ala; X$_2$ is Ala; and X$_3$ is Ala;

APTSSSTKKT QLQLEHLLLX$_1$LQMILNGINN YKNPKLTRML TX$_2$KFYMPKKA TELKHLQCLE EELKPLEEVL NLAQSKNFHL RPRDLISNIN VIVLELKGSE TTFMCEYADE TAT I VEFLNR WI TFCX$_3$S I I S TLT (SEQ ID NO:115), where X$_1$ is any amino acid other than Asp; where X$_2$ is any amino acid other than Phe; and where X$_3$ is any amino acid other than Gln. In some cases, X$_1$ is Ala. In some cases, X$_2$ is Ala. In some cases, X$_3$ is Ala. In some cases, X$_1$ is Ala; X$_2$ is Ala; and X$_3$ is Ala;

APTSSSTKKT QLQLEHLLLX$_1$LQMILNGINN YKNPKLTRML TX$_2$KFX$_3$MPKKA TELKHLQCLE EELKPLEEVL NLAQSKNFHL RPRDLISNIN VIVLELKGSE TTFMCEYADE TAT I VEFLNR WI TFCQS I I S TLT (SEQ ID NO:116), where X$_1$ is any amino acid other than Asp; where X$_2$ is any amino acid other than Phe; and where X$_3$ is any amino acid other than Tyr. In some cases, X$_1$ is Ala. In some cases, X$_2$ is Ala. In some cases, X$_3$ is Ala. In some cases, X$_1$ is Ala; X$_2$ is Ala; and X$_3$ is Ala;

APTSSSTKKT QLQLEX$_1$LLLX$_2$LQMILNGINN YKNPKLTRML TX$_3$KFX$_4$MPKKA TELKHLQCLE EELKPLEEVL NLAQSKNFHL RPRDLISNIN VIVLELKGSE TTFMCEYADE TAT I VEFLNR WI TFCQS I I S TLT (SEQ ID NO:117), where X$_1$ is any amino acid other than His; where X$_2$ is any amino acid other than Asp; where X$_3$ is any amino acid other than Phe; and where X$_4$ is any amino acid other than Tyr. In some cases, X$_1$ is Ala. In some cases, X$_2$ is Ala. In some cases, X$_3$ is Ala. In some cases, X$_4$ is Ala. In some cases, X$_1$ is Ala; X$_2$ is Ala; X$_3$ is Ala; and X$_4$ is Ala;

APTSSSTKKT QLQLEHLLLX$_1$LQMILNGINN YKNPKLTRML TX$_2$KFX$_3$MPKKA TELKHLQCLE EELKPLEEVL NLAQSKNFHL RPRDLISNIN VIVLELKGSE TTFMCEYADE TAT I VEFLNR WI TFCX$_4$S I I S TLT (SEQ ID NO:118), where X$_1$ is any amino acid other than Asp; where X$_2$ is any amino acid other than Phe; where X$_3$ is any amino acid other than Tyr; and where X$_4$ is any amino acid other than Gln. In some cases, X$_1$ is Ala. In some cases, X$_2$ is Ala. In some cases, X$_3$ is Ala. In some cases, X$_4$ is Ala. In some cases, X$_1$ is Ala; X$_2$ is Ala; X$_3$ is Ala; and X$_4$ is Ala;

APTSSSTKKT QLQLEX$_1$LLLX$_2$LQMILNGINN YKNPKLTRML TX$_3$KFX$_4$MPKKA TELKHLQCLE EELKPLEEVL NLAQSKNFHL RPRDLISNIN VIVLELKGSE TTFMCEYADE TAT I VEFLNR WI TFCX$_5$S I I S TLT (SEQ ID NO:119), where X$_1$ is any amino acid other than His; where X$_2$ is any amino acid other than Asp; where X$_3$ is any amino acid other than Phe; where X$_4$ is any amino acid other than Tyr; and where X$_5$ is any amino acid other than Gln. In some cases, X$_1$ is Ala. In some cases, X$_2$ is Ala. In some cases, X$_3$ is Ala. In some cases, X$_4$ is Ala. In some cases, X$_5$ is Ala. In some cases, X$_1$ is Ala; X$_2$ is Ala; X$_3$ is Ala; X$_4$ is Ala; X$_5$ is Ala; and APTSSSTKKT QLQLEX$_1$LLLD LQMILNGINN YKNPKLTRML TX$_2$KFYMPKKA TELKHLQCLE EELKPLEEVL NLAQSKNFHL RPRDLISNIN VIVLELKGSE TTFMCEYADE TATIVEFLNR WITFCX$_3$SIIS TLT (SEQ ID NO:120), where X$_1$ is any amino acid other than His; where X$_2$ is any amino acid other than Phe; and where X$_3$ is any amino acid other than Gln. In some cases, X$_1$ is Ala. In some cases, X$_2$ is Ala. In some cases, X₃ is Ala. In some cases, X₁ is Ala; X₂ is Ala; and X₃ is Ala.

In some cases, a suitable variant IL-2 polypeptide comprises the amino acid sequence: APTSSSTKKT QLQL-EALLLD LQMILNGINN YKNPKLTRML TAKFYMPKKA TELKHLQCLEEELKPLEEVL NLAQSKNFHL RPRDLISNIN VIVLELKGSE TTFMC-EYADE TATIVEFLNRWITFCQSIIS TLT (SEQ ID NO:121), i.e., the variant IL-2 polypeptide has the amino acid sequence of wild-type IL-2 but with H16A and F42A substitutions (shown in bold).

Wild-type TGF-β and variant TGF-β polypeptides

In some cases, at least one of the one or more immunomodulatory polypeptides present in a TMMP of the present disclosure comprises the amino acid sequence of a wild-type TGF-13 polypeptide. In other instances, at least one of the one or more immunomodulatory polypeptides present in a TMMP of the present disclosure is a variant TGF-13 polypeptide. Wild-type TGF-13 and variant TGF-13 polypeptides bind to TGF receptor.

As noted above, in some cases, the immunomodulatory polypeptide present in a TMMP of the present disclosure is a TGF-13 polypeptide. Amino acid sequences of TGF-13 polypeptides are known in the art. In some cases, the immunomodulatory polypeptide present in a TMMP of the present disclosure is a TGF-01 polypeptide. immunomodulatory polypeptide present in a TMMP of the present disclosure is a TGF-02 polypeptide. immunomodulatory polypeptide present in a TMMP of the present disclosure is a TGF-03 polypeptide. A suitable TGF-13 polypeptide can comprise an amino acid sequence having at least 60%, at least 70%, at least 80%, at least 90%, at least 95%, at least 98%, at least 99%, or 100%, amino acid sequence identity to the mature form of a human TGF-β1 polypeptide, a human TGF-β32 polypeptide, or a human TGF-03 polypeptide. A suitable TGF-13 polypeptide can have a length of from about 100 amino acids to about 125 amino acids; for example, a suitable TGF-13 polypeptide can have a length of from about 100 amino acids to about 105 amino acids, from about 105 amino acids to about 110 amino acids, from about 110 amino acids to about 115 amino acids, from about 115 amino acids to about 120 amino acids, or from about 120 amino acids to about 125 amino acids.

A suitable TGF-01 polypeptide can comprise an amino acid sequence having at least 60%, at least 70%, at least 80%, at least 90%, at least 95%, at least 98%, at least 99%, or 100%, amino acid sequence identity to the following TGF-01 amino acid sequence: AL DTNYCFSSTE KNCCVRQLYI DFRKDLGWKW IHEPKGYHAN FCLGPCPYIW SLDTQYSKVL ALYNQHNPGA SAAPCCVPQA LEPLPIVYYV GRKPKVEQLS NMIVRSCKCS (SEQ ID NO: 122); or the foregoing sequence comprising a C77S substitution; where the TGF-01 polypeptide has a length of about 112 amino acids.

A suitable TGF-02 polypeptide can comprise an amino acid sequence having at least 60%, at least 70%, at least 80%, at least 90%, at least 95%, at least 98%, at least 99%, or 100%, amino acid sequence identity to the following TGF-02 amino acid sequence: ALDAAYCF RNVQDNC-CLR PLYIDFKRDL GWKWIHEPKG YNANFCAGAC PYLWSSDTQH SRVLSLYNTI NPEASASPCC VSQDLE-PLTI LYYIGKTPKI EQLSNMIVKS CKCS (SEQ ID NO: 123); or the foregoing sequence comprising a C79S substitution, where the TGF-β2 polypeptide has a length of about 112 amino acids.

A suitable TGF-β3 polypeptide can comprise an amino acid sequence having at least 60%, at least 70%, at least 80%, at least 90%, at least 95%, at least 98%, at least 99%, or 100% amino acid sequence identity to the following TGF-β3 amino acid sequence: ALDTNYCFRN LEEN-CCVRPL YIDFRQDLGW KWVHEPKGYY ANFCSGPCPY LRSADTTHST VLGLYNTLNP EASASPCCVP QDLEPLTILY YVGRTPKVEQ LSNMVVKSCK CS (SEQ ID NO:124); or the foregoing sequence comprising a C77S substitution, where the TGF-β3 polypeptide has a length of about 112 amino acids.

FasL and FasL Variants

In some cases, at least one of the one or more immunomodulatory polypeptides present in a TMMP of the present disclosure comprises the amino acid sequence of a wild-type Fas ligand (FasL) polypeptide. In other instances, at least one of the one or more immunomodulatory polypeptides present in a TMMP of the present disclosure is a variant FasL polypeptide. Wild-type FasL and variant FasL polypeptides bind to Fas receptor (FasR). FasL is also known as CD95L or CD178.

Human FasL polypeptide can have the following amino acid sequence: MQQPFNYPYP QIYWVDSSAS SPWAPPGTVL PCPTSVPRRP GQRRPPPPPP PPPLPPPPPP PPLPPLPLPP LKKRGNHSTG LCLL-VMFFMV LVALVGLGLG MFQLFHLQKE LAEL-RESTSQ MHTASSLEKQ IGHPSPPPEK KELRKVAHLT GKSNSRSMPL EWEDTYGIVL LSGVKYKKGG LVI-NETGLYF VYSKVYFRGQ SCNNLPLSHK VYMRN-SKYPQ DLVMMEGKMM SYCTTGQMWA RSSYL-GAVFN LTSADHLYVN VSELSLVNFE ESQTFFGLYK L (SEQ ID NO: 125). In some cases, a FasL polypeptide suitable for inclusion in a TMMP of the present disclosure comprises an amino acid sequence having at least 60%, at least 70%, at least 80%, at least 90%, at least 95%, at least 98%, at least 99%, or 100%, amino acid sequence identity to a contiguous stretch of from about 150 amino acids to about 175, from about 175 amino acids to about 200 amino acids, from about 200 amino acids to about 250 amino acids, or from about 250 amino acids to about 281 amino acids, of the following amino acid sequence: MQQPFNYPYP QIYWVDSSAS SPWAPPGTVL PCPTSVPRRP GQRRPPPPPP PPPLPPPPPP PPLPPLPLPP LKKRGNH-STG LCLLVMFFMV LVALVGLGLG MFQLFHLQKE LAELRESTSQ MHTASSLEKQ IGHPSPPPEK KELRK-VAHLT GKSNSRSMPL EWEDTYGIVL LSGVKYKKGG LVINETGLYF VYSKVYFRGQ SCNNLPLSHK VYMRN-SKYPQ DLVMMEGKMM SYCTTGQMWA RSSYL-GAVFN LTSADHLYVN VSELSLVNFE ESQTFFGLYK L (SEQ ID NO:125).

In some cases, a FasL polypeptide suitable for inclusion in a TMMP of the present disclosure comprises an amino acid sequence having at least 60%, at least 70%, at least 80%, at least 90%, at least 95%, at least 98%, at least 99%, or 100%, amino acid sequence identity to the following amino acid sequence: IGHPSPPPEK KELRKVAHLT GKSNSRSMPL EWEDTYGIVL LSGVKYKKGG LVI-NETGLYF VYSKVYFRGQ SCNNLPLSHK VYMRN-SKYPQ DLVMMEGKMM SYCTTGQMWA RSSYL-GAVFN LTSADHLYVN VSELSLVNFE ESQTFFGLYK (SEQ ID NO:237); and has a length of about 150, 151, or 152 amino acids.

In some cases, a FasL polypeptide suitable for inclusion in a TMMP of the present disclosure comprises an amino acid sequence having at least 60%, at least 70%, at least 80%, at least 90%, at least 95%, at least 98%, at least 99%, or 100%, amino acid sequence identity to the following amino acid sequence: QLFHLQKELAELRESTS QMHTAS SLEKQIGHPSPPPEKKELRKVAHLTGKSNSRSMPLEW EDTY GIVLLSGVKYKKGGLVINETGLYFVYSKVY-FRGQSCNNLPLSHKVYMRNSKYPQDLVMMEGK MMSYCTTGQMWARSSYLGAVFNLTSADHLYVNV-SELSLVNFEESQTFFGLYKL (SEQ ID NO: 126); and can have a length of about 179 amino acids.

A FasR polypeptide can comprise an amino acid sequence having at least 60%, at least 70%, at least 80%, at least 90%, at least 95%, at least 98%, at least 99%, or 100%, amino acid sequence identity to the following amino acid sequence: MLGIWTLLPL VLTSVARLSS KSVNAQVTDI NSK- GLELRKT VTTVETQNLE GLHHDGQFCH KPCPPGERKA RDCTVNGDEP DCVPCQEGKE YTDKAHFSSK CRRCRLCDEG HGLEVEINCT RTQNTKCRCK PNFFCNSTVC EHCDPCTKCE HGIIKE- CTLT SNTKCKEEGS RSNLGWLCLL LLPIPLIVWV KRKEVQKTCR KHRKENQGSH ESPTLNPETV AINLSDVDLS KYITTIAGVM TLSQVKGFVR KNGVNEAKID EIKNDNVQDT AEQKVQLLRN WHQLHGKKEA YDTLIKDLKK ANLCTLAEKI QTIILKDITS DSENSNFRNE IQSLV (SEQ ID NO:127).

Exemplary TMMPs

As noted above, a TMMP of the present disclosure comprises a heterodimer (e.g., comprises two heterodimers), where the heterodimer comprises a first polypeptide chain and a second polypeptide chain that are disulfide bonded to one another.

TMMPs that are Disulfide Bonded Via a Cys in the MHC Class II Alpha Chain and a Cys in the MHC Class II Beta Chain As noted above, in some cases, a TMMP of the present disclosure comprises a heterodimer comprising a first polypeptide chain comprising: i) a T1D peptide; and ii) a first MHC class II polypeptide; and b) a second polypeptide comprising a second MHC class II polypeptide, where the first and/or the second polypeptides comprise one or more immunomodulatory polypeptides, optionally wherein the first and/or the second polypeptide comprises an Ig Fc polypeptide; where the first MHC class II polypeptide comprises a substitution of an amino acid (other than a Cys) with a Cys (a "first Cys"), and the second MHC class II polypeptide comprises a substitution of an amino acid (other than a Cys) with a Cys (a "second" Cys), where the first polypeptide and the second polypeptide are joined by a disulfide bond formed between the first Cys and the second Cys.

The first MHC class II polypeptide can be a DRB MHC class II polypeptide comprising an amino acid sequence having at least 80%, at least 85%, at least 90%, at least 95%, at least 98%, or at least 99% amino acid sequence identity to the amino acid sequence depicted in FIG. 14A; and having an amino acid substitution selected from P5C, F7C, Q10C, N19C, G20C, H33C, G151C, D152C, and W153C. The second MHC class II polypeptide can be a DRA MHC class II polypeptide comprising an amino acid sequence having at least 80%, at least 85%, at least 90%, at least 95%, at least 98%, or at least 99%, amino acid sequence identity to the amino acid sequence depicted in FIG. 13A; and having an amino acid substitution selected from E3C, E4C, F12C, G28C, D29C, I72C, K75C, T80C, P81C, I82C, T93C, N94C, and S95C.

As one example, in some cases, the first MHC class II polypeptide is a DRB MHC class II polypeptide comprising a substitution at a residue selected from the group consisting of P5C, H33C, G151C, and W153, and the second MHC class II polypeptide is a DRA MHC class II polypeptide comprising a substitution selected from the group consisting of P81C, I82C, and D29C. For example, the MHC class II β chain polypeptide can comprise an amino acid sequence having at least 80%, at least 85%, at least 90%, at least 95%, at least 98%, or at least 99% amino acid sequence identity to the amino acid sequence depicted in FIG. 14A, where the polypeptide comprises a Cys at a residue position selected from the group consisting of 5, 33, 151, and 153; and the MHC class II α chain polypeptide can comprise an amino acid sequence having at least 80%, at least 85%, at least 90%, at least 95%, at least 98%, or at least 99% amino acid sequence identity to the amino acid sequence depicted in FIG. 13A, where the polypeptide comprises a Cys at a residue selected from the group consisting of 81, 82, and 29.

As another example, the disulfide can be formed between one of the specific pairs of Cys residues in Table 3, below:

TABLE 3

| DRB MHC Class II Polypeptide Substitution | DRA MHC Class II Polypeptide Substitution |
| --- | --- |
| N19C | E3C |
| G20C | E3C |
| N19C | E4C |
| G20C | E4C |
| F7C | F12C |
| Q10C | F12C |
| G151C | G28C |
| D152C | G28C |
| W153C | G28C |
| G151C | D29C |
| D152C | D29C |
| W153C | D29C |
| F7C | T80C |
| P5C | T80C |
| H33C | T80C |
| P5C | P81C |
| H33C | P81C |
| F7C | P81C |
| H33C | I82C |
| F7C | I82C |
| P5C | I82C |
| Q156C | T93C |
| W153C | T93C |
| Q156C | N94C |
| N120C | N94C |
| Q156C | S95C |
| N120C | S95C |

For example, the DRB MHC class II polypeptide can comprise an amino acid sequence having at least 80%, at least 85%, at least 90%, at least 95%, at least 98%, or at least 99% amino acid sequence identity to the amino acid sequence depicted in FIG. 14A, and the DRA MHC class II polypeptide can comprise an amino acid sequence having at least 80%, at least 85%, at least 90%, at least 95%, at least 98%, or at least 99% amino acid sequence identity to the amino acid sequence depicted in FIG. 13A, wherein the β chain polypeptide and α chain polypeptides are joined by a disulfide formed between a pair of Cys residues selected from the group consisting of: β chain polypeptide residue 5 and α chain polypeptide residue 81; β chain polypeptide residue 33 and α chain polypeptide residue 81; 0 chain polypeptide residue 33 and α chain polypeptide residue 82; β chain polypeptide residue 151 and α chain polypeptide residue 29; and β chain polypeptide residue 153 and α chain polypeptide residue 29.

TMMP Bonded Through a Disulfide Bond Between β P5C and α P81C

As one example, a TMMP of the present disclosure comprises a heterodimer comprising: a) a first polypeptide comprising, in order from N-terminus to C-terminus: i) a T1D peptide; and ii) a DRB MHC class II polypeptide comprising a P5C substitution; and b) a second polypeptide comprising, in order form N-terminus to C-terminus: i) one or more immunomodulatory polypeptides; ii) a DRA MHC class II polypeptide comprising a P81C substitution; and (optionally) iii) an Ig Fc polypeptide. (See FIG. 5, MOD Position 1.) As another example, a TMMP of the present disclosure comprises a heterodimer comprising: a) a first polypeptide comprising, in order from N-terminus to C-terminus: i) a T1D peptide; and ii) a DRB MHC class II polypeptide comprising a P5C substitution; and b) a second polypeptide comprising, in order form N-terminus to C-terminus: i) a DRA MHC class II polypeptide comprising a P81C substitution; ii) an Ig Fc polypeptide; and iii) one or more immunomodulatory polypeptides. (See FIG. 5, MOD Position 3.) Alternatively, the one or more immunomodulatory polypeptides can be at Position 2, 4 or 5 as those positions are described above and depicted schematically in FIG. 5. In the above embodiments, the first polypeptide and the second polypeptide are linked via a disulfide bond between the Cys at residue 5 in the DRB MHC class II polypeptide and the Cys at residue 81 in the DRA MHC class II polypeptide. In any of the above embodiments, linkers that do not comprise a Cys optionally can be used to connect the components of the first or second polypeptide. In any of the above embodiments, in some cases, the one or more immunomodulatory polypeptides is a PD-L1 polypeptide or variant thereof, a TGF-β polypeptide or variant thereof, an IL-2 polypeptide or variant thereof, or a FasL polypeptide or variant thereof. In some cases, the Ig Fc polypeptide is present and is a human IgG1 Fc polypeptide, optionally comprising L234A and L235A substitutions (L14A and L15A of the amino acid sequence depicted in FIG. 12A). In some cases, the DRB MHC class II polypeptide comprises an amino acid sequence having at least 80%, at least 85%, at least 90%, at least 95%, at least 98%, or at least 99% amino acid sequence identity to the amino acid sequence depicted in FIG. 14B, and comprises a Cys at position 5. In some cases, the DRA MHC class II polypeptide comprises an amino acid sequence having at least 80%, at least 85%, at least 90%, at least 95%, at least 98%, or at least 99% amino acid sequence identity to the amino acid sequence depicted in FIG. 13J, and comprises a Cys at position 81. In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO: 90: proIns 76-90: K88S), and GAGSLQPLALEGSLQKRG (SEQ ID NO:93; proIns 73-90). In some cases, the T1D peptide is a GAD peptide. In some cases, the T1D peptide is a GAD peptide selected from

```
                            (SEQ ID NO: 87; GAD65 555-567)
NFFRMVISNPAAT
and (SEQ ID NO: 88; GAD65 555-567; F557I)
NFIRMVISNPAAT.
```

TMMP Bonded Through a Disulfide Bond Between β H33C and α P81C

As one example, a TMMP of the present disclosure comprises a heterodimer comprising: a) a first polypeptide comprising, in order from N-terminus to C-terminus: i) a T1D peptide; and ii) a DRB MHC class II polypeptide comprising an H33C substitution; and b) a second polypeptide comprising, in order form N-terminus to C-terminus: i) one or more immunomodulatory polypeptides; ii) a DRA MHC class II polypeptide comprising a P81C substitution; and (optionally) iii) an Ig Fc polypeptide. (See FIG. 5, MOD Position 1.) As another example, a TMMP of the present disclosure comprises a heterodimer comprising: a) a first polypeptide comprising, in order from N-terminus to C-terminus: i) a T1D peptide; and ii) a DRB MHC class II polypeptide comprising an H33C substitution; and b) a second polypeptide comprising, in order from N-terminus to C-terminus: i) a DRA MHC class II polypeptide comprising a P81C substitution; ii) an Ig Fc polypeptide; and iii) one or more immunomodulatory polypeptides. (See FIG. 5, MOD Position 3). Alternatively, the one or more immunomodulatory polypeptides can be at Position 2, 4 or 5 as those positions are described above and depicted schematically in FIG. 5. In the above embodiments, the first polypeptide and the second polypeptide are linked via a disulfide bond between the Cys at residue 33 in the DRB MHC class II polypeptide and the Cys at residue 81 in the DRA MHC class II polypeptide. In any of the above embodiments, linkers that do not comprise a Cys can be used to connect the components of the first or second polypeptide. In any of the above embodiments, in some cases, the one or more immunomodulatory polypeptides is a PD-L1 polypeptide or variant thereof, a TGF-β polypeptide or variant thereof, an IL-2 polypeptide or variant thereof, or a FasL polypeptide or variant thereof. In some cases, the Ig Fc polypeptide is present and is a human IgG1 Fc polypeptide, optionally comprising L234A and L235A substitutions (L14A and L15A of the amino acid sequence depicted in FIG. 12A). In some cases, the DRB MHC class II polypeptide comprises an amino acid sequence having at least 80%, at least 85%, at least 90%, at least 95%, at least 98%, at least 99%, or 100%, amino acid sequence identity to the amino acid sequence depicted in FIG. 14G, and comprises a Cys at position 33. In some cases, the DRA MHC class II polypeptide comprises an amino acid sequence having at least 80%, at least 85%, at least 90%, at least 95%, at least 98%, at least 99%, or 100%, amino acid sequence identity to the amino acid sequence depicted in FIG. 13J, and comprises a Cys at position 81. In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93; proIns 73-90). In some cases, the T1D peptide is a GAD peptide. In some cases, the T1D peptide is a GAD peptide selected from

```
                            (SEQ ID NO: 87; GAD65 555-567)
NFFRMVISNPAAT
and (SEQ ID NO: 88; GAD65 555-567; F557I)
NFIRMVISNPAAT.
```

TMMP Bonded Through a Disulfide Bond Between β H33C and α I82C

As one example, a TMMP of the present disclosure comprises a heterodimer comprising: a) a first polypeptide comprising, in order from N-terminus to C-terminus: i) a T1D peptide; and ii) a DRB MHC class II polypeptide comprising an H33C substitution; and b) a second polypeptide comprising, in order form N-terminus to C-terminus: i) one or more immunomodulatory polypeptides; ii) a DRA MHC class II polypeptide comprising an I82C substitution;

and (optionally) iii) an Ig Fc polypeptide. (See FIG. 5, MOD Position 1.) As another example, a TMMP of the present disclosure comprises a heterodimer comprising: a) a first polypeptide comprising, in order from N-terminus to C-terminus: i) a T1D peptide; and ii) a DRB MHC class II polypeptide comprising an H33C substitution; and b) a second polypeptide comprising, in order form N-terminus to C-terminus: i) a DRA MHC class II polypeptide comprising an 182C substitution; ii) an Ig Fc polypeptide; and iii) one or more immunomodulatory polypeptides. (See FIG. 5, MOD Position 3.) Alternatively, the one or more immunomodulatory polypeptides can be at Position 2, 4 or 5 as those positions are described above and depicted schematically in FIG. 5. In the above embodiments, the first polypeptide and the second polypeptide are linked via a disulfide bond between the Cys at residue 33 in the DRB MHC class II polypeptide and the Cys at residue 82 in the DRA MHC class II polypeptide. In any of the above embodiments, linkers that do not comprise a Cys optionally can be used to connect the components of the first or second polypeptide. In any of the above embodiments, in some cases, the one or more immunomodulatory polypeptides is a PD-L1 polypeptide or variant thereof, a TGF-β polypeptide or variant thereof, an IL-2 polypeptide or variant thereof, or a FasL polypeptide or variant thereof. In some cases, the Ig Fc polypeptide is present and is a human IgG1 Fc polypeptide, optionally comprising L234A and L235A substitutions (L14A and L15A of the amino acid sequence depicted in FIG. 12A). In some cases, the DRB MHC class II polypeptide comprises an amino acid sequence having at least 80%, at least 85%, at least 90%, at least 95%, at least 98%, at least 99%, or 100%, amino acid sequence identity to the amino acid sequence depicted in FIG. 14G, and comprises a Cys at position 33. In some cases, the DRA MHC class II polypeptide comprises an amino acid sequence having at least 80%, at least 85%, at least 90%, at least 95%, at least 98%, at least 99%, or 100%, amino acid sequence identity to the amino acid sequence depicted in FIG. 13K, and comprises a Cys at position 82. In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93; proIns 73-90). In some cases, the T1D peptide is a GAD peptide. In some cases, the T1D peptide is a GAD peptide selected from

```
                        (SEQ ID NO: 87; GAD65 555-567)
NFFRMVISNPAAT
and (SEQ ID NO: 88; GAD65 555-567; F557I)
NFIRMVISNPAAT.
```

TMMP Bonded Through a Disulfide Bond Between β G151C and α D29C

As one example, a TMMP of the present disclosure comprises a heterodimer comprising: a) a first polypeptide comprising, in order from N-terminus to C-terminus: i) a T1D peptide; and ii) a DRB MHC class II polypeptide comprising a G151C substitution; and b) a second polypeptide comprising, in order form N-terminus to C-terminus: i) one or more immunomodulatory polypeptides; ii) a DRA MHC class II polypeptide comprising a D29C substitution; and (optionally) iii) an Ig Fc polypeptide. (See FIG. 5, MOD Position 1.) As another example, a TMMP of the present disclosure comprises a heterodimer comprising: a) a first polypeptide comprising, in order from N-terminus to C-terminus: i) a T1D peptide; and ii) a DRB MHC class II polypeptide comprising a G151C substitution; and b) a second polypeptide comprising, in order form N-terminus to C-terminus: i) a DRA MHC class II polypeptide comprising a D29C substitution; ii) an Ig Fc polypeptide; and iii) one or more immunomodulatory polypeptides. (See FIG. 5, MOD Position 3.) [Alternatively, the one or more immunomodulatory polypeptides can be at Position 2, 4 or 5 as those positions are described above and depicted schematically in FIG. 5. In the above embodiments, the first polypeptide and the second polypeptide are linked via a disulfide bond between the Cys at residue 151 in the DRB MHC class II polypeptide and the Cys at residue 29 in the DRA MHC class II polypeptide. In any of the above embodiments, linkers that do not comprise a Cys optionally can be used to connect the components of the first or second polypeptide. In any of the above embodiments, in some cases, the one or more immunomodulatory polypeptides is a PD-L1 polypeptide or variant thereof, a TGF-β polypeptide or variant thereof, an IL-2 polypeptide or variant thereof, or a FasL polypeptide or variant thereof. In some cases, the Ig Fc polypeptide is present and is a human IgG1 Fc polypeptide, optionally comprising L234A and L235A substitutions (L14A and L15A of the amino acid sequence depicted in FIG. 12A). In some cases, the DRB MHC class II polypeptide comprises an amino acid sequence having at least 80%, at least 85%, at least 90%, at least 95%, at least 98%, or at least 99%, amino acid sequence identity to the amino acid sequence depicted in FIG. 14H, and comprises a Cys at position 151. In some cases, the DRA MHC class II polypeptide comprises an amino acid sequence having at least 80%, at least 85%, at least 90%, at least 95%, at least 98%, at least 99%, or 100%, amino acid sequence identity to the amino acid sequence depicted in FIG. 13F, and comprises a Cys at position 29. In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93; proIns 73-90). In some cases, the T1D peptide is a GAD peptide. In some cases, the T1D peptide is a GAD peptide selected from

```
                        (SEQ ID NO: 87; GAD65 555-567)
NFFRMVISNPAAT
and (SEQ ID NO: 88; GAD65 555-567; F557I)
NFIRMVISNPAAT.
```

TMMP Bonded Through a Disulfide Bond Between β W153C and α D29C

As one example, a TMMP of the present disclosure comprises a heterodimer comprising: a) a first polypeptide comprising, in order from N-terminus to C-terminus: i) a T1D peptide; and ii) a DRB MHC class II polypeptide comprising a W513C substitution; and b) a second polypeptide comprising, in order form N-terminus to C-terminus: i) one or more immunomodulatory polypeptides; ii) a DRA MHC class II polypeptide comprising a D29C substitution; and (optionally) iii) an Ig Fc polypeptide. (See FIG. 5, MOD Position 1.) As another example, a TMMP of the present disclosure comprises a heterodimer comprising: a) a first polypeptide comprising, in order from N-terminus to C-terminus: i) a T1D peptide; and ii) a DRB MHC class II polypeptide comprising a W513C substitution; and b) a second polypeptide comprising, in order form N-terminus to C-terminus: i) a DRA MHC class II α chain polypeptide comprising a D29C substitution; ii) an Ig Fc polypeptide; and iii) one or more immunomodulatory polypeptides. (See FIG. 5, MOD Position 3) Alternatively, the one or more immunomodulatory polypeptides can be at Position 2, 4 or 5 as those positions are described above and depicted schematically in FIG. 5. In the above embodiments, the first polypeptide and the second polypeptide are linked via a disulfide bond between the Cys at residue 153 in the DRB MHC class II polypeptide and the Cys at residue 29 in the DRA MHC class II polypeptide. In any of the above embodiments, linkers that do not comprise a Cys optionally can be used to connect the components of the first or second polypeptide. In any of the above embodiments, in some cases, the one or more immunomodulatory polypeptides is a PD-L1 polypeptide or variant thereof, a TGF-β polypeptide or variant thereof, an IL-2 polypeptide or variant thereof, or a FasL polypeptide or variant thereof. In some cases, the Ig Fc polypeptide is present and is a human IgG1 Fc polypeptide, optionally comprising L234A and L235A substitutions (L14A and L15A of the amino acid sequence depicted in FIG. 12A). In some cases, the DRB MHC class II polypeptide comprises an amino acid sequence having at least 80%, at least 85%, at least 90%, at least 95%, at least 98%, at least 99%, or 100%, amino acid sequence identity to the amino acid sequence depicted in FIG. 14J, and comprises a Cys at position 153. In some cases, the DRA MHC class II polypeptide comprises an amino acid sequence having at least 80%, at least 85%, at least 90%, at least 95%, at least 98%, or at least 99% amino acid sequence identity to the amino acid sequence depicted in FIG. 13F, and comprises a Cys at position 29. In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93; proIns 73-90). In some cases, the T1D peptide is a GAD peptide. In some cases, the T1D peptide is a GAD peptide selected from

```
                        (SEQ ID NO: 87; GAD65 555-567)
NFFRMVISNPAAT
and (SEQ ID NO: 88; GAD65 555-567; F557I)
NFIRMVISNPAAT.
```

TMMPs that are Disulfide Bonded Via a Cys in a Linker Between the T1D Peptide and the First MHC Class II Polypeptide and a Cys in the Second MHC Class II Polypeptide As noted above, in some cases, a TMMP of the present disclosure comprises a heterodimer comprising a first polypeptide chain comprising: i) a T1D peptide; ii) a peptide linker comprising a Cys; and iii) a first MHC class II polypeptide; and b) a second polypeptide comprising a second MHC class II polypeptide, where the first and/or the second polypeptides comprise one or more immunomodulatory polypeptides, optionally wherein the first or the second polypeptide comprises an Ig Fc polypeptide, where the second MHC class II polypeptide comprises a substitution of an amino acid (other than a Cys) with a Cys; and where the first and the second polypeptides are linked via a disulfide bond between the Cys in the peptide linker and the Cys provided by the substitution in the second MHC class II polypeptide.

For example, in some cases, the peptide linker can comprise an amino acid sequence selected from: (CGGGS)(GGGGS)n (SEQ ID NO: 1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10, with n=2 or 3 generally being useful); the first MHC class II polypeptide is a DRB MHC class II polypeptide; and the second MHC class II polypeptide is a DRA MHC class II polypeptide that comprises a substitution of an amino acid (other than a Cys) with a Cys.

Specific examples of the Cys-containing linkers between the T1D peptide and a DRB MHC class II polypeptide and Cys residues in the DRA MHC class II polypeptide that can form a disulfide bond are provided in Table 4, below:

TABLE 4

| Cys-Containing Linker Between the T1D peptide and the DRB MHC Class II Polypeptide | DRA MHC class II polypeptide substitution |
|---|---|
| (CGGGS)(GGGGS)n (SEQ ID NO: 1) | I72C |
| (GCGGS)(GGGGS)n (SEQ ID NO: 2) | I72C |
| (GGCGS)(GGGGS)n (SEQ ID NO: 3) | I72C |
| (GGGCS)(GGGGS)n (SEQ ID NO: 4) | I72C |
| (GGGGC)(GGGGS)n (SEQ ID NO: 5) | I72C |
| (CGGGS)(GGGGS)n (SEQ ID NO: 1) | K75C |
| (GCGGS)(GGGGS)n (SEQ ID NO: 2) | K75C |
| (GGCGS)(GGGGS)n (SEQ ID NO: 3) | K75C |
| (GGGCS)(GGGGS)n (SEQ ID NO: 4) | K75C |
| (GGGGC)(GGGGS)n (SEQ ID NO: 5) | K75C |

In some cases, where the first and second MHC class II polypeptides are DRB and DRA polypeptides, respectively, the DRB MHC class II polypeptide can comprise an amino acid sequence having at least 80%, at least 85%, at least 90%, at least 95%, at least 98%, at least 99%, or 100%, amino acid sequence identity to the amino acid sequence depicted in FIG. 14A. The DRA MHC class II polypeptide can comprise an amino acid sequence having at least 80%, at least 85%, at least 90%, at least 95%, at least 98%, or at least 99%, amino acid sequence identity to the amino acid sequence depicted in FIG. 13A, and can comprise a Cys at, e.g., position 72 or position 75. In any of the above embodiments, n=0, 1, 2, 3, 4 or more, with 2 or 3 typically being used to create a total linker length of 15 or 20 amino acids, although longer lengths may be possible. In any of the above embodiments, linkers that do not comprise a Cys optionally can be used to connect the other components of the first or second polypeptide. In some cases, the Ig Fc polypeptide is present and is a human IgG1 Fc polypeptide, optionally comprising L234A and L235A substitutions (L14A and L15A of the amino acid sequence depicted in FIG. 12A). In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93; proIns 73-90). In some cases, the T1D peptide is a GAD peptide. In some cases, the T1D peptide is a GAD peptide selected from NFFRMVISNPAAT (SEQ ID NO:87; GAD65 555-567) and NFIRMVISNPAAT (SEQ ID NO:88; GAD65 555-567; F557I). In any of the above embodiments, in some cases, the one or more immunomodulatory polypeptides is a PD-L1 polypeptide or variant thereof, a TGF-β polypeptide or variant thereof, an IL-2 polypeptide or variant thereof, or a FasL polypeptide or variant thereof. The one or more immunomodulatory polypeptides can be at Position 1, Position 2, Position 3, Position 4, or Position 5; where the immunomodulatory polypeptide positions are described above and depicted schematically in FIG. 5.

The following are examples of the TMMPs described above in which the first and the second polypeptides are linked via a disulfide bond between the Cys in the peptide linker and the Cys provided by the substitution in the second MHC class II polypeptide, and wherein the first polypeptide is a DRB MHC class II polypeptide (i.e., a DR β chain polypeptide), and the second polypeptide is a DRA MHC class II polypeptide (i.e., a DR α chain polypeptide).

As one example, a TMMP of the present disclosure comprises a heterodimer comprising one of the following five first polypeptides and one of the following two second polypeptides to create a heterodimer having one or more immunomodulatory polypeptides at MOD position 1 or 3:

- a1) a first polypeptide comprising, in order from N-terminus to C-terminus: i) a T1D peptide; ii) a linker comprising the amino acid sequence (CGGGS)(GGGGS)n (SEQ ID NO: 1), where n is an integer from 1 to 10; and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A); or alternatively
- a2) a first polypeptide comprising, in order from N-terminus to C-terminus: i) a T1D peptide; ii) a linker comprising the amino acid sequence (GCGGS)(GGGGS)$_n$ (SEQ ID NO:2), where n is an integer from 1 to 10; and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A); or alternatively
- a3) a first polypeptide comprising, in order from N-terminus to C-terminus: i) a T1D peptide; ii) a linker comprising the amino acid sequence (GGCGS)(GGGGS)n (SEQ ID NO:3), where n is an integer from 1 to 10; and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A); or alternatively
- a4) a first polypeptide comprising, in order from N-terminus to C-terminus: i) a T1D peptide; ii) a linker comprising the amino acid sequence (GGGCS)(GGGGS)n (SEQ ID NO:4), where n is an integer from 1 to 10; and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A); or alternatively
- a5) a first polypeptide comprising, in order from N-terminus to C-terminus: i) a T1D peptide; ii) a linker comprising the amino acid sequence (GGGGC)(GGGGS)$_n$ (SEQ ID NO:5), where n is an integer from 1 to 10; and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A); and
- b1) a second polypeptide comprising, in order from N-terminus to C-terminus: i) an MHC class II α chain comprising a Cys at position 72 (e.g., a DRA MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 13G, and comprising a Cys at position 72); an ii) an Ig Fc polypeptide; and iii) one or more immunomodulatory polypeptides. (See FIG. 5, MOD Position 1.); or, alternatively
- b2) a second polypeptide comprising, in order from N-terminus to C-terminus: i) an MHC class II α chain comprising a Cys at position 75 (e.g., a DRA MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 13G, and comprising a Cys at position 75); an ii) an Ig Fc polypeptide; and iii) one or more immunomodulatory polypeptides. (See FIG. 5, MOD Position 1); or, alternatively
- b3) a second polypeptide comprising, in order from N-terminus to C-terminus: i) an MHC class II α chain comprising a Cys at position 72 (e.g., a DRA MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 3G, and comprising a Cys at position 72); an ii) an Ig Fc polypeptide; and iii) one or more immunomodulatory polypeptides. (See FIG. 5, MOD Position 3.); or, alternatively
- b4) a second polypeptide comprising, in order from N-terminus to C-terminus: i) an MHC class II α chain comprising a Cys at position 75 (e.g., a DRA MHC class II polypeptide comprising an amino acid sequence having at least 80%, at least 85%, at least 90%, at least 95%, at least 98%, at least 99%, or 100% amino acid sequence identity to the amino acid sequence depicted in FIG. 13G, and comprising a Cys at position 75); an ii) an Ig Fc polypeptide; and iii) one or more immunomodulatory polypeptides. (See FIG. 5, MOD Position 3.)

Each of the above combinations of first and second polypeptides for making a TMMP is thus expressly disclosed, i.e., a1-b1, a2-b1, a3-b1, a4-b1, a5-b1, a1-b2, a2-b2, a3-b2, a4-b2 and a5-b2, a1-b3, a2-b3, a3-b3, a4-b3, a5-b3, and a1-b4, a2-b4, a3-b4, a4-b4, and a5-b4.

Alternatively, the one or more immunomodulatory polypeptides in the second polypeptide can be at Position 2, Position 4, or Position 5, which are described above and depicted schematically in FIG. 5.

As noted above, in any of the above embodiments, n=0, 1, 2, 3, 4 or more, with 2 or 3 typically being used to create a total linker length of 15 or 20 amino acids, although longer lengths may be used. In any of the above embodiments, linkers that do not comprise a Cys optionally can be used to connect the other components of the second polypeptide (e.g., a (G4S)n (SEQ ID NO:71) linker can be used between the PD-L1 polypeptide and the DRA MHC class II polypeptide, where n=1, 2, 3, 4, 5, 6, 7, 8, 9, or 10, and a GGSAAAGG (SEQ ID NO:83) linker or AAAGG (SEQ ID NO:82) linker can be used between the DRA MHC class II polypeptide and the Ig Fc polypeptide). In the above embodiments, in some cases, the Ig Fc polypeptide is a human IgG1 Fc polypeptide comprising L234A and L235A substitutions (L14A and L15A of the amino acid sequence depicted in FIG. 12A). In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93; proIns 73-90). In some cases, the T1D peptide is a GAD peptide. In some cases, the T1D peptide is a GAD peptide selected from NFFRMVISNPAAT (SEQ ID NO:87; GAD65 555-567) and NFIRMVISNPAAT (SEQ ID NO:88; GAD65 555-567; F557I).

In any of the above embodiments, in some cases, the one or more immunomodulatory polypeptides is a PD-L1 polypeptide or variant thereof, a TGF-β polypeptide or variant thereof, an IL-2 polypeptide or variant thereof, or a FasL polypeptide or variant thereof. In some cases, when the one or more immunomodulatory polypeptides is a PD-L1 polypeptide or variant thereof, the PD-L1 polypeptide

```
                                        (SEQ ID NO: 99)
FTVTVPKDLYVVEYGSNMTIECKFPVEKQLDLAALIVYWEMEDKNIIQFV

HGEEDLKVQHSSYRQRARLLKDQLSLGNAALQITDVKLQDAGVYRCMISY

GGADYKRITVKVNAPYNKINQRILVVDPVTSEHELTCQAEGYPKAEVIWT

SSDHQVLSGKTTTTNSKREEKLFNVTSTLRINTTTNEIFYCTFRRLDPEE

NHTAELVIPELPLAHPPNER.
```

In some cases, when the one or more immunomodulatory polypeptides comprises an IL-2 polypeptide or variant thereof, the IL-2 polypeptide comprises the following amino acid sequence: APTSSSTKKT QLQLEALLLD LQMILNGINN YKNPKLTRML TAKFYMPKKA TELKHLQCLEEELKPLEEVL NLAQSKNFHL RPRDLISNIN VIVLELKGSE TTFMCEYADE TATIVEFLNRWITFCQSIIS TLT (SEQ ID NO: 121), where the IL-2 polypeptide is a variant comprising Hi 6A and F42A substitutions relative to wild-type IL-2.

Hence, for example, a TMMP in accordance with the above embodiments can comprise the combination of first polypeptide chain α3 and second polypeptide chain b2, wherein i) the MHC class II β chain polypeptide is a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A, ii) the MHC class II α chain polypeptide is a DRA MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 13G, and comprising a Cys at position 75, iii) the T1D peptide is SLQPLALEGSLQSRG (SEQ ID NO:90; proIns 76-90; K88S), iv) the linker between the T1D peptide and the DRB MHC class II polypeptide is (GGCGS)(GGGGS)$_n$ (SEQ ID NO: 128), where n=2 (for a total of 15 amino acids in the linker between the T1D peptide and the DRB MHC class II polypeptide), v) the Ig Fc polypeptide is a human IgG1 Fc polypeptide comprising L234A and L235A substitutions (L14A and L15A of the amino acid sequence depicted in FIG. 12A), v) the one or more immunomodulatory polypeptides comprise a PD-L1 polypeptide comprising the sequence:

```
                                        (SEQ ID NO: 99)
FTVTVPKDLYVVEYGSNMTIECKFPVEKQLDLAALIVYWEMEDKNIIQFV

HGEEDLKVQHSSYRQRARLLKDQLSLGNAALQITDVKLQDAGVYRCMISY

GGADYKRITVKVNAPYNKINQRILVVDPVTSEHELTCQAEGYPKAEVIWT

SSDHQVLSGKTTTTNSKREEKLFNVTSTLRINTTTNEIFYCTFRRLDPEE

NHTAELVIPELPLAHPPNER,
``` vi) there is a (G4S)4 (SEQ ID NO:75) linker between the PD-L1 polypeptide and the DRA MHC class II polypeptide, vii) there is a GGSAAAGG (SEQ ID NO:83) linker between the DRA MHC class II polypeptide and the Ig Fc polypeptide, and viii) there is a disulfide bond joining the Cys in the (GGCGS)(GGGGS)2 (SEQ ID NO:128) linker and the Cys at the K75C substitution in the DRA MHC class II polypeptide.

As another example, a TMMP of the present disclosure can comprise: a) a first polypeptide comprising the amino acid sequence of construct "2938" depicted in FIG. 15A; and b) a second polypeptide comprising the amino acid sequence of construct "3893" depicted in FIG. 15B.

Antigen-Presenting, Disulfide-Linked Heterodimers (I.E., Mod-Less TMMPs)

Figure 16A:
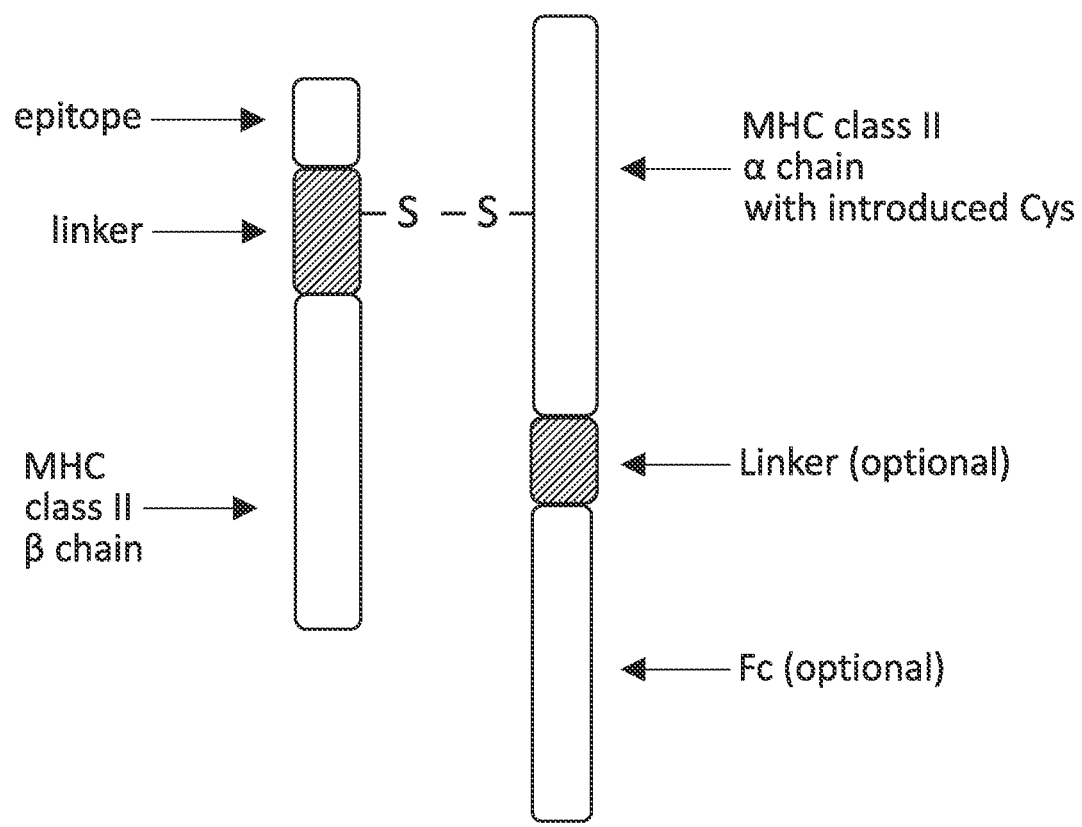
FIG. 16A-16C are schematic depictions of disulfide-linked antigen-presenting polypeptides (APPs) of the present disclosure.
Figure 16B:
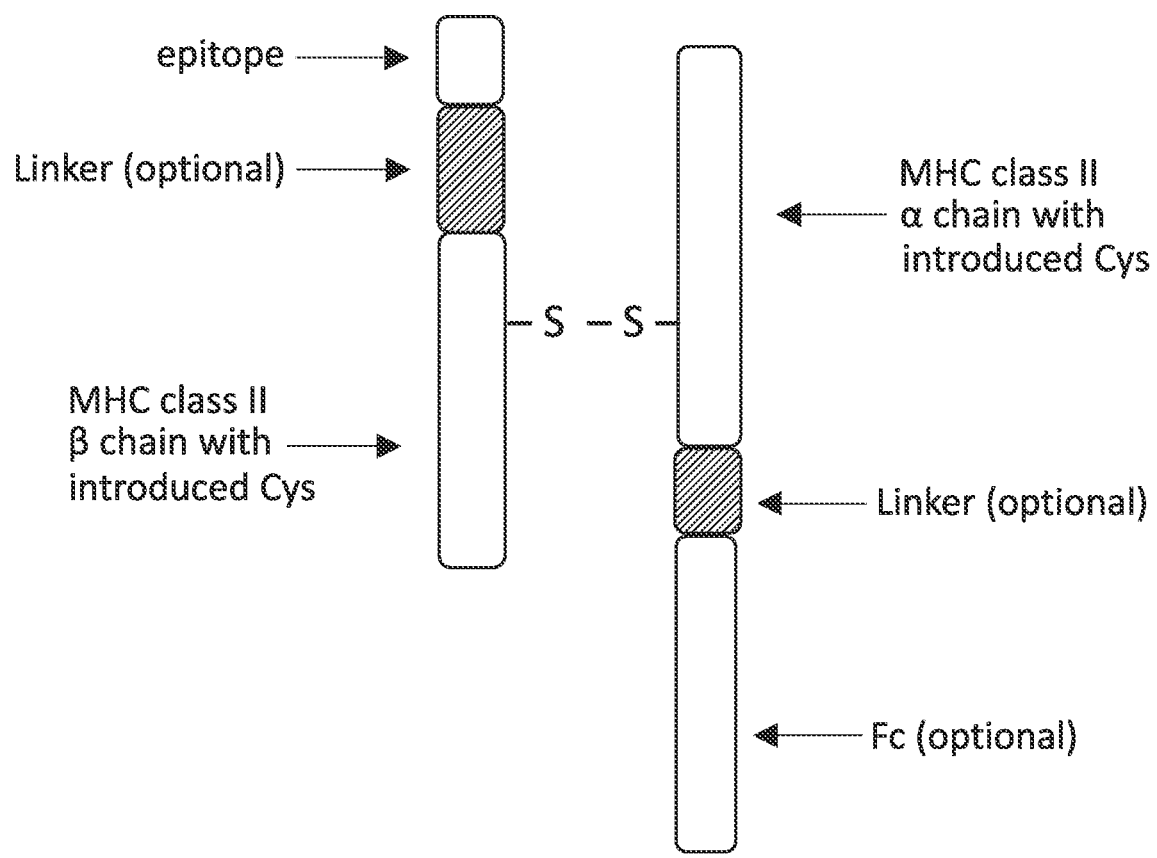
Figure 16C:
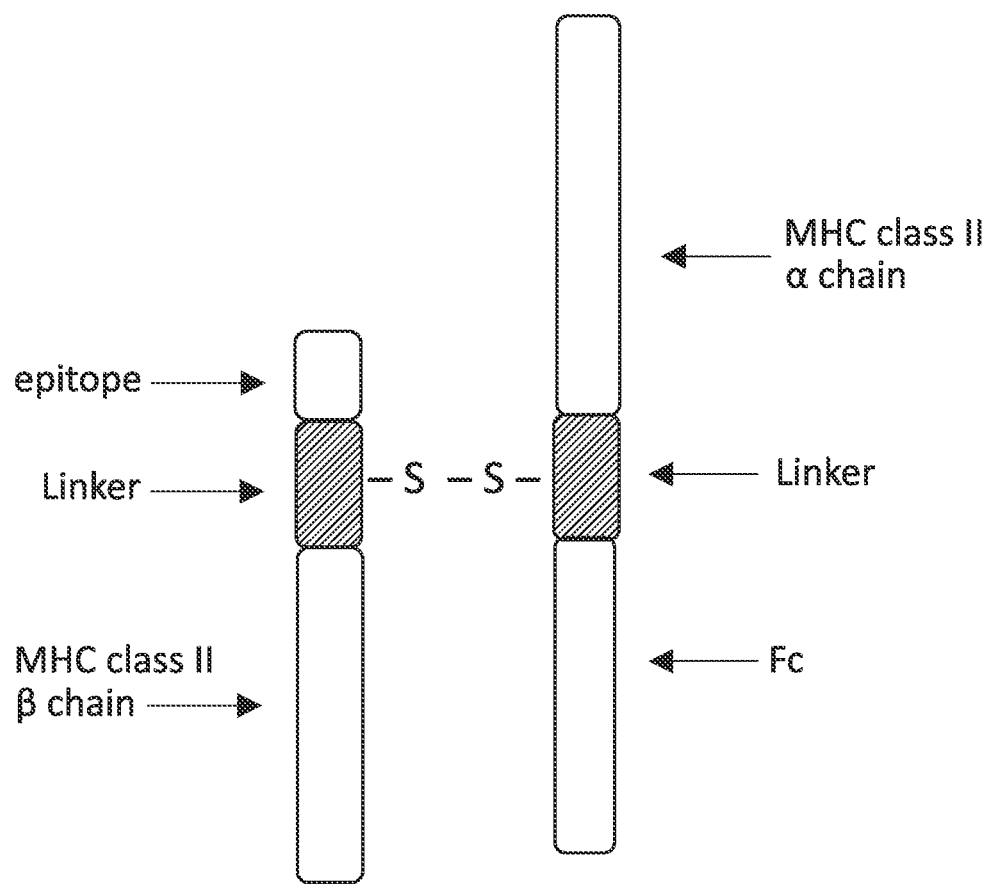

The present disclosure provides an antigen-presenting polypeptide (APP) that comprises a heterodimer (e.g., comprises a heterodimer or a homodimer of two heterodimers), where the heterodimer comprises: a) a first polypeptide comprising a T1D peptide; and ii) a first MHC class II polypeptide; and b) a second polypeptide comprising a second MHC class II polypeptide, where the heterodimer does not include an immunomodulatory polypeptide, where the first polypeptide and the second polypeptide are disulfide linked to one another, optionally where the first or the second polypeptide comprises an Ig Fc polypeptide. An APP of the present disclosure is depicted schematically in FIG. 16A-16C. An APP of the present disclosure is useful for diagnostic applications and therapeutic applications. As discussed below, when used for diagnostic applications, the APP also can comprise a detectable label so that binding of the APP to a target T cell is detected by detecting the detectable label.

Any of the TMMPs described above may be used without the immunomodulatory polypeptide(s) component as an APP. Further, because the APP comprises an Ig Fc polypeptide, an APP typically will be a homodimer comprising two heterodimers that are joined by disulfide bonds that spontaneously form between the two Ig Fc polypeptides. The APP comprises a suitable T1D peptides as described above. In some cases, the first MHC class II polypeptide is an MHC class II β chain polypeptide such as a DRB MHC class II polypeptide. In some cases, the second MHC class II polypeptide is an MHC class II α chain polypeptide such as a DRA MHC class II polypeptide. Suitable Ig Fc polypeptides are as described above. In some cases, the Ig Fc polypeptide is one that induces cell lysis through activation of complement-dependent cytotoxicity (CDC). In some cases, the Ig Fc polypeptide is one that can elicit antibody-dependent cellular cytotoxicity (ADCC). In some cases, the Ig Fc polypeptide binds complement or a complement component. In some cases, the Ig Fc polypeptide is one that substantially does not induce cell lysis through activation of CDC. When the Ig Fc polypeptide is one that that induces cell lysis through activation of CDC, and/or elicits ADCC, the APP can bind to and destroy the target T cell. An APP used for diagnostic purposes typically will have an Ig Fc polypeptide is one that substantially does not induce cell lysis through activation of CDC or elicit ADCC.

In some cases, therefore, an APP of the present disclosure comprises a heterodimer comprising: a) a first polypeptide comprising, in order from N-terminus to C-terminus: i) a T1D peptide; and ii) a first MHC class II polypeptide comprising a substitution of an amino acid (other than a Cys) with a Cys (a "first Cys"); and b) a second polypeptide comprising, in order form N-terminus to C-terminus: i) a second MHC class II polypeptide comprising a substitution of an amino acid (other than a Cys) with a Cys (a "second Cys"); and ii) an Ig Fc polypeptide, where the first polypeptide and the second polypeptide are disulfide bonded via the first Cys and the second Cys. The first MHC class II polypeptide can be a DRB MHC class II polypeptide comprising an amino acid sequence having at least 80%, at least 85%, at least 90%, at least 95%, at least 98%, or at least 99%, amino acid sequence identity to the amino acid sequence depicted in FIG. 14A; and having an amino acid substitution selected from P5C, F7C, Q10C, N19C, G20C, H33C, G151C, D152C, and W153C. The second MHC class II polypeptide can be a DRA MHC class II polypeptide comprising an amino acid sequence having at least 80%, at least 85%, at least 90%, at least 95%, at least 98%, or at least 99%, amino acid sequence identity to the amino acid sequence depicted in FIG. 13A; and having an amino acid substitution selected from E3C, E4C, F12C, G28C, D29C, I72C, K75C, T80C, P81C, I82C, T93C, N94C, and S95C. In some cases, the Ig Fc polypeptide induces cell lysis through activation of complement-dependent cytotoxicity (CDC) and/or elicits antibody-dependent cellular cytotoxicity (ADCC). In some cases, the Ig Fc polypeptide is a variant that substantially does not induce cell lysis through activation of CDC, e.g., an IgG1 Fc polypeptide comprising L234A and L235A substitutions (L14A and L15A of the amino acid sequence depicted in FIG. 12A). In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93; proIns 73-90). In some cases, the T1D peptide is a GAD peptide. In some cases, the T1D peptide is a GAD peptide selected from NFFRMVISNPAAT (SEQ ID NO:87; GAD65 555-567) and NFIRMVISNPAAT (SEQ ID NO:88; GAD65 555-567; F557I).

In some cases, an APP of the present disclosure comprises a heterodimer comprising: a) a first polypeptide comprising, in order from N-terminus to C-terminus: i) a T1D peptide; ii) a linker comprising a Cys (a "linker Cys"), and iii) a first MHC class II polypeptide; and b) a second polypeptide comprising, in order form N-terminus to C-terminus: i) a second MHC class II polypeptide comprising a substitution of an amino acid (other than a Cys) with a Cys (a "second Cys"); and ii) an Ig Fc polypeptide, where the first polypeptide and the second polypeptide are disulfide bonded via the linker Cys and the second Cys. The first MHC class II polypeptide can be a DRB MHC class II polypeptide comprising an amino acid sequence having at least 80%, at least 85%, at least 90%, at least 95%, at least 98%, at least 99%, or at least 100% amino acid sequence identity to the amino acid sequence depicted in FIG. 14A. The second MHC class II polypeptide can be a DRA MHC class II polypeptide comprising an amino acid sequence having at least 80%, at least 85%, at least 90%, at least 95%, at least 98%, or at least 99%, amino acid sequence identity to the amino acid sequence depicted in FIG. 13A; and having an amino acid substitution selected from I72C or K75C. In some cases, the Ig Fc polypeptide induces cell lysis through activation of complement-dependent cytotoxicity (CDC) and/or elicits antibody-dependent cellular cytotoxicity (ADCC). In some cases, the Ig Fc polypeptide is a variant that substantially does not induce cell lysis through activation of CDC, e.g., an IgG1 Fc polypeptide comprising L234A and L235A substitutions (L14A and L15A of the amino acid sequence depicted in FIG. 12A). In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93; proIns 73-90). In some cases, the T1D peptide is a GAD peptide. In some cases, the T1D peptide is a GAD peptide selected from

```
                    (SEQ ID NO: 87; GAD65 555-567)
NFFRMVISNPAAT
and (SEQ ID NO: 88; GAD65 555-567; F557I)
NFIRMVISNPAAT.
```

For example, in some cases, the peptide linker can comprise an amino acid sequence selected from: (CGGGS)(GGGGS)n (SEQ ID NO: 1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where n is 1, 2, 3, 4, 5, 6, 7, 8, 9, or 10, with n=2 or 3 generally being useful); the first MHC class II polypeptide is a DRB MHC class II polypeptide; and the second MHC class II polypeptide is a DRA MHC class II polypeptide that comprises a substitution of an amino acid (other than a Cys) with a Cys.

Specific examples of the Cys-containing linkers between the T1D peptide and a DRB MHC class II polypeptide and Cys residues in the DRA MHC class II polypeptide that can form a disulfide bond are provided in the Table 5, below:

TABLE 5

| Cys-Containing Linker Between the T1D peptide and the DRB MHC Class II Polypeptide | DRA MHC class II polypeptide substitution |
|---|---|
| (CGGGS)(GGGGS)n (SEQ ID NO: 1) | I72C |
| (GCGGS)(GGGGS)n (SEQ ID NO: 2) | I72C |
| (GGCGS)(GGGGS)n (SEQ ID NO: 3) | I72C |
| (GGGCS)(GGGGS)n (SEQ ID NO: 4) | I72C |
| (GGGGC)(GGGGS)n (SEQ ID NO: 5) | I72C |
| (CGGGS)(GGGGS)n (SEQ ID NO: 1) | K75C |
| (GCGGS)(GGGGS)n (SEQ ID NO: 2) | K75C |
| (GGCGS)(GGGGS)n (SEQ ID NO: 3) | K75C |
| (GGGCS)(GGGGS)n (SEQ ID NO: 4) | K75C |
| (GGGGC)(GGGGS)n (SEQ ID NO: 5) | K75C |

As noted above, in any of the above APP embodiments, n=0, 1, 2, 3, 4 or more, with 2 or 3 typically being used to create a total linker length of 15 or 20 amino acids, although longer lengths may be possible. In any of the above embodiments, linkers that do not comprise a Cys optionally can be used to connect the other components of second polypeptide. In some cases, the Ig Fc polypeptide induces cell lysis through activation of complement-dependent cytotoxicity (CDC) and/or elicits antibody-dependent cellular cytotoxicity (ADCC). In some cases, the Ig Fc polypeptide is present and is a human IgG1 Fc polypeptide, optionally comprising L234A and L235A substitutions (L14A and L15A of the amino acid sequence depicted in FIG. 12A). In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO:94; proIns 76-90; K88S), and GAGSLQPLALEGSLQKRG (SEQ ID NO:93; proIns 73-90). In some cases, the T1D peptide is a GAD peptide. In some cases, the T1D peptide is a GAD peptide selected from NFFRMVISNPAAT (SEQ ID NO:87; GAD65 555-567) and NFIRMVISNPAAT (SEQ ID NO:88; GAD65 555-567; F557I).

The following are examples of the APPs described above in which the first and the second polypeptides are linked via a disulfide bond between the Cys in the peptide linker and the Cys provided by the substitution in the second MHC class II polypeptide, and wherein the first polypeptide is a DRB MHC class II polypeptide (i.e., a DR β chain polypeptide), and the second polypeptide is a DRA MHC class II polypeptide (i.e., a DR α chain polypeptide).

As one example, an APP of the present disclosure comprises a heterodimer comprising one of the following five first polypeptides and one of the following two second polypeptides:

a1) a first polypeptide comprising, in order from N-terminus to C-terminus: i) a T1D peptide; ii) a linker comprising the amino acid sequence (CGGGS)(GGGGS)n (SEQ ID NO: 1), where n is an integer from 1 to 10; and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A); or alternatively a2) a first polypeptide comprising, in order from N-terminus to C-terminus: i) a T1D peptide; ii) a linker comprising the amino acid sequence (GCGGS)(GGGGS)n (SEQ ID NO:2), where n is an integer from 1 to 10; and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A); or alternatively a3) a first polypeptide comprising, in order from N-terminus to C-terminus: i) a T1D peptide; ii) a linker comprising the amino acid sequence (GGCGS)(GGGGS)n (SEQ ID NO:3), where n is an integer from 1 to 10; and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 4A); or alternatively a4) a first polypeptide comprising, in order from N-terminus to C-terminus: i) a T1D peptide; ii) a linker comprising the amino acid sequence (GGGCS)(GGGGS)n (SEQ ID NO:4), where n is an integer from 1 to 10; and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A); or alternatively a5) a first polypeptide comprising, in order from N-terminus to C-terminus: i) a T1D peptide; ii) a linker comprising the amino acid sequence (GGGGC)(GGGGS)n (SEQ ID NO:5), where n is an integer from 1 to 10; and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A); and b1) a second polypeptide comprising, in order from N-terminus to C-terminus: i) an MHC class II α chain comprising a Cys at position 72 (e.g., a DRA MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 13G, and comprising a Cys at position 72); and an ii) an Ig Fc polypeptide; or, alternatively b2) a second polypeptide comprising, in order from N-terminus to C-terminus: i) an MHC class II α chain comprising a Cys at position 75 (e.g., a DRA MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 13G, and comprising a Cys at position 75); and
ii) an Ig Fc polypeptide.

Each of the above combinations of first and second polypeptides for making an APP is thus expressly disclosed, i.e., a1-b1, a2-b1, a3-b1, a4-b1, a5-b1, and a1-b2, a2-b2, a3-b2, a4-b2 and a5-b2.

As noted above, in any of the above embodiments, n=0, 1, 2, 3, 4 or more, with 2 or 3 typically being used to create a total linker length of 15 or 20 amino acids, although longer lengths may be usable. In any of the above embodiments, linkers that do not comprise a Cys optionally can be used to connect the components of the second polypeptide (e.g., a GGSAAAGG (SEQ ID NO: 83) linker or AAAGG (SEQ ID NO:82) linker can be used between the DRA MHC class II polypeptide and the Ig Fc polypeptide). In the above embodiments, in some cases, the Ig Fc polypeptide is a human IgG1 Fc polypeptide comprising L234A and L235A substitutions (L14A and L15A of the amino acid sequence depicted in FIG. 12A). In some cases, the Ig Fc polypeptide induces cell lysis through activation of complement-dependent cytotoxicity (CDC) and/or elicits antibody-dependent cellular cytotoxicity (ADCC). In some cases, the T1D peptide is a proinsulin peptide. In some cases, the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93; proIns 73-90). In some cases, the T1D peptide is a GAD peptide. In some cases, the T1D peptide is a GAD peptide selected from NFFRMVISNPAAT (SEQ ID NO:87; GAD65 555-567) and NFIRMVISNPAAT (SEQ ID NO:88; GAD65 555-567; F557I).

Hence, for example, a TMMP in accordance with the above embodiments can comprise the combination of first polypeptide chain α3 and second polypeptide chain b2, wherein
i) the MHC class II β chain polypeptide is a DRB MHC class II polypeptide comprising an amino acid sequence having at least 80%, at least 85%, at least 90%, at least 95%, at least 98%, at least 99%, or 100% amino acid sequence identity to the amino acid sequence depicted in FIG. 14A,
ii) the MHC class II α chain polypeptide is a DRA MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 13G, and comprising a Cys at position 75,
iii) the T1D peptide is SLQPLALEGSLQSRG (SEQ ID NO:90; proIns 76-90; K88S),
iv) the linker between the T1D peptide and the DRB MHC class II polypeptide is (GGCGS)(GGGGS)n (SEQ ID NO: 128), where n=2 (for a total of 15 amino acids in the linker between the T1D peptide and the DRB MHC class II polypeptide),
v) the Ig Fc polypeptide is a human IgG1 Fc polypeptide comprising the amino acid sequence depicted in FIG. 12A, or a variant thereof such as the amino acid sequence depicted in FIG. 12A comprising L234A and L235A substitutions (L14A and L15A of the amino acid sequence depicted in FIG. 12A),
vi) there is a GGSAAAGG (SEQ ID NO:83) linker between the DRA MHC class II polypeptide and the Ig Fc polypeptide, and
viii) there is a disulfide bond joining the Cys in the (GGCGS)(GGGGS)2 (SEQ ID NO:128) linker and the Cys at the K75C substitution in the DRA MHC class II polypeptide.

A disulfide-bonded APP of the present disclosure will in some cases exhibit greater stability than a control non-disulfide-bonded APP. An example of a control APP is an APP comprising first and second polypeptide chains 2744 and 2932 (depicted in FIG. 15AA and FIG. 15Z, respectively), or 2639 and 2932 (depicted in FIG. 15C and FIG. 15Z, respectively). A disulfide-bonded APP of the present disclosure will in some cases exhibit at least 10%, at least 15%, at least 20%, at least 25%, at least 30%, at least 50%, at least 75%, at least 2-fold, at least 5-fold, at least 10-fold, at least 50-fold, at least 100-fold, or greater than 100-fold, greater stability in the PBS buffer solution containing 500 mM NaCl (described above) in vitro over a specified period of time and at a specified temperature (e.g., in a solution at a temperature of from 37° C. to 42° C. for a period of time of from 1 hour to 28 days; e.g., for 1 hour at 37° C.; 1 day at 37° C.; 5 days at 37° C.; 1 hour at 42° C.; 1 day at 42° C.; 5 days at 42° C.; 5 days at 37° C.; 10 days at 37° C.; 14 days at 37° C.; 28 days at 37° C.; and the like) than a control non-disulfide-bonded APP. A disulfide-bonded APP of the present disclosure will in some cases exhibit greater expression than a control non-disulfide-bonded APP. A disulfide-bonded APP of the present disclosure will in some cases exhibit both greater stability and greater expression than a control non-disulfide-bonded APP. For example, in some cases, an APP of the present disclosure is expressed (produced) in a Chinese hamster ovary (CHO) cell in vitro at a level that is at least 10%, at least 20%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 20-fold, at least 50-fold, at least 100-fold, or more than 100-fold, higher than the expression level of a control APP lacking the at least one disulfide bond when expressed under the same conditions and in the same CHO cells. Expression levels can be determined by: i) producing the APP in a CHO cell in vitro; and ii) determining the amount of APP produced by the mammalian cell. For example, the APP can be isolated from the CHO cells and/or from culture medium in which the CHO cells are cultured, where isolation of the APP can be carried out by affinity chromatography, e.g., on a Protein A column, a Protein G column, or the like. An example of a suitable mammalian cell is a CHO cell; e.g., an Expi-CHO-S™ cell (e.g., ThermoFisher Scientific, Catalog #A29127).

As one example, an APP of the present disclosure comprises: a) a first polypeptide comprising the amino acid sequence of construct 2986, depicted in FIG. 15I, comprising an F7C substitution (Cys-7) in the MHC class II β chain relative to the MHC class II β chain sequence depicted in FIG. 14A; and b) a second polypeptide comprising the amino acid sequence of construct 2983, depicted in FIG. 15H, comprising a P81C substitution (Cys-81) in the MHC class II α chain relative to the MHC class II α chain sequence depicted in FIG. 13A, where the first polypeptide and the second polypeptide are covalently linked to one another via a disulfide bond between Cys-7 and Cys-81.

As another example, an APP of the present disclosure comprises: a) a first polypeptide comprising the amino acid sequence of construct 2987, depicted in FIG. 15J, comprising an P5C substitution (Cys-5) in the MHC class II β chain relative to the MHC class II β chain sequence depicted in FIG. 14A; and b) a second polypeptide comprising the amino acid sequence of construct 2983, depicted in FIG. 15H, comprising a P81C substitution (Cys-81) in the MHC class II α chain relative to the MHC class II α chain sequence depicted in FIG. 13A, where the first polypeptide and the second polypeptide are covalently linked to one another via a disulfide bond between Cys-5 and Cys-81.

As another example, an APP of the present disclosure comprises: a) a first polypeptide comprising the amino acid sequence of construct 3027, depicted in FIG. 15K, comprising an H33C substitution (Cys-33) in the MHC class II β chain relative to the MHC class II β chain sequence depicted in FIG. 14A; and b) a second polypeptide comprising the amino acid sequence of construct 2983, depicted in FIG. 15H, comprising a P81C substitution (Cys-81) in the MHC class II α chain relative to the MHC class II α chain sequence depicted in FIG. 13A, where the first polypeptide and the second polypeptide are covalently linked to one another via a disulfide bond between Cys-33 and Cys-81.

As another example, an APP of the present disclosure comprises: a) a first polypeptide comprising the amino acid sequence of construct 2988, depicted in FIG. 15M, comprising an N19C substitution (N19C) in the MHC class II β chain relative to the MHC class II β chain sequence depicted in FIG. 14A; and b) a second polypeptide comprising the amino acid sequence of construct 2984, depicted in FIG. 15L, comprising an E4C substitution (Cys-4) in the MHC class II α chain relative to the MHC class II α chain sequence depicted in FIG. 13A, where the first polypeptide and the second polypeptide are covalently linked to one another via a disulfide bond between Cys-19 and Cys-4.

As another example, an APP of the present disclosure comprises: a) a first polypeptide comprising the amino acid sequence of construct 3032, depicted in FIG. 15N, comprising a G20C substitution (Cys-20) in the MHC class II β chain relative to the MHC class II β chain sequence depicted in FIG. 14A; and b) a second polypeptide comprising the amino acid sequence of construct 2984, depicted in FIG. 15L, comprising an E4C substitution (Cys-4) in the MHC class II α chain relative to the MHC class II α chain sequence depicted in FIG. 13A, where the first polypeptide and the second polypeptide are covalently linked to one another via a disulfide bond between Cys-20 and Cys-4.

As another example, an APP of the present disclosure comprises: a) a first polypeptide comprising the amino acid sequence of construct 2989, depicted in FIG. 15P, comprising a Q56C substitution (Cys-156) in the MHC class II β chain relative to the MHC class II β chain sequence depicted in FIG. 14A; and b) a second polypeptide comprising the amino acid sequence of construct 2985, depicted in FIG. 15O, comprising a T93C substitution (Cys-93) in the MHC class II α chain relative to the MHC class II α chain sequence depicted in FIG. 13A, where the first polypeptide and the second polypeptide are covalently linked to one another via a disulfide bond between Cys-156 and Cys-93.

As another example, an APP of the present disclosure comprises: a) a first polypeptide comprising the amino acid sequence of construct 3030, depicted in FIG. 15Q, comprising a W153C substitution (Cys-153) in the MHC class II β chain relative to the MHC class II β chain sequence depicted in FIG. 14A; and b) a second polypeptide comprising the amino acid sequence of construct 2985, depicted in FIG. 15O, comprising a T93C substitution (Cys-93) in the MHC class II α chain relative to the MHC class II α chain sequence depicted in FIG. 13A, where the first polypeptide and the second polypeptide are covalently linked to one another via a disulfide bond between Cys-153 and Cys-93.

As another example, an APP of the present disclosure comprises: a) a first polypeptide comprising the amino acid sequence of construct 2986, depicted in FIG. 15I, comprising an F7C substitution (Cys-7) in the MHC class II β chain relative to the MHC class II β chain sequence depicted in FIG. 14A; and b) a second polypeptide comprising the amino acid sequence of construct 3018, depicted in FIG. 15R, comprising an F12C substitution (Cys-12) in the MHC class II α chain relative to the MHC class II α chain sequence depicted in FIG. 13A, where the first polypeptide and the second polypeptide are covalently linked to one another via a disulfide bond between Cys-7 and Cys-12.

As another example, an APP of the present disclosure comprises: a) a first polypeptide comprising the amino acid sequence of construct 3026, depicted in FIG. 15S, comprising a Q10C substitution (Cys-10) in the MHC class II β chain relative to the MHC class II β chain sequence depicted in FIG. 14A; and b) a second polypeptide comprising the amino acid sequence of construct 3018, depicted in FIG. 15R, comprising an F12C substitution (Cys-12) in the MHC class II α chain relative to the MHC class II α chain sequence depicted in FIG. 13A, where the first polypeptide and the second polypeptide are covalently linked to one another via a disulfide bond between Cys-10 and Cys-12.

As another example, an APP of the present disclosure comprises: a) a first polypeptide comprising the amino acid sequence of construct 2986, depicted in FIG. 15I, comprising an F7C substitution (Cys-7) in the MHC class II β chain relative to the MHC class II β chain sequence depicted in FIG. 14A; and b) a second polypeptide comprising the amino acid sequence of construct 3019, depicted in FIG. 15T, comprising a T80C substitution (Cys-80) in the MHC class II α chain relative to the MHC class II α chain sequence depicted in FIG. 13A, where the first polypeptide and the second polypeptide are covalently linked to one another via a disulfide bond between Cys-7 and Cys-80.

As another example, an APP of the present disclosure comprises: a) a first polypeptide comprising the amino acid sequence of construct 2987, depicted in FIG. 15J, comprising a P5C substitution (Cys-5) in the MHC class II 13 chain relative to the MHC class II 13 chain sequence depicted in FIG. 14A; and b) a second polypeptide comprising the amino acid sequence of construct 3019, depicted in FIG. 15T, comprising a T80C substitution (Cys-80) in the MHC class II α chain relative to the MHC class II α chain sequence depicted in FIG. 13A, where the first polypeptide and the second polypeptide are covalently linked to one another via a disulfide bond between Cys-5 and Cys-80.

As another example, an APP of the present disclosure comprises: a) a first polypeptide comprising the amino acid sequence of construct 3027, depicted in FIG. 15K, comprising an I82C substitution (Cys-82) in the MHC class II β chain relative to the MHC class II β chain sequence depicted in FIG. 14A; and b) a second polypeptide comprising the amino acid sequence of construct 3019, depicted in FIG. 15T, comprising a T80C substitution (Cys-80) in the MHC class II α chain relative to the MHC class II α chain sequence depicted in FIG. 13A, where the first polypeptide and the second polypeptide are covalently linked to one another via a disulfide bond between Cys-82 and Cys-80.

As another example, an APP of the present disclosure comprises: a) a first polypeptide comprising the amino acid sequence of construct 2986, depicted in FIG. 15I, comprising an F7C substitution (Cys-7) in the MHC class II β chain relative to the MHC class II β chain sequence depicted in FIG. 14A; and b) a second polypeptide comprising the amino acid sequence of construct 3018, depicted in FIG.

15R, comprising an F12C substitution (Cys-12) in the MHC class II α chain relative to the MHC class II α chain sequence depicted in FIG. 13A, where the first polypeptide and the second polypeptide are covalently linked to one another via a disulfide bond between Cys-7 and Cys-12.

As another example, an APP of the present disclosure comprises: a) a first polypeptide comprising the amino acid sequence of construct 3026, depicted in FIG. 15S, comprising a Q10C substitution (Cys-10) in the MHC class II β chain relative to the MHC class II β chain sequence depicted in FIG. 14A; and b) a second polypeptide comprising the amino acid sequence of construct 3018, depicted in FIG. 15R, comprising an F12C substitution (Cys-12) in the MHC class II α chain relative to the MHC class II α chain sequence depicted in FIG. 13A, where the first polypeptide and the second polypeptide are covalently linked to one another via a disulfide bond between Cys-10 and Cys-12.

As another example, an APP of the present disclosure comprises: a) a first polypeptide comprising the amino acid sequence of construct 2986, depicted in FIG. 15I, comprising an F7C substitution (Cys-7) in the MHC class II β chain relative to the MHC class II β chain sequence depicted in FIG. 14A; and b) a second polypeptide comprising the amino acid sequence of construct 3019, depicted in FIG. 15T, comprising a T80C substitution (Cys-80) in the MHC class II α chain relative to the MHC class II α chain sequence depicted in FIG. 13A, where the first polypeptide and the second polypeptide are covalently linked to one another via a disulfide bond between Cys-7 and Cys-80.

As another example, an APP of the present disclosure comprises: a) a first polypeptide comprising the amino acid sequence of construct 2987, depicted in FIG. 15J, comprising a P5C substitution (Cys-5) in the MHC class II β chain relative to the MHC class II β chain sequence depicted in FIG. 14A; and b) a second polypeptide comprising the amino acid sequence of construct 3019, depicted in FIG. 15T, comprising a T80C substitution (Cys-80) in the MHC class II α chain relative to the MHC class II α chain sequence depicted in FIG. 13A, where the first polypeptide and the second polypeptide are covalently linked to one another via a disulfide bond between Cys-5 and Cys-80.

As another example, an APP of the present disclosure comprises: a) a first polypeptide comprising the amino acid sequence of construct 3027, depicted in FIG. 15K, comprising an I82C substitution (Cys-82) in the MHC class II β chain relative to the MHC class II β chain sequence depicted in FIG. 14A; and b) a second polypeptide comprising the amino acid sequence of construct 3019, depicted in FIG. 15T, comprising a T80C substitution (Cys-80) in the MHC class II α chain relative to the MHC class II α chain sequence depicted in FIG. 13A, where the first polypeptide and the second polypeptide are covalently linked to one another via a disulfide bond between Cys-82 and Cys-80.

As another example, an APP of the present disclosure comprises: a) a first polypeptide comprising the amino acid sequence of construct 2986, depicted in FIG. 15I, comprising an F7C substitution (Cys-7) in the MHC class II β chain relative to the MHC class II β chain sequence depicted in FIG. 14A; and b) a second polypeptide comprising the amino acid sequence of construct 3020, depicted in FIG. 15U, comprising an I82C substitution (Cys-82) in the MHC class II α chain relative to the MHC class II α chain sequence depicted in FIG. 13A, where the first polypeptide and the second polypeptide are covalently linked to one another via a disulfide bond between Cys-7 and Cys-82.

As another example, an APP of the present disclosure comprises: a) a first polypeptide comprising the amino acid sequence of construct 2987, depicted in FIG. 15J, comprising a P5C substitution (Cys-5) in the MHC class II β chain relative to the MHC class II β chain sequence depicted in FIG. 14A; and b) a second polypeptide comprising the amino acid sequence of construct 3020, depicted in FIG. 15U, comprising an I82C substitution (Cys-82) in the MHC class II α chain relative to the MHC class II α chain sequence depicted in FIG. 13A, where the first polypeptide and the second polypeptide are covalently linked to one another via a disulfide bond between Cys-5 and Cys-82.

As another example, an APP of the present disclosure comprises: a) a first polypeptide comprising the amino acid sequence of construct 3027, depicted in FIG. 15V, comprising an H33C substitution (Cys-33) in the MHC class II β chain relative to the MHC class II β chain sequence depicted in FIG. 14A; and b) a second polypeptide comprising the amino acid sequence of construct 3020, depicted in FIG. 15U, comprising an I82C substitution (Cys-82) in the MHC class II α chain relative to the MHC class II α chain sequence depicted in FIG. 13A, where the first polypeptide and the second polypeptide are covalently linked to one another via a disulfide bond between Cys-33 and Cys-82.

As another example, an APP of the present disclosure comprises: a) a first polypeptide comprising the amino acid sequence of construct 3028, depicted in FIG. 15X, comprising a G151C substitution (Cys-151) in the MHC class II β chain relative to the MHC class II β chain sequence depicted in FIG. 14A; and b) a second polypeptide comprising the amino acid sequence of construct 3021, depicted in FIG. 15W, comprising a G28C substitution (Cys-28) in the MHC class II α chain relative to the MHC class II α chain sequence depicted in FIG. 13A, where the first polypeptide and the second polypeptide are covalently linked to one another via a disulfide bond between Cys-151 and Cys-28.

As another example, an APP of the present disclosure comprises: a) a first polypeptide comprising the amino acid sequence of construct 3029, depicted in FIG. 15Y, comprising a D152C substitution (Cys-152) in the MHC class II β chain relative to the MHC class II β chain sequence depicted in FIG. 14A; and b) a second polypeptide comprising the amino acid sequence of construct 3021, depicted in FIG. 15W, comprising a G28C substitution (Cys-28) in the MHC class II α chain relative to the MHC class II α chain sequence depicted in FIG. 13A, where the first polypeptide and the second polypeptide are covalently linked to one another via a disulfide bond between Cys-152 and Cys-28.

As another example, an APP of the present disclosure comprises: a) a first polypeptide comprising the amino acid sequence of construct 3030, depicted in FIG. 15Q, comprising a W153C substitution (Cys-153) in the MHC class II β chain relative to the MHC class II β chain sequence depicted in FIG. 14A; and b) a second polypeptide comprising the amino acid sequence of construct 3021, depicted in FIG. 15W, comprising a G28C substitution (Cys-28) in the MHC class II α chain relative to the MHC class II α chain sequence depicted in FIG. 13A, where the first polypeptide and the second polypeptide are covalently linked to one another via a disulfide bond between Cys-153 and Cys-28.

As another example, an APP of the present disclosure comprises: a) a first polypeptide comprising the amino acid sequence of construct 3028, depicted in FIG. 15X, comprising a G151C substitution (Cys-151) in the MHC class II β chain relative to the MHC class II β chain sequence depicted in FIG. 14A; and b) a second polypeptide comprising the amino acid sequence of construct 3022, depicted in FIG. 15BB, comprising a D29C substitution (Cys-29) in the MHC class II α chain relative to the MHC class II α chain sequence depicted in FIG. 13A, where the first polypeptide and the second polypeptide are covalently linked to one another via a disulfide bond between Cys-151 and Cys-29.

As another example, an APP of the present disclosure comprises: a) a first polypeptide comprising the amino acid sequence of construct 3029, depicted in FIG. 15Y, comprising a D152C substitution (Cys-152) in the MHC class II β chain relative to the MHC class II β chain sequence depicted in FIG. 14A; and b) a second polypeptide comprising the amino acid sequence of construct 3022, depicted in FIG. 15BB, comprising a D29C substitution (Cys-29) in the MHC class II α chain relative to the MHC class II α chain sequence depicted in FIG. 13A, where the first polypeptide and the second polypeptide are covalently linked to one another via a disulfide bond between Cys-152 and Cys-29.

As another example, an APP of the present disclosure comprises: a) a first polypeptide comprising the amino acid sequence of construct 3030, depicted in FIG. 15Q, comprising a W153C substitution (Cys-153) in the MHC class II β chain relative to the MHC class II β chain sequence depicted in FIG. 14A; and b) a second polypeptide comprising the amino acid sequence of construct 3022, depicted in FIG. 15BB, comprising a D29C substitution (Cys-29) in the MHC class II α chain relative to the MHC class II α chain sequence depicted in FIG. 13A, where the first polypeptide and the second polypeptide are covalently linked to one another via a disulfide bond between Cys-153 and Cys-29.

As another example, an APP of the present disclosure comprises: a) a first polypeptide comprising the amino acid sequence of construct 2989, depicted in FIG. 15P, comprising a Q156C substitution (Cys-156) in the MHC class II β chain relative to the MHC class II β chain sequence depicted in FIG. 14A; and b) a second polypeptide comprising the amino acid sequence of construct 3023, depicted in FIG. 15CC, comprising an N94C substitution (Cys-94) in the MHC class II α chain relative to the MHC class II α chain sequence depicted in FIG. 13A, where the first polypeptide and the second polypeptide are covalently linked to one another via a disulfide bond between Cys-156 and Cys-94.

As another example, an APP of the present disclosure comprises: a) a first polypeptide comprising the amino acid sequence of construct 3031, depicted in FIG. 15DD, comprising an N120C substitution (Cys-120) in the MHC class II β chain relative to the MHC class II β chain sequence depicted in FIG. 14A; and b) a second polypeptide comprising the amino acid sequence of construct 3023, depicted in FIG. 15CC, comprising an N94C substitution (Cys-94) in the MHC class II α chain relative to the MHC class II α chain sequence depicted in FIG. 13A, where the first polypeptide and the second polypeptide are covalently linked to one another via a disulfide bond between Cys-120 and Cys-94.

As another example, an APP of the present disclosure comprises: a) a first polypeptide comprising the amino acid sequence of construct 2989, depicted in FIG. 15P, comprising a Q156C substitution (Cys-156) in the MHC class II β chain relative to the MHC class II β chain sequence depicted in FIG. 14A; and b) a second polypeptide comprising the amino acid sequence of construct 3024, depicted in FIG. 15EE, comprising an S95C substitution (Cys-95) in the MHC class II α chain relative to the MHC class II α chain sequence depicted in FIG. 13A, where the first polypeptide and the second polypeptide are covalently linked to one another via a disulfide bond between Cys-156 and Cys-95.

As another example, an APP of the present disclosure comprises: a) a first polypeptide comprising the amino acid sequence of construct 3031, depicted in FIG. 15DD, comprising an N120C substitution (Cys-120) in the MHC class II β chain relative to the MHC class II β chain sequence depicted in FIG. 14A; and b) a second polypeptide comprising the amino acid sequence of construct 3024, depicted in FIG. 15EE, comprising an S95C substitution (Cys-95) in the MHC class II α chain relative to the MHC class II α chain sequence depicted in FIG. 13A, where the first polypeptide and the second polypeptide are covalently linked to one another via a disulfide bond between Cys-120 and Cys-95.

As another example, an APP of the present disclosure comprises: a) a first polypeptide comprising the amino acid sequence of construct 2988, depicted in FIG. 15M, comprising an N19C substitution (Cys-19) in the MHC class II β chain relative to the MHC class II β chain sequence depicted in FIG. 14A; and b) a second polypeptide comprising the amino acid sequence of construct 3025, depicted in FIG. 15FF, comprising an E3C substitution (Cys-3) in the MHC class II α chain relative to the MHC class II α chain sequence depicted in FIG. 13A, where the first polypeptide and the second polypeptide are covalently linked to one another via a disulfide bond between Cys-19 and Cys-3.

As another example, an APP of the present disclosure comprises: a) a first polypeptide comprising the amino acid sequence of construct 3032, depicted in FIG. 15N, comprising a G20C substitution (Cys-20) in the MHC class II β chain relative to the MHC class II β chain sequence depicted in FIG. 14A; and b) a second polypeptide comprising the amino acid sequence of construct 3025, depicted in FIG. 15FF, comprising an E3C substitution (Cys-3) in the MHC class II α chain relative to the MHC class II α chain sequence depicted in FIG. 13A, where the first polypeptide and the second polypeptide are covalently linked to one another via a disulfide bond between Cys-20 and Cys-3.

Nucleic Acids

The present disclosure provides a nucleic acid comprising a nucleotide sequence encoding a TMPP or an APP of the present disclosure. For example, the present disclosure provides a single nucleic acid comprising nucleotide sequences encoding both the first polypeptide and the second polypeptide of a TMPP or APP of the present disclosure. As another example, the present disclosure provides: a) a first nucleic acid comprising a nucleotide sequence encoding the first polypeptide of a TMMP or APP of the present disclosure; and b) a second nucleic acid comprising a nucleotide sequence encoding the second polypeptide of a TMMP or APP of the present disclosure. In some cases, the nucleic acid is a recombinant expression vector; thus, the present disclosure provides a recombinant expression vector comprising a nucleotide sequence encoding a TMPP or APP of the present disclosure. The discussion, below, of nucleic acids refers to nucleic acids encoding TMPPs of the present disclosure; however, the discussion applies as well to nucleic acids encoding APPs of the present disclosure.

Separate Nucleic Acids Encoding Individual Polypeptide Chains of a TMPP or APP

The present disclosure provides nucleic acids comprising nucleotide sequences encoding a TMMP or APP of the present disclosure. As noted above, in some cases, the individual polypeptide chains of a TMMP of the present disclosure are encoded in separate nucleic acids. In some cases, nucleotide sequences encoding the separate polypeptide chains of a TMMP or APP of the present disclosure are operably linked to transcriptional control elements, e.g., promoters, such as promoters that are functional in a eukaryotic cell, where the promoter can be a constitutive promoter or an inducible promoter.

For example, the present disclosure provides a first nucleic acid and a second nucleic acid, where the first nucleic acid comprises a nucleotide sequence encoding the first polypeptide of a TMMP or APP of the present disclosure, and where the second nucleic acid comprises a nucleotide sequence encoding the second polypeptide of the TMMP or APP. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

Nucleic Acid Encoding Two or More Polypeptides Present in a TMMP or APP

The present disclosure provides a nucleic acid comprising nucleotide sequences encoding the first polypeptide and the second polypeptide of a TMMP or APP of the present disclosure. In some cases, the nucleotide sequences encoding the first polypeptide and the second polypeptide of a TMMP or APP of the present disclosure includes a proteolytically cleavable linker interposed between the nucleotide sequence encoding the first polypeptide and the nucleotide sequence encoding the second polypeptide. In some cases, the nucleotide sequences encoding the first polypeptide and the second polypeptide of a TMMP or APP of the present disclosure includes an internal ribosome entry site (IRES) interposed between the nucleotide sequence encoding the first polypeptide and the nucleotide sequence encoding the second polypeptide. In some cases, the nucleotide sequences encoding the first polypeptide and the second polypeptide of a TMMP or APP of the present disclosure includes a ribosome skipping signal (or cis-acting hydrolase element, CHYSEL) interposed between the nucleotide sequence encoding the first polypeptide and the nucleotide sequence encoding the second polypeptide. Examples of nucleic acids are described below, where a proteolytically cleavable linker is provided between nucleotide sequences encoding the first polypeptide and the second polypeptide of a TMMP or APP of the present disclosure; in any of these embodiments, an IRES or a ribosome skipping signal can be used in place of the nucleotide sequence encoding the proteolytically cleavable linker.

In some cases, a first nucleic acid (e.g., a recombinant expression vector, an mRNA, a viral RNA, etc.) comprises a nucleotide sequence encoding a first polypeptide chain of a TMMP or APP of the present disclosure; and a second nucleic acid (e.g., a recombinant expression vector, an mRNA, a viral RNA, etc.) comprises a nucleotide sequence encoding a second polypeptide chain of a TMMP or APP of the present disclosure. In some cases, the nucleotide sequence encoding the first polypeptide, and the second nucleotide sequence encoding the second polypeptide, are each operably linked to transcriptional control elements, e.g., promoters, such as promoters that are functional in a eukaryotic cell, where the promoter can be a constitutive promoter or an inducible promoter.

Recombinant Expression Vectors

The present disclosure provides recombinant expression vectors comprising nucleic acids of the present disclosure. In some cases, the recombinant expression vector is a non-viral vector. In some cases, the recombinant expression vector is a viral construct, e.g., a recombinant adeno-associated virus construct (see, e.g., U.S. Pat. No. 7,078, 387), a recombinant adenoviral construct, a recombinant lentiviral construct, a recombinant retroviral construct, a non-integrating viral vector, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. Numerous suitable expression vectors are known to those of skill in the art, and many are commercially available.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some cases, a nucleotide sequence encoding a TMMP or APP of the present disclosure is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some cases, a nucleotide sequence encoding a DNA-targeting RNA and/or a site-directed modifying polypeptide is operably linked to multiple control elements that allow expression of the nucleotide sequence encoding a DNA-targeting RNA and/or a site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

Genetically Modified Host Cells

The present disclosure provides a genetically modified host cell, where the host cell is genetically modified with a nucleic acid(s) of the present disclosure.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCL1.3), human embryonic kidney (HEK) cells (ATCC No. CRL1573), HLHepG2 cells, and the like.

Genetically modified host cells can be used to produce a TMMP or an APP of the present disclosure. For example, a genetically modified host cell can be used to produce a TMMP of the present disclosure, or an APP of the present disclosure. An expression vector(s) comprising nucleotide sequences encoding the polypeptide(s) is/are introduced into a host cell, generating a genetically modified host cell, which genetically modified host cell produces the polypeptide(s).

Methods of Producing a TMMP or an APP

The present disclosure provides methods of producing TMMP or an APP of the present disclosure. The methods generally involve culturing, in a culture medium, a host cell (e.g., a genetically modified host cell of the present disclosure) that is genetically modified with a recombinant expression vector(s) comprising a nucleotide sequence(s) encoding the TMMP or the APP; and isolating the TMMP or the APP from the genetically modified host cell and/or the culture medium. As noted above, in some cases, the individual polypeptide chains of a TMMP or APP of the present disclosure are encoded in separate recombinant expression vectors. In some cases, all polypeptide chains of a TMMP or APP of the present disclosure are encoded in a single recombinant expression vector.

Isolation of the TMMP or the APP from the expression host cell (e.g., from a lysate of the expression host cell) and/or the culture medium in which the host cell is cultured, can be carried out using standard methods of protein purification.

For example, a lysate may be prepared of the expression host and the lysate purified using high performance liquid chromatography (HPLC), exclusion chromatography (e.g., size exclusion chromatography), gel electrophoresis, affinity chromatography, or other purification technique. Alternatively, where the TMMP or APP is secreted from the expression host cell into the culture medium, the TMMP or APP can be purified from the culture medium using HPLC, exclusion chromatography, gel electrophoresis, affinity chromatography, or other purification technique. In some cases, the TMMP or APP is purified, e.g., a composition is generated that comprises at least 80% by weight, at least about 85% by weight, at least about 95% by weight, or at least about 99.5% by weight, of the TMMP or APP in relation to contaminants related to the method of preparation of the product and its purification. The percentages can be based upon total protein.

In some cases, e.g., where the TMMP or APP comprises an affinity tag, the TMMP or APP can be purified using an immobilized binding partner of the affinity tag. For example, where a TMMP or an APP comprises an Ig Fc polypeptide, the TMMP or the APP can be isolated from genetically modified mammalian host cell and/or from culture medium in which the mammalian cells are cultured, where isolation of the TMMP or APP can be carried out by affinity chromatography, e.g., on a Protein A column, a Protein G column, or the like. An example of a suitable mammalian cell is a CHO cell; e.g., an Expi-CHO-S™ cell (e.g., ThermoFisher Scientific, Catalog #A29127).

The first and second polypeptides will self-assemble into heterodimers by spontaneously forming disulfide bonds between the above-discussed Cys residues in the first and second polypeptides. As also noted above, when both heterodimers include Ig Fc polypeptides, disulfide bonds will spontaneously form between the respective Ig Fc polypeptides to covalently link the two heterodimers to one another (depicted schematically in FIG. 1E).

Compositions

The present disclosure provides compositions, including pharmaceutical compositions, comprising a TMMP or an APP of the present disclosure. The present disclosure provides compositions, including pharmaceutical compositions, comprising a nucleic acid or a recombinant expression vector of the present disclosure. The discussion, below, of compositions refers to compositions comprising a TMMP of the present disclosure; however, the discussion applies equally to an APP of the present disclosure.

Compositions Comprising a TMMP or an APP

A composition of the present disclosure can comprise, in addition to a TMMP of the present disclosure, or an APP of the present disclosure, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and *Handbook of Pharmaceutical Excipients* (2000) A. H. Kibbe et al., eds., $3^{rd}$ ed. Amer. Pharmaceutical Assoc.

A pharmaceutical composition can comprise: i) a TMMP of the present disclosure; and ii) a pharmaceutically acceptable excipient. A pharmaceutical composition can comprise: i) an APP of the present disclosure; and ii) a pharmaceutically acceptable excipient. In some cases, a subject pharmaceutical composition will be suitable for administration to a subject, e.g., will be sterile. For example, in some embodiments, a subject pharmaceutical composition will be suitable for administration to a human subject, e.g., where the composition is sterile and is free of detectable pyrogens and/or other toxins.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where a TMMP of the present disclosure is administered as an injectable (e.g. subcutaneously, intraperitoneally, intramuscularly, intralymphatically, and/or intravenously) directly into a tissue, a formulation can be provided as a ready-to-use dosage form, or as non-aqueous form (e.g. a reconstitutable storage-stable powder) or aqueous form, such as liquid composed of pharmaceutically acceptable carriers and excipients. The protein-containing formulations may also be provided so as to enhance serum half-life of the subject protein following administration. For example, the protein may be provided in a liposome formulation, prepared as a colloid, or other conventional techniques for extending serum half-life. A variety of methods are available for preparing liposomes, as described in, e.g., Szoka et al. 1980 Ann. Rev. Biophys. Bioeng. 9:467, U.S. Pat. Nos. 4,235,871, 4,501,728 and 4,837,028. The preparations may also be provided in controlled release or slow-release forms.

In some cases, a composition of the present disclosure comprises: a) a TMMP of the present disclosure; and b) saline (e.g., 0.9% NaCl). In some cases, the composition is sterile. In some cases, the composition is suitable for administration to a human subject, e.g., where the composition is sterile and is free of detectable pyrogens and/or other toxins. Thus, the present disclosure provides a composition comprising: a) a TMMP of the present disclosure; and b) saline (e.g., 0.9% NaCl), where the composition is sterile and is free of detectable pyrogens and/or other toxins.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of a TMMP of the present disclosure in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The present disclosure provides a container comprising a composition of the present disclosure, e.g., a liquid composition. The container can be, e.g., a syringe, an ampoule, and the like. In some cases, the container is sterile. In some cases, both the container and the composition are sterile.

Compositions Comprising a Nucleic Acid or a Recombinant Expression Vector

The present disclosure provides compositions, e.g., pharmaceutical compositions, comprising a nucleic acid or a recombinant expression vector of the present disclosure. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A composition of the present disclosure can include: a) one or more nucleic acids or one or more recombinant expression vectors comprising nucleotide sequences encoding a TMMP or an APP of the present disclosure; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris (hydroxymethyl)-aminomethane (Tris), etc.). Suitable salts include, e.g., NaCl, $MgCl_2$, KCl, $MgSO_4$, etc.

A pharmaceutical formulation of the present disclosure can include a nucleic acid or recombinant expression vector of the present disclosure in an amount of from about 0.001% to about 90% (w/w). In the description of formulations, below, "subject nucleic acid or recombinant expression vector" will be understood to include a nucleic acid or recombinant expression vector of the present disclosure. For example, in some cases, a subject formulation comprises a nucleic acid or recombinant expression vector of the present disclosure.

A subject nucleic acid or recombinant expression vector can be admixed, encapsulated, conjugated or otherwise associated with other compounds or mixtures of compounds; such compounds can include, e.g., liposomes or receptor-targeted molecules. A subject nucleic acid or recombinant expression vector can be combined in a formulation with one or more components that assist in uptake, distribution and/or absorption.

A subject nucleic acid or recombinant expression vector composition can be formulated into any of many possible dosage forms such as, but not limited to, tablets, capsules, gel capsules, liquid syrups, soft gels, suppositories, and enemas. A subject nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a subject nucleic acid or recombinant expression vector can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present disclosure may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanolamine, N,N-dimethylacetamide, N,N-dimethylformamide, 2-pyrrolidone and derivatives thereof, tetrahydrofurfuryl alcohol, and AZONE™.

Methods

A TMMP of the present disclosure is useful for modulating an activity of a T cell. Thus, the present disclosure provides methods of modulating an activity of a T cell, the methods generally involving contacting a target T cell with a TMMP of the present disclosure.

An APP of the present disclosure is useful for various research, therapeutic, and diagnostic purposes. For example, an APP of the present disclosure can be used to label, directly or indirectly, an antigen-specific T cell. An APP of the present disclosure can provide effector functions in an antigen-specific manner.

Methods of Modulating T Cell Activity

The present disclosure provides a method of selectively modulating the activity of an epitope-specific T cell, the method comprising contacting the T cell with a TMMP of the present disclosure, where contacting the T cell with a TMMP of the present disclosure selectively modulates the activity of the epitope-specific T cell. In some cases, the contacting occurs in vivo. In some cases, the contacting occurs in vitro.

In some cases, a TMMP of the present disclosure reduces activity of an autoreactive T cell and/or an autoreactive B cell. In some cases, a TMMP of the present disclosure increases the number and/or activity of a regulatory T cell (Treg), resulting in reduced activity of an autoreactive T cell and/or an autoreactive B cell.

In some cases, the T cell being contacted with a TMMP of the present disclosure is a regulatory T cell (Treg). Tregs are $CD4^+$, $FOXP3^+$, and $CD25^+$. Tregs can suppress autoreactive T cells. In some cases, a method of the present disclosure activates Tregs, thereby reducing autoreactive T cell activity.

The present disclosure provides a method of increasing proliferation of Tregs, the method comprising contacting Tregs with a TMMP of the present disclosure, where the contacting increases proliferation of Tregs. The present disclosure provides a method of increasing the number of Tregs in an individual, the method comprising administering to the individual a TMMP of the present disclosure, where the administering results in an increase in the number of Tregs in the individual. For example, the number of Tregs can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold.

Methods of Detecting an Antigen-Specific T Cell

The present disclosure provides a method of detecting an antigen-specific T-cell. The methods comprise contacting a T cell with an APP of the present disclosure; and detecting binding of the APP to the T cell.

The present disclosure provides a method of detecting an antigen-specific T cell, the method comprising contacting a T cell with an APP of the present disclosure, wherein binding of the APP to the T cell indicates that the T cell is specific for the epitope present in the APP.

In some cases, the APP comprises a detectable label. Suitable detectable labels include, but are not limited to, a radioisotope, a fluorescent polypeptide, or an enzyme that generates a fluorescent product, and an enzyme that generates a colored product. Where the APP comprises a detectable label, binding of the APP to the T cell is detected by detecting the detectable label.

In some cases, an APP of the present disclosure comprises a detectable label suitable for use in in vivo imaging, e.g., suitable for use in positron emission tomography (PET), single photon emission tomography (SPECT), near infrared (NIR) optical imaging, x-ray imaging, computer-assisted tomography (CAT), or magnetic resonance imaging (MRI), or other in vivo imaging method. Examples of suitable labels for in vivo imaging include gadolinium chelates (e.g., gadolinium chelates with DTPA (diethylenetriamine penta-acetic acid), DTPA-bismethylamide (BMA), DOTA (dodecane tetraacetic acid), or HP-DO3A (1,4,7-tris(carboxymethyl)-10-

(2'-hydroxypropyl)-1,4,7,10-tetraazacycl ododecane)), iron chelates, magnesium chelates, manganese chelates, copper chelates, chromium chelates, iodine-based materials, and radionuclides. Suitable radionuclides include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{64}$Cu, $^{67}$Cu, $^{75}$Br, $^{77}$Br, $^{99}$mTc, $^{14}$C, $^{13}$N, $^{15}$O, $^{32}$P, $^{33}$P and $^{18}$F. In some cases, the detectable label is a positron-emitting isotope such as $^{11}$C, $^{13}$N, $^{15}$O, $^{18}$F, $^{64}$Cu, $^{68}$Ga, $^{78}$Br, $^{82}$Rb, $^{86}$Y $^{90}$Y, $^{22}$Na, $^{26}$Al, $^{40}$K, $^{83}$Sr, $^{89}$Zr, or $^{124}$I. In some cases, the detectable label is $^{64}$Cu.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilized ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

In some cases, binding of the APP to the T cell is detected using a detectably labeled antibody specific for the APP. An antibody specific for the APP can comprise a detectable label such as a radioisotope, a fluorescent polypeptide, or an enzyme that generates a fluorescent product, or an enzyme that generates a colored product.

In some cases, the T cell being detected is present in a sample comprising a plurality of T cells. For example, a T cell being detected can be present in a sample comprising from 10 to $10^9$ T cells, e.g., from 10 to $10^2$, from $10^2$ to $10^4$, from $10^4$ to $10^6$, from $10^6$ to $10^7$, from $10^7$ to $10^8$, or from $10^8$ to $10^9$, or more than $10^9$, T cells.

Treatment Methods

The present disclosure provides treatment methods, the methods comprising administering to the individual an amount of a TMMP of the present disclosure, or one or more nucleic acids or expression vectors encoding the TMMP effective to selectively modulate the activity of an epitope-specific T cell in an individual and to treat the individual. In some cases, a treatment method of the present disclosure comprises administering to an individual in need thereof one or more recombinant expression vectors comprising nucleotide sequences encoding a TMMP of the present disclosure. In some cases, a treatment method of the present disclosure comprises administering to an individual in need thereof one or more mRNA molecules comprising nucleotide sequences encoding a TMMP of the present disclosure. In some cases, a treatment method of the present disclosure comprises administering to an individual in need thereof a TMMP of the present disclosure. A TMMP of the present disclosure is useful for treating type 1 diabetes (T1D).

The present disclosure provides a method of selectively modulating the activity of an epitope-specific T cell in an individual, the method comprising administering to the individual an effective amount of a TMMP of the present disclosure, or one or more nucleic acids (e.g., expression vectors; mRNA; etc.) comprising nucleotide sequences encoding the TMMP, where the TMMP selectively modulates the activity of the epitope-specific T cell in the individual. Selectively modulating the activity of an epitope-specific T cell can treat a disease or disorder in the individual. Thus, the present disclosure provides a treatment method comprising administering to an individual in need thereof an effective amount of a TMMP of the present disclosure. A treatment method of the present disclosure, comprising administering an effective amount of a TMMP of the present disclosure, is suitable for treating T1D.

In some cases, the immunomodulatory polypeptide is an inhibitory polypeptide, and a T TMMP of the present disclosure inhibits activity of the epitope-specific T cell. In some cases, the epitope is a self-epitope, and a TMMP of the present disclosure selectively inhibits the activity of a T cell specific for the self-epitope.

The present disclosure provides a method of treating T1D in an individual, the method comprising administering to the individual an effective amount of a TMMP of the present disclosure, or one or more nucleic acids comprising nucleotide sequences encoding the TMMP, where the TMMP comprises a T1D peptide (as described above), and where the TMMP comprises an inhibitory immunomodulatory polypeptide. In some cases, an "effective amount" of a TMMP of the present disclosure is an amount that, when administered in one or more doses to an individual in need thereof, reduces the number of self-reactive (i.e., reactive with a T1D-associated antigen) CD4$^+$ and/or CD8$^+$ T cells by at least 10%, at least 15%, at least 20%, at least 25%, at least 30%, at least 40%, at least 50%, at least 60%, at least 70%, at least 80%, at least 90%, or at least 95%, compared to number of self-reactive T cells in the individual before administration of the TMMP, or in the absence of administration with the TMMP. In some cases, an "effective amount" of a TMMP of the present disclosure is an amount that, when administered in one or more doses to an individual in need thereof, reduces production of Th2 cytokines in the individual. In some cases, an "effective amount" of a TMMP of the present disclosure is an amount that, when administered in one or more doses to an individual in need thereof, ameliorates one or more symptoms associated with T1D in the individual. In some instances, the TMMP reduces the number of CD4$^+$ self-reactive T cells (i.e., the number of CD4$^+$ T cells reactive with a T1D-associated antigen), which in turn leads to a reduction in CD8$^+$ self-reactive T cells. In some instances, the TMMP increases the number of CD4$^+$ Tregs, which in turn reduces the number of CD4$^+$ self-reactive T cells and/or CD8$^+$ T self-reactive T cells.

As noted above, in some cases, in carrying out a subject treatment method, a TMMP of the present disclosure is administered to an individual in need thereof, as the polypeptide per se. In other instances, in carrying out a subject treatment method, one or more nucleic acids comprising nucleotide sequences encoding a TMMP is/are administering to an individual in need thereof. Thus, in other instances, one or more nucleic acids of the present disclosure, e.g., one or more recombinant expression vectors of the present disclosure, is/are administered to an individual in need thereof.

The present disclosure also provides treatment methods, the methods comprising administering to the individual an amount of an APP of the present disclosure, or one or more nucleic acids or expression vectors encoding the APP effective to selectively engage with an epitope-specific T cell in an individual in order to treat the individual, e.g., by depleting epitope-specific T cells when the Ig Fc polypeptide is one that that induces cell lysis through activation of CDC, and/or elicits ADCC. In some cases, a treatment method of the present disclosure comprises administering to an individual in need thereof one or more recombinant expression vectors comprising nucleotide sequences encoding an APP of the present disclosure. In some cases, a treatment method of the present disclosure comprises administering to an individual in need thereof one or more mRNA molecules comprising nucleotide sequences encoding an APP of the present disclosure. In some cases, a treatment method of the present disclosure comprises administering to an individual in need thereof an APP of the present disclosure. An APP of the present disclosure is useful for treating type 1 diabetes (T1D) by selectively engaging with an epitope-specific T cell in an individual, including by, e.g., depleting epitope-specific T cells when the Ig Fc polypeptide is one that that induces cell lysis through activation of CDC, and/or elicits ADCC.

The present disclosure provides a method of treating T1D in an individual, the method comprising administering to the individual an effective amount of an APP of the present disclosure, or one or more nucleic acids comprising nucleotide sequences encoding the APP, where the APP comprises a T1D peptide (as described above). In some cases, an "effective amount" of an APP of the present disclosure is an amount that, when administered in one or more doses to an individual in need thereof, reduces the number of self-reactive (i.e., reactive with a T1D-associated antigen) $CD4^+$ and/or $CD8^+$ T cells by at least 10%, at least 15%, at least 20%, at least 25%, at least 30%, at least 40%, at least 50%, at least 60%, at least 70%, at least 80%, at least 90%, or at least 95%, compared to number of self-reactive T cells in the individual before administration of the APP, or in the absence of administration with the APP. In some cases, an "effective amount" of an APP of the present disclosure is an amount that, when administered in one or more doses to an individual in need thereof, reduces production of Th2 cytokines in the individual. In some cases, an "effective amount" of an APP of the present disclosure is an amount that, when administered in one or more doses to an individual in need thereof, ameliorates one or more symptoms associated with T1D in the individual. In some instances, the APP reduces the number of $CD4^+$ self-reactive T cells (i.e., the number of $CD4^+$ T cells reactive with a T1D-associated antigen), which in turn leads to a reduction in $CD8^+$ self-reactive T cells. In some instances (e.g., when the Ig Fc polypeptide of the APP substantially does not induce cell lysis through activation of CDC, and/or elicits ADCC), the APP increases the number of $CD4^+$ Tregs, which in turn reduces the number of $CD4^+$ self-reactive T cells and/or $CD8^+$ T self-reactive T cells.

As noted above, in some cases, in carrying out a subject treatment method, an APP of the present disclosure is administered to an individual in need thereof, as the polypeptide per se. In other instances, in carrying out a subject treatment method, one or more nucleic acids comprising nucleotide sequences encoding an APP is/are administering to an individual in need thereof. Thus, in other instances, one or more nucleic acids of the present disclosure, e.g., one or more recombinant expression vectors of the present disclosure, is/are administered to an individual in need thereof.

Formulations

Suitable formulations are described above, where suitable formulations include a pharmaceutically acceptable excipient. In some cases, a suitable formulation comprises: a) a TMMP or APP of the present disclosure; and b) a pharmaceutically acceptable excipient. In some cases, a suitable formulation comprises: a) a nucleic acid comprising a nucleotide sequence encoding a TMMP or APP of the present disclosure; and b) a pharmaceutically acceptable excipient; in some instances, the nucleic acid is an mRNA. In some cases, a suitable formulation comprises: a) a first nucleic acid comprising a nucleotide sequence encoding the first polypeptide of a TMMP or APP of the present disclosure; b) a second nucleic acid comprising a nucleotide sequence encoding the second polypeptide of a TMMP or APP of the present disclosure; and c) a pharmaceutically acceptable excipient. In some cases, a suitable formulation comprises: a) a recombinant expression vector comprising a nucleotide sequence encoding a TMMP or APP of the present disclosure; and b) a pharmaceutically acceptable excipient. In some cases, a suitable formulation comprises: a) a first recombinant expression vector comprising a nucleotide sequence encoding the first polypeptide of a TMMP or APP of the present disclosure; b) a second recombinant expression vector comprising a nucleotide sequence encoding the second polypeptide of a TMMP or APP of the present disclosure; and c) a pharmaceutically acceptable excipient.

Suitable pharmaceutically acceptable excipients are described above.

Dosages

A suitable dosage can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A TMMP or APP (whether as a single heterodimer or, as described above, as a homodimer comprising two heterodimers linked together) of the present disclosure may be administered in amounts between 1 ng/kg body weight and 20 mg/kg body weight per dose, e.g. between 0.1 mg/kg body weight to 10 mg/kg body weight, e.g. from 0.1 mg/kg body weight to 0.5 mg/kg body weight, from 0.5 mg/kg body weight to 1 mg/kg body weight, from 1.0 mg/kg body weight to 5 mg/kg body weight, from 5 mg/kg body weight to 10 mg/kg body weight, from 10 mg/kg body weight to 15 mg/kg body weight, and from 15 mg/kg body weight to 20 mg/kg body weight; however, doses below 0.1 mg/kg body weight or above 20 mg/kg are envisioned, especially considering the aforementioned factors. Amounts thus include from about 0.1 mg/kg body weight to about 0.5 mg/kg body weight, from about 0.5 mg/kg body weight to about 1 mg/kg body weight, from about 1.0 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight. If the regimen is a continuous infusion, it can also be in the range of 1 µg to 10 mg per kilogram of body weight per minute.

Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the T1D disease state, wherein a TMMP or APP of the present disclosure is administered in maintenance doses, ranging from those recited above, i.e., 0.1 mg/kg body weight to about 0.5 mg/kg body weight, from about 0.5 mg/kg body weight to about 1 mg/kg body weight, from about 1.0 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

Those of skill will readily appreciate that dose levels can vary as a function of the specific TMMP or APP, the severity of the symptoms and the susceptibility of the subject to side effects. Preferred dosages for a given compound are readily determinable by those of skill in the art by a variety of means.

In some cases, multiple doses of a TMMP or APP of the present disclosure, a nucleic acid of the present disclosure, or a recombinant expression vector of the present disclosure are administered. The frequency of administration of a TMMP or APP of the present disclosure, a nucleic acid of the present disclosure, or a recombinant expression vector of the present disclosure can vary depending on any of a variety of factors, e.g., severity of the symptoms, patient response, etc. For example, in some cases, a TMMP or APP of the present disclosure, a nucleic acid of the present disclosure, or a recombinant expression vector of the present disclosure is administered once per month, twice per month, three times per month, every other week (qow), one every three weeks, once every four weeks, once per week (qw), twice per week (biw), three times per week (tiw), four times per week, five times per week, six times per week, every other day (qod), daily (qd), twice a day (qid), or three times a day (tid).

The duration of administration of a TMMP or APP of the present disclosure, a nucleic acid of the present disclosure, or a recombinant expression vector of the present disclosure, e.g., the period of time over which a TMMP or APP of the present disclosure, a nucleic acid of the present disclosure, or a recombinant expression vector of the present disclosure is administered, can vary, depending on any of a variety of factors, e.g., patient response, etc. For example, a TMMP or APP of the present disclosure, a nucleic acid of the present disclosure, or a recombinant expression vector of the present disclosure can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more, including continued administration for the patient's life.

Where treatment is of a finite duration, following successful treatment, it may be desirable to have the patient undergo maintenance therapy to prevent the recurrence of the T1D disease state, wherein a TMMP or APP of the present disclosure is administered in maintenance doses, ranging from those recited above, i.e., 0.1 mg/kg body weight to about 0.5 mg/kg body weight, from about 0.5 mg/kg body weight to about 1 mg/kg body weight, from about 1.0 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

Routes of Administration

An active agent (a TMMP or APP of the present disclosure, a nucleic acid of the present disclosure, or a recombinant expression vector of the present disclosure) is administered to an individual using any available method and route suitable for drug delivery, including in vivo and in vitro methods, as well as systemic and localized routes of administration. A TMMP or APP of the present disclosure, a nucleic acid of the present disclosure, or a recombinant expression vector of the present disclosure can be administered to a host using any available conventional methods and routes suitable for delivery of conventional drugs, including systemic or localized routes. In general, routes of administration contemplated for use in a method of the present disclosure include, but are not necessarily limited to, enteral, parenteral, and inhalational routes.

Conventional and pharmaceutically acceptable routes of administration include intramuscular, intratracheal, intralymphatic, subcutaneous, intradermal, topical application, intravenous, intraarterial, rectal, nasal, oral, and other enteral and parenteral routes of administration. Of these, intravenous, intramuscular and subcutaneous may be more commonly employed. Routes of administration may be combined, if desired, or adjusted depending upon the TMMP or APP and/or the desired effect. A TMMP or APP of the present disclosure, or a nucleic acid or recombinant expression vector of the present disclosure, can be administered in a single dose or in multiple doses.

In some cases, a TMMP or APP of the present disclosure, a nucleic acid of the present disclosure, or a recombinant expression vector of the present disclosure is administered intravenously. In some cases, a TMMP or APP of the present disclosure, a nucleic acid of the present disclosure, or a recombinant expression vector of the present disclosure is administered intramuscularly. In some cases, a TMMP or APP of the present disclosure, a nucleic acid of the present disclosure, or a recombinant expression vector of the present disclosure is administered intralymphatically. In some cases, a TMMP of the present disclosure, a nucleic acid of the present disclosure, or a recombinant expression vector of the present disclosure is administered subcutaneously.

Subjects Suitable for Treatment

Subjects suitable for treatment with a method of the present disclosure include individuals who have T1D, including individuals who have been diagnosed as having T1D, and individuals who have been treated for T1D but who failed to respond to the treatment. Suitable subjects also may include individuals who have been diagnosed as being likely to develop T1D or who have symptoms indicating the imminent onset of T1D.

Methods of Selectively Delivering an Immunomodulatory Polypeptide

The present disclosure provides a method of delivering an immunomodulatory polypeptide (such as a wild-type (wt) or variant of immunomodulatory polypeptide described herein, e.g., PD-L1, IL-2, TGFβ, or FasL) to a selected T cell or a selected T cell population, e.g., in a manner such that a TCR specific for a given T1D epitope is targeted. The present disclosure provides a method of delivering a wt or variant immunomodulatory polypeptide disclosed herein selectively to a target T cell bearing a TCR specific for the epitope present in a TMMP of the present disclosure. In this context, the term "selective delivery" means that the immunomodulatory polypeptide is not delivered to all T cells, but rather that the majority of T cells to which the immunomodulatory polypeptide is delivered are T cells specific for the T1D peptide, thereby minimizing the modulation of non-target T cells. Thus, e.g., less than 50%, less than 40%, less than 30%, less than 25%, less than 20%, less than 15%, less than 10%, less than 5%, or less than 4%, 3%, 2% or 1%, of the non-target T cells bind the TMMP and, as a result, the immunomodulatory polypeptide is not delivered to the non-target T cells that do not bind the TMMP.

The method comprises contacting a population of T cells, in vivo or in vitro, with a TMMP of the present disclosure. The population of T cells can be a mixed population that comprises: i) the target T cell; and ii) non-target T cells that are not specific for the epitope (e.g., T cells that are specific for an epitope(s) other than the epitope to which the epitope-specific T cell binds). The epitope-specific T cell is specific for the T1D peptide epitope present in the TMMP binds to the TMMP. Contacting the population of T cells with the TMMP thus delivers the immunomodulatory polypeptide present in the TMMP selectively to the T cell(s) that are specific for the epitope present in the TMMP. Thus, e.g., less than 50%, less than 40%, less than 30%, less than 25%, less than 20%, less than 15%, less than 10%, less than 5%, or less than 4%, 3%, 2% or 1%, of the non-target T cells bind the TMMP and, as a result, the immunomodulatory polypeptide is not delivered to the non-target T cells that are not bound to the TMMP.

In some cases, the population of T cells is in vivo. In some cases, the population of T cells is in vitro, and a biological response (e.g., T cell activation and/or expansion and/or phenotypic differentiation) of the target T cell population to the TMMP of the present disclosure is elicited in the context of an in vitro culture. For example, a mixed population of T cells can be obtained from an individual, and can be contacted with the TMMP in vitro. Such contacting can comprise single or multiple exposures of the population of T cells to a defined dose(s) and/or exposure schedule(s). In some cases, said contacting results in selectively modulating target T cells within the population of T cells and results, e.g., in generation of a population of activated and/or expanded target T cells. As an example, a mixed population of T cells can be peripheral blood mononuclear cells (PBMC). For example, PBMC from a patient can be obtained by standard blood drawing and PBMC enrichment techniques before being exposed to 0.1-1000 nM of a TMMP of the present disclosure under standard lymphocyte culture conditions. At time points before, during, and after exposure of the mixed T cell population at a defined dose and schedule, the abundance of target T cells in the in vitro culture can be monitored by specific peptide-MHC multimers and/or phenotypic markers and/or functional activity (e.g. cytokine ELISpot assays). In some cases, upon achieving an optimal abundance and/or phenotype of antigen specific cells in vitro, all or a portion of the population of activated and/or expanded target T cells is administered to the individual (the individual from whom the mixed population of T cells was obtained).

In some cases, the population of T cells is in vitro. For example, a mixed population of T cells is obtained from an individual, and is contacted with a TMMP of the present disclosure in vitro. Such contacting, which can comprise single or multiple exposures of the T cells to a defined dose(s) and/or exposure schedule(s) in the context of in vitro cell culture, can be used to determine whether the mixed population of T cells includes T cells that are specific for the epitope presented by the TMMP. The presence of T cells that are specific for the T1D peptide of the TMMP can be determined by assaying a sample comprising a mixed population of T cells, which population of T cells comprises T cells that are not specific for the epitope (non-target T cells) and may comprise T cells that are specific for the epitope (target T cells). Known assays can be used to detect activation and/or proliferation of the target T cells, thereby providing an in vitro assay that can determine whether a particular TMMP possesses an epitope that binds to T cells present in the individual and thus whether the TMMP has potential use as a therapeutic composition for that individual. Suitable known assays for detection of activation and/or proliferation of target T cells include, e.g., flow cytometric characterization of T cell phenotype and/or antigen specificity and/or proliferation. Such an assay to detect the presence of epitope-specific T cells, e.g., a companion diagnostic, can further include additional assays (e.g. effector cytokine ELISpot assays) and/or appropriate controls (e.g. antigen-specific and antigen-nonspecific multimeric peptide-HLA staining reagents) to determine whether the TMMP is selectively binding/activating and/or expanding the target T cell. Thus, for example, the present disclosure provides a method of detecting, in a mixed population of T cells obtained from an individual, the presence of a target T cell that binds an epitope of interest, the method comprising: a) contacting in vitro the mixed population of T cells with a TMMP of the present disclosure, wherein the multimeric polypeptide comprises the epitope of interest; and b) detecting activation and/or proliferation of T cells in response to said contacting, wherein activated and/or proliferated T cells indicates the presence of the target T cell. Alternatively, and/or in addition, if activation and/or expansion (proliferation) of the desired T cell population is obtained using the TMMP, then all or a portion of the population of T cells comprising the activated/expanded T cells can be administered back to the individual as a therapy.

In some instances, the population of T cells is in vivo in an individual. In such instances, a method of the present disclosure for selectively delivering an immunomodulatory polypeptide as described herein to an epitope-specific T cell comprises administering the TMMP to the individual.

The epitope-specific T cell to which an immunomodulatory polypeptide is being selectively delivered is also referred to herein as a "target T cell." In some cases, the target T cell is a regulatory T cell (Treg). In some cases, the Treg inhibits or suppresses activity of an autoreactive T cell.

The present disclosure provides a method of delivering an inhibitory immunomodulatory polypeptide (such as wt or variant of PD-L1 or FasL) to a selected T cell or a selected T cell population, e.g., in a manner such that a TCR specific for a given epitope is targeted. The present disclosure provides a method of delivering such an inhibitory immunomodulatory polypeptide selectively to a target T cell bearing a TCR specific for the epitope present in a TMMP of the present disclosure. The method comprises contacting a population of T cells with a TMMP of the present disclosure. The population of T cells can be a mixed population that comprises: i) the target T cell; and ii) non-target T cells that are not specific for the epitope (e.g., T cells that are specific for an epitope(s) other than the epitope to which the epitope-specific T cell binds). The epitope-specific T cell is specific for the epitope-presenting peptide present in the TMMP, and binds to the TMMP. Contacting the population of T cells with the TMMP thus delivers the inhibitory immunomodulatory polypeptide present in the TMMP selectively to the T cell(s) that are specific for the T1D peptide present in the TMMP.

For example, a TMMP of the present disclosure is contacted with a population of T cells comprising: i) a target T cell(s) that is specific for the epitope present in the TMMP; and ii) a non-target T cell(s), e.g., a T cell(s) that is specific for a second epitope(s) that is not the epitope present in the TMMP. Contacting the population results in selective delivery of an inhibitory immunomodulatory polypeptide(s) an inhibitory immunomodulatory polypeptide (such as wt or variant of PD-L1 or FasL) which is present in the TMMP, to the target T cell. Thus, e.g., less than 50%, less than 40%, less than 30%, less than 25%, less than 20%, less than 15%, less than 10%, less than 5%, or less than 4%, 3%, 2% or 1%, of the non-target T cells bind the TMMP and, as a result, the immunomodulatory polypeptide is not delivered to the non-target T cells.

In some cases, the population of T cells is in vitro. In some cases, the population of T cells is in vitro, and a biological response (e.g., T cell activation and/or expansion and/or phenotypic differentiation) of the target T cell population to the TMMP of the present disclosure is elicited in the context of an in vitro culture. For example, a mixed population of T cells can be obtained from an individual, and can be contacted with the TMMP in vitro. Such contacting can comprise single or multiple exposures of the population of T cells to a defined dose(s) and/or exposure schedule(s). In some cases, said contacting results in selectively binding/activating and/or expanding target T cells within the population of T cells, and results in generation of a population of activated and/or expanded target T cells. As an example, a mixed population of T cells can be peripheral blood mononuclear cells (PBMC). For example, PBMC from a patient can be obtained by standard blood drawing and PBMC enrichment techniques before being exposed to 0.1-1000 nM of a TMMP of the present disclosure under standard lymphocyte culture conditions. At time points before, during, and after exposure of the mixed T cell population at a defined dose and schedule, the abundance of target T cells in the in vitro culture can be monitored by specific peptide-MHC multimers and/or phenotypic markers and/or functional activity (e.g. cytokine ELISpot assays). In some cases, upon achieving an optimal abundance and/or phenotype of antigen specific cells in vitro, all or a portion of the population of activated and/or expanded target T cells is administered to the individual (the individual from whom the mixed population of T cells was obtained).

In some cases, the population of T cells is in vitro. For example, a mixed population of T cells is obtained from an individual, and is contacted with a TMMP of the present disclosure in vitro. Such contacting, which can comprise single or multiple exposures of the T cells to a defined dose(s) and/or exposure schedule(s) in the context of in vitro cell culture, can be used to determine whether the mixed population of T cells includes T cells that are specific for the epitope presented by the TMMP. The presence of T cells that are specific for the T1D peptide epitope of the TMMP can be determined by assaying a sample comprising a mixed population of T cells, which population of T cells comprises T cells that are not specific for the epitope (non-target T cells) and may comprise T cells that are specific for the epitope (target T cells). Known assays can be used to detect activation and/or proliferation of the target T cells, thereby providing an in vitro assay that can determine whether a particular TMMP possesses an epitope that binds to T cells present in the individual and thus whether the TMMP has potential use as a therapeutic composition for that individual. Suitable known assays for detection of activation and/or proliferation of target T cells include, e.g., flow cytometric characterization of T cell phenotype and/or antigen specificity and/or proliferation. Such an assay to detect the presence of epitope-specific T cells, e.g., a companion diagnostic, can further include additional assays (e.g. effector cytokine ELISpot assays) and/or appropriate controls (e.g. antigen-specific and antigen-nonspecific multimeric peptide-HLA staining reagents) to determine whether the TMMP is selectively binding/activating and/or expanding the target T cell. Thus, for example, the present disclosure provides a method of detecting, in a mixed population of T cells obtained from an individual, the presence of a target T cell that binds an epitope of interest, the method comprising: a) contacting in vitro the mixed population of T cells with a TMMP of the present disclosure, wherein the multimeric polypeptide comprises the epitope of interest; and b) detecting activation and/or proliferation of T cells in response to said contacting, wherein activated and/or proliferated T cells indicates the presence of the target T cell. Alternatively, and/or in addition, if activation and/or expansion (proliferation) of the desired T cell population is obtained using the TMMP, then all or a portion of the population of T cells comprising the activated/expanded T cells can be administered back to the individual as a therapy.

In some instances, the population of T cells is in vivo in an individual. In such instances, a method of the present disclosure for selectively delivering an inhibitory immunomodulatory polypeptide (such as wt or variant of PD-L1 or FasL) to an epitope-specific T cell comprises administering the TMMP to the individual.

The epitope-specific T cell to which an inhibitory immunomodulatory polypeptide is being selectively delivered is also referred to herein as a "target T cell." In some cases, the target T cell is a regulatory T cell (Treg). In some cases, the Treg inhibits or suppresses activity of an autoreactive T cell. In some cases, the target T cell is a $CD4^+$ T cell. In some cases, the target T cell is a $CD4^+$ T cell that is specific for an autoantigen.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A T-cell modulatory multimeric polypeptide (TMMP) comprising at least one heterodimer, wherein each heterodimer comprises:
   a) a first polypeptide comprising:
      i) a peptide that displays a type 1 diabetes associated epitope capable of being bound by a T-cell receptor (a "T1D peptide"); and
      ii) a first major histocompatibility complex (MHC) class II polypeptide; and
      iii) optionally a linker that links the T1D peptide to the first MHC class II polypeptide; and
   b) a second polypeptide comprising a second MHC class II polypeptide,
      wherein one or both polypeptides of the heterodimer comprises one or more immunomodulatory polypeptides,
      wherein the first and the second polypeptide of the heterodimer are covalently linked to one another via at least one disulfide bond, and
      wherein one polypeptide of the heterodimer optionally comprises an immunoglobulin (Ig) Fc polypeptide or a non-Ig scaffold, and wherein when the optional Ig Fc is present, it is optionally joined to the first or second polypeptide via a linker.
2. A TMMP of aspect 1, wherein
   a1) the first polypeptide comprises, in order from N-terminus to C-terminus:
      i) the T1D peptide; and
      ii) an MHC class II β polypeptide; and
   b1) the second polypeptide comprises, in order from N-terminus to C-terminus:
      i) the one or more immunomodulatory polypeptides;
      ii) an MHC class II α polypeptide; and
      iii) an Ig Fc polypeptide; or
   a2) the first polypeptide comprises, in order from N-terminus to C-terminus:
      i) the T1D peptide; and
      ii) an MHC class II β polypeptide; and
   b2) the second polypeptide comprises, in order from N-terminus to C-terminus:
      i) an MHC class II α polypeptide;
      ii) an Ig Fc polypeptide; and
      iii) the one or more immunomodulatory polypeptides; or
   a3) the first polypeptide comprises, in order from N-terminus to C-terminus:
      i) the T1D peptide;
      ii) an MHC class II β polypeptide; and
   b3) the second polypeptide comprises, in order from N-terminus to C-terminus:
      i) an MHC class II α polypeptide;
      ii) the one or more immunomodulatory polypeptides; and
      iii) an Ig Fc polypeptide; or
   a4) the first polypeptide comprises, in order from N-terminus to C-terminus:
      i) the one or more immunomodulatory polypeptides;
      ii) the T1D peptide; and
      iii) an MHC class II β polypeptide; and
   b4) the second polypeptide comprises, in order from N-terminus to C-terminus:
      i) an MHC class II α polypeptide; and
      ii) an Ig Fc polypeptide; or
   a5) the first polypeptide comprises, in order from N-terminus to C-terminus:
      i) the T1D peptide;
      ii) an MHC class II β polypeptide; and
      iii) the one or more immunomodulatory polypeptides; and
   b5) the second polypeptide comprises, in order from N-terminus to C-terminus:
      i) an MHC class II α polypeptide; and
      ii) an Ig Fc polypeptide;
      wherein, in any of the above TMMPs, the components of the first polypeptide optionally may be joined by one or more linkers, and the components of the second polypeptide optionally may be joined by one or more linkers.
3. A TMMP of aspect 2, wherein the MHC class II α polypeptide comprises an amino acid sequence having at least 95%, at least 98% or at least 99%, amino acid sequence identity to a DRA1*01:01 polypeptide; and the MHC class II β polypeptide comprises an amino acid sequence having at least 95%, at least 98%, or at least 99% amino acid sequence identity to a DRB 1*04:01 polypeptide.
4. A TMMP of any one of aspects 1-3, wherein the one or more immunomodulatory polypeptides are selected from the group consisting of an IL-2 polypeptide, PD-L1 polypeptide, a FasL polypeptide, a TGF-β polypeptide, and combinations thereof.
5. A TMMP of any one of aspects 1-3, wherein at least one of the one or more immunomodulatory polypeptides is a PD-L1 polypeptide.
6. A TMMP of aspect 5, wherein the immunomodulatory polypeptide comprises a PD-L1 polypeptide extracellular domain.
7. A TMMP of aspect 6, wherein the immunomodulatory polypeptide comprises an amino acid sequence having at least 95%, at least 98%, at least 99%, or 100% amino acid sequence identity to the PD-L1 amino acid sequence depicted in FIG. 13O, and has a length of 200 amino acids or about 220 amino acids.
8. A TMMP of any one of aspects 1-7, wherein the T1D peptide has a length of from about 4 amino acids to about 25 amino acids.
9. A TMMP of any one of aspects 1-8, wherein the T1D peptide comprises is a proinsulin peptide or a glutamic acid decarboxylase (GAD) peptide.
10. A TMMP of aspect 9, wherein: (a) the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93;
proIns 73-90); or (b) wherein the T1D peptide is a GAD peptide selected from NFFRMVISNPAAT (SEQ ID NO:87; GAD65 555-567) and NFIRMVISNPAAT (SEQ ID NO:88; GAD65 555-567; F557I).
11. A TMMP of any one of aspects 1-8, wherein the T1D peptide comprises the amino acid sequence SLQPLALEGSLQSRG (SEQ ID NO:90).
12. A TMMP of any one of aspects 1-11, wherein the first MHC class II polypeptide is an MHC class II β chain polypeptide (comprising an amino acid sequence having at least 95%, at least 98%, or at least 99% amino acid sequence identity to a DRB1*04:01 polypeptide), and wherein the second MHC class II polypeptide is an MHC class II α chain polypeptide (e.g., having at least 95%, at least 98% or at least 99%, amino acid sequence identity to a DRA1*01:01 polypeptide).

13. A TMMP of any one of aspects 1-12, wherein the first MHC class II polypeptide comprises a Cys-containing linker between the T1D peptide and the MHC Class II β chain polypeptide, and wherein a disulfide bond is formed between the Cys in the linker and a Cys in the second MHC class II polypeptide.

14. A TMMP of aspect 13, wherein the linker comprises an amino acid sequence selected from (CGGGS) (GGGGS)n (SEQ ID NO: 1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where the linker is from about 15 amino acids to about 20 amino acids, such as (GGCGS)(GGGGS)n where n=2 (SEQ ID NO:128) or n=3 (SEQ ID NO:129)).

15. A TMMP of aspect 13, wherein the second MHC class II polypeptide is a variant MHC class II polypeptide that comprises a non-naturally occurring Cys residue.

16. A TMMP of aspect 15, wherein the second MHC class II polypeptide is a DRA MHC class II polypeptide (e.g., having at least 95%, at least 98% or at least 99%, amino acid sequence identity to a DRAT*01:01 polypeptide).

17. A TMMP of aspect 15 or aspect 16, wherein the non-naturally occurring Cys residue is located at an amino acid residue from amino acids 55 to 110 of the second MHC Class II polypeptide.

18. A TMMP of any one of aspects 15-17, wherein the second MHC class II polypeptide is a variant DRA MHC class II polypeptide comprising a Cys at position 72 or 75 based on the amino acid numbering depicted in FIG. 13A.

19. A TMMP of aspect 18, wherein the variant DRA MHC class II polypeptide comprises a K75C substitution or an I72C substitution (e.g., a DRA MHC class II polypeptide comprising an amino acid sequence having at least 80%, at least 85%, at least 90%, at least 95%, at least 98%, at least 99%, or 100% amino acid sequence identity to the amino acid sequence depicted in FIG. 13G or 13H).

20. A TMMP of aspects 14-19, wherein the TMMP comprises:
a1) a first polypeptide comprising, in order from N-terminus to C-terminus: i) a T1D peptide; ii) a linker comprising an amino acid sequence selected from the group consisting of (CGGGS)(GGGGS)n (SEQ ID NO:1), (GCGGS)(GGGGS)n (SEQ ID NO:2), (GGCGS)(GGGGS)n (SEQ ID NO:3), (GGGCS) (GGGGS)n (SEQ ID NO:4), and (GGGGC)(GGGGS)n (SEQ ID NO:5), where n is an integer from 1 to 10 (e.g., where the linker is from about 15 amino acids to about 20 amino acids, such as (GGCGS)(GGGGS)n where n=2 (SEQ ID NO:128) or n=3 (SEQ ID NO:129)); and iii) a DRB MHC class II polypeptide comprising an amino acid sequence having at least 80%, at least 85%, at least 90%, at least 95%, at least 98%, at least 99%, or 100% amino acid sequence identity to the amino acid sequence depicted in FIG. 14A; and b 1) a second polypeptide comprising, in order from N-terminus to C-terminus: i) a DRA MHC class II polypeptide comprising an amino acid sequence having at least 80%, at least 85%, at least 90%, at least 95%, at least 98% or at least 99%, amino acid sequence identity to the amino acid sequence depicted in FIG. 13G, and comprising a Cys at position 72 or 75; an ii) a variant human IgG1 Fc polypeptide that substantially does not induce cell lysis through activation of CDC (e.g., a human IgG1 Fc polypeptide comprising L234A and L235A substitutions shown as L14A and L15A of the amino acid sequence depicted in FIG. 12A); and iii) one or more immunomodulatory polypeptides, wherein the one or more immunomodulatory polypeptides is a wt or variant PD-L1 polypeptide (e.g., comprising an amino acid sequence having at least 80%, at least 85%, at least 90%, at least 95%, at least 98%, at least 99%, or 100% sequence identity to the PD-L1 amino acid sequence depicted in FIG. 13O, and having a length of about 220 amino acids); or, alternatively
b2) a second polypeptide comprising, in order from N-terminus to C-terminus: i) a DRA MHC class II polypeptide comprising an amino acid sequence having at least 80%, at least 85%, at least 90%, at least 95%, at least 98%, at least 99%, or 100% amino acid sequence identity to the amino acid sequence depicted in FIG. 13G or 13H, and comprising a Cys at position 72 or 75; an ii) a variant human IgG1 Fc polypeptide that substantially does not induce cell lysis through activation of CDC (e.g., a human IgG1 Fc polypeptide comprising L234A and L235A substitutions, shown as L14A and L15A of the amino acid sequence depicted in FIG. 12A); and iii) one or more immunomodulatory polypeptides, wherein the one or more immunomodulatory polypeptides is a wt or variant PD-L1 polypeptide (e.g., comprising an amino acid sequence having at least 80%, at least 85%, at least 90%, at least 95%, at least 98%, at least 99%, or 100% sequence identity to the PD-L1 amino acid sequence depicted in FIG. 13O, and having a length of about 220 amino acids).

21. A TMMP of aspect 1, wherein:
i) the first polypeptide comprises the amino acid sequence of the 3893 polypeptide depicted in FIG. 15B; and
ii) the first polypeptide comprises the amino acid sequence of the 2938 polypeptide depicted in FIG. 15A.

22. A TMMP of any one of aspects 1-12, wherein the disulfide bond is formed between:
i) a Cys in the first MHC class II polypeptide; and
ii) a Cys in the second MHC class II polypeptide.

23. A TMMP of aspect 22, wherein: i) the first MHC class II polypeptide is a variant MHC class II polypeptide (e.g., an MHC class II β chain polypeptide such as a DRB MHC class II polypeptide) that comprises a non-naturally occurring Cys residue; and ii) the second MHC class II polypeptide is a variant MHC class II polypeptide (e.g., an MHC class II α chain polypeptide such as a DRA MHC class II polypeptide) that comprises a non-naturally occurring Cys residue.

24. A TMMP of aspect 23, wherein the MHC class II polypeptide is a variant DRB MHC class II polypeptide (e.g., comprising an amino acid sequence having at least 95%, at least 98%, or at least 99% amino acid sequence identity to a DRB1*04:01 polypeptide) that comprises an amino acid substitution selected from the group consisting of PSC, F7C, Q10C, N19C, G20C, H33C, G151C, D152C, and W153C.

25. A TMMP of aspect 23 or aspect 24, wherein the MHC class II polypeptide is a variant DRA MHC class II polypeptide (e.g., having at least 95%, at least 98% or at least 99%, amino acid sequence identity to a DRA1*01:01 polypeptide) that comprises an amino acid substitution selected from E3C, E4C, F12C, G28C, D29C, I72C, K75C, T80C, P81C, I82C, T93C, N94C, and S95C.

26. A TMMP of aspect 24 or 25, wherein:
a) the amino acid substitution in the DRA MHC class II polypeptide is P81C; and the amino acid substitution in the DRB MHC class II polypeptide is F7C;
b) the amino acid substitution in the DRA MHC class II polypeptide is P81C; and the amino acid substitution in the DRB MHC class II polypeptide is P5C;
c) the amino acid substitution in the DRA MHC class II polypeptide is P81C; and the amino acid substitution in the DRB MHC class II polypeptide is H33C;
d) the amino acid substitution in the DRA MHC class II polypeptide is E4C; and the amino acid substitution in the DRB MHC class II polypeptide is N19C;
e) the amino acid substitution in the DRA MHC class II polypeptide is E4C; and the amino acid substitution in the DRB MHC class II polypeptide is G20C;
f) the amino acid substitution in the DRA MHC class II polypeptide is T93C; and the amino acid substitution in the DRB MHC class II polypeptide is Q156C;
g) the amino acid substitution in the DRA MHC class II polypeptide is T93C; and the amino acid substitution in the DRB MHC class II polypeptide is W153C;
h) the amino acid substitution in the DRA MHC class II polypeptide is F12C; and the amino acid substitution in the DRB MHC class II polypeptide is F7C;
i) the amino acid substitution in the DRA MHC class II polypeptide is F12C; and the amino acid substitution in the DRB MHC class II polypeptide is Q10C;
j) the amino acid substitution in the DRA MHC class II polypeptide is T80C; and the amino acid substitution in the DRB MHC class II polypeptide is F7C;
k) the amino acid substitution in the DRA MHC class II polypeptide is T80C; and the amino acid substitution in the DRB MHC class II polypeptide is P5C;
l) the amino acid substitution in the DRA MHC class II polypeptide is T80C; and the amino acid substitution in the DRB MHC class II polypeptide is I82C;
m) the amino acid substitution in the DRA MHC class II polypeptide is I82C; and the amino acid substitution in the DRB MHC class II polypeptide is F7C;
n) the amino acid substitution in the DRA MHC class II polypeptide is I82C; and the amino acid substitution in the DRB MHC class II polypeptide is P5C;
o) the amino acid substitution in the DRA MHC class II polypeptide is I82C; and the amino acid substitution in the DRB MHC class II polypeptide is H33C;
p) the amino acid substitution in the DRA MHC class II polypeptide is G28C; and the amino acid substitution in the DRB MHC class II polypeptide is G151C;
q) the amino acid substitution in the DRA MHC class II polypeptide is G28C; and the amino acid substitution in the DRB MHC class II polypeptide is D152C;
r) the amino acid substitution in the DRA MHC class II polypeptide is G28C; and the amino acid substitution in the DRB MHC class II polypeptide is W153C;
s) the amino acid substitution in the DRA MHC class II polypeptide is D29C; and the amino acid substitution in the DRB MHC class II polypeptide is G151C;
t) the amino acid substitution in the DRA MHC class II polypeptide is D29C; and the amino acid substitution in the DRB MHC class II polypeptide is D152C;
u) the amino acid substitution in the DRA MHC class II polypeptide is D29C; and the amino acid substitution in the DRB MHC class II polypeptide is W153C;
v) the amino acid substitution in the DRA MHC class II polypeptide is N94C; and the amino acid substitution in the DRB MHC class II polypeptide is Q156C;
w) the amino acid substitution in the DRA MHC class II polypeptide is N94C; and the amino acid substitution in the DRB MHC class II polypeptide is N120C;
y) the amino acid substitution in the DRA MHC class II polypeptide is S95C; and the amino acid substitution in the DRB MHC class II polypeptide is Q156C;
z) the amino acid substitution in the DRA MHC class II polypeptide is S95C; and the amino acid substitution in the DRB MHC class II polypeptide is N120C;
aa) the amino acid substitution in the DRA MHC class II polypeptide is E3C; and the amino acid substitution in the DRB MHC class II polypeptide is N19C; or
bb) the amino acid substitution in the DRA MHC class II polypeptide is E3C; and the amino acid substitution in the DRB MHC class II polypeptide is G20C.

27. A TMMP comprising two heterodimers according to any one of aspects 1-26, wherein each heterodimer comprises an Ig Fc polypeptide (e.g., a variant human IgG1 Fc polypeptide that substantially does not induce cell lysis through activation of CDC such as a human IgG1 Fc polypeptide comprising L234A and L235A substitutions, shown as L14A and L15A of the amino acid sequence depicted in FIG. 12A), and wherein the heterodimers are disulfide bonded to each other though their respective Ig Fc components.

28. A composition comprising:
a) a TMMP of any one of aspects 1-27; and
b) a pharmaceutically acceptable excipient.

29. One or more nucleic acids comprising nucleotide sequences encoding a T-cell modulatory multimeric polypeptide of any one of aspects 1-27.

30. One or more expression vectors comprising the one or more nucleic acids of aspect 29.

31. A host cell genetically modified with the one or more nucleic acids of aspect 29 or the one or more expression vectors of aspect 30.

32. A method of selectively modulating the activity of CD4$^+$ T cells specific for a type 1 diabetes-associated epitope in an individual, the method comprising contacting the CD4+ T cells with a TMMP of any one of aspects 1-27.

33. A method of reducing the number and/or activity of CD4+ and/or CD8+ self-reactive T cells specific for a type 1 diabetes-associated epitope in an individual, the method comprising contacting the CD4$^+$ T cells with a TMMP of any one of aspects 1-27.

34. A method of treating type 1 diabetes (T1D) in an individual, the method comprising administering to an individual in need thereof an effective amount of a TMMP of any one of aspects 1-27, or an effective amount of the composition of aspect 28.

35. An antigen-presenting polypeptide (APP) comprising:
a) a first polypeptide comprising:
   i) a peptide that displays a type 1 diabetes associated epitope capable of being bound by a T-cell receptor (a "T1D peptide"); and
   ii) a first major histocompatibility complex (MHC) class II polypeptide; and
   iii) optionally a linker that links the T1D peptide to the first MHC class II polypeptide; and
b) a second polypeptide comprising a second MHC class II polypeptide, wherein the first and the second polypeptide of the heterodimer are covalently linked to one another via at least one disulfide bond,
wherein one of the polypeptides of the heterodimer comprises an immunoglobulin (Ig) Fc polypeptide, optionally joined to the first or second polypeptide via a linker, and
wherein the APP does not include an immunomodulatory polypeptide.

36. An APP of aspect 35, wherein the first MHC class II polypeptide is an MHC class II β chain polypeptide and wherein the second MHC class II polypeptide is an MHC class II α chain polypeptide.

37. An APP of aspect 36, wherein the MHC class II α polypeptide comprises an amino acid sequence having at least 95%, at least 98% or at least 99%, amino acid sequence identity to a DRA1*01:01 polypeptide; and the MHC class II β polypeptide comprises an amino acid sequence having at least 95%, at least 98%, or at least 99% amino acid sequence identity to a DRB 1*04:01 polypeptide.

38. An APP of any one of aspects 35-37, wherein the T1D peptide has a length of from about 4 amino acids to about 25 amino acids.

39. An APP of any one of aspects 35-38, wherein the T1D peptide comprises is a proinsulin peptide or a glutamic acid decarboxylase (GAD) peptide.

40. An APP of aspect 39, wherein the T1D peptide is a proinsulin peptide selected from SLQPLALEGSLQKRG (SEQ ID NO:94; proIns 76-90), SLQPLALEGSLQSRG (SEQ ID NO:90; proIns 76-90; K88S), and GAGSLQPLALEGSLQKRG (SEQ ID NO:93; proIns 73-90).

41. An APP of aspect 39, wherein the T1D peptide is a GAD peptide selected from

```
                         (SEQ ID NO: 87; GAD65 555-567)
NFFRMVISNPAAT
and (SEQ ID NO: 88; GAD65 555-567; F557I)
NFIRMVISNPAAT.
```

42. An APP of any one of aspects 36-41, wherein the first polypeptide comprises a Cys-containing linker between the T1D peptide and the MHC Class II β chain polypeptide, and wherein a disulfide bond is formed between the Cys in the linker and a Cys in the second MHC class II polypeptide.

43. An APP of aspect 42, wherein the linker comprises an amino acid sequence selected from (CGGGS)(GGGGS)n (SEQ ID NO: 1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where the linker is from about 15 amino acids to about 20 amino acids, such as (GGCGS)(GGGGS)n where n=2 (SEQ ID NO:128) or n=3 (SEQ ID NO:129)).

44. An APP of aspect 42 or aspect 43, wherein the second MHC class II polypeptide is a variant MHC class II polypeptide that comprises a non-naturally occurring Cys residue.

45. An APP of aspect 44, wherein the second MHC class II polypeptide is a DRA MHC class II polypeptide (e.g., having at least 95%, at least 98% or at least 99% amino acid sequence identity to a DRAT*01:01 polypeptide).

46. An APP of aspect 44 or 45, wherein the non-naturally occurring Cys residue is located at an amino acid residue from amino acids 55 to 110 of the second MHC Class II polypeptide.

47. An APP of any one of aspects 42-46, wherein the second MHC class II polypeptide is a variant DRA MHC class II polypeptide comprising a Cys at position 72 or 75 based on the amino acid numbering depicted in FIG. 13A.

48. An APP of any one of aspects 42-47, wherein the variant DRA MHC class II polypeptide comprises a K75C substitution or an I72C substitution (e.g., a DRA MHC class II polypeptide comprising an amino acid sequence having at least 80%, at least 85%, at least 90%, at least 95%, at least 98%, at least 99%, or 100% amino acid sequence identity to the amino acid sequence depicted in FIG. 13G or 13H).

49. An APP of any one of aspects 42-48, comprising:
a1) a first polypeptide comprising, in order from N-terminus to C-terminus: i) a T1D peptide; ii) a linker comprising an amino acid sequence selected from the group consisting of (CGGGS)(GGGGS)n (SEQ ID NO:1), (GCGGS)(GGGGS)n (SEQ ID NO:2), (GGCGS)(GGGGS)n (SEQ ID NO:3), (GGGCS)(GGGGS)n (SEQ ID NO:4), and (GGGGC)(GGGGS)n (SEQ ID NO:5), where n is an integer from 1 to 10 (e.g., where the linker is from about 15 amino acids to about 20 amino acids, such as (GGCGS)(GGGGS)n where n=2 (SEQ ID NO:128) or n=3 (SEQ ID NO:129); and iii) an MHC class II β chain polypeptide (e.g., a DRB MHC class II polypeptide comprising an amino acid sequence having at least 80%, at least 85%, at least 90%, at least 95%, at least 98%, at least 99%, or 100%, amino acid sequence identity to the amino acid sequence depicted in FIG. 14A); and
b1) a second polypeptide comprising, in order from N-terminus to C-terminus: i) an MHC class II α chain comprising Cys at position 72 or 75 (e.g., a DRA MHC class II polypeptide comprising an amino acid sequence having at least 80%, at least 85%, at least 90%, at least 95%, at least 98%, at least 99%, or 100% amino acid sequence identity to the amino acid sequence depicted in FIG. 13G or 13H, and comprising a Cys at position 72 or 75); and an ii) a variant human IgG1 Fc polypeptide that substantially does not induce cell lysis through activation of CDC (e.g., a human IgG1 Fc polypeptide comprising L234A and L235A substitutions, shown as L14A and L15A of the amino acid sequence depicted in FIG. 12A).

50. An APP of any one of aspects 35-41, wherein the disulfide bond is formed between:
i) a Cys in the first MHC class II polypeptide; and
ii) a Cys in the second MHC class II polypeptide.

51. An APP of aspect 50, wherein: i) the first MHC class II polypeptide is a variant MHC class II polypeptide that comprises a non-naturally occurring Cys residue; and ii) the second MHC class II polypeptide is a variant MHC class II polypeptide that comprises a non-naturally occurring Cys residue.

52. An APP of aspect 50 or aspect 51, wherein the first MHC class II polypeptide is a DRB MHC class II polypeptide, and wherein the second MHC class II polypeptide is a DRA MHC class II polypeptide.

53. An APP of aspect 52, wherein the DRB MHC class II polypeptide comprises an amino acid substitution selected from the group consisting of P5C, F7C, Q10C, N19C, G20C, H33C, G151C, D152C, and W153C.

54. An APP of aspect 52 or aspect 53, wherein DRA MHC class II polypeptide comprises an amino acid substitution selected from the group consisting of E3C, E4C, F12C, G28C, D29C, I72C, K75C, T80C, P81C, I82C, T93C, N94C, and S95C.

55. An APP of aspect 53 or 54, wherein:
a) the amino acid substitution in the DRA MHC class II polypeptide is P81C; and the amino acid substitution in the DRB MHC class II polypeptide is F7C;
b) the amino acid substitution in the DRA MHC class II polypeptide is P81C; and the amino acid substitution in the DRB MHC class II polypeptide is P5C;
c) the amino acid substitution in the DRA MHC class II polypeptide is P81C; and the amino acid substitution in the DRB MHC class II polypeptide is H33C;
d) the amino acid substitution in the DRA MHC class II polypeptide is E4C; and the amino acid substitution in the DRB MHC class II polypeptide is N19C;
e) the amino acid substitution in the DRA MHC class II polypeptide is E4C; and the amino acid substitution in the DRB MHC class II polypeptide is G20C;
f) the amino acid substitution in the DRA MHC class II polypeptide is T93C; and the amino acid substitution in the DRB MHC class II polypeptide is Q156C;
g) the amino acid substitution in the DRA MHC class II polypeptide is T93C; and the amino acid substitution in the DRB MHC class II polypeptide is W153C;
h) the amino acid substitution in the DRA MHC class II polypeptide is F12C; and the amino acid substitution in the DRB MHC class II polypeptide is F7C;
i) the amino acid substitution in the DRA MHC class II polypeptide is F12C; and the amino acid substitution in the DRB MHC class II polypeptide is Q10C;
j) the amino acid substitution in the DRA MHC class II polypeptide is T80C; and the amino acid substitution in the DRB MHC class II polypeptide is F7C;
k) the amino acid substitution in the DRA MHC class II polypeptide is T80C; and the amino acid substitution in the DRB MHC class II polypeptide is P5C;
l) the amino acid substitution in the DRA MHC class II polypeptide is T80C; and the amino acid substitution in the DRB MHC class II polypeptide is I82C;
m) the amino acid substitution in the DRA MHC class II polypeptide is I82C; and the amino acid substitution in the DRB MHC class II polypeptide is F7C;
n) the amino acid substitution in the DRA MHC class II polypeptide is I82C; and the amino acid substitution in the DRB MHC class II polypeptide is P5C;
o) the amino acid substitution in the DRA MHC class II polypeptide is I82C; and the amino acid substitution in the DRB MHC class II polypeptide is H33C;
p) the amino acid substitution in the DRA MHC class II polypeptide is G28C; and the amino acid substitution in the DRB MHC class II polypeptide is G151C;
q) the amino acid substitution in the DRA MHC class II polypeptide is G28C; and the amino acid substitution in the DRB MHC class II polypeptide is D152C;
r) the amino acid substitution in the DRA MHC class II polypeptide is G28C; and the amino acid substitution in the DRB MHC class II polypeptide is W153C;
s) the amino acid substitution in the DRA MHC class II polypeptide is D29C; and the amino acid substitution in the DRB MHC class II polypeptide is G151C;
t) the amino acid substitution in the DRA MHC class II polypeptide is D29C; and the amino acid substitution in the DRB MHC class II polypeptide is D152C;
u) the amino acid substitution in the DRA MHC class II polypeptide is D29C; and the amino acid substitution in the DRB MHC class II polypeptide is W153C;
v) the amino acid substitution in the DRA MHC class II polypeptide is N94C; and the amino acid substitution in the DRB MHC class II polypeptide is Q156C;
w) the amino acid substitution in the DRA MHC class II polypeptide is N94C; and the amino acid substitution in the DRB MHC class II polypeptide is N120C;
y) the amino acid substitution in the DRA MHC class II polypeptide is S95C; and the amino acid substitution in the DRB MHC class II polypeptide is Q156C;
z) the amino acid substitution in the DRA MHC class II polypeptide is S95C; and the amino acid substitution in the DRB MHC class II polypeptide is N120C;
aa) the amino acid substitution in the DRA MHC class II polypeptide is E3C; and the amino acid substitution in the DRB MHC class II polypeptide is N19C; or
bb) the amino acid substitution in the DRA MHC class II polypeptide is E3C; and the amino acid substitution in the DRB MHC class II polypeptide is G20C.

56. An APP of any one of aspects 35-55, wherein the second polypeptide comprises the Ig Fc polypeptide.

57. An APP of any one of aspects 35-56, wherein the Ig Fc polypeptide induces cell lysis through activation of complement-dependent cytotoxicity (CDC) and/or elicits antibody-dependent cellular cytotoxicity (ADCC).

58. An APP of any one of aspects 35-56, further comprising a detectable label that permits binding of the APP to a target T cell to be detected.

59. An APP comprising two heterodimers according to any of aspects 35-58, wherein each heterodimer comprises an Ig Fc polypeptide, and wherein the heterodimers are disulfide bonded to each other though their respective Ig Fc components.

60. A composition comprising:
a) an APP of any one of aspects 35-59; and
b) a pharmaceutically acceptable excipient.

61. One or more nucleic acids comprising nucleotide sequences encoding an APP of any one of aspects 35-59.

62. One or more expression vectors comprising the one or more nucleic acids of aspect 61.

63. A host cell genetically modified with the one or more nucleic acids of aspect 61 or the one or more expression vectors of aspect 62.

64. A method of reducing the number and/or activity of CD4$^+$ and/or CD8$^+$ self-reactive T cells specific for a type 1 diabetes-associated epitope in an individual, the method comprising contacting the CD4$^+$ T cells with an APP of aspect 57.

65. A method of treating type 1 diabetes (T1D) in an individual, the method comprising administering to an individual in need thereof an effective amount of an APP of aspect 57.

66. A method of detecting a CD4$^+$ T cell specific for a type 1 diabetes-associated epitope in an individual, the method comprising the steps of contacting the CD4$^+$ T cell with an APP of aspect 58, and detecting the presence of the label.

67. A TMMP according to aspect 27, wherein at least 50%, at least 60%, at least 70%, at least 80%, or at least 90% of an initial quantity of TMMP monomer remains present as a monomer in a PBS buffer solution after 3 days at 37° C. at a TMMP concentration of 9.5 mg/mL, 1 mg/mL, or 0.1 mg/mL, wherein the PBS buffer solution, not including the TMMP monomer, comprises sodium chloride (500 mM), sodium phosphate dibasic (10 mM), potassium phosphate monobasic (2 mM), potassium chloride (2.7 mM), and water, and has a pH of 7.5±0.15, and wherein the amount of monomer is determined using size exclusion chromatography using a Superdex 200 Increase (3.2×300 mm) column (e.g., from GE Healthcare), with a running buffer of the PBS buffer solution, and wherein the flow rate is 0.15 ml/minute.

68. A TMMP according to aspect 27, wherein at least 50%, at least 60%, at least 70%, or at least 80% of an initial quantity of TMMP monomer remains present as a monomer in a PBS buffer solution after 5 days at 37° C. at a TMMP concentration of 9.5 mg/mL, 1 mg/mL, or 0.1 mg/mL, wherein the PBS buffer solution, not including the TMMP monomer, comprises sodium chloride (500 mM), sodium phosphate dibasic (10 mM), potassium phosphate monobasic (2 mM), potassium chloride (2.7 mM), and water, and has a pH of 7.5±0.15, and wherein the amount of monomer is determined using size exclusion chromatography using a Superdex 200 Increase (3.2×300 mm) column (e.g., from GE Healthcare), with a running buffer of the PBS buffer solution, and wherein the flow rate is 0.15 ml/minute.

69. A TMMP according to aspect 27, wherein at least 50%, at least 60%, or at least 70% of an initial quantity of TMMP monomer remains present as a monomer in a PBS buffer solution after 3 days at 42° C. at a TMMP concentration of 9.5 mg/mL, 1 mg/mL, or 0.1 mg/mL, wherein the PBS buffer solution, not including the TMMP monomer, comprises sodium chloride (500 mM), sodium phosphate dibasic (10 mM), potassium phosphate monobasic (2 mM), potassium chloride (2.7 mM), and water, and has a pH of 7.5±0.15, and wherein the amount of monomer is determined using size exclusion chromatography using a Superdex 200 Increase (3.2×300 mm) column (e.g., from GE Healthcare), with a running buffer of the PBS buffer solution, and wherein the flow rate is 0.15 ml/minute.

70. A TMMP according to aspect 27, wherein at least 50%, at least 60%, at least 70%, at least 80%, or at least 90% of an initial quantity of TMMP monomer remains present as a monomer in a PBS buffer solution after 5 days at 42° C.; at a TMMP concentration of 9.5 mg/mL, 1 mg/mL, or 0.1 mg/mL, wherein the PBS buffer solution, not including the TMMP monomer, comprises sodium chloride (500 mM), sodium phosphate dibasic (10 mM), potassium phosphate monobasic (2 mM), potassium chloride (2.7 mM), and water, and has a pH of 7.5±0.15, and wherein the amount of monomer is determined using size exclusion chromatography using a Superdex 200 Increase (3.2×300 mm) column (e.g., from GE Healthcare), with a running buffer of the PBS buffer solution, and wherein the flow rate is 0.15 ml/minute.

71. A TMMP according to any one of aspects 67-70, wherein the TMMP is in the PBS buffer solution at a concentration of 9.5 mg/mL.

72. A TMMP according to any one of aspects 67-70, wherein the TMMP is in the PBS buffer solution at a concentration of 1 mg/mL.

73. A TMMP according to any one of aspects 67-70, wherein the TMMP is in the PBS buffer solution at a concentration of 0.1 mg/mL.

EXAMPLES

The following examples are put forth so as to provide those of ordinary skill in the art with a complete disclosure and description of how to make and use aspects of the present disclosure, and are not intended to limit the scope of what the inventors regard as their disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Disulfide Bond Placement

One set of constructs ("body disulfide" set) was made that included two heterodimers, each heterodimer including: a) a first polypeptide comprising: i) a peptide epitope (e.g., a proinsulin peptide or a GAD65 peptide); and ii) an hDRB 1*0401β chain polypeptide comprising an amino acid substitution providing a Cys (a "first Cys"); and b) a second polypeptide comprising: i) an hDRA1*0101α chain polypeptide comprising an amino acid substitution providing a Cys (a "second Cys"); and ii) an Ig Fc polypeptide, where the first and second polypeptides are covalently linked to one another via a disulfide between the first Cys and the second Cys. A second set of constructs ("linker disulfide set") was made that included two heterodimers, each heterodimer including: a) a first polypeptide comprising: i) a peptide epitope (e.g., a proinsulin peptide or a GAD65 peptide); ii) a peptide linker comprising a Cys; and iii) an hDRB 1*0401β chain polypeptide; and b) a second polypeptide comprising: i) an hDRA1*0101α chain polypeptide comprising an amino acid substitution providing a Cys; and ii) an Ig Fc polypeptide, where the first and second polypeptides are covalently linked to one another via a disulfide between the Cys in the peptide linker and the Cys provided by the amino acid substitution in the α chain.

The ability of the first and the second polypeptides to form disulfide-linked heterodimers was tested by running the constructs on sodium dodecyl sulfate (SDS) polyacrylamide gels (PAGE) containing dithiothreitol (reducing) or not containing dithiothreitol (non-reducing).

A protein consisting of 2 heterodimers, and a total of 4 polypeptide chains, is referred to in this Example as a "monomer." Whether a protein was present in solution as a monomer was determined using size exclusion chromatography (SEC). SEC was performed using the PBS containing 500 mM NaCl (described above) as the running buffer; and a flow rate of 0.15 ml/minute.

Figure 17C:
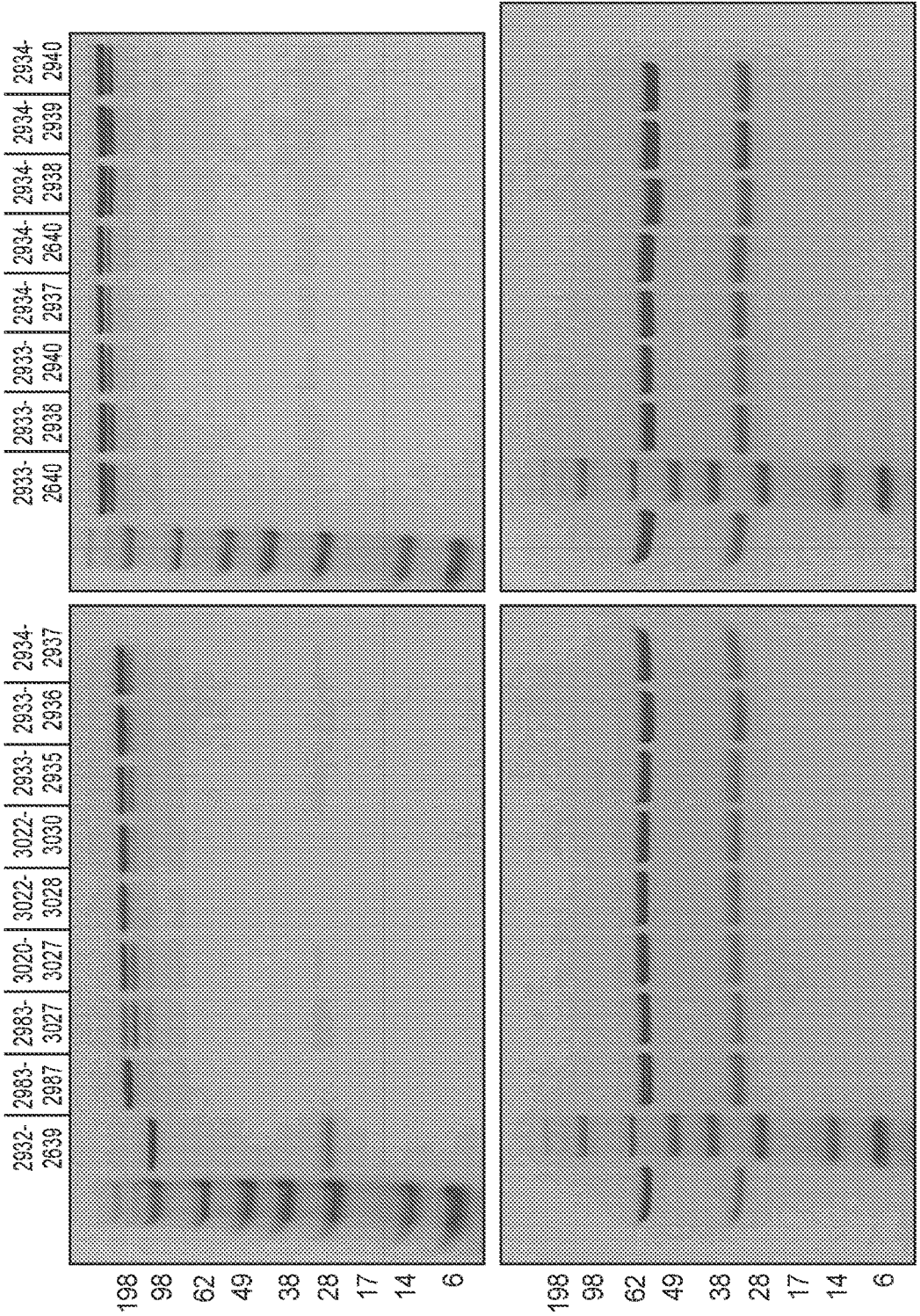

FIG. 17A depicts various "body disulfide" and "linker disulfide" constructs, the position of the Cys residues forming a disulfide bond between the two polypeptides of a heterodimer, the yield from a Protein A column, and the percent monomer. Amino acid sequences of the various polypeptide chains of the constructs are depicted in FIG. 15. FIG. 17B depicts expression level from the Protein A column. FIG. 17C shows reducing (lower panels) and non-reducing (upper panels) SDS-PAGE results for the various proteins.

FIG. 18A-18B depict various "body disulfide" constructs and features of the two polypeptides of the heterodimers. Amino acid sequences of the various polypeptide chains of the constructs are depicted in FIG. 15. The constructs were analyzed on reducing and non-reducing SDS-PAGE. The results are shown in FIG. 18C.

Example 2: MOD Placement

Various constructs were made to test the effect of the position of the immunomodulatory polypeptide ("MOD") in a TMMP. The various possibilities tested are Positions 1-5, depicted schematically in FIG. 5. TMMPs were generated that comprise: a) PD-L1 as the MOD, at various positions; b) GAD65 (555-567) as the T1D peptide; and c) MHC class II DRA α chain and DRB β chains. The two polypeptide chains of the heterodimers were not covalently linked. Amino acid sequences of the polypeptide chains of the constructs are depicted in FIG. 15.

Figure 19D:
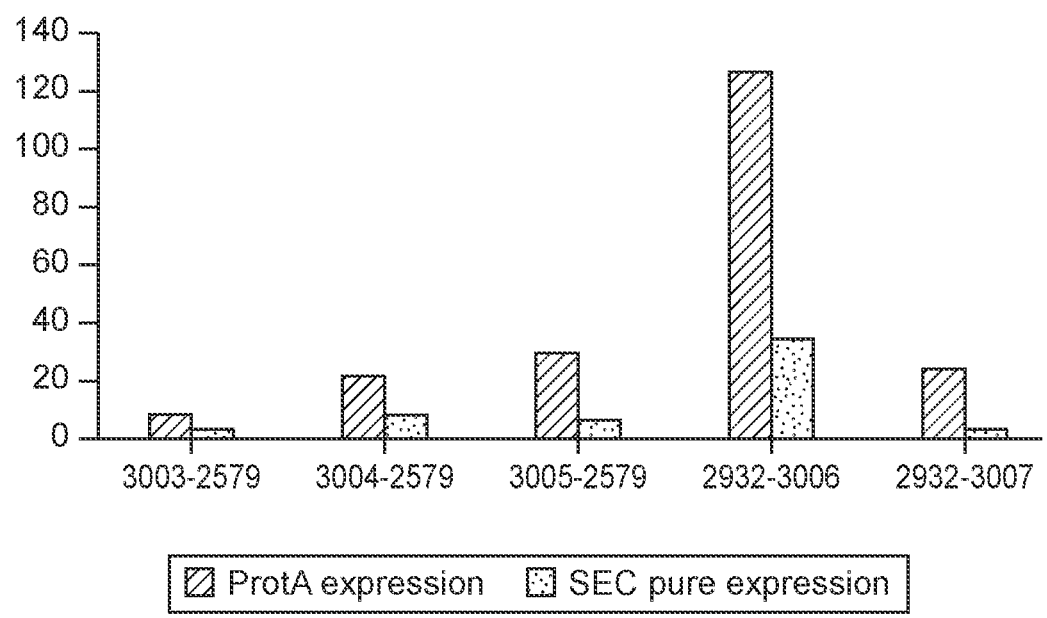

The results are shown in FIG. 18A-19D. FIG. 19A shows expression levels of the various constructs. FIG. 19B depicts reducing and non-reducing SDS-PAGE results. FIG. 19C depicts SEC data used to determine the % monomer. FIG. 19D shows expression levels determined by either Protein A column yields or SEC data.

Figure 20D:
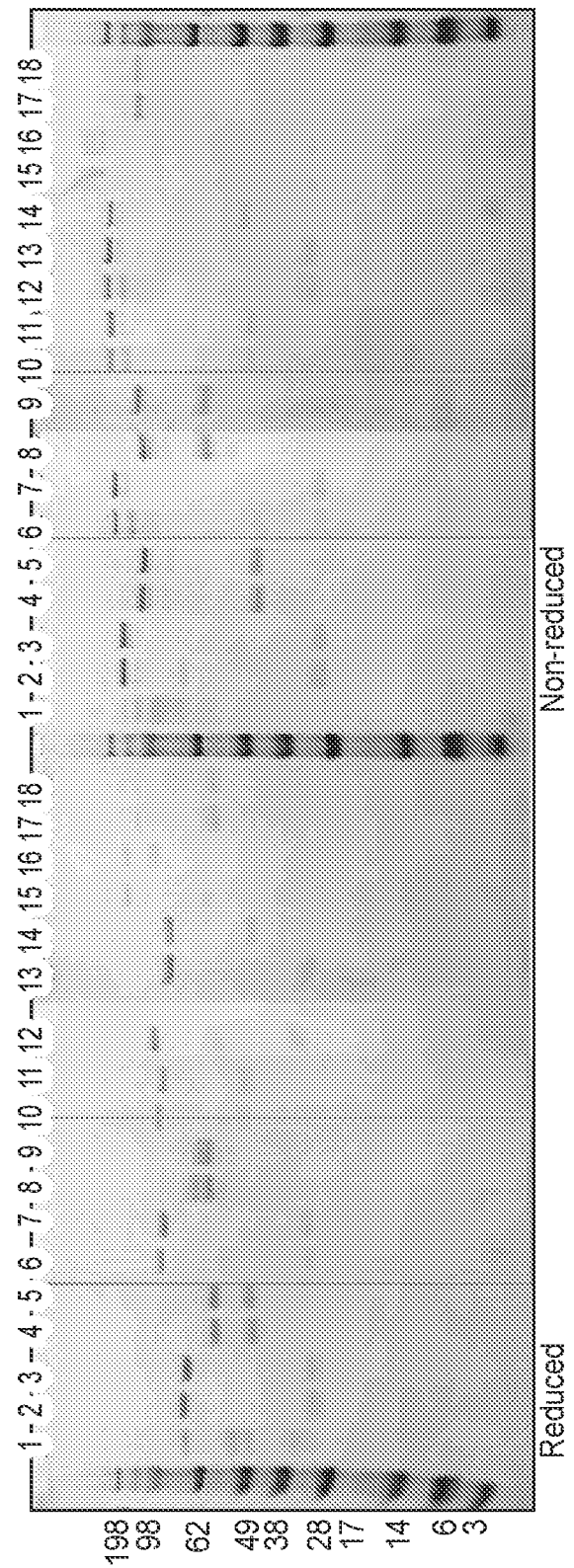

Additional constructs were made and tested. Features of the constructs are shown in FIG. 20A-20B. Production levels of the constructs are shown in FIG. 20C. Results of non-reducing and reducing SDS-PAGE analysis of the constructs are shown in FIG. 20D.

Example 3: In Vitro Stability

Figure 21A:
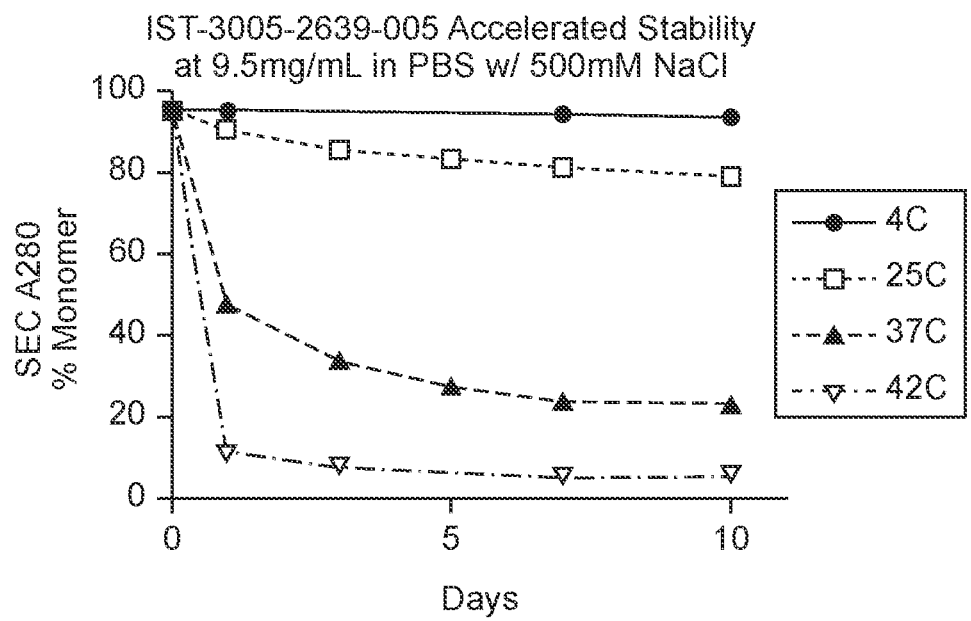
Figure 21B:
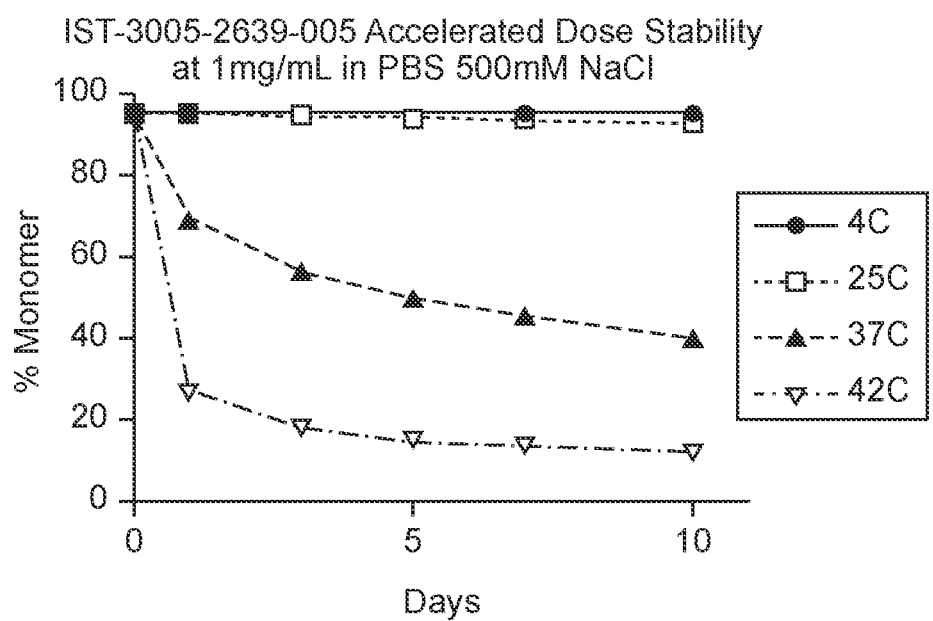
Figure 21C:
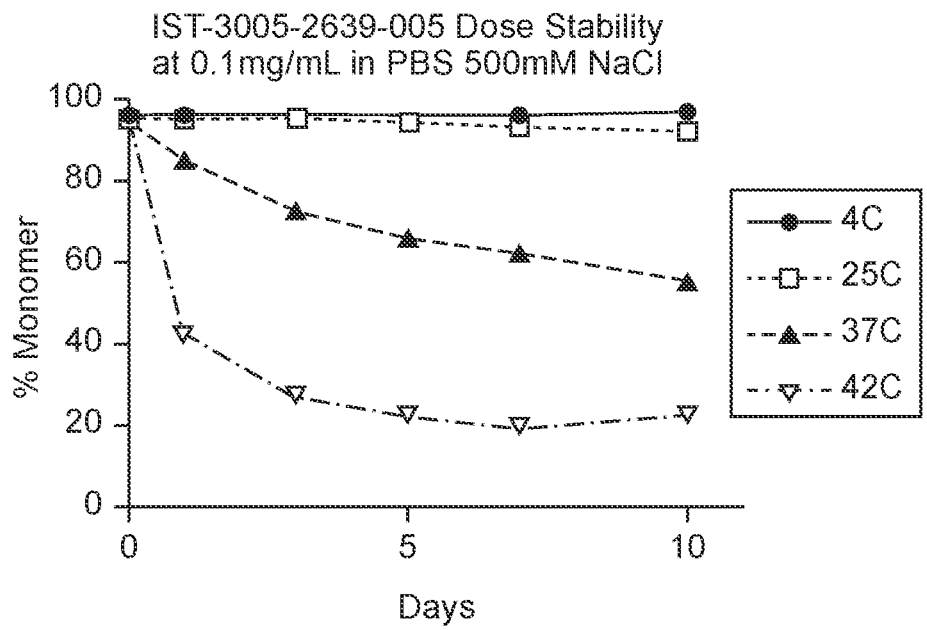
Figure 21D:
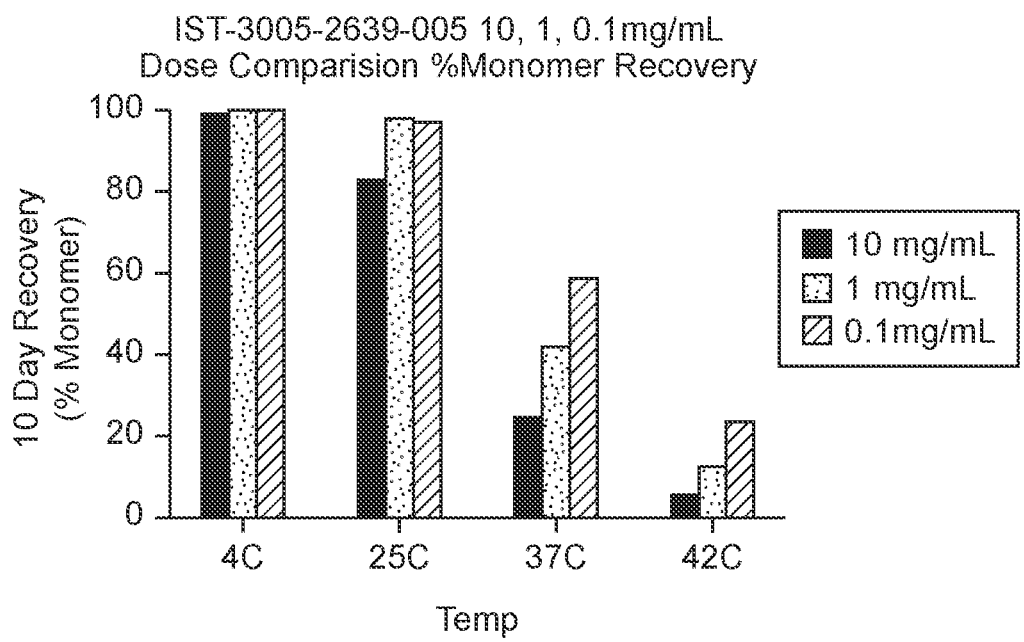

The in vitro stability of TMMP 3005-2639 was tested. TMMP 3005-2639 in a solution of PBS containing 500 mM NaCl (described above), at TMMP concentrations of 9.5 mg/mL, 1 mg/mL, or 0.1 mg/mL, was kept at 4° C., 25° C., 37° C., or 42° C. for up to 10 days. At various time points, the % monomer was determined. The results are shown in FIG. 21A-21E. FIG. 21A-21C show the % monomer at 9.5 mg/mL (FIG. 21A), 1 mg/mL (FIG. 21B), and 0.1 mg/mL (FIG. 21C). FIG. 30D shows % monomer recovery at the various concentrations and temperatures. The % monomer recovery data from FIG. 21D are summarized in FIG. 21E. The data show that increased aggregation upon thermal stress is proportional to increased concentration and temperature.

Figure 22A:
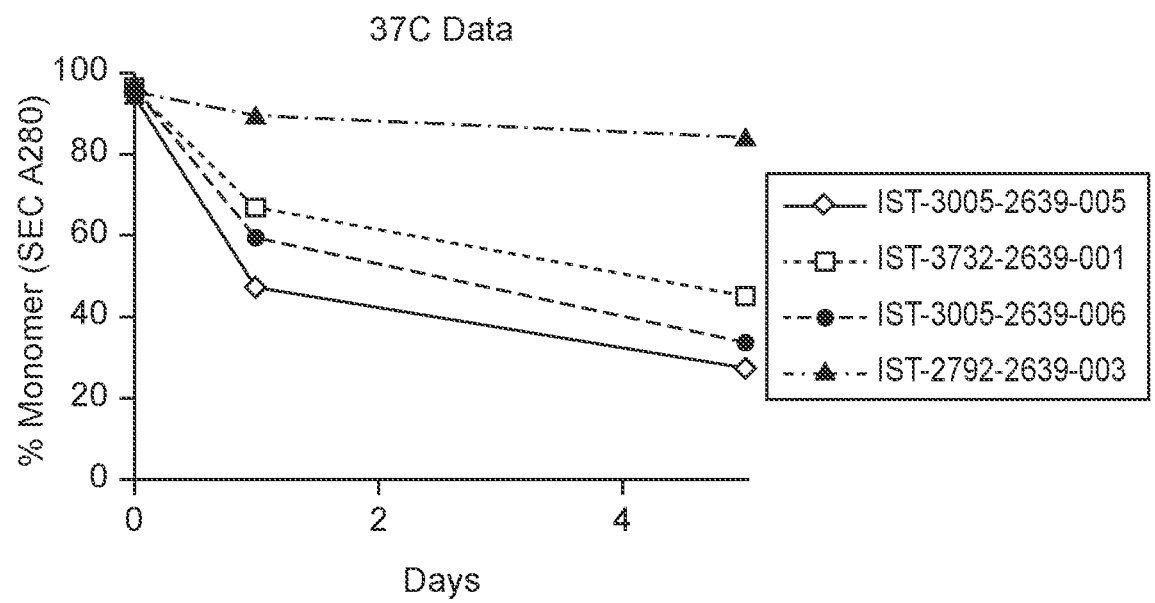
FIG. 22A-22B depict the results of stability analysis of disulfide-stabilized TMMPs with the immunomodulatory polypeptide (MOD) at Position 3.
Figure 22B:
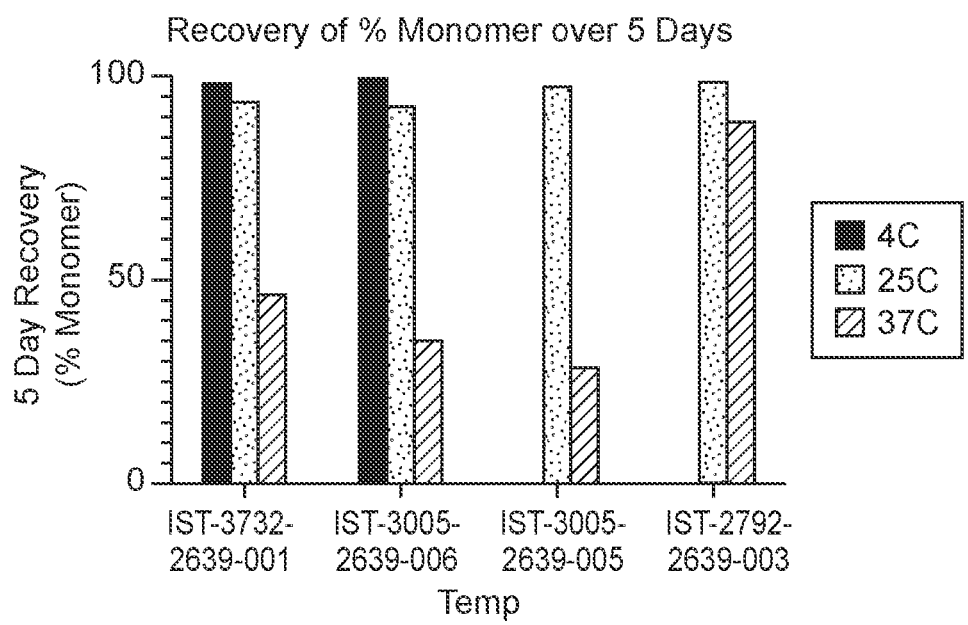

The in vitro stability of disulfide-stabilized TMMP, in which the MOD is at Position 3, was tested. The disulfide-stabilized TMMP was 3732-2639 (FIG. 15NN and FIG. 15C). Control TMMPs, in which the first and second polypeptides were not disulfide bonded, were also tested. The control TMMPs were: i) 2792-2639 (FIG. 1500 and FIG. 15C); and ii) 3005-2639 (FIG. 15D and FIG. 15C). Two different batches of TMMP 3005-2639, where the batches were designated "005" and "006," were tested. The data are shown in FIG. 22A and FIG. 22B. FIG. 22A depicts the % monomer remaining after 5 days at 37° C. FIG. 22B depict the % monomer after 5 days at 4° C., 25° C., and 37° C. The data indicate that disulfide linkage between the first polypeptide and the second polypeptide of a TMMP increases stability.

The in vitro stability of various disulfide-stabilized TMMPs, in which the MOD (PD-L1) is at Position 1, and in which the disulfide bond was between i) a Cys in the linker between the proIns epitope (proIns 76-90 (K88S)) and the MHC class II β chain; and ii) a Cys in the MHC class II α chain, was tested. The TMMPs were: i) 3892-2640 (FIG. 15PP and FIG. 15JJ); ii) 3893-2938 (FIG. 15B and FIG. 15A); and iii) 3893-2640 (FIG. 15B and FIG. 15JJ). A control TMMP, 3005-2639 (FIG. 15D and FIG. 15C), in which the first and second polypeptides were not disulfide bonded, was also tested. The in vitro stability of a TMMP concentration of 9.5 mg/mL was tested for the following conditions: i) 37° C. for 3 days; ii) 37° C. for 5 days; iii) 42° C. for 3 days; and iv) 42° C. for 5 days. The data are shown in FIG. 23. The data indicate that disulfide linkage between the first polypeptide and the second polypeptide of a TMMP increases stability.

Example 4: Expression Levels

Expression levels of various TMMPs are shown in the table presented in FIG. 24. It is noted that expression levels can vary with the conditions and scale employed. For example, while further expression results in a larger scale showed that 3003-2639 remained low, expression of 3005-2639 was able to achieve 30-40 mg/L expression titer.

Example 5: Effect of TMMPs on Functional Responses of Epitope-Specific CD4+ T Cells In Vitro The effect of TMMPs on functional responses of proinsulin-specific CD4+ T cells was assessed. The ability of Proins-PDL1 Pos3 (3005-2639) and Proins-PDL1 Pos 1 (3893-2938) to suppress Proinsulin-specific CD4 cells was assessed in an overnight suppression assay. TMMP 3005-2639 comprises two heterodimers; each heterodimer comprises: a) a 3005 polypeptide (FIG. 15D); and b) a 2639 polypeptide (FIG. 15C), where the 3005 polypeptide and the 2639 polypeptide are non-covalently associated. TMMP 3892-2938 comprises two heterodimers; each heterodimer comprises: a) a 3893 polypeptide (FIG. 15B); and b) a 2938 polypeptide (FIG. 15A), where the 3893 polypeptide and the 2938 polypeptide are covalently linked via a disulfide bond.

Peripheral blood mononuclear cells (PBMCs) from multiple healthy or T1D patients were expanded with proinsulin (PI) 76-90K88S peptide and recombinant human IL-2 (rhIL-2) in RPMI+10% human serum for 14 days. Expanded PBMCs were washed and incubated (2e6 cells/well, 24 well plate) with increasing concentrations of indicated TMMPs overnight at 37° C., 5% $CO_2$. The TMMP-treated cells were washed, and functional response of antigen-specific cells was assessed using an IFNγ ELISPOT upon re-stimulation with PI 76-90K88S peptide. Additionally, the TMMP-treated, washed cells were cultured in presence of autologous PBMCs (1:1) and rhIL-2 to assess duration of suppressive effect. IFNγ ELISPOT was performed at the indicated time points.

Figure 25:
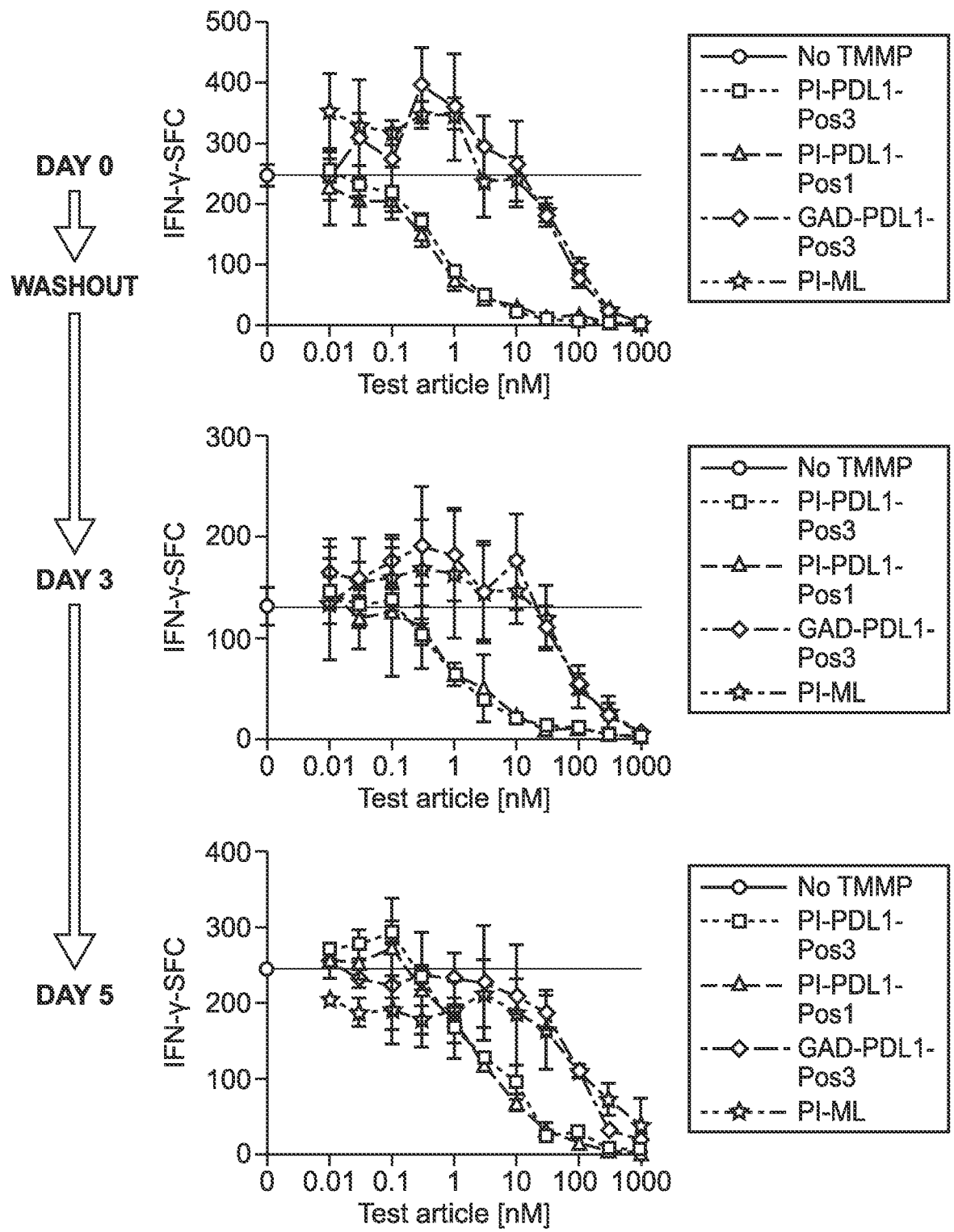
FIG. 25 depicts functional response of Proinsulin-specific CD4+ T cells following administration with TMMP 3005-2639 or TMMP 3893-2938 as compared to control molecules.
Figure 26:
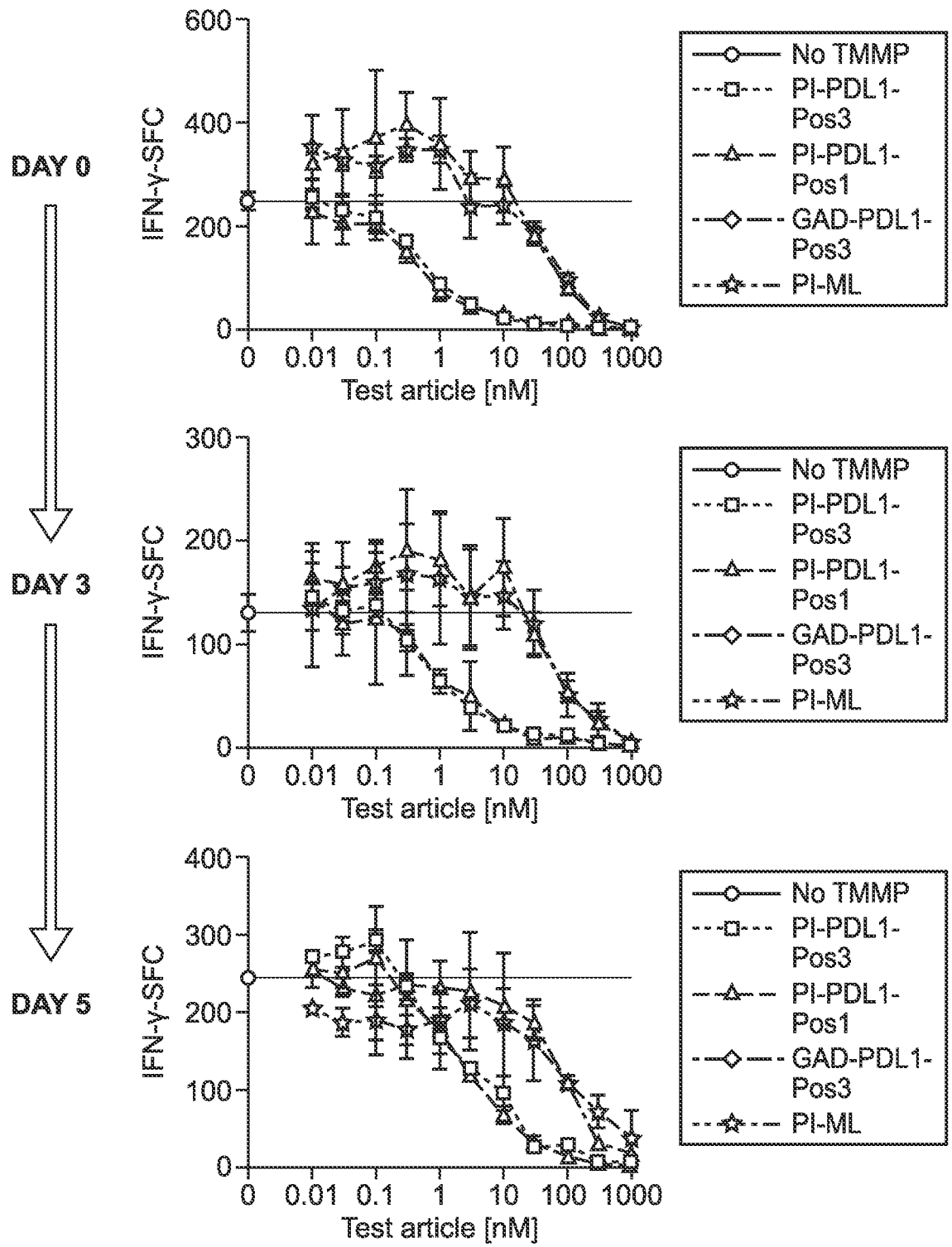
FIG. 26 depicts antigen-specific, PD-L1-dependent suppression of PI-specific CD4+ T cells following administration of TMMP.
Figure 26:
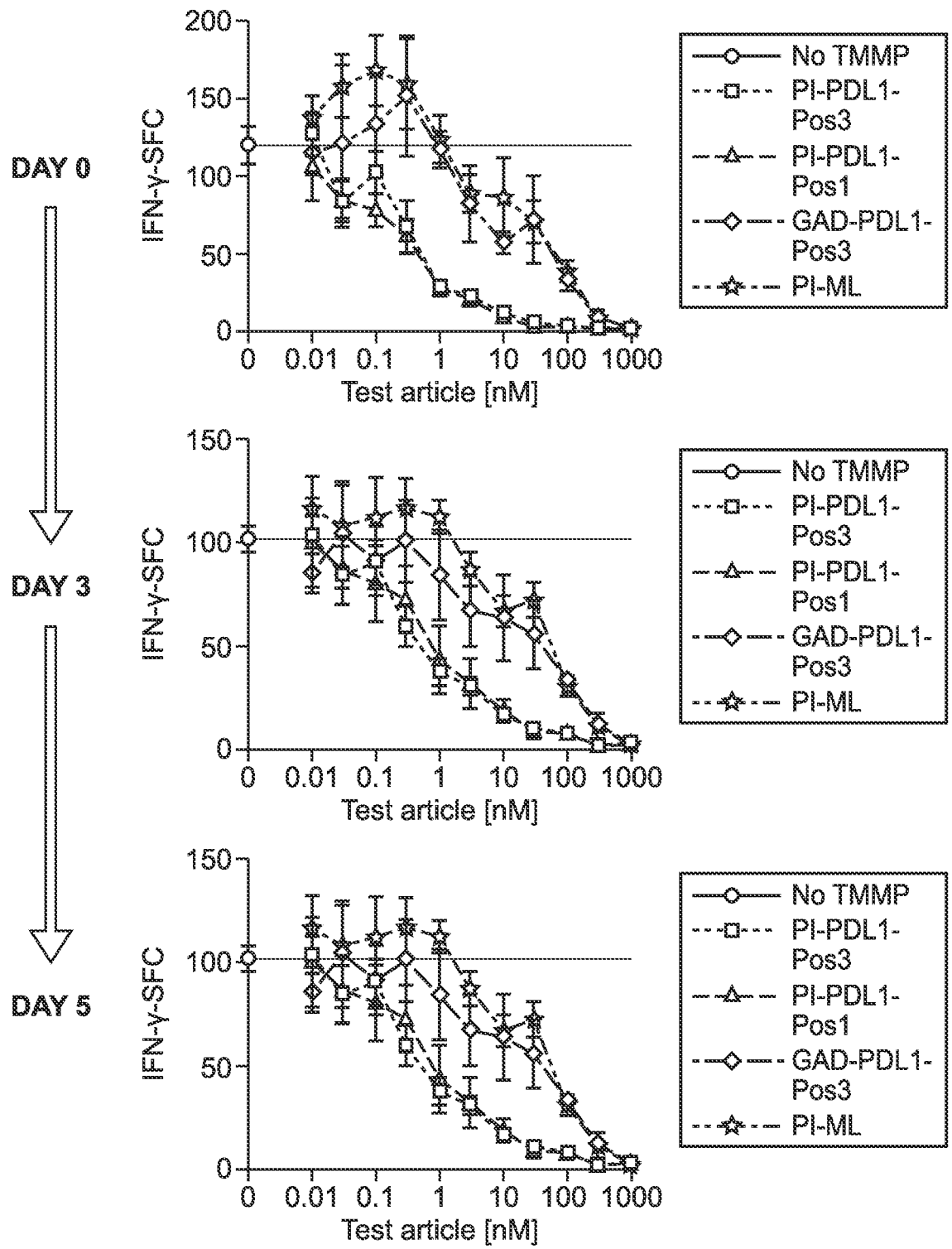
Figure 26:
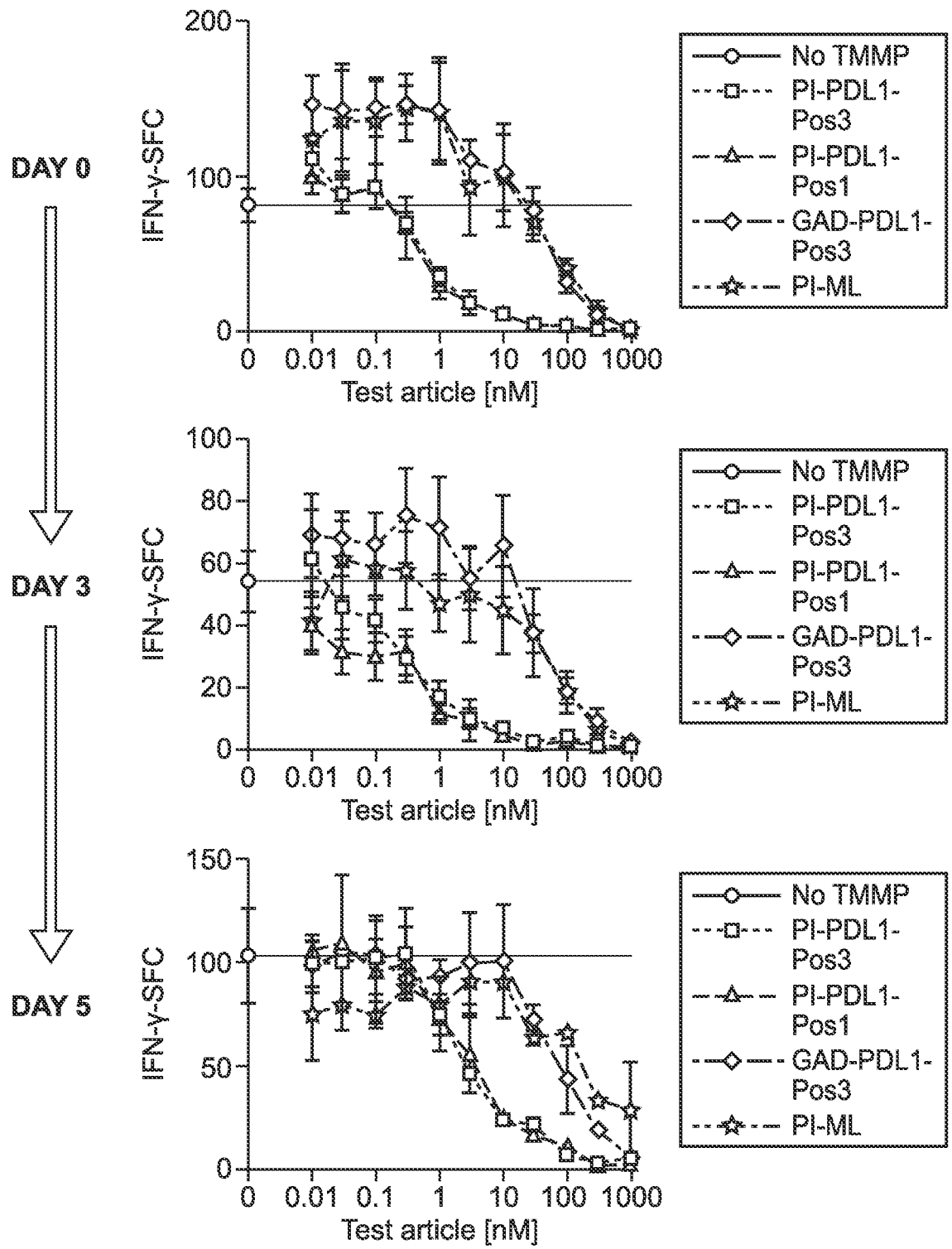
Figure 26:
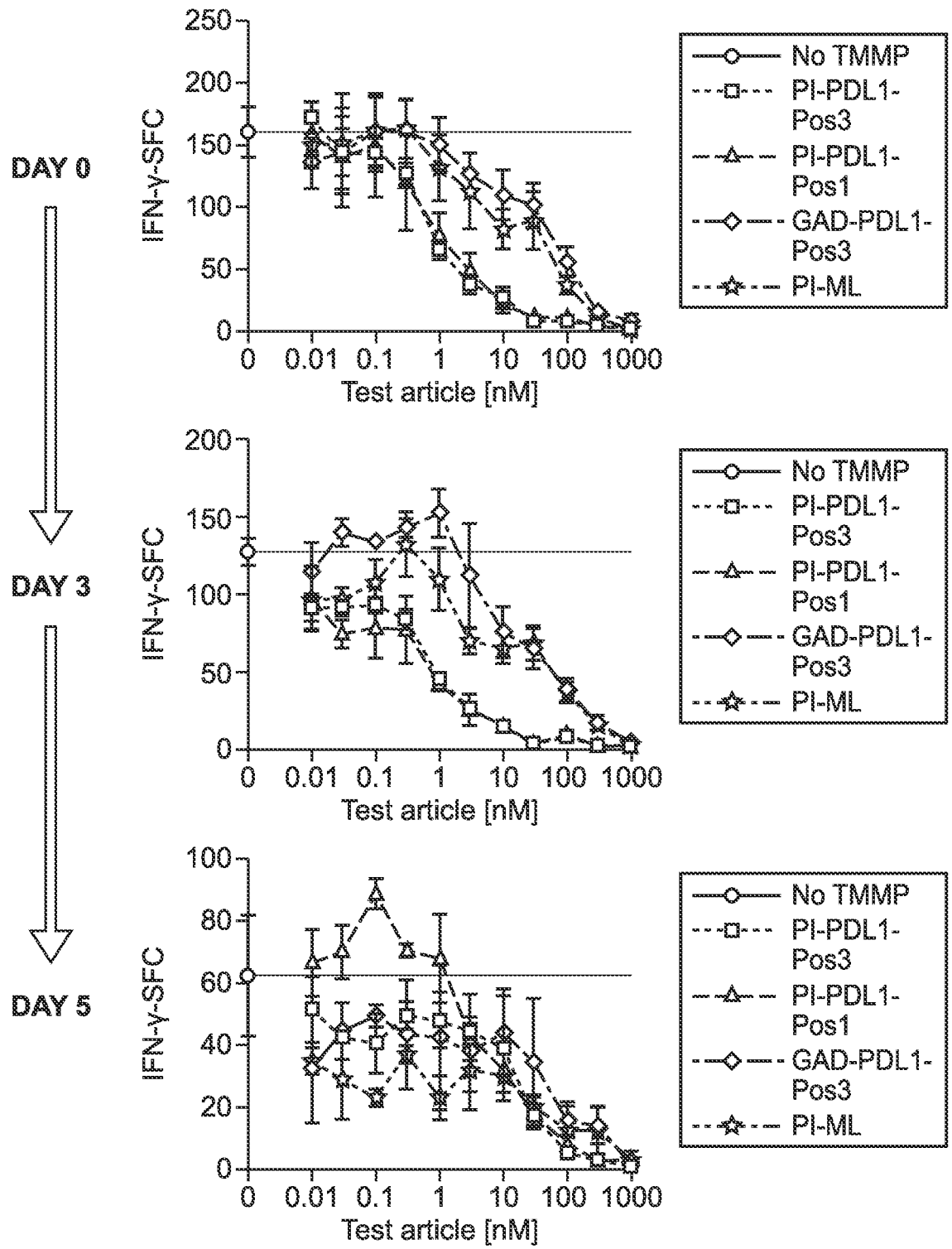

The results are shown in FIG. 25 and FIG. 26. As shown in FIG. 25, functional response of Proinsulin-specific CD4+ T cells were strongly suppressed by overnight treatment with 3005-2639 and 3893-2938 as compared to control molecules and remained suppressed 3-5 days post-treatment. As shown in FIG. 26, the antigen-specific, PD-L1-dependent suppression of PI-specific CD4+ T cells was observed across multiple donors.

Example 6: Suppression of Epitope-Specific CD4+ T Cells In Vitro

The ability of GAD65-PDL1 Pos3 (3005-2580) to suppress GAD65-specific CD4 cells was assessed in an overnight suppression assay. The TMMP comprises two heterodimers; each heterodimer comprises: a) a 3005 polypeptide (FIG. 15D); and b) a 2580 polypeptide (FIG. 15G). PBMCs from a T1D patient were expanded with GAD65 555-567F557I peptide and recombinant human IL-2 in RPMI+10% human serum for 14 days. Expanded PBMCs were washed and incubated (2e6 cells/well, 24 well plate) with increasing concentrations of indicated TMMPs overnight at 37° C., 5% $CO_2$. The TMMP-treated cells were washed, and functional response of antigen-specific cells was assessed using an IFNγ ELISPOT upon re-stimulation with GAD65 555-567F557I peptide. Additionally, the TMMP-treated, washed cells were cultured in presence of autologous PBMCs (1:1) and rhIL-2 to assess duration of suppressive effect. IFNγ ELISPOT was performed at the indicated time points.

Figure 27:
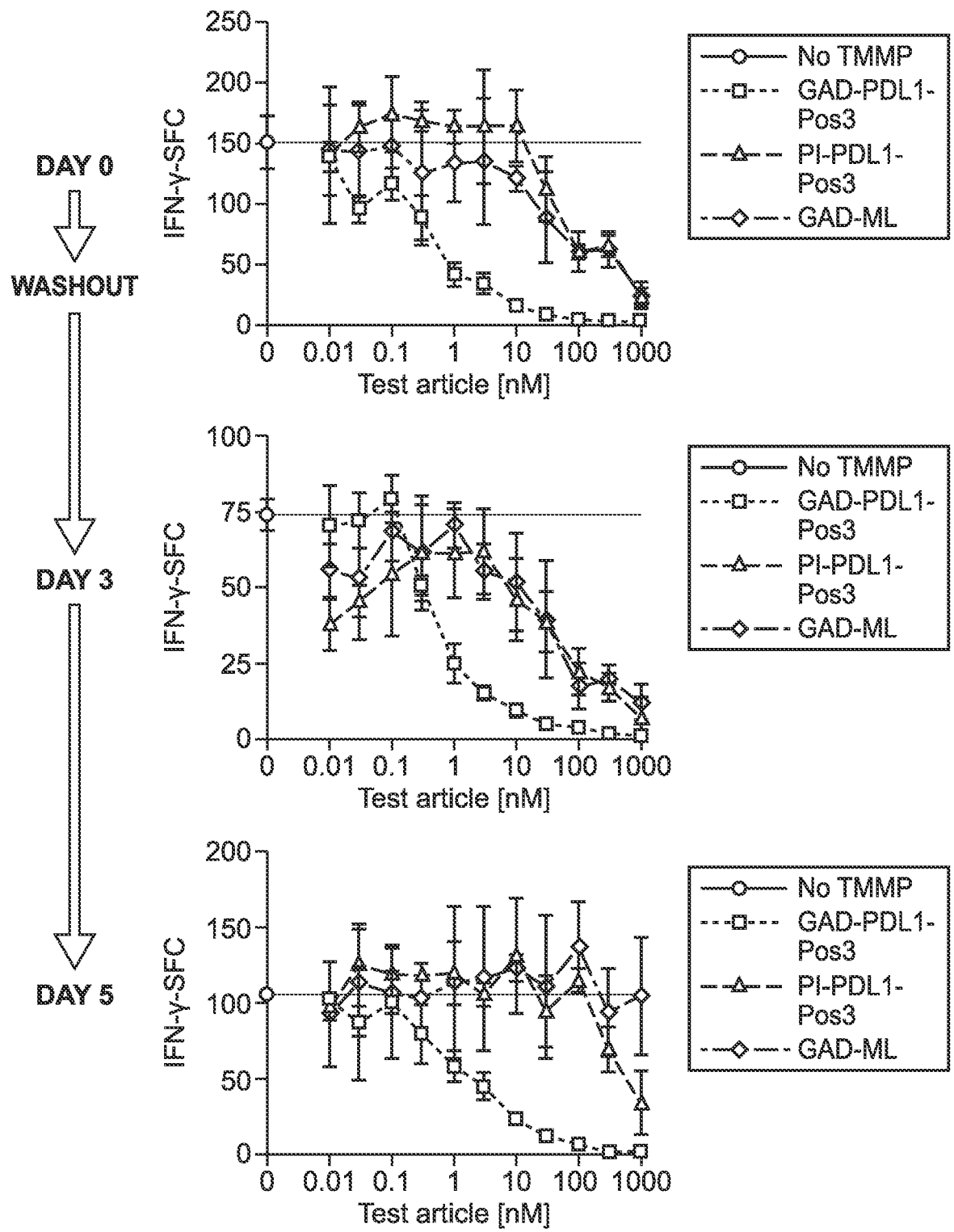
FIG. 27 depicts suppression of functional response of GAD65-specific CD4+ T cells by overnight treatment with TMMP 3005-2580 as compared to control molecules.

The results are shown in FIG. 27. Functional response of GAD65-specific $CD4^+$ T cells were strongly suppressed by overnight treatment with 3005-2580 as compared to control molecules and remained suppressed 3-5 days post-treatment.

Example 7: Suppression of Epitope-Specific $CD4^+$ T Cells In Vitro

The ability of Proins-PDL1 Pos3 (3005-2639) and Proins-PDL1 Pos 1 (3893-2938) to suppress Proinsulin-specific CD4 cells in the presence of peptide stimulation was assessed in a 5-day assay. PBMCs from multiple healthy or T1D patients were expanded with PI 76-90K88S peptide and recombinant human IL-2 in RPMI+10% human serum for 14 days. CD4 cells were purified by negative selection from expanded PBMCs and stimulated with PI 76-90K88S peptide loaded autologous dendritic cells (DCs) in presence of increasing concentrations of indicated TMMPs (DCs were prepared as follows—autologous monocytes were isolated by negative selection and matured with IL4+ granulocyte-monocyte colony stimulating factor (GMCSF) for 24 hrs, followed by activation with TNFα, IL1β, IL6, and $PGE_2$ for 24 hrs). After 5 days of culture, TMMP-treated cells were washed, and functional response of antigen-specific cells was assessed using an IFNγ ELISPOT upon re-stimulation with PI 76-90K88S peptide. Additionally, the TMMP-treated, washed cells were cultured in presence of autologous PBMCs (1:1) and rhIL-2 to assess duration of suppressive effect. IFNγ ELISPOT was performed at the indicated time points.

Figure 28:
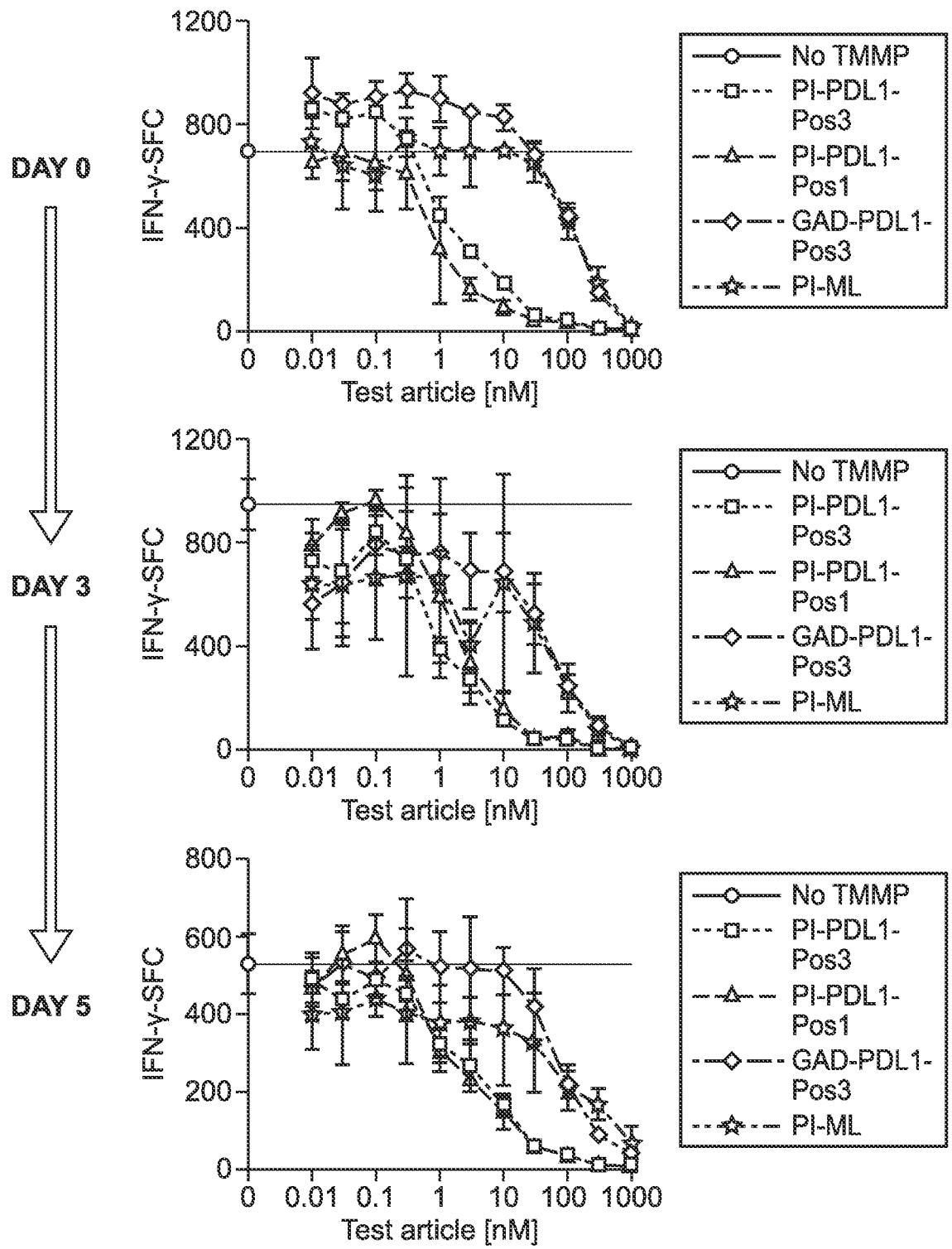
FIG. 28 depicts suppression of functional response of Proinsulin-specific CD4+ T cells stimulated for 5 days by treatment with TMMP 3005-2639 or TMMP 3893-2938 as compared to control molecules.
Figure 28:
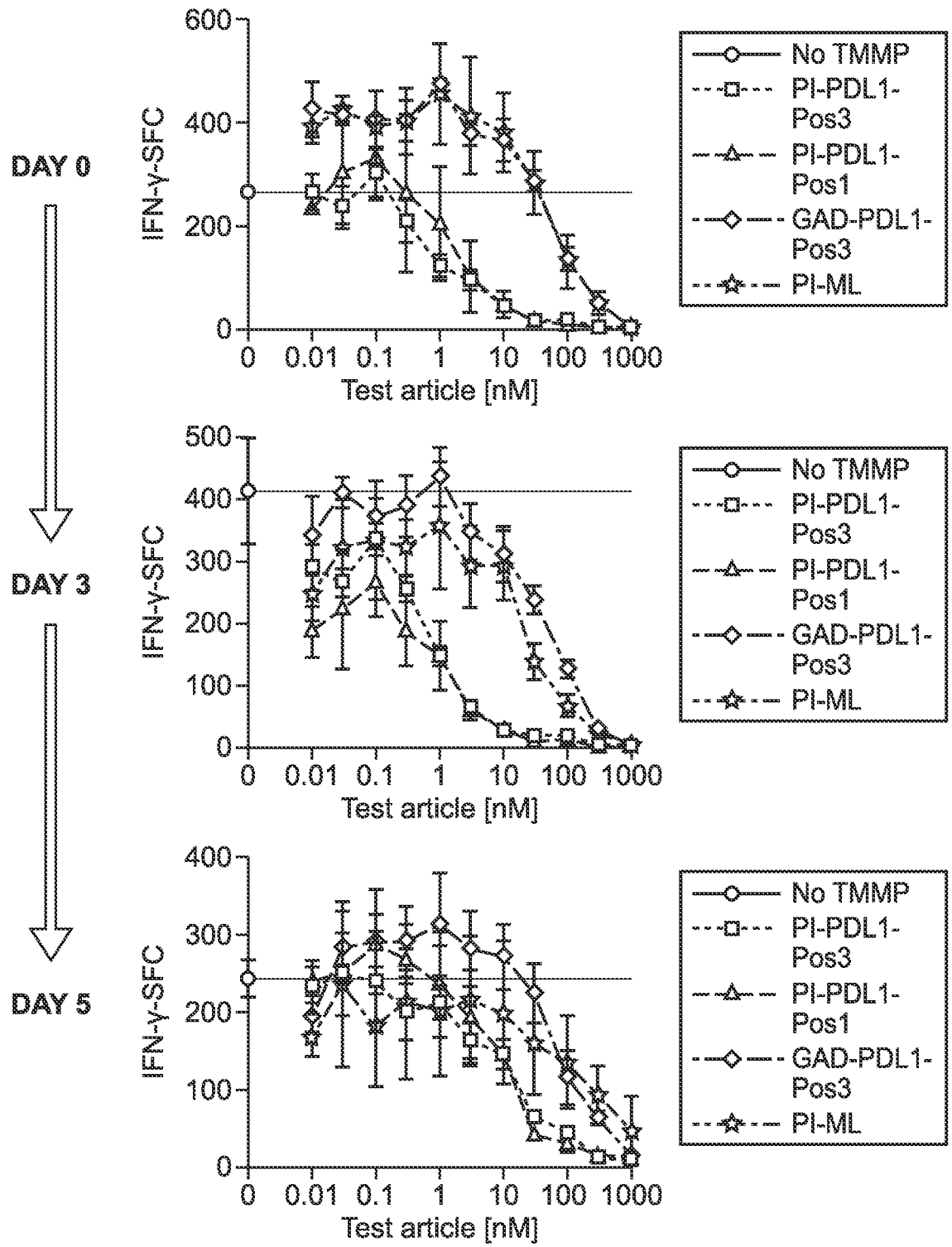
Figure 28:
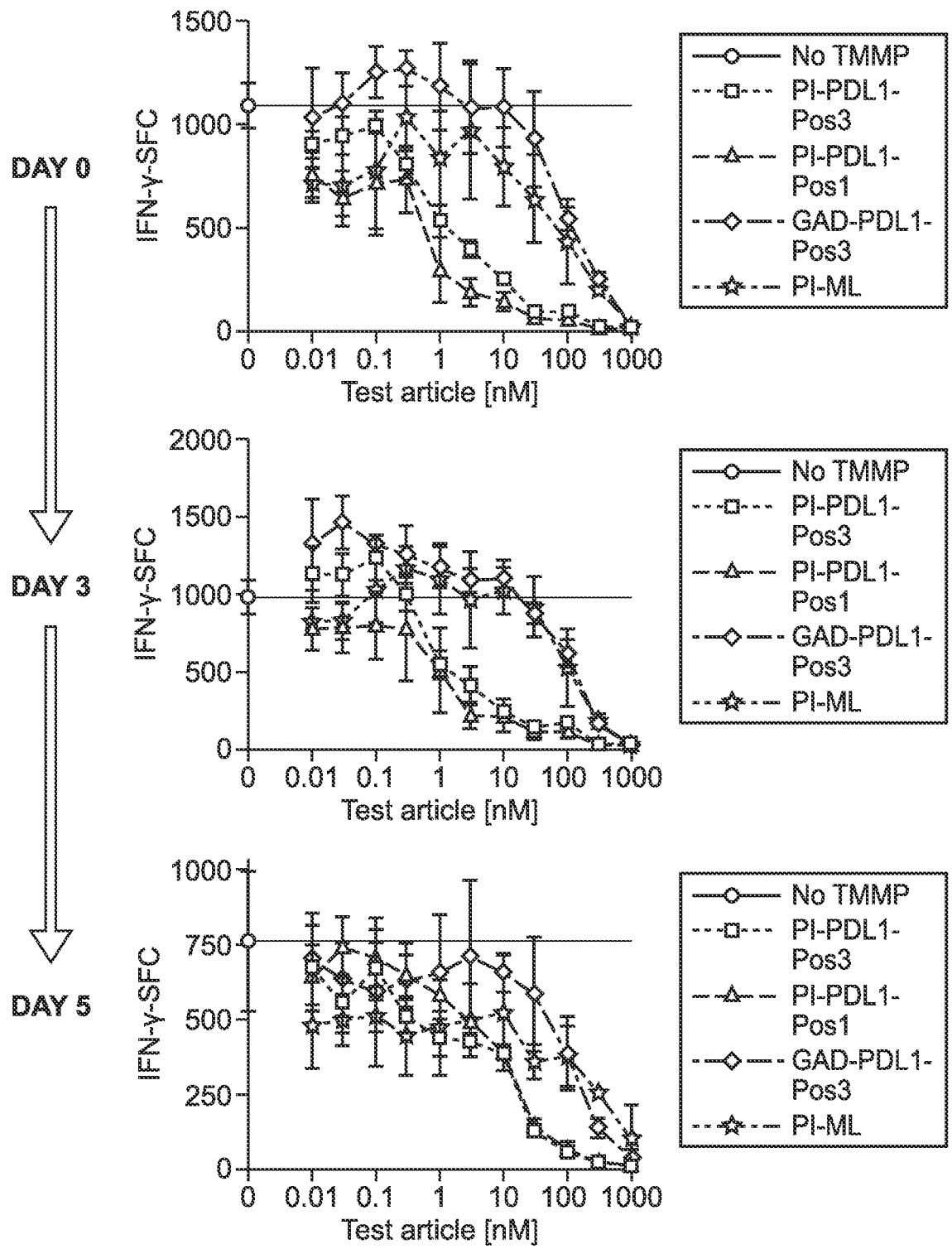
Figure 28:
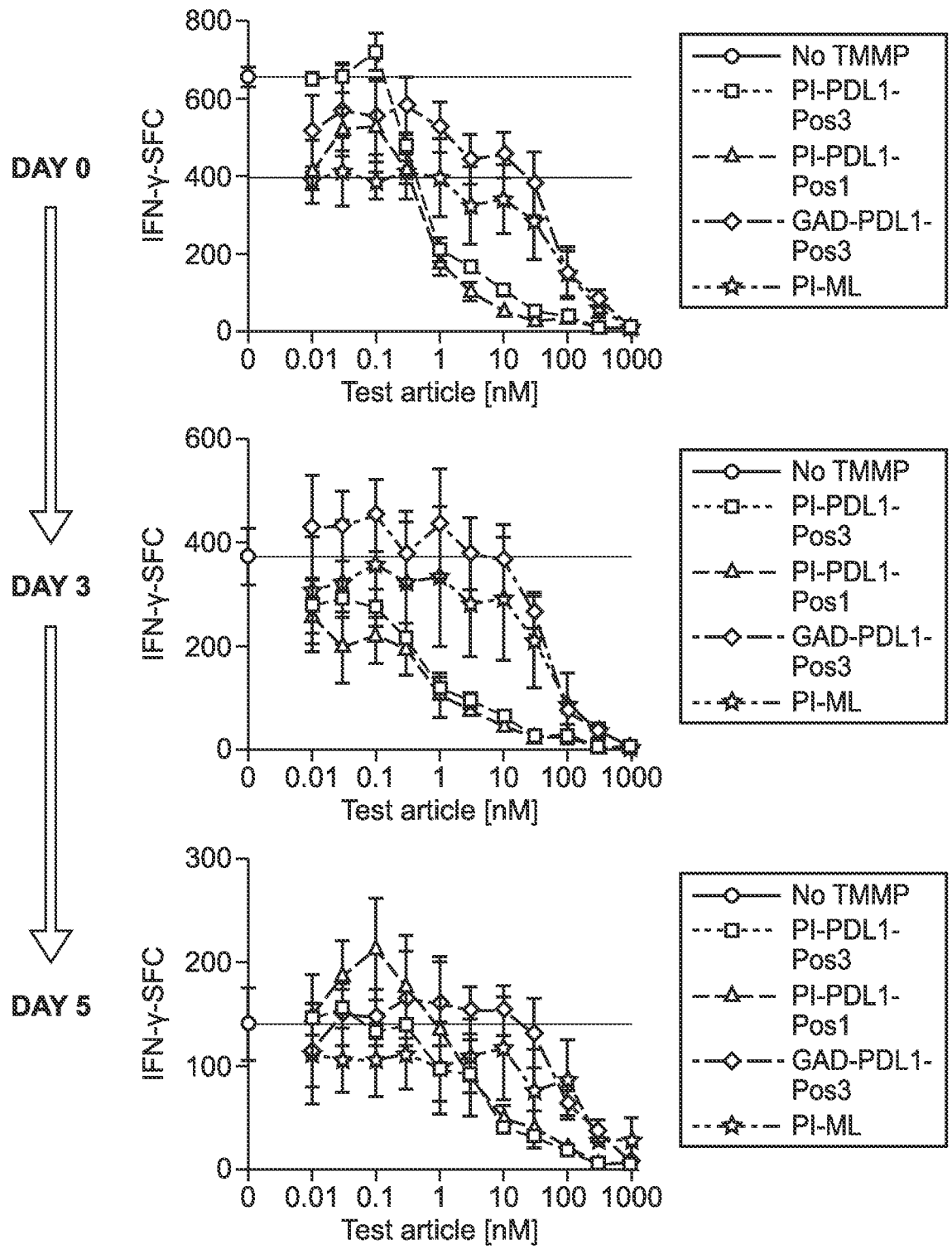

The results are shown in FIG. 28. Functional response of Proinsulin-specific $CD4^+$ T cells stimulated for 5 days are strongly suppressed by treatment with 3005-2639 and 3893-2938 as compared to control molecules and remain suppressed 3-5 days post-treatment. The antigen-specific, PD-L1-dependent suppression of PI-specific $CD4^+$ T cells was observed across multiple donors.

Example 8: Pharmacokinetic Analysis and In Vivo Activity

A pharmacokinetic analysis of TMMP 3893-2938 was conducted. The effect of TMMP 3893-2938 on proinsulin-specific responses in vivo was assessed.
Pharmacokinetics of TMMP 3893-2938 and TMMP 3005-2639

The pharmacokinetics of TMMP 3005-2639 (FIG. 15C-15D) and TMMP 3893-2938 (FIG. 15A-15B); depicted schematically in FIG. 29) were assessed in female albino C57Bl/6 mice. TMMPs were administered intravenously at 5 mg/kg, and serum samples were collected for up to 72 hours post-dose. The concentration of each TMMP in serum was determined relative to a standard curve using a ligand binding assay, in which each TMMP was captured by an anti-PDL1 antibody, and then detected using a sulfotagged anti-DR4 antibody.

The data are shown in FIG. 29. The data indicate that the pharmacokinetics of TMMP 3893-2938 are similar to those of TMMP 3005-2639.

In vivo activity of 3893-2938

Figure 30:
FIG. 30 depicts the study design for in vivo analysis of TMMP 3893-2938.

The in vivo activity of Proins-DR4-PDL1 TMMP 3893-2938 was tested in human HLA-DRB 1*04 transgenic mice. The study design is depicted in FIG. 30. Mice were simultaneously immunized with Proins (PI; 76-90, K88S) and influenza HA (307-319) peptides in Complete Freund's Adjuvant (CFA) on Day 0. On Day 11 (before treatment with TMMPs) blood samples were drawn from mice, PBMCs purified, and seeded in an IL-2 ELISpot assay. PBMCs were stimulated with PMA/ionomycin, an irrelevant HIV peptide, Proins (PI; 76-90, K88S), or HA (307-319) peptides.

The data are shown in FIG. 31. The frequencies of Proins- and HA-reactive T cells are shown for each animal. All animals demonstrated successful immunization with the relevant immunizing peptides. While variable per group, each animal exhibited similar functional responses to both Proins and HA peptide stimulation 11 days post-immunization.

From the same experiment as above, on Day 11 post-immunization the mice were treated intravenously with (1) vehicle, or (2) 20 mg/kg of Proins-DR4-PDL1 IST-3005-2639, or (3) 20 mg/kg of Proins-DR4-PDL1 IST-3893-2938, or (4) 2 mg/kg of Proins-DR4-PDL1 IST-3893-2938, or (5) 0.2 mg/kg of Proins-DR4-PDL1 IST-3893-2938, or (6) 20 mg/kg of Proins-DR4-PDL1 IST-3893-2938 after being immunized with PI peptide alone. On Day 12 (post-treatment) blood samples were drawn from mice, PBMCs purified, and seeded in an IL-2 ELISpot assay. PBMCs were stimulated as above.

The data are shown in FIG. 32. The frequencies of Proins- and HA-reactive T cells are shown for each animal. A single treatment with Proins-DR4-PDL1 TMMP (TMMP-3005-2639 or TMMP-3893-2938) on Day 11 post-immunization resulted in a dose-dependent reduction in the frequency of Proins-reactive T cells on Day 12 post-immunization. This suppression of Proins-reactive T cells was antigen specific, as HA-reactive T cells were not suppressed. TMMP 3893-2938 (in which the two polypeptides of the heterodimer disulfide linked) demonstrated comparable suppression to TMMP 3005-2639 (in which the two polypeptides of the heterodimer are non-covalently associated). Comparable suppression of proinsulin-specific responses was observed, regardless whether animals were co-immunized against HA. Proins-specific responses were suppressed in a dose-dependent manner by TMMP 3893-2938.

Figure 33:
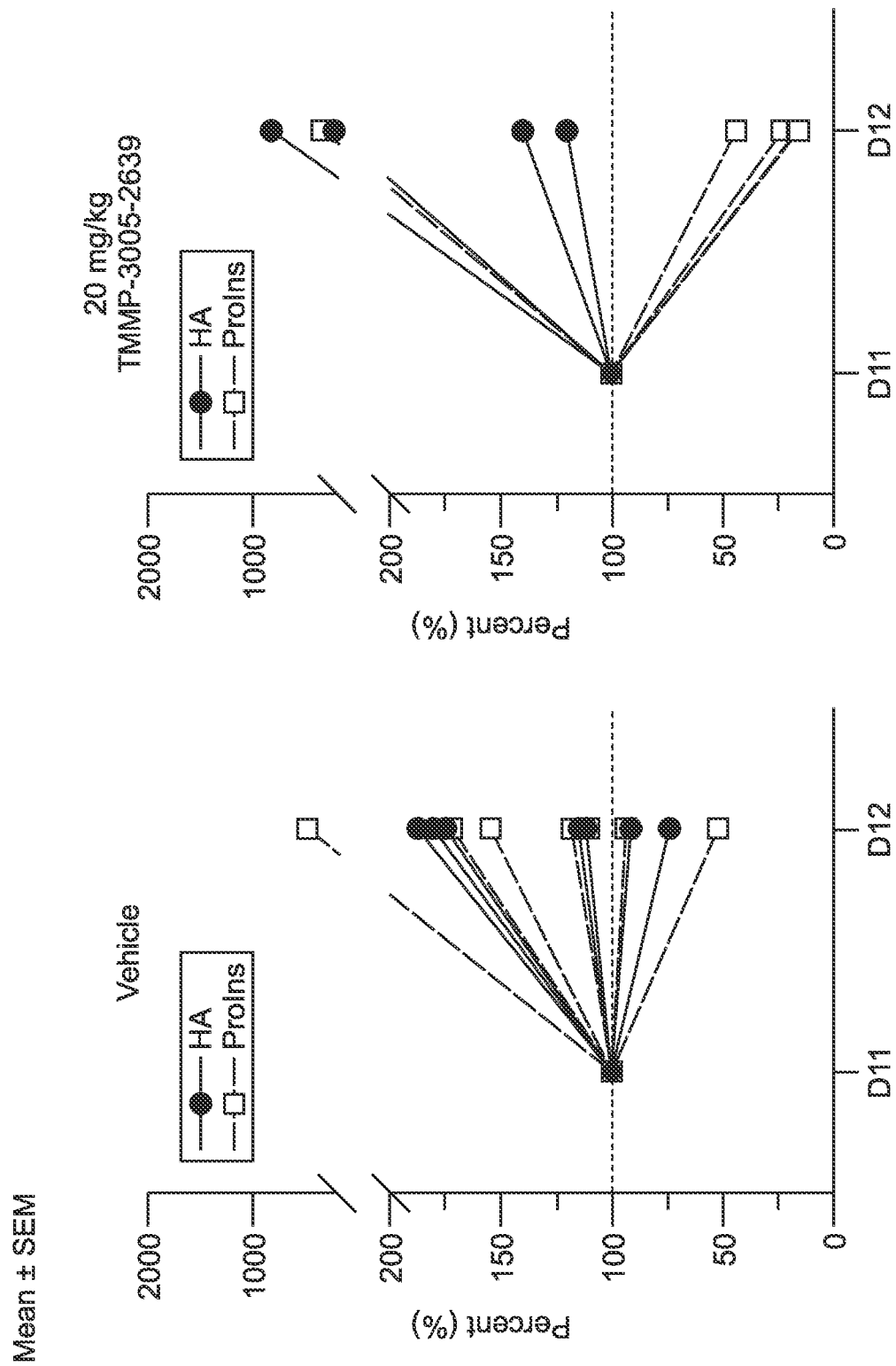
FIG. 33 depicts the percent relative change in frequency of proinsulin (PI)- and HA-reactive T cells following treatment with TMMPs, relative to pre-treatment.
Figure 33:
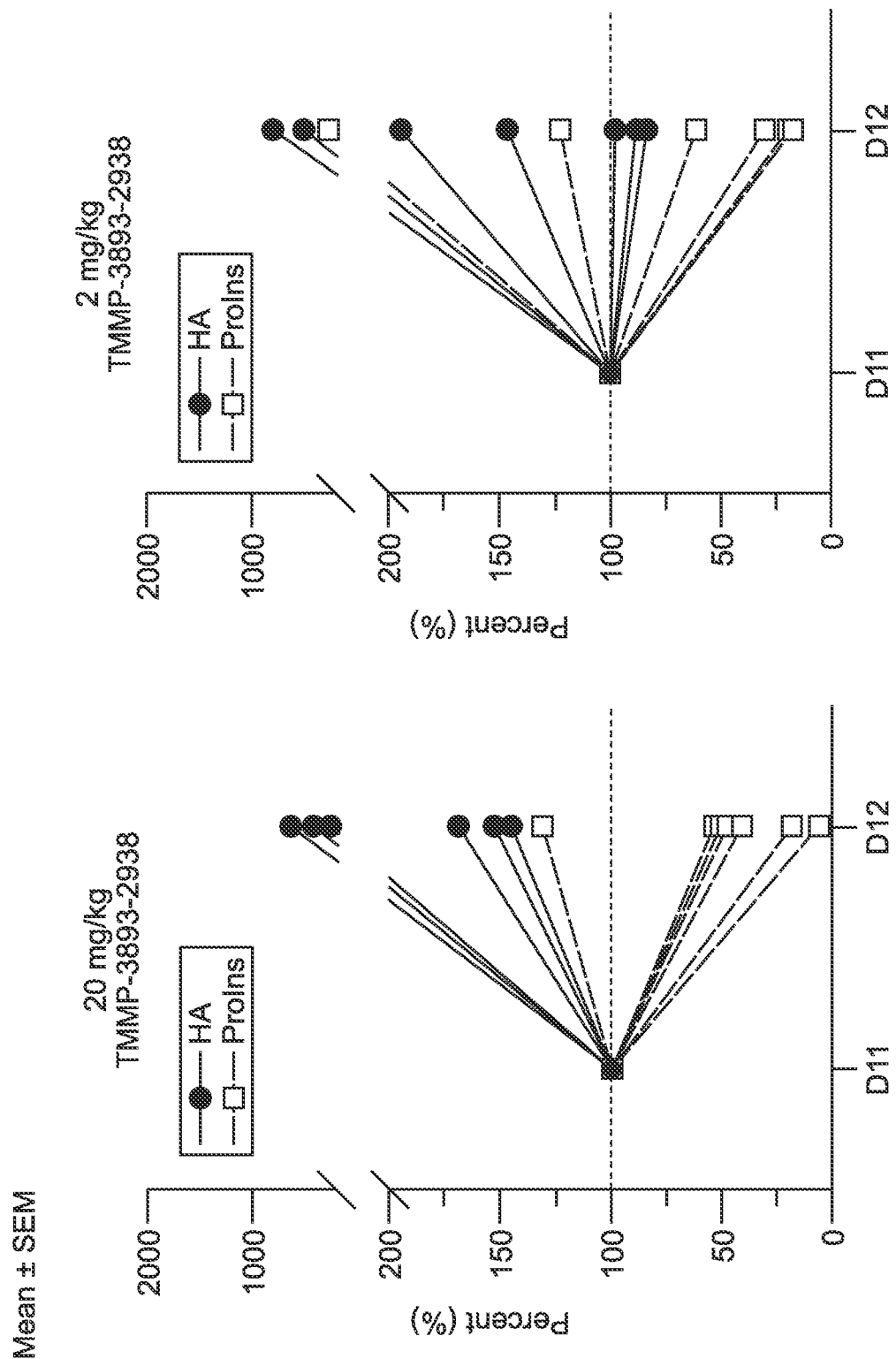
Figure 33:
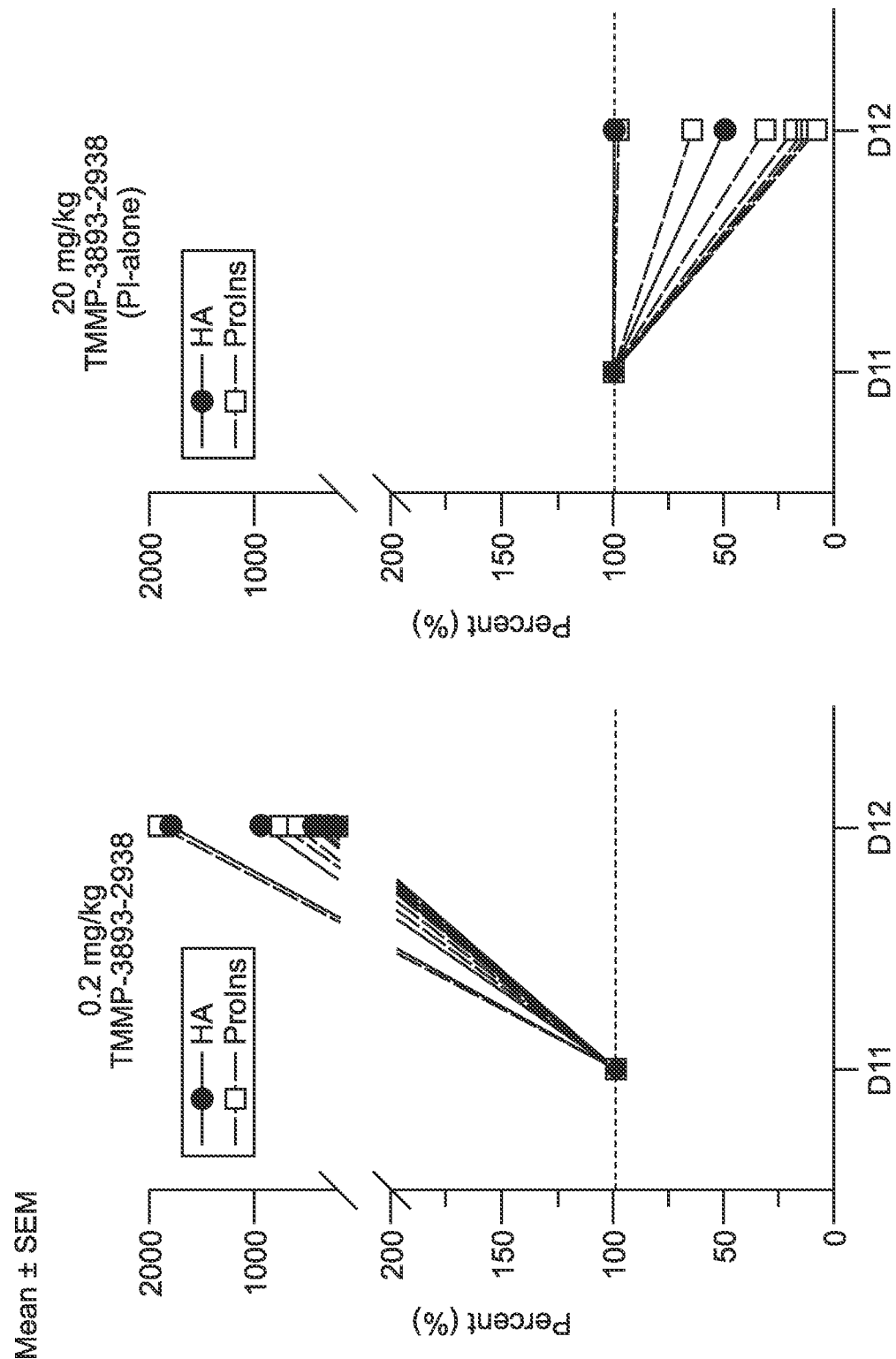

The results depicted in FIG. 32 were quantified by another means. The data are shown in FIG. 33. The percent relative change in frequency of PI and HA reactive cells post-treatment (Day 12) is shown relative to the pre-treatment (Day 11) sample from each individual mouse. This result demonstrates that a 20 mg/kg dose of TMMP 3005-2639 or TMMP 3892-2938 results in reduced frequency of PI-reactive cells while the frequency of HA-reactive cells continues to increase, confirming the antigen-specificity of this treatment effect.
Suppression of Proins-Specific Cytokine Production Following a Single Dose of TMMP Inhibition of cytokine-producing T cells by TMMP treatment was further demonstrated using intracellular cytokine staining and flow cytometry. Spleens were harvested from all animals in the above experiment on Day 12 post-immunization (post-treatment). Spleens were then dissociated into single cell suspensions and stimulated with Proins (PI; 76-90, K88S) or HA (307-319) peptides and cytokine production was analyzed by flow cytometry.

The data are shown in FIG. 34. Splenic CD4⁺ T cells from immunized animals produced IL-2 and/or IFNγ plus TNFα upon stimulation with Proins or HA peptides. In these animals, treatment with Proins-DR4-PDL1 TMMP 3005-2639 or TMMP 3893-2938 reduced the frequency of splenic CD4⁺ T cells producing cytokine in response to Proins stimulation. In contrast, the frequency of HA-reactive CD4⁺ T cells was not altered by treatment with Proins-DR4-PDL1 TMMP. These data confirm the ELISpot data showing suppression of Proins-specific responses by both TMMP 3893-2938 and TMMP 3005-2639, and demonstrate suppression of multiple cytokines by treatment with either TMMP 3893-2938 or TMMP 3005-2639.

ProIns-specific T cells are CD4+, CD44$^{hi}$, and PD-1⁺.

Figure 35:
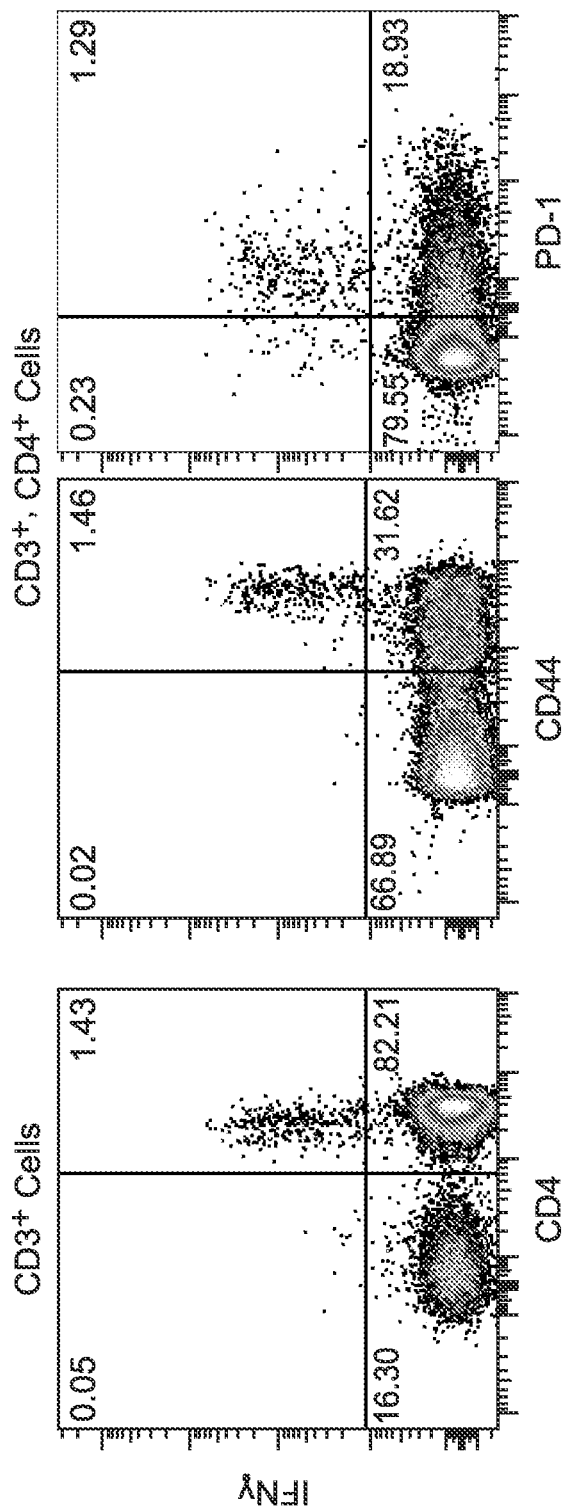
FIG. 35 depicts data showing that cytokine-producing cells are CD4+, $CD44^{hi}$, and PD-1+.

Cell surface marker expression in the Proins-reactive CD4⁺ T cells in the above experiment was further quantified by measuring the geometric mean fluorescence intensity (gMFI) of staining in cytokine-positive cells. The data are shown in FIG. 35. CD3+CD4⁺ T cells producing IFNγ in response to PI peptide stimulation were observed to express high levels of CD44 and PD1.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A T-cell modulatory multimeric polypeptide (TMMP) that is a homodimer of two heterodimers, wherein each heterodimer comprises a first polypeptide having the amino acid sequence set forth in SEQ ID NO: 185 and a second polypeptide having the amino acid sequence set forth in SEQ ID NO: 186, and wherein the heterodimers are covalently linked to one another through disulfide bonds formed between the Ig Fc polypeptides in the second polypeptide of each heterodimer.

2. A pharmaceutical composition comprising a TMMP of claim 1.

* * * * *

SEQUENCE LISTING

```
Sequence total quantity: 237
SEQ ID NO: 1            moltype = AA  length = 55
FEATURE                 Location/Qualifiers
source                  1..55
                        mol_type = protein
                        organism = synthetic construct
VARIANT                 11..55
                        note = Wherein up to 9 copies of GGGGS may be omitted
SEQUENCE: 1
CGGGSGGGGS GGGGSGGGGS GGGGSGGGGS GGGGSGGGGS GGGGSGGGGS GGGGS          55

SEQ ID NO: 2            moltype = AA  length = 55
FEATURE                 Location/Qualifiers
source                  1..55
                        mol_type = protein
                        organism = synthetic construct
VARIANT                 11..55
                        note = Wherein up to 9 copies of GGGGS may be omitted
SEQUENCE: 2
GCGGSGGGGS GGGGSGGGGS GGGGSGGGGS GGGGSGGGGS GGGGSGGGGS GGGGS          55

SEQ ID NO: 3            moltype = AA  length = 55
FEATURE                 Location/Qualifiers
source                  1..55
                        mol_type = protein
                        organism = synthetic construct
VARIANT                 11..55
                        note = Wherein up to 9 copies of GGGGS may be omitted
SEQUENCE: 3
GGCGSGGGGS GGGGSGGGGS GGGGSGGGGS GGGGSGGGGS GGGGSGGGGS GGGGS          55

SEQ ID NO: 4            moltype = AA  length = 55
FEATURE                 Location/Qualifiers
source                  1..55
                        mol_type = protein
                        organism = synthetic construct
VARIANT                 11..55
                        note = Wherein up to 9 copies of GGGGS may be omitted
SEQUENCE: 4
GGGCSGGGGS GGGGSGGGGS GGGGSGGGGS GGGGSGGGGS GGGGSGGGGS GGGGS          55

SEQ ID NO: 5            moltype = AA  length = 55
FEATURE                 Location/Qualifiers
source                  1..55
                        mol_type = protein
                        organism = synthetic construct
VARIANT                 11..55
                        note = Wherein up to 9 copies of GGGGS may be omitted
SEQUENCE: 5
GGGGCGGGGS GGGGSGGGG SGGGGSGGGG SGGGGSGGGGS GGGGSGGGGS GGGGS          55

SEQ ID NO: 6            moltype = AA  length = 178
FEATURE                 Location/Qualifiers
source                  1..178
```

```
                              mol_type = protein
                              organism = synthetic construct
SEQUENCE: 6
IKEEHVIIQA EFYLNPDQSG EFMFDFDGDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHW     178

SEQ ID NO: 7               moltype = AA  length = 178
FEATURE                    Location/Qualifiers
source                     1..178
                              mol_type = protein
                              organism = synthetic construct
SEQUENCE: 7
IKEEHVIIQA EFYLNPDQSG EFMFDFDGDE IFHVDMAKKE TVWRLEEFGR FASFEAQGAL    60
ANIAVDKANL ECMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHW     178

SEQ ID NO: 8               moltype = AA  length = 178
FEATURE                    Location/Qualifiers
source                     1..178
                              mol_type = protein
                              organism = synthetic construct
SEQUENCE: 8
IKEEHVIIQA EFYLNPDQSG EFMFDFDGDE IFHVDMAKKE TVWRLEEFGR FASFEAQGAL    60
ANIAVDKANL EIMTCRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHW     178

SEQ ID NO: 9               moltype = AA  length = 189
FEATURE                    Location/Qualifiers
source                     1..189
                              mol_type = protein
                              organism = Homo sapiens
SEQUENCE: 9
IKEEHVIIQA EFYLNPDQSG EFMFDFDGDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                          189

SEQ ID NO: 10              moltype = AA  length = 189
FEATURE                    Location/Qualifiers
source                     1..189
                              mol_type = protein
                              organism = synthetic construct
SEQUENCE: 10
IKEEHVIIQA EFYLNPDQSG EFMFDFDGCE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                          189

SEQ ID NO: 11              moltype = AA  length = 189
FEATURE                    Location/Qualifiers
source                     1..189
                              mol_type = protein
                              organism = synthetic construct
SEQUENCE: 11
IKEEHVIIQA EFYLNPDQSG EFMFDFDGDE IFHVDMAKKE TVWRLEEFGR FASFEAQGAL    60
ANIAVDKANL ECMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                          189

SEQ ID NO: 12              moltype = AA  length = 189
FEATURE                    Location/Qualifiers
source                     1..189
                              mol_type = protein
                              organism = synthetic construct
SEQUENCE: 12
IKEEHVIIQA EFYLNPDQSG EFMFDFDGDE IFHVDMAKKE TVWRLEEFGR FASFEAQGAL    60
ANIAVDKANL EIMTCRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                          189

SEQ ID NO: 13              moltype = AA  length = 189
FEATURE                    Location/Qualifiers
source                     1..189
                              mol_type = protein
                              organism = synthetic construct
SEQUENCE: 13
IKEEHVIIQA EFYLNPDQSG EFMFDFDGDE IFHVDMAKKE TVWRLEEFGR FASFEAQGAL    60
ANIAVDKANL EIMTKRSNYT CITNVPPEVT VLTNSPVELR EPNVLICFID KFTPPVVNVT   120
```

```
WLRNGKPVTT GVSETVFLPR EDHLFRKFHY LPFLPSTEDV YDCRVEHWGL DEPLLKHWEF   180
DAPSPLPET                                                          189

SEQ ID NO: 14           moltype = AA  length = 189
FEATURE                 Location/Qualifiers
source                  1..189
                        mol_type = protein
                        organism = synthetic construct
SEQUENCE: 14
IKEEHVIIQA EFYLNPDQSG EFMFDFDGDE IFHVDMAKKE TVWRLEEFGR FASFEAQGAL    60
ANIAVDKANL EIMTKRSNYT PCTNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                          189

SEQ ID NO: 15           moltype = AA  length = 79
FEATURE                 Location/Qualifiers
source                  1..79
                        mol_type = protein
                        organism = synthetic construct
SEQUENCE: 15
VIIQAEFYLN PDQSGEFMFD FDGDEIFHVD MAKKETVWRL EEFGRFASFE AQGALANIAV    60
DKANLEIMTK RSNYTPITN                                                79

SEQ ID NO: 16           moltype = AA  length = 84
FEATURE                 Location/Qualifiers
source                  1..84
                        mol_type = protein
                        organism = synthetic construct
SEQUENCE: 16
IKEEHVIIQA EFYLNPDQSG EFMFDFDGCE IFHVDMAKKE TVWRLEEFGR FASFEAQGAL    60
ANIAVDKANL EIMTKRSNYT PITN                                          84

SEQ ID NO: 17           moltype = AA  length = 84
FEATURE                 Location/Qualifiers
source                  1..84
                        mol_type = protein
                        organism = synthetic construct
SEQUENCE: 17
IKEEHVIIQA EFYLNPDQSG EFMFDFDGDE IFHVDMAKKE TVWRLEEFGR FASFEAQGAL    60
ANIAVDKANL ECMTKRSNYT PITN                                          84

SEQ ID NO: 18           moltype = AA  length = 84
FEATURE                 Location/Qualifiers
source                  1..84
                        mol_type = protein
                        organism = synthetic construct
SEQUENCE: 18
IKEEHVIIQA EFYLNPDQSG EFMFDFDGDE IFHVDMAKKE TVWRLEEFGR FASFEAQGAL    60
ANIAVDKANL EIMTCRSNYT PITN                                          84

SEQ ID NO: 19           moltype = AA  length = 84
FEATURE                 Location/Qualifiers
source                  1..84
                        mol_type = protein
                        organism = synthetic construct
SEQUENCE: 19
IKEEHVIIQA EFYLNPDQSG EFMFDFDGDE IFHVDMAKKE TVWRLEEFGR FASFEAQGAL    60
ANIAVDKANL EIMTKRSNYT CITN                                          84

SEQ ID NO: 20           moltype = AA  length = 84
FEATURE                 Location/Qualifiers
source                  1..84
                        mol_type = protein
                        organism = synthetic construct
SEQUENCE: 20
IKEEHVIIQA EFYLNPDQSG EFMFDFDGDE IFHVDMAKKE TVWRLEEFGR FASFEAQGAL    60
ANIAVDKANL EIMTKRSNYT PCTN                                          84

SEQ ID NO: 21           moltype = AA  length = 94
FEATURE                 Location/Qualifiers
source                  1..94
                        mol_type = protein
                        organism = synthetic construct
SEQUENCE: 21
VPPEVTVLTN SPVELREPNV LICFIDKFTP PVVNVTWLRN GKPVTTGVSE TVFLPREDHL    60
FRKFHYLPFL PSTEDVYDCR VEHWGLDEPL LKHW                                94

SEQ ID NO: 22           moltype = AA  length = 181
FEATURE                 Location/Qualifiers
```

```
                                  -continued source                    1..181
                          mol_type = protein
                          organism = Homo sapiens
SEQUENCE: 22
AGAIKADHVS TYAAFVQTHR PTGEFMFEFD EDEMFYVDLD KKETVWHLEE FGQAFSFEAQ    60
GGLANIAILN NNLNTLIQRS NHTQATNDPP EVTVFPKEPV ELGQPNTLIC HIDKFFPPVL   120
NVTWLCNGEL VTEGVAESLF LPRTDYSFHK FHYLTFVPSA EDFYDCRVEH WGLDQPLLKH   180
W                                                                  181

SEQ ID NO: 23             moltype = AA   length = 85
FEATURE                   Location/Qualifiers
source                    1..85
                          mol_type = protein
                          organism = synthetic construct
SEQUENCE: 23
AIKADHVSTY AAFVQTHRPT GEFMFEFDED EMFYVDLDKK ETVWHLEEFG QAFSFEAQGG    60
LANIAILNNN LNTLIQRSNH TQATN                                         85

SEQ ID NO: 24             moltype = AA   length = 94
FEATURE                   Location/Qualifiers
source                    1..94
                          mol_type = protein
                          organism = synthetic construct
SEQUENCE: 24
DPPEVTVFPK EPVELGQPNT LICHIDKFFP PVLNVTWLCN GELVTEGVAE SLFLPRTDYS    60
FHKFHYLTFV PSAEDFYDCR VEHWGLDQPL LKHW                               94

SEQ ID NO: 25             moltype = AA   length = 260
FEATURE                   Location/Qualifiers
source                    1..260
                          mol_type = protein
                          organism = Homo sapiens
SEQUENCE: 25
MRPEDRMFHI RAVILRALSL AFLLSLRGAG AIKADHVSTY AAFVQTHRPT GEFMFEFDED    60
EQFYVDLDKK ETVWHLEEFG RAFSFEAQGG LANIAILNNN LNTLIQRSNH TQAANDPPEV   120
TVFPKEPVEL GQPNTLICHI DRFPPVLNV TWLCNGEPVT EGVAESLFLP RTDYSFHKFH   180
YLTFVPSAED VYDCREHWG LDQPLLKHWE AQEPIQMPET TETVLCALGL VLGLVGIIVG   240
TVLIIKSLRS GHDPRAQGPL                                              260

SEQ ID NO: 26             moltype = AA   length = 181
FEATURE                   Location/Qualifiers
source                    1..181
                          mol_type = protein
                          organism = synthetic construct
SEQUENCE: 26
EDIVADHVAS CGVNLYQFYG PSGQYTHEFD GDEQFYVDLE RKETAWRWPE FSKFGGFDPQ    60
GALRNMAVAK HNLNIMIKRY NSTAATNEVP EVTVFSKSPV TLGQPNTLIC LVDNIFPPVV   120
NITWLSNGQS VTEGVSETSF LSKSDHSFFK ISYLTFLPSA DEIYDCKVEH WGLDQPLLKH   180
W                                                                  181

SEQ ID NO: 27             moltype = AA   length = 87
FEATURE                   Location/Qualifiers
source                    1..87
                          mol_type = protein
                          organism = synthetic construct
SEQUENCE: 27
EDIVADHVAS CGVNLYQFYG PSGQYTHEFD GDEQFYVDLE RKETAWRWPE FSKFGGFDPQ    60
GALRNMAVAK HNLNIMIKRY NSTAATN                                       87

SEQ ID NO: 28             moltype = AA   length = 87
FEATURE                   Location/Qualifiers
source                    1..87
                          mol_type = protein
                          organism = synthetic construct
SEQUENCE: 28
EDIVADHVAS CGVNLYQFYG PSGQYTHEFD GDEQFYVDLE RKETAWRWPE FSKFGGFDPQ    60
GALRNMAVAK HNLNIMIKRY NSTAATN                                       87

SEQ ID NO: 29             moltype = AA   length = 94
FEATURE                   Location/Qualifiers
source                    1..94
                          mol_type = protein
                          organism = synthetic construct
SEQUENCE: 29
EVPEVTVFSK SPVTLGQPNT LICLVDNIFP PVVNITWLSN GQSVTEGVSE TSFLSKSDHS    60
FFKISYLTFL PSADEIYDCK VEHWGLDQPL KHW                                94

SEQ ID NO: 30             moltype = AA   length = 199
FEATURE                   Location/Qualifiers
```

```
source                  1..199
                        mol_type = protein
                        organism = Homo sapiens
SEQUENCE: 30
GDTRPRFLEQ VKHECHFFNG TERVRFLDRY FYHQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPASIEVR WFRNGQEEKT GVVSTGLIQN GDWTFQTLVM LETVPRSGEV YTCQVEHPSL   180
TSPLTVEWRA RSESAQSKM                                                199

SEQ ID NO: 31           moltype = AA   length = 29
FEATURE                 Location/Qualifiers
source                  1..29
                        mol_type = protein
                        organism = synthetic construct
SEQUENCE: 31
MVCLKLPGGS SLAALTVTLM VLSSRLAFA                                      29

SEQ ID NO: 32           moltype = AA   length = 19
FEATURE                 Location/Qualifiers
source                  1..19
                        mol_type = protein
                        organism = synthetic construct
SEQUENCE: 32
MVCLKLPGGS CMAALTVTL                                                 19

SEQ ID NO: 33           moltype = AA   length = 19
FEATURE                 Location/Qualifiers
source                  1..19
                        mol_type = protein
                        organism = synthetic construct
SEQUENCE: 33
MVCLKLPGGS YMAKLTVTL                                                 19

SEQ ID NO: 34           moltype = AA   length = 197
FEATURE                 Location/Qualifiers
source                  1..197
                        mol_type = protein
                        organism = synthetic construct
SEQUENCE: 34
DTRPRFLEQV KHECHFFNGT ERVRFLDRYF YHQEEYVRFD SDVGEYRAVT ELGRPDAEYW    60
NSQKDLLEQK RAAVDTYCRH NYGVGESFTV QRRVYPEVTV YPAKTQPLQH HNLLVCSVNG   120
FYPGSIEVRW FRNGQEEKTG VVSTGLIQNG DWTFQTLVML ETVPRSGEVY TCQVEHPSLT   180
SPLTVEWRAR SESAQSK                                                  197

SEQ ID NO: 35           moltype = AA   length = 199
FEATURE                 Location/Qualifiers
source                  1..199
                        mol_type = protein
                        organism = synthetic construct
SEQUENCE: 35
GDTRCRFLEQ VKHECHFFNG TERVRFLDRY FYHQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPASIEVR WFRNGQEEKT GVVSTGLIQN GDWTFQTLVM LETVPRSGEV YTCQVEHPSL   180
TSPLTVEWRA RSESAQSKM                                                199

SEQ ID NO: 36           moltype = AA   length = 199
FEATURE                 Location/Qualifiers
source                  1..199
                        mol_type = protein
                        organism = synthetic construct
SEQUENCE: 36
GDTRPRFLEQ VKHECHFFNG TERVRFLDRY FYHQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPASIEVR WFRNGQEEKT GVVSTGLIQN CDWTFQTLVM LETVPRSGEV YTCQVEHPSL   180
TSPLTVEWRA RSESAQSKM                                                199

SEQ ID NO: 37           moltype = AA   length = 199
FEATURE                 Location/Qualifiers
source                  1..199
                        mol_type = protein
                        organism = synthetic construct
SEQUENCE: 37
GDTRPRFLEQ VKHECHFFNG TERVRFLDRY FYHQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPASIEVR WFRNGQEEKT GVVSTGLIQN GDCTFQTLVM LETVPRSGEV YTCQVEHPSL   180
TSPLTVEWRA RSESAQSKM                                                199

SEQ ID NO: 38           moltype = AA   length = 94
FEATURE                 Location/Qualifiers
```

```
source                  1..94
                        mol_type = protein
                        organism = synthetic construct
SEQUENCE: 38
DTRPRFLEQV KHECHFFNGT ERVRFLDRYF YHQEEYVRFD SDVGEYRAVT ELGRPDAEYW   60
NSQKDLLEQK RAAVDTYCRH NYGVGESFTV QRRV                              94

SEQ ID NO: 39           moltype = AA  length = 95
FEATURE                 Location/Qualifiers
source                  1..95
                        mol_type = protein
                        organism = synthetic construct
SEQUENCE: 39
GDTRCRFLEQ VKHECHFFNG TERVRFLDRY FYHQEEYVRF DSDVGEYRAV TELGRPDAEY   60
WNSQKDLLEQ KRAAVDTYCR HNYGVGESFT VQRRV                             95

SEQ ID NO: 40           moltype = AA  length = 103
FEATURE                 Location/Qualifiers
source                  1..103
                        mol_type = protein
                        organism = synthetic construct
SEQUENCE: 40
YPEVTVYPAK TQPLQHHNLL VCSVNGFYPG SIEVRWFRNG QEEKTGVVST GLIQNGDWTF   60
QTLVMLETVP RSGEVYTCQV EHPSLTSPLT VEWRARSESA QSK                    103

SEQ ID NO: 41           moltype = AA  length = 104
FEATURE                 Location/Qualifiers
source                  1..104
                        mol_type = protein
                        organism = synthetic construct
SEQUENCE: 41
YPEVTVYPAK TQPLQHHNLL VCSVNGFYPA SIEVRWFRNG QEEKTGVVST GLIQNCDWTF   60
QTLVMLETVP RSGEVYTCQV EHPSLTSPLT VEWRARSESA QSKM                   104

SEQ ID NO: 42           moltype = AA  length = 104
FEATURE                 Location/Qualifiers
source                  1..104
                        mol_type = protein
                        organism = synthetic construct
SEQUENCE: 42
YPEVTVYPAK TQPLQHHNLL VCSVNGFYPA SIEVRWFRNG QEEKTGVVST GLIQNGDCTF   60
QTLVMLETVP RSGEVYTCQV EHPSLTSPLT VEWRARSESA QSKM                   104

SEQ ID NO: 43           moltype = AA  length = 197
FEATURE                 Location/Qualifiers
source                  1..197
                        mol_type = protein
                        organism = synthetic construct
SEQUENCE: 43
DTRPRFLELR KSECHFFNGT ERVRYLDRYF HNQEEFLRFD SDVGEYRAVT ELGRPVAESW   60
NSQKDLLEQK RGRVDNYCRH NYGVGESFTV QRRVHPQVTV YPAKTQPLQH HNLLVCSVSG   120
FYPGSIEVRW FRNGQEEKAG VVSTGLIQNG DWTFQTLVML ETVPRSGEVY TCQVEHPSVT   180
SALTVEWRAR SESAQSK                                                 197

SEQ ID NO: 44           moltype = AA  length = 94
FEATURE                 Location/Qualifiers
source                  1..94
                        mol_type = protein
                        organism = synthetic construct
SEQUENCE: 44
DTRPRFLELR KSECHFFNGT ERVRYLDRYF HNQEEFLRFD SDVGEYRAVT ELGRPVAESW   60
NSQKDLLEQK RGRVDNYCRH NYGVGESFTV QRRV                              94

SEQ ID NO: 45           moltype = AA  length = 103
FEATURE                 Location/Qualifiers
source                  1..103
                        mol_type = protein
                        organism = synthetic construct
SEQUENCE: 45
HPQVTVYPAK TQPLQHHNLL VCSVSGFYPG SIEVRWFRNG QEEKAGVVST GLIQNGDWTF   60
QTLVMLETVP RSGEVYTCQV EHPSVTSALT VEWRARSESA QSK                    103

SEQ ID NO: 46           moltype = AA  length = 208
FEATURE                 Location/Qualifiers
source                  1..208
                        mol_type = protein
                        organism = synthetic construct
SEQUENCE: 46
TVLSSPLALA GDTQPRFLEQ AKCECHFLNG TERVWNLIRY IYNQEEYARY NSDLGEYQAV   60
```

```
TELGRPDAEY WNSQKDLLER RRAEVDTYCR YNYGVVESFT VQRRVQPKVT VYPSKTQPLQ    120
HHNLLVCSVN GFYPGSIEVR WFRNGQEEKA GVVSTGLIQN GDWTFQTLVM LETVPRSGEV    180
YTCQVEHPSM MSPLTVQWSA RSESAQSK                                      208

SEQ ID NO: 47              moltype = AA   length = 105
FEATURE                    Location/Qualifiers
source                     1..105
                           mol_type = protein
                           organism = synthetic construct
SEQUENCE: 47
TVLSSPLALA GDTQPRFLEQ AKCECHFLNG TERVWNLIRY IYNQEEYARY NSDLGEYQAV    60
TELGRPDAEY WNSQKDLLER RRAEVDTYCR YNYGVVESFT VQRRV                    105

SEQ ID NO: 48              moltype = AA   length = 103
FEATURE                    Location/Qualifiers
source                     1..103
                           mol_type = protein
                           organism = synthetic construct
SEQUENCE: 48
QPKVTVYPSK TQPLQHHNLL VCSVNGFYPG SIEVRWFRNG QEEKAGVVST GLIQNGDWTF    60
QTLVMLETVP RSGEVYTCQV EHPSMMSPLT VQWSARSESA QSK                      103

SEQ ID NO: 49              moltype = AA   length = 207
FEATURE                    Location/Qualifiers
source                     1..207
                           mol_type = protein
                           organism = synthetic construct
SEQUENCE: 49
MVLSSPLALA GDTRPRFLQQ DKYECHFFNG TERVRFLHRD IYNQEEDLRF DSDVGEYRAV    60
TELGRPDAEY WNSQKDFLED RRAAVDTYCR HNYGVGESFT VQRRVEPKVT VYPARTQTLQ    120
HHNLLVCSVN GFYPGSIEVR WFRNSQEEKA GVVSTGLIQN GDWTFQTLVM LETVPRSGEV    180
YTCQVEHPSV TSPLTVEWRA QSESAQS                                       207

SEQ ID NO: 50              moltype = AA   length = 105
FEATURE                    Location/Qualifiers
source                     1..105
                           mol_type = protein
                           organism = synthetic construct
SEQUENCE: 50
MVLSSPLALA GDTRPRFLQQ DKYECHFFNG TERVRFLHRD IYNQEEDLRF DSDVGEYRAV    60
TELGRPDAEY WNSQKDFLED RRAAVDTYCR HNYGVGESFT VQRRV                    105

SEQ ID NO: 51              moltype = AA   length = 102
FEATURE                    Location/Qualifiers
source                     1..102
                           mol_type = protein
                           organism = synthetic construct
SEQUENCE: 51
EPKVTVYPAR TQTLQHHNLL VCSVNGFYPG SIEVRWFRNS QEEKAGVVST GLIQNGDWTF    60
QTLVMLETVP RSGEVYTCQV EHPSVTSPLT VEWRAQSESA QS                       102

SEQ ID NO: 52              moltype = AA   length = 186
FEATURE                    Location/Qualifiers
source                     1..186
                           mol_type = protein
                           organism = synthetic construct
SEQUENCE: 52
RATPENYLFQ GRQECYAFNG TQRFLERYIY NREEFARFDS DVGEFRAVTE LGRPAAEYWN    60
SQKDILEEKR AVPDRMCRHN YELGGPMTLQ RRVQPRVNVS PSKKGPLQHH NLLVCHVTDF    120
YPGSIQVRWF LNGQEETAGV VSTNLIRNGD WTFQILVMLE MTPQQGDVYT CQVEHTSLDS    180
PVTVEW                                                               186

SEQ ID NO: 53              moltype = AA   length = 92
FEATURE                    Location/Qualifiers
source                     1..92
                           mol_type = protein
                           organism = synthetic construct
SEQUENCE: 53
RATPENYLFQ GRQECYAFNG TQRFLERYIY NREEFARFDS DVGEFRAVTE LGRPAAEYWN    60
SQKDILEEKR AVPDRMCRHN YELGGPMTLQ RR                                  92

SEQ ID NO: 54              moltype = AA   length = 94
FEATURE                    Location/Qualifiers
source                     1..94
                           mol_type = protein
                           organism = synthetic construct
SEQUENCE: 54
VQPRVNVSPS KKGPLQHHNL LVCHVTDFYP GSIQVRWFLN GQEETAGVVS TNLIRNGDWT    60
FQILVMLEMT PQQGDVYTCQ VEHTSLDSPV TVEW                                94
```

```
SEQ ID NO: 55          moltype = AA  length = 188
FEATURE                Location/Qualifiers
source                 1..188
                       mol_type = protein
                       organism = synthetic construct
SEQUENCE: 55
RDSPEDFVFQ FKGMCYFTNG TERVRLVTRY IYNREEYARF DSDVGVYRAV TPQGRPDAEY    60
WNSQKEVLEG TRAELDTVCR HNYEVAFRGI LQRRVEPTVT ISPSRTEALN HHNLLVCSVT   120
DFYPGQIKVR WFRNDQEETA GVVSTPLIRN GDWTFQILVM LEMTPQRGDV YTCHVEHPSL   180
QSPITVEW                                                            188

SEQ ID NO: 56          moltype = AA  length = 94
FEATURE                Location/Qualifiers
source                 1..94
                       mol_type = protein
                       organism = synthetic construct
SEQUENCE: 56
RDSPEDFVFQ FKGMCYFTNG TERVRLVTRY IYNREEYARF DSDVGVYRAV TPQGRPDAEY    60
WNSQKEVLEG TRAELDTVCR HNYEVAFRGI LQRR                                94

SEQ ID NO: 57          moltype = AA  length = 94
FEATURE                Location/Qualifiers
source                 1..94
                       mol_type = protein
                       organism = synthetic construct
SEQUENCE: 57
VEPTVTISPS RTEALNHHNL LVCSVTDFYP GQIKVRWFRN DQEETAGVVS TPLIRNGDWT    60
FQILVMLEMT PQRGDVYTCH VEHPSLQSPI TVEW                                94

SEQ ID NO: 58          moltype = AA  length = 223
FEATURE                Location/Qualifiers
source                 1..223
                       mol_type = protein
                       organism = synthetic construct
SEQUENCE: 58
PPCPSCPAPE FLGGPSVFLF PPKPKDTLMI SRTPEVTCVV VDVSQEDPEV QFNWYVDGVE    60
VHNAKTKPRE EQFNSTYRVV SVLTVLHQDW LNGKEYKCKV SNKGLPSSIE KTISKAKGQP   120
REPQVYTLPP SQEEMTKNQV SLTCLVKGFY PSDIAVEWES NGQPENNYKT TPPVLDSDGS   180
FFLYSRLTVD KSRWQEGNVF SCSVMHEALH NHYTQKSLSL SPG                     223

SEQ ID NO: 59          moltype = AA  length = 226
FEATURE                Location/Qualifiers
source                 1..226
                       mol_type = protein
                       organism = synthetic construct
SEQUENCE: 59
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPG                  226

SEQ ID NO: 60          moltype = AA  length = 5
FEATURE                Location/Qualifiers
source                 1..5
                       mol_type = protein
                       organism = synthetic construct
SEQUENCE: 60
GSGGS                                                                 5

SEQ ID NO: 61          moltype = AA  length = 4
FEATURE                Location/Qualifiers
source                 1..4
                       mol_type = protein
                       organism = synthetic construct
SEQUENCE: 61
GGGS                                                                  4

SEQ ID NO: 62          moltype = AA  length = 4
FEATURE                Location/Qualifiers
source                 1..4
                       mol_type = protein
                       organism = synthetic construct
SEQUENCE: 62
GGSG                                                                  4

SEQ ID NO: 63          moltype = AA  length = 5
FEATURE                Location/Qualifiers
source                 1..5
```

```
                        mol_type = protein
                        organism = synthetic construct
SEQUENCE: 63
GGSGG                                                                    5

SEQ ID NO: 64           moltype = AA   length = 5
FEATURE                 Location/Qualifiers
source                  1..5
                        mol_type = protein
                        organism = synthetic construct
SEQUENCE: 64
GSGSG                                                                    5

SEQ ID NO: 65           moltype = AA   length = 5
FEATURE                 Location/Qualifiers
source                  1..5
                        mol_type = protein
                        organism = synthetic construct
SEQUENCE: 65
GSGGG                                                                    5

SEQ ID NO: 66           moltype = AA   length = 5
FEATURE                 Location/Qualifiers
source                  1..5
                        mol_type = protein
                        organism = synthetic construct
SEQUENCE: 66
GGGSG                                                                    5

SEQ ID NO: 67           moltype = AA   length = 5
FEATURE                 Location/Qualifiers
source                  1..5
                        mol_type = protein
                        organism = synthetic construct
SEQUENCE: 67
GSSSG                                                                    5

SEQ ID NO: 68           moltype = AA   length = 41
FEATURE                 Location/Qualifiers
source                  1..41
                        mol_type = protein
                        organism = synthetic construct
VARIANT                 6..41
                        note = Wherein up to 9 copies of SSSS may be omitted
SEQUENCE: 68
GSSSSSSSSS SSSSSSSSSS SSSSSSSSSS SSSSSSSSSS S                            41

SEQ ID NO: 69           moltype = AA   length = 20
FEATURE                 Location/Qualifiers
source                  1..20
                        mol_type = protein
                        organism = synthetic construct
SEQUENCE: 69
GSSSSGSSSS GSSSSGSSSS                                                    20

SEQ ID NO: 70           moltype = AA   length = 25
FEATURE                 Location/Qualifiers
source                  1..25
                        mol_type = protein
                        organism = synthetic construct
SEQUENCE: 70
GSSSSGSSSS GSSSSGSSSS GSSSS                                              25

SEQ ID NO: 71           moltype = AA   length = 50
FEATURE                 Location/Qualifiers
source                  1..50
                        mol_type = protein
                        organism = synthetic construct
VARIANT                 6..50
                        note = Wherein up to 9 copies of GGGGS may be omitted
SEQUENCE: 71
GGGGSGGGGS GGGGSGGGGS GGGGSGGGGS GGGGSGGGGS GGGGSGGGGS                   50

SEQ ID NO: 72           moltype = AA   length = 5
FEATURE                 Location/Qualifiers
source                  1..5
                        mol_type = protein
                        organism = synthetic construct
SEQUENCE: 72
```

```
GGGGS                                                                                5

SEQ ID NO: 73          moltype = AA   length = 10
FEATURE                Location/Qualifiers
source                 1..10
                       mol_type = protein
                       organism = synthetic construct
SEQUENCE: 73
GGGGSGGGGS                                                                          10

SEQ ID NO: 74          moltype = AA   length = 15
FEATURE                Location/Qualifiers
source                 1..15
                       mol_type = protein
                       organism = synthetic construct
SEQUENCE: 74
GGGGSGGGGS GGGGS                                                                    15

SEQ ID NO: 75          moltype = AA   length = 20
FEATURE                Location/Qualifiers
source                 1..20
                       mol_type = protein
                       organism = synthetic construct
SEQUENCE: 75
GGGGSGGGGS GGGGSGGGGS                                                               20

SEQ ID NO: 76          moltype = AA   length = 25
FEATURE                Location/Qualifiers
source                 1..25
                       mol_type = protein
                       organism = synthetic construct
SEQUENCE: 76
GGGGSGGGGS GGGGSGGGGS GGGGS                                                         25

SEQ ID NO: 77          moltype = AA   length = 30
FEATURE                Location/Qualifiers
source                 1..30
                       mol_type = protein
                       organism = synthetic construct
SEQUENCE: 77
GGGGSGGGGS GGGGSGGGGS GGGGSGGGGS                                                    30

SEQ ID NO: 78          moltype = AA   length = 35
FEATURE                Location/Qualifiers
source                 1..35
                       mol_type = protein
                       organism = synthetic construct
SEQUENCE: 78
GGGGSGGGGS GGGGSGGGGS GGGGSGGGGS GGGGS                                              35

SEQ ID NO: 79          moltype = AA   length = 40
FEATURE                Location/Qualifiers
source                 1..40
                       mol_type = protein
                       organism = synthetic construct
SEQUENCE: 79
GGGGSGGGGS GGGGSGGGGS GGGGSGGGGS GGGGSGGGGS                                         40

SEQ ID NO: 80          moltype = AA   length = 45
FEATURE                Location/Qualifiers
source                 1..45
                       mol_type = protein
                       organism = synthetic construct
SEQUENCE: 80
GGGGSGGGGS GGGGSGGGGS GGGGSGGGGS GGGGSGGGGS GGGGS                                   45

SEQ ID NO: 81          moltype = AA   length = 50
FEATURE                Location/Qualifiers
source                 1..50
                       mol_type = protein
                       organism = synthetic construct
SEQUENCE: 81
GGGGSGGGGS GGGGSGGGGS GGGGSGGGGS GGGGSGGGGS GGGGSGGGGS                              50

SEQ ID NO: 82          moltype = AA   length = 5
FEATURE                Location/Qualifiers
source                 1..5
                       mol_type = protein
                       organism = synthetic construct
```

| | | |
|---|---|---|
| SEQUENCE: 82 | | |
| AAAGG | | 5 |
| | | |
| SEQ ID NO: 83 | moltype = AA  length = 8 | |
| FEATURE | Location/Qualifiers | |
| source | 1..8 | |
| | mol_type = protein | |
| | organism = synthetic construct | |
| SEQUENCE: 83 | | |
| GGSAAAGG | | 8 |
| | | |
| SEQ ID NO: 84 | moltype = AA  length = 17 | |
| FEATURE | Location/Qualifiers | |
| source | 1..17 | |
| | mol_type = protein | |
| | organism = Homo sapiens | |
| SEQUENCE: 84 | | |
| GAGSLQPLAL EGSLQKR | | 17 |
| | | |
| SEQ ID NO: 85 | moltype = AA  length = 15 | |
| FEATURE | Location/Qualifiers | |
| source | 1..15 | |
| | mol_type = protein | |
| | organism = Homo sapiens | |
| SEQUENCE: 85 | | |
| GIVDQCCTSI CSLYQ | | 15 |
| | | |
| SEQ ID NO: 86 | moltype = AA  length = 15 | |
| FEATURE | Location/Qualifiers | |
| source | 1..15 | |
| | mol_type = protein | |
| | organism = Homo sapiens | |
| SEQUENCE: 86 | | |
| GIVEQCCTSI CSLYQ | | 15 |
| | | |
| SEQ ID NO: 87 | moltype = AA  length = 13 | |
| FEATURE | Location/Qualifiers | |
| source | 1..13 | |
| | mol_type = protein | |
| | organism = Homo sapiens | |
| SEQUENCE: 87 | | |
| NFFRMVISNP AAT | | 13 |
| | | |
| SEQ ID NO: 88 | moltype = AA  length = 13 | |
| FEATURE | Location/Qualifiers | |
| source | 1..13 | |
| | mol_type = protein | |
| | organism = Homo sapiens | |
| SEQUENCE: 88 | | |
| NFIRMVISNP AAT | | 13 |
| | | |
| SEQ ID NO: 89 | moltype = AA  length = 20 | |
| FEATURE | Location/Qualifiers | |
| source | 1..20 | |
| | mol_type = protein | |
| | organism = Homo sapiens | |
| SEQUENCE: 89 | | |
| SFYLKNVQTQ ETRTLTQFHF | | 20 |
| | | |
| SEQ ID NO: 90 | moltype = AA  length = 15 | |
| FEATURE | Location/Qualifiers | |
| source | 1..15 | |
| | mol_type = protein | |
| | organism = Homo sapiens | |
| SEQUENCE: 90 | | |
| SLQPLALEGS LQSRG | | 15 |
| | | |
| SEQ ID NO: 91 | moltype = AA  length = 18 | |
| FEATURE | Location/Qualifiers | |
| source | 1..18 | |
| | mol_type = protein | |
| | organism = Homo sapiens | |
| SEQUENCE: 91 | | |
| GSLQPLALEG SLQSRGIV | | 18 |
| | | |
| SEQ ID NO: 92 | moltype = AA  length = 110 | |
| FEATURE | Location/Qualifiers | |
| source | 1..110 | |
| | mol_type = protein | |

```
                                  organism  = Homo sapiens
SEQUENCE: 92
MALWMRLLPL LALLALWGPD PAAAFVNQHL CGSHLVEALY LVCGERGFFY TPKTRREAED    60
LQVGQVELGG GPGAGSLQPL ALEGSLQKRG IVEQCCTSIC SLYQLENYCN              110

SEQ ID NO: 93             moltype = AA   length = 18
FEATURE                   Location/Qualifiers
source                    1..18
                          mol_type = protein
                          organism = Homo sapiens
SEQUENCE: 93
GAGSLQPLAL EGSLQKRG                                                  18

SEQ ID NO: 94             moltype = AA   length = 15
FEATURE                   Location/Qualifiers
source                    1..15
                          mol_type = protein
                          organism = Homo sapiens
SEQUENCE: 94
SLQPLALEGS LQKRG                                                     15

SEQ ID NO: 95             moltype = AA   length = 13
FEATURE                   Location/Qualifiers
source                    1..13
                          mol_type = protein
                          organism = Homo sapiens
SEQUENCE: 95
QPLALEGSLQ KRG                                                       13

SEQ ID NO: 96             moltype = AA   length = 13
FEATURE                   Location/Qualifiers
source                    1..13
                          mol_type = protein
                          organism = Homo sapiens
SEQUENCE: 96
QPLALEGSLQ SRG                                                       13

SEQ ID NO: 97             moltype = AA   length = 245
FEATURE                   Location/Qualifiers
source                    1..245
                          mol_type = protein
                          organism = Homo sapiens
SEQUENCE: 97
MRIFAVFIFM TYWHLLNAFT VTVPKDLYVV EYGSNMTIEC KFPVEKQLDL AALIVYWEME    60
DKNIIQFVHG EEDLKVQHSS YRQRARLLKD QLSLGNAALQ ITDVKLQDAG VYRCMISYGG   120
ADYKRITVKV NAPYNKINQR ILVVDPVTSE HELTCQAEGY PKAEVIWTSS DHQVLSGKTT   180
TTNSKREEKL FNVTSTLRIN TTTNEIFYCT FRRLDPEENH TAELVIPGNI LNVSIKICLT   240
LSPST                                                               245

SEQ ID NO: 98             moltype = AA   length = 219
FEATURE                   Location/Qualifiers
source                    1..219
                          mol_type = protein
                          organism = Homo sapiens
SEQUENCE: 98
FTVTVPKDLY VVEYGSNMTI ECKFPVEKQL DLAALIVYWE MEDKNIIQFV HGEEDLKVQH    60
SSYRQRARLL KDQLSLGNAA LQITDVKLQD AGVYRCMISY GGADYKRITV KVNAPYNKIN   120
QRILVVDPVT SEHELTCQAE GYPKAEVIWT SSDHQVLSGK TTTTNSKREE KLFNVTSTLR   180
INTTTNEIFY CTFRRLDPEE NHTAELVIPG NILNVSIKI                          219

SEQ ID NO: 99             moltype = AA   length = 220
FEATURE                   Location/Qualifiers
source                    1..220
                          mol_type = protein
                          organism = Homo sapiens
SEQUENCE: 99
FTVTVPKDLY VVEYGSNMTI ECKFPVEKQL DLAALIVYWE MEDKNIIQFV HGEEDLKVQH    60
SSYRQRARLL KDQLSLGNAA LQITDVKLQD AGVYRCMISY GGADYKRITV KVNAPYNKIN   120
QRILVVDPVT SEHELTCQAE GYPKAEVIWT SSDHQVLSGK TTTTNSKREE KLFNVTSTLR   180
INTTTNEIFY CTFRRLDPEE NHTAELVIPE LPLAHPPNER                         220

SEQ ID NO: 100            moltype = AA   length = 268
FEATURE                   Location/Qualifiers
source                    1..268
                          mol_type = protein
                          organism = Homo sapiens
SEQUENCE: 100
PGWFLDSPDR PWNPPTFSPA LLVVTEGDNA TFTCSFSNTS ESFVLNWYRM SPSNQTDKLA    60
AFPEDRSQPG QDCRFRVTQL PNGRDFHMSV VRARRNDSGT YLCGAISLAP KAQIKESLRA   120
```

```
ELRVTERRAE VPTAHPSPSP RPAGQFQTLV VGVVGGLLGS LVLLVWVLAV ICSRAARGTI    180
GARRTGQPLK EDPSAVPVFS VDYGELDFQW REKTPEPPVP CVPEQTEYAT IVFPSGMGTS    240
SPARRGSADG PRSAQPLRPE DGHCSWPL                                      268

SEQ ID NO: 101          moltype = AA   length = 133
FEATURE                 Location/Qualifiers
source                  1..133
                        mol_type = protein
                        organism = Homo sapiens
SEQUENCE: 101
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLT                                                      133

SEQ ID NO: 102          moltype = AA   length = 251
FEATURE                 Location/Qualifiers
source                  1..251
                        mol_type = protein
                        organism = Homo sapiens
SEQUENCE: 102
ELCDDDPPEI PHATFKAMAY KEGTMLNCEC KRGFRRIKSG SLYMLCTGNS SHSSWDNQCQ     60
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SCLVTTTDFQ IQTEMAATME TSIFTTEYQV AVAGCVFLLI SVLLLSGLTW    240
QRRQRKSRRT I                                                        251

SEQ ID NO: 103          moltype = AA   length = 524
FEATURE                 Location/Qualifiers
source                  1..524
                        mol_type = protein
                        organism = Homo sapiens
SEQUENCE: 103
VNGTSQFTCF YNSRANISCV WSQDGALQDT SCQVHAWPDR RRWNQTCELL PVSQASWACN     60
LILGAPDSQK LTTVDIVTLR VLCREGVRWR VMAIQDFKPF ENLRLMAPIS LQVVHVETHR    120
CNISWEISQA SHYFERHLEF EARTLSPGHT WEEAPLLTLK QKQEWICLET LTPDTQYEFQ    180
VRVKPLQGEF TTWSPWSQPL AFRTKPAALG KDTIPWLGHL LVGLSGAFGF IILVYLLINC    240
RNTGPWLKKV LKCNTPDPSK FFSQLSSEHG GDVQKWLSSP FPSSSFSPGG LAPEISPLEV    300
LERDKVTQLL LQQDKVPEPA SLSSNHSLTS CFTNQGYFFF HLPDALEIEA CQVYFTYDPY    360
SEEDPDEGVA GAPTGSSPQP LQPLSGEDDA YCTFPSRDDL LLFSPSLLGG PSPPSTAPGG    420
SGAGEERMPP SLQERVPRDW DPQPLGPPTP GVPDLVDFQP PPELVLREAG EEVPDAGPRE    480
GVSFPWSRPP GQGEFRALNA RLPLNTDAYL SLQELQGQDP THLV                    524

SEQ ID NO: 104          moltype = AA   length = 347
FEATURE                 Location/Qualifiers
source                  1..347
                        mol_type = protein
                        organism = Homo sapiens
SEQUENCE: 104
LNTTILTPNG NEDTTADFFL TTMPTDSLSV STLPLPEVQC FVFNVEYMNC TWNSSSEPQP     60
TNLTLHYWYK NSDNDKVQKC SHYLFSEEIT SGCQLQKKEI HLYQTFVVQL QDPREPRRQA    120
TQMLKLQNLV IPWAPENLTL HKLSESQLEL NWNNRFLNHL LEHLVQYRTD WDHSWTEQSV    180
DYRHKFSLPS VDGQKRYTFR VRSRFNPLCG SAQHWSEWSH PIHWGSNTSK ENPFLFALEA    240
VVISVGSMGL IISLLCVYFW LERTMPRIPT LKNLEDLVTE YHGNFSAWSG VSKGLAESLQ    300
PDYSERLCLV SEIPPKGGAL GEGPGASPCN QHSPYWAPPC YTLKPET                 347

SEQ ID NO: 105          moltype = AA   length = 133
FEATURE                 Location/Qualifiers
VARIANT                 42
                        note = X is any amino acid other than Phe. In some cases, X
                         is Ala
source                  1..133
                        mol_type = protein
                        organism = synthetic construct
SEQUENCE: 105
APTSSSTKKT QLQLEHLLLD LQMILNGINN YKNPKLTRML TXKFYMPKKA TELKHLQCLE     60
EELKPLEEVL NLAQSKNFHL RPRDLISNIN VIVLELKGSE TTFMCEYADE TATIVEFLNR    120
WITFCQSIIS TLT                                                      133

SEQ ID NO: 106          moltype = AA   length = 133
FEATURE                 Location/Qualifiers
VARIANT                 20
                        note = X is any amino acid other than Asp. In some cases, X
                         is Ala
source                  1..133
                        mol_type = protein
                        organism = synthetic construct
SEQUENCE: 106
APTSSSTKKT QLQLEHLLLX LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
```

```
                                                          -continued
WITFCQSIIS TLT                                                       133

SEQ ID NO: 107          moltype = AA  length = 133
FEATURE                 Location/Qualifiers
VARIANT                 15
                        note = X is any amino acid other than Glu. In some cases, X
                          is Ala
source                  1..133
                        mol_type = protein
                        organism = synthetic construct
SEQUENCE: 107
APTSSSTKKT QLQLXHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 108          moltype = AA  length = 133
FEATURE                 Location/Qualifiers
VARIANT                 16
                        note = X is any amino acid other than His. In some cases, X
                          is Ala, Arg, Asn, Asp, Cys, Glu, Gln, Gly, Lys, Leu, Met,
                          Phe, Pro, Ser, Thr, Tyr, Trp or Val
source                  1..133
                        mol_type = protein
                        organism = synthetic construct
SEQUENCE: 108
APTSSSTKKT QLQLEXLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 109          moltype = AA  length = 133
FEATURE                 Location/Qualifiers
VARIANT                 45
                        note = X is any amino acid other than Tyr. In some cases, X
                          is Ala
source                  1..133
                        mol_type = protein
                        organism = synthetic construct
SEQUENCE: 109
APTSSSTKKT QLQLEHLLLD LQMILNGINN YKNPKLTRML TFKFXMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 110          moltype = AA  length = 133
FEATURE                 Location/Qualifiers
VARIANT                 126
                        note = X is any amino acid other than Gln. In some cases, X
                          is Ala
source                  1..133
                        mol_type = protein
                        organism = synthetic construct
SEQUENCE: 110
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                      133

SEQ ID NO: 111          moltype = AA  length = 133
FEATURE                 Location/Qualifiers
VARIANT                 16
                        note = X is any amino acid other than His. In some cases, X
                          is Ala or Thr
VARIANT                 42
                        note = X is any amino acid other than Phe. In some cases, X
                          is Ala
source                  1..133
                        mol_type = protein
                        organism = synthetic construct
SEQUENCE: 111
APTSSSTKKT QLQLEXLLLD LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 112          moltype = AA  length = 133
FEATURE                 Location/Qualifiers
VARIANT                 20
                        note = X is any amino acid other than Asp. In some cases, X
                          is Ala
VARIANT                 42
                        note = X is any amino acid other than Phe. In some cases, X
                          is Ala
```

```
source                     1..133
                           mol_type = protein
                           organism = synthetic construct
SEQUENCE: 112
APTSSSTKKT QLQLEHLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 113             moltype = AA  length = 133
FEATURE                    Location/Qualifiers
VARIANT                    15
                           note = X is any amino acid other than Glu. In some cases, X
                             is Ala
VARIANT                    20
                           note = X is any amino acid other than Asp. In some cases, X
                             is Ala
VARIANT                    42
                           note = X is any amino acid other than Phe. In some cases, X
                             is Ala
source                     1..133
                           mol_type = protein
                           organism = synthetic construct
SEQUENCE: 113
APTSSSTKKT QLQLXHLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 114             moltype = AA  length = 133
FEATURE                    Location/Qualifiers
VARIANT                    16
                           note = X is any amino acid other than His. In some cases, X
                             is Ala
VARIANT                    20
                           note = X is any amino acid other than Asp. In some cases, X
                             is Ala
VARIANT                    42
                           note = X is any amino acid other than Phe. In some cases, X
                             is Ala
source                     1..133
                           mol_type = protein
                           organism = synthetic construct
SEQUENCE: 114
APTSSSTKKT QLQLEXLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 115             moltype = AA  length = 133
FEATURE                    Location/Qualifiers
VARIANT                    20
                           note = X is any amino acid other than Asp. In some cases, X
                             is Ala
VARIANT                    42
                           note = X is any amino acid other than Phe. In some cases, X
                             is Ala
VARIANT                    126
                           note = X is any amino acid other than Gln. In some cases, X
                             is Ala
source                     1..133
                           mol_type = protein
                           organism = synthetic construct
SEQUENCE: 115
APTSSSTKKT QLQLEHLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                     133

SEQ ID NO: 116             moltype = AA  length = 133
FEATURE                    Location/Qualifiers
VARIANT                    20
                           note = X is any amino acid other than Asp. In some cases, X
                             is Ala
VARIANT                    42
                           note = X is any amino acid other than Phe. In some cases, X
                             is Ala
VARIANT                    45
                           note = X is any amino acid other than Tyr. In some cases, X
                             is Ala
source                     1..133
                           mol_type = protein
                           organism = synthetic construct
```

```
SEQUENCE: 116
APTSSSTKKT QLQLEHLLLX LQMILNGINN YKNPKLTRML TXKFXMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 117          moltype = AA  length = 133
FEATURE                 Location/Qualifiers
VARIANT                 16
                        note = X is any amino acid other than His. In some cases, X
                          is Ala
VARIANT                 20
                        note = X is any amino acid other than Asp. In some cases, X
                          is Ala
VARIANT                 42
                        note = X is any amino acid other than Phe. In some cases, X
                          is Ala
VARIANT                 45
                        note = X is any amino acid other than Tyr. In some cases, X
                          is Ala
source                  1..133
                        mol_type = protein
                        organism = synthetic construct
SEQUENCE: 117
APTSSSTKKT QLQLEXLLLX LQMILNGINN YKNPKLTRML TXKFXMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 118          moltype = AA  length = 133
FEATURE                 Location/Qualifiers
VARIANT                 20
                        note = X is any amino acid other than Asp. In some cases, X
                          is Ala
VARIANT                 42
                        note = X is any amino acid other than Phe. In some cases, X
                          is Ala
VARIANT                 45
                        note = X is any amino acid other than Tyr. In some cases, X
                          is Ala
VARIANT                 126
                        note = X is any amino acid other than Gln. In some cases, X
                          is Ala
source                  1..133
                        mol_type = protein
                        organism = synthetic construct
SEQUENCE: 118
APTSSSTKKT QLQLEHLLLX LQMILNGINN YKNPKLTRML TXKFXMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                     133

SEQ ID NO: 119          moltype = AA  length = 133
FEATURE                 Location/Qualifiers
VARIANT                 16
                        note = X is any amino acid other than His. In some cases, X
                          is Ala
VARIANT                 20
                        note = X is any amino acid other than Asp. In some cases, X
                          is Ala
VARIANT                 42
                        note = X is any amino acid other than Phe. In some cases, X
                          is Ala
VARIANT                 45
                        note = X is any amino acid other than Tyr. In some cases, X
                          is Ala
VARIANT                 126
                        note = X is any amino acid other than Gln. In some cases, X
                          is Ala
source                  1..133
                        mol_type = protein
                        organism = synthetic construct
SEQUENCE: 119
APTSSSTKKT QLQLEXLLLX LQMILNGINN YKNPKLTRML TXKFXMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                     133

SEQ ID NO: 120          moltype = AA  length = 133
FEATURE                 Location/Qualifiers
VARIANT                 16
                        note = X is any amino acid other than His. In some cases, X
                          is Ala
```

```
VARIANT                     42
                            note = X is any amino acid other than Phe. In some cases, X
                              is Ala
VARIANT                     126
                            note = X is any amino acid other than Gln. In some cases, X
                              is Ala
source                      1..133
                            mol_type = protein
                            organism = synthetic construct
SEQUENCE: 120
APTSSSTKKT QLQLEXLLLD LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                     133

SEQ ID NO: 121              moltype = AA  length = 133
FEATURE                     Location/Qualifiers
source                      1..133
                            mol_type = protein
                            organism = synthetic construct
SEQUENCE: 121
APTSSSTKKT QLQLEALLLD LQMILNGINN YKNPKLTRML TAKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 122              moltype = AA  length = 112
FEATURE                     Location/Qualifiers
source                      1..112
                            mol_type = protein
                            organism = synthetic construct
SEQUENCE: 122
ALDTNYCFSS TEKNCCVRQL YIDFRKDLGW KWIHEPKGYH ANFCLGPCPY IWSLDTQYSK    60
VLALYNQHNP GASAAPCCVP QALEPLPIVY YVGRKPKVEQ LSNMIVRSCK CS           112

SEQ ID NO: 123              moltype = AA  length = 112
FEATURE                     Location/Qualifiers
source                      1..112
                            mol_type = protein
                            organism = synthetic construct
SEQUENCE: 123
ALDAAYCFRN VQDNCCLRPL YIDFKRDLGW KWIHEPKGYN ANFCAGACPY LWSSDTQHSR    60
VLSLYNTINP EASASPCCVS QDLEPLTILY YIGKTPKIEQ LSNMIVKSCK CS           112

SEQ ID NO: 124              moltype = AA  length = 112
FEATURE                     Location/Qualifiers
source                      1..112
                            mol_type = protein
                            organism = synthetic construct
SEQUENCE: 124
ALDTNYCFRN LEENCCVRPL YIDFRQDLGW KWVHEPKGYY ANFCSGPCPY LRSADTTHST    60
VLGLYNTLNP EASASPCCVP QDLEPLTILY YVGRTPKVEQ LSNMVVKSCK CS           112

SEQ ID NO: 125              moltype = AA  length = 281
FEATURE                     Location/Qualifiers
source                      1..281
                            mol_type = protein
                            organism = synthetic construct
SEQUENCE: 125
MQQPFNYPYP QIYWVDSSAS SPWAPPGTVL PCPTSVPRRP GQRRPPPPPP PPPLPPPPPP    60
PPLPPLPLPP LKKRGNHSTG LCLLVMFFMV LVALVGLGLG MFQLFHLQKE LAELRESTSQ   120
MHTASSLEKQ IGHPSPPPEK KELRKVAHLT GKSNSRSMPL EWEDTYGIVL LSGVKYKKGG   180
LVINETGLYF VYSKVYFRGQ SCNNLPLSHK VYMRNSKYPQ DLVMMEGKMM SYCTTGQMWA   240
RSSYLGAVFN LTSADHLYVN VSELSLVNFE ESQTFFGLYK L                      281

SEQ ID NO: 126              moltype = AA  length = 179
FEATURE                     Location/Qualifiers
source                      1..179
                            mol_type = protein
                            organism = synthetic construct
SEQUENCE: 126
QLFHLQKELA ELRESTSQMH TASSLEKQIG HPSPPPEKKE LRKVAHLTGK SNSRSMPLEW    60
EDTYGIVLLS GVKYKKGGLV INETGLYFVY SKVYFRGQSC NNLPLSHKVY MRNSKYPQDL   120
VMMEGKMMSY CTTGQMWARS SYLGAVFNLT SADHLYVNVS ELSLVNFEES QTFFGLYKL   179

SEQ ID NO: 127              moltype = AA  length = 335
FEATURE                     Location/Qualifiers
source                      1..335
                            mol_type = protein
                            organism = synthetic construct
SEQUENCE: 127
```

```
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HGLEVEINCT   120
RTQNTKCRCK PNFFCNSTVC EHCDPCTKCE HGIIKECTLT SNTKCKEEGS RSNLGWLCLL   180
LLPIPLIVWV KRKEVQKTCR KHRKENQGSH ESPTLNPETV AINLSDVDLS KYITTIAGVM   240
TLSQVKGFVR KNGVNEAKID EIKNDNVQDT AEQKVQLLRN WHQLHGKKEA YDTLIKDLKK   300
ANLCTLAEKI QTIILKDITS DSENSNFRNE IQSLV                              335

SEQ ID NO: 128          moltype = AA  length = 15
FEATURE                 Location/Qualifiers
source                  1..15
                        mol_type = protein
                        organism = synthetic construct
SEQUENCE: 128
GGCGSGGGGS GGGGS                                                    15

SEQ ID NO: 129          moltype = AA  length = 20
FEATURE                 Location/Qualifiers
source                  1..20
                        mol_type = protein
                        organism = synthetic construct
SEQUENCE: 129
GGCGSGGGGS GGGGSGGGGS                                               20

SEQ ID NO: 130          moltype = AA  length = 254
FEATURE                 Location/Qualifiers
source                  1..254
                        mol_type = protein
                        organism = synthetic construct
SEQUENCE: 130
MAISGVPVLG FFIIAVLMSA QESWAIKEEH VIIQAEFYLN PDQSGEFMFD FDGDEIFHVD    60
MAKKETVWRL EEFGRFASFE AQGALANIAV DKANLEIMTK RSNYTPITNV PPEVTVLTNS   120
PVELREPNVL ICFIDKFTPP VVNVTWLRNG KPVTTGVSET VFLPREDHLF RKFHYLPFLP   180
STEDVYDCRV EHWGLDEPLL KHWEFDAPSP LPETTENVVC ALGLTVGLVG IIIGTIFIIK   240
GLRKSNAAER RGPL                                                    254

SEQ ID NO: 131          moltype = AA  length = 266
FEATURE                 Location/Qualifiers
source                  1..266
                        mol_type = protein
                        organism = Homo sapiens
SEQUENCE: 131
MVCLRLPGGS CMAVLTVTLM VLSSPLALAG DTRPRFLEYS TSECHFFNGT ERVRYLDRYF    60
HNQEENVRFD SDVGEFRAVT ELGRPDAEYW NSQKDLLEQK RGRVDNYCRH NYGVVESFTV   120
QRRVHPKVTV YPSKTQPLQH HNLLVCSVSG FYPGSIEVRW FRNGQEEKTG VVSTGLIHNG   180
DWTFQTLVML ETVPRSGEVY TCQVEHPSVT SPLTVEWRAR SESAQSKMLS GVGGFVLGLL   240
FLGAGLFIYF RNQKGHSGLQ PRGFLS                                       266

SEQ ID NO: 132          moltype = AA  length = 266
FEATURE                 Location/Qualifiers
source                  1..266
                        mol_type = protein
                        organism = Homo sapiens
SEQUENCE: 132
MVCLKFPGGS CMAALTVTLM VLSSPLALAG DTRPRFLEQV KHECHFFNGT ERVRFLDRYF    60
YHQEEYVRFD SDVGEYRAVT ELGRPDAEYW NSQKDLLEQK RAAVDTYCRH NYGVVESFTV   120
QRRVYPEVTV YPAKTQPLQH HNLLVCSVNG FYPGSIEVRW FRNGQEEKTG VVSTGLIQNG   180
DWTFQTLVML ETVPRSGEVY TCQVEHPSLT SPLTVEWRAR SESAQSKMLS GVGGFVLGLL   240
FLGAGLFIYF RNQKGHSGLQ PTGFLS                                       266

SEQ ID NO: 133          moltype = AA  length = 266
FEATURE                 Location/Qualifiers
source                  1..266
                        mol_type = protein
                        organism = Homo sapiens
SEQUENCE: 133
MVCLKFPGGS CMAALTVTLM VLSSPLALAG DTRPRFLEQV KHECHFFNGT ERVRFLDRYF    60
YHQEEYVRFD SDVGEYRAVT ELGRPDAEYW NSQKDILEDE RAAVDTYCRH NYGVVESFTV   120
QRRVYPEVTV YPAKTQPLQH HNLLVCSVNG FYPGSIEVRW FRNGQEEKTG VVSTGLIQNG   180
DWTFQTLVML ETVPRSGEVY TCQVEHPSLT SPLTVEWRAR SESAQSKMLS GVGGFVLGLL   240
FLGAGLFIYF RNQKGHSGLQ PTGFLS                                       266

SEQ ID NO: 134          moltype = AA  length = 266
FEATURE                 Location/Qualifiers
source                  1..266
                        mol_type = protein
                        organism = Homo sapiens
SEQUENCE: 134
MVCLKFPGGS CMAALTVTLM VLSSPLALAG DTRPRFLEQV KHECHFFNGT ERVRFLDRYF    60
YHQEEYVRFD SDVGEYRAVT ELGRPSAEYW NSQKDLLEQR RAAVDTYCRH NYGVESFTV    120
```

```
QRRVYPEVTV YPAKTQPLQH HNLLVCSVNG FYPGSIEVRW FRNGQEEKTG VVSTGLIQNG   180
DWTFQTLVML ETVPRSGEVY TCQVEHPSLT SPLTVEWRAR SESAQSKMLS GVGGFVLGLL   240
FLGAGLFIYF RNQKGHSGLQ PTGFLS                                       266

SEQ ID NO: 135          moltype = AA   length = 266
FEATURE                 Location/Qualifiers
source                  1..266
                        mol_type = protein
                        organism = Homo sapiens
SEQUENCE: 135
MVCLRLPGGS CMAVLTVTLM VLSSPLALAG DTRPRFLEYS TGECYFFNGT ERVRFLDRYF    60
YNQEEYVRFD SDVGEYRAVT ELGRPSAEYW NSQKDFLEDR RALVDTYCRH NYGVGESFTV   120
QRRVHPKVTV YPSKTQPLQH HNLLVCSVSG FYPGSIEVRW FRNGQEEKTG VVSTGLIHNG   180
DWTFQTLVML ETVPRSGEVY TCQVEHPSVT SPLTVEWSAR SESAQSKMLS GVGGFVLGLL   240
FLGAGLFIYF RNQKGHSGLQ PTGFLS                                       266

SEQ ID NO: 136          moltype = AA   length = 266
FEATURE                 Location/Qualifiers
source                  1..266
                        mol_type = protein
                        organism = Homo sapiens
SEQUENCE: 136
MVCLKLPGGS CMAALTVTLM VLSSPLALAG DTQPRFLKQD KFECHFFNGT ERVRYLHRGI    60
YNQEENVRFD SDVGEYRAVT ELGRPVAESW NSQKDFLERR RAEVDTVCRH NYGVGESFTV   120
QRRVHPEVTV YPAKTQPLQH HNLLVCSVSG FYPGSIEVRW FRNGQEEKAG VVSTGLIQNG   180
DWTFQTLVML ETVPRSGEVY TCQVEHPSVM SPLTVEWRAR SESAQSKMLS GVGGFVLGLL   240
FLGAGLFIYF RNQKGHSGLQ PTGFLS                                       266

SEQ ID NO: 137          moltype = AA   length = 266
FEATURE                 Location/Qualifiers
source                  1..266
                        mol_type = protein
                        organism = Homo sapiens
SEQUENCE: 137
MVCLKLPGGS CMTALTVTLM VLSSPLALAG DTRPRFLWQP KRECHFFNGT ERVRFLDRYF    60
YNQEESVRFD SDVGEYRAVT ELGRPDAEYW NSQKDFLEDR RAAVDTYCRH NYGVGESFTV   120
QRRVQPKVTV YPSKTQPLQH HNLLVCSVSG FYPGSIEVRW FLNGQEEKAG MVSTGLIQNG   180
DWTFQTLVML ETVPRSGEVY TCQVEHPSVT SPLTVEWRAR SESAQSKMLS GVGGFVLGLL   240
FLGAGLFIYF RNQKGHSGLQ PTGFLS                                       266

SEQ ID NO: 138          moltype = AA   length = 60
FEATURE                 Location/Qualifiers
source                  1..60
                        mol_type = protein
                        organism = Homo sapiens
SEQUENCE: 138
DWTFQTLVML ETVPRSGEVY TCQVEHPSVT SPLTVEWSAR SESAQSKMLS GVGGFVLGLL    60

SEQ ID NO: 139          moltype = AA   length = 266
FEATURE                 Location/Qualifiers
source                  1..266
                        mol_type = protein
                        organism = Homo sapiens
SEQUENCE: 139
MVCLKLPGGS SLAALTVTLM VLSSRLAFAG DTRPRFLELR KSECHFFNGT ERVRYLDRYF    60
HNQEEFLRFD SDVGEYRAVT ELGRPVAESW NSQKDLLEQK RGRVDNYCRH NYGVGESFTV   120
QRRVHPQVTV YPAKTQPLQH HNLLVCSVSG FYPGSIEVRW FRNGQEEKAG VVSTGLIQNG   180
DWTFQTLVML ETVPRSGEVY TCQVEHPSVT SALTVEWRAR SESAQSKMLS GVGGFVLGLL   240
FLGAGLFIYF RNQKGHSGLQ PTGFLS                                       266

SEQ ID NO: 140          moltype = AA   length = 266
FEATURE                 Location/Qualifiers
source                  1..266
                        mol_type = protein
                        organism = Homo sapiens
SEQUENCE: 140
MVCLKLPGGS SLAALTVTLM VLSSRLAFAG DTRPRFLELR KSECHFFNGT ERVRYLDRYF    60
HNQEEFLRFD SDVGEYRAVT ELGRPVAESW NSQKDLLEQK RGQVDNYCRH NYGVVESFTV   120
QRRVHPQVTV YPAKTQPLQH HNLLVCSVSG FYPGSIEVRW FRNGQEEKAG VVSTGLIQNG   180
DWTFQTLVML ETVPRSGEVY TCQVEHPSVT SALTVEWRAR SESAQSKMLS GVGGFVLGLL   240
FLGAGLFIYF RNQKGHSGLQ PTGFLS                                       266

SEQ ID NO: 141          moltype = AA   length = 266
FEATURE                 Location/Qualifiers
source                  1..266
                        mol_type = protein
                        organism = Homo sapiens
SEQUENCE: 141
MVCLKLPGGS SLAALTVTLM VLSSRLAFAG DTRPRFLELL KSECHFFNGT ERVRFLERHF    60
```

```
HNQEEYARFD SDVGEYRAVR ELGRPDAEYW NSQKDLLEQK RGQVDNYCRH NYGVVESFTV    120
QRRVHPQVTV YPAKTQPLQH HNLLVCSVSG FYPGSIEVRW FRNGQEEKAG VVSTGLIQNG    180
DWTFQTLVML ETFPRSGEVY TCQVEHPSVT SPLTVEWSAR SESAQSKMLS GVGGFVLGLL    240
FLGAGLFIYF RNQKGHSGLQ PTGFLS                                        266

SEQ ID NO: 142          moltype = AA   length = 266
FEATURE                 Location/Qualifiers
source                  1..266
                        mol_type = protein
                        organism = Homo sapiens
SEQUENCE: 142
MVCLKLPGGS SLAALTVTLM VLSSRLAFAG DTRPRFLELL KSECHFFNGT ERVRFLERYF     60
HNQEEFVRFD SDVGEYRAVT ELGRPVAESW NSQKDLLEQK RGQVDNYCRH RGVVESFTV    120
QRRVHPQVTV YPAKTQPLQH HNLLVCSVSG FYPGSIEVRW FRNGQEEKTG VVSTGLIHNG    180
DWTFQTLVML ETVPRSGEVY TCQVEHPSVT SPLTVEWRAR SESAQSKMLS GVGGFVLGLL    240
FLGAGLFIYF RNQKGHSGLQ PTGFLS                                        266

SEQ ID NO: 143          moltype = AA   length = 266
FEATURE                 Location/Qualifiers
source                  1..266
                        mol_type = protein
                        organism = Homo sapiens
SEQUENCE: 143
MVCLKLPGGS CMAALTVTLT VLSSPLALAG DTQPRFLEQA KCECHFLNGT ERVWNLIRYI     60
YNQEEYARYN SDLGEYQAVT ELGRPDAEYW NSQKDLLERR RAEVDTYCRY NYGVVESFTV   120
QRRVQPKVTV YPSKTQPLQH HNLLVCSVNG FYPGSIEVRW FRNGQEEKAG VVSTGLIQNG    180
DWTFQTLVML ETVPRSGEVY TCQVEHPSMM SPLTVQWSAR SESAQSKMLS GVGGFVLGLL    240
FLGTGLFIYF RNQKGHSGLQ PTGLLS                                        266

SEQ ID NO: 144          moltype = AA   length = 266
FEATURE                 Location/Qualifiers
source                  1..266
                        mol_type = protein
                        organism = Homo sapiens
SEQUENCE: 144
MVCLKLPGGS YMAKLTVTLM VLSSPLALAG DTRPRFLQQD KYECHFFNGT ERVRFLHRDI     60
YNQEEDLRFD SDVGEYRAVT ELGRPDAEYW NSQKDFLEDR RAAVDTYCRH NYGVGESFTV   120
QRRVEPKVTV YPARTQPLQH HNLLVCSVNG FYPGSIEVRW FRNSQEEKAG VVSTGLIQNG    180
DWTFQTLVML ETVPRSGEVY TCQVEHPSVT SPLTVEWRAQ SESAQSKMLS GVGGFVLGLL    240
FLGAGLFIYF KNQKGHSGLH PTGLVS                                        266

SEQ ID NO: 145          moltype = AA   length = 260
FEATURE                 Location/Qualifiers
source                  1..260
                        mol_type = protein
                        organism = Homo sapiens
SEQUENCE: 145
MRPEDRMFHI RAVILRALSL AFLLSLRGAG AIKADHVSTY AAFVQTHRPT GEFMFEFDED     60
EMFYVDLDKK ETVWHLEEFG QAFSFEAQGG LANIAILNNN LNTLIQRSNH TQATNDPPEV   120
TVFPKEPVEL GQPNTLICHI DKFFPPVLNV TWLCNGELVT EGVAESLFLP RTDYSFHKFH    180
YLTFVPSAED FYDCRVEHWG LDQPLLKHWE AQEPIQMPET TETVLCALGL VLGLVGIIVG    240
TVLIIKSLRS GHDPRAQGTL                                                260

SEQ ID NO: 146          moltype = AA   length = 258
FEATURE                 Location/Qualifiers
source                  1..258
                        mol_type = protein
                        organism = Homo sapiens
SEQUENCE: 146
MMVLQVSAAP RTVALTALLM VLLTSVVQGR ATPENYLFQG RQECYAFNGT QRFLERYIYN     60
REELVRFDSD VGEFRAVTEL GRPEAEYWNS QKDILEEERA VPDRMCRHNY ELGGPMTLQR   120
RVQPRVNVSP SKKGPLQHHN LLVCHVTDFY PGSIQVRWFL NGQEETAGVV STNLIRNGDW    180
TFQILVMLEM TPQQGDVYTC QVEHTSLDSP VTVEWKAQSD SARSKTLTGA GGFVLGLIIC    240
GVGIFMHRRS KKVQRGSA                                                 258

SEQ ID NO: 147          moltype = AA   length = 258
FEATURE                 Location/Qualifiers
source                  1..258
                        mol_type = protein
                        organism = Homo sapiens
SEQUENCE: 147
MMVLQVSAAP RTVALTALLM VLLTSVVQGR ATPENYVYQL RQECYAFNGT QRFLERYIYN     60
REEFVRFDSD VGEFRAVTEL GRPDEDYWNS QKDLLEEKRA ELDEAVTLQR              120
RVQPKVNVSP SKKGPLQHHN LLVCHVTDFY PGSIQVRWFL NGQEETAGVV STNLIRNGDW    180
TFQILVMLEM TPQQGDVYIC QVEHTSLDSP VTVEWKAQSD SARSKTLTGA GGFVLGLIIC    240
GVGIFMHRRS KKVQRGSA                                                 258

SEQ ID NO: 148          moltype = AA   length = 135
FEATURE                 Location/Qualifiers
```

| | | |
|---|---|---|
| source | 1..135<br>mol_type = protein<br>organism = Homo sapiens | |
| SEQUENCE: 148 | | |
| MILNKALLLG ALALTTVMSP CGGEDIVADH VASCGVNLYQ FYGPSGQYTH EFDGDEEFYV | | 60 |
| SPVTLGQPNT LICLVDNIFP PVVNITWLSN GQSVTEGVSE TSFLSKSDHS FFKISYLTFL | | 120 |
| QGLRSVGASR HQGPL | | 135 |

| | | |
|---|---|---|
| SEQ ID NO: 149<br>FEATURE<br>source | moltype = AA  length = 134<br>Location/Qualifiers<br>1..134<br>mol_type = protein<br>organism = Homo sapiens | |
| SEQUENCE: 149 | | |
| MILNKALMLG ALALTTVMSP CGGEDIVADH VASYGVNLYQ SYGPSGQYSH EFDGDEEFYV | | 60 |
| SPVTLGQPNT LICLVDNIFP PVVNITWLSN GHSVTEGVST SFLSKSDHSF FKISYLTFLR | | 120 |
| GLRSVGASRH QGPL | | 134 |

| | | |
|---|---|---|
| SEQ ID NO: 150<br>FEATURE<br>source | moltype = AA  length = 135<br>Location/Qualifiers<br>1..135<br>mol_type = protein<br>organism = Homo sapiens | |
| SEQUENCE: 150 | | |
| MILNKALLLG ALALTTVMSP CGGEDIVADH VASYGVNLYQ SYGPSGQYTH EFDGDEQFYV | | 60 |
| SPVTLGQPNT LICLVDNIFP PVVNITWLSN GHSVTEGVSE TSFLSKSDHS FFKISYLTFL | | 120 |
| RGLRSVGASR HQGPL | | 135 |

| | | |
|---|---|---|
| SEQ ID NO: 151<br>FEATURE<br>source | moltype = AA  length = 135<br>Location/Qualifiers<br>1..135<br>mol_type = protein<br>organism = Homo sapiens | |
| SEQUENCE: 151 | | |
| MILNKALMLG ALALTTVMSP CGGEDIVADH VASYGVNLYQ SYGPSGQYTH EFDGDEQFYV | | 60 |
| SPVTLGQPNI LICLVDNIFP PVVNITWLSN GHSVTEGVSE TSFLSKSDHS FFKISYLTLL | | 120 |
| RGLRSVGASR HQGPL | | 135 |

| | | |
|---|---|---|
| SEQ ID NO: 152<br>FEATURE<br>source | moltype = AA  length = 261<br>Location/Qualifiers<br>1..261<br>mol_type = protein<br>organism = Homo sapiens | |
| SEQUENCE: 152 | | |
| MSWKKALRIP GGLRAATVTL MLSMLSTPVA EGRDSPEDFV YQFKGMCYFT NGTERVRLVS | | 60 |
| RSIYNREEIV RFDSDVGEFR AVTLLGLPAA EYWNSQKDIL ERKRAAVDRV CRHNYQLELR | | 120 |
| TTLQRRVEPT VTISPSRTEA LNHHNLLVCS VTDFYPAQIK VRWFRNDQEE TAGVVSTPLI | | 180 |
| RNGDWTFQIL VMLEMTPQRG DVYTCHVEHP SLQSPITVEW RAQSESAQSK MLSGIGGFVL | | 240 |
| GLIFLGLGLI IHHRSQKGLL H | | 261 |

| | | |
|---|---|---|
| SEQ ID NO: 153<br>FEATURE<br>source | moltype = AA  length = 261<br>Location/Qualifiers<br>1..261<br>mol_type = protein<br>organism = Homo sapiens | |
| SEQUENCE: 153 | | |
| MSWKKALRIP GGLRVATVTL MLAMLSTPVA EGRDSPEDFV YQFKGMCYFT NGTERVRLVT | | 60 |
| RYIYNREEYA RFDSDVGVYR AVTPLGPPAA EYWNSQKEVL ERTRAELDTV CRHNYQLELR | | 120 |
| TTLQRRVEPT VTISPSRTEA LNHHNLLVCS VTDFYPAQIK VRWFRNDQEE TTGVVSTPLI | | 180 |
| RNGDWTFQIL VMLEMTPQRG DVYTCHVEHP SLQNPIIVEW RAQSESAQSK MLSGIGGFVL | | 240 |
| GLIFLGLGLI IHHRSQKGLL H | | 261 |

| | | |
|---|---|---|
| SEQ ID NO: 154<br>FEATURE<br>source | moltype = AA  length = 261<br>Location/Qualifiers<br>1..261<br>mol_type = protein<br>organism = Homo sapiens | |
| SEQUENCE: 154 | | |
| MSWKKALRIP GGLRVATVTL MLAMLSTPVA EGRDSPEDFV YQFKGMCYFT NGTERVRLVT | | 60 |
| RYIYNREEYA RFDSDVGVYR AVTPLGPPDA EYWNSQKEVL ERTRAELDTV CRHNYQLELR | | 120 |
| TTLQRRVEPT VTISPSRTEA LNHHNLLVCS VTDFYPAQIK VRWFRNDQEE TTGVVSTPLI | | 180 |
| RNGDWTFQIL VMLEMTPQRG DVYTCHVEHP SLQNPIIVEW RAQSESAQSK MLSGIGGFVL | | 240 |
| GLIFLGLGLI IHHRSQKGLL H | | 261 |

| | |
|---|---|
| SEQ ID NO: 155<br>FEATURE<br>source | moltype = AA  length = 261<br>Location/Qualifiers<br>1..261<br>mol_type = protein<br>organism = Homo sapiens |

```
SEQUENCE: 155
MSWKKALRIP GGLRVATVTL MLAMLSTPVA EGRDSPEDFV FQFKGMCYFT NGTELVRGVT    60
RYIYNREEYA RFDSDVGVYR AVTPLGRLDA EYWNSQKDIL EEDRASVDTV CRHNYQLELR   120
TTLQRRVEPT VTISPSRTEA LNHHNLLVCS VTDFYPAQIK VRWFRNDQEE TTGVVSTPLI   180
RNGDWTFQIL VMLEMTPQRG DVYTCHVEHP SLQNPIIVEW RAQSESAQSK MLSGIGGFVL   240
GLIFLGLGLI IHHRSQKGLL H                                            261

SEQ ID NO: 156           moltype = AA  length = 261
FEATURE                  Location/Qualifiers
source                   1..261
                         mol_type = protein
                         organism = Homo sapiens
SEQUENCE: 156
MSWKKALRIP GGLRVATVTL MLAMLSTPVA EGRDSPEDFV FQFKGMCYFT NGTERVRGVT    60
RYIYNREEYA RFDSDVGVYR AVTPLGRLDA EYWNSQKDIL EEDRASVDTV CRHNYQLELR   120
TTLQRRVEPT VTISPSRTEA LNHHNLLVCS VTDFYPAQIK VRWFRNDQEE TTGVVSTPLI   180
RNGDWTFQIL VMLEMTPQRG DVYTCHVEHP SLQNPIIVEW RAQSESAQSK MLSGIGGFVL   240
GLIFLGLGLI IHHRSQKGLL H                                            261

SEQ ID NO: 157           moltype = AA  length = 261
FEATURE                  Location/Qualifiers
source                   1..261
                         mol_type = protein
                         organism = Homo sapiens
SEQUENCE: 157
MSWKKSLRIP GDLRVATVTL MLAILSSSLA EGRDSPEDFV YQFKGLCYFT NGTERVRGVT    60
RHIYNREEYV RFDSDVGVYR AVTPQGRPVA EYWNSQKEVL EGARASVDRV CRHNYEVAYR   120
GILQRRVEPT VTISPSRTEA LNHHNLLICS VTDFYPSQIK VRWFRNDQEE TAGVVSTPLI   180
RNGDWTFQIL VMLEMTPQRG DVYTCHVEHP SLQSPITVEW RAQSESAQSK MLSGVGGFVL   240
GLIFLGLGLI IRQRSRKGLL H                                            261

SEQ ID NO: 158           moltype = AA  length = 29
FEATURE                  Location/Qualifiers
source                   1..29
                         mol_type = protein
                         organism = Homo sapiens
SEQUENCE: 158
GLIFLGLGLI IRQRSRKGPQ GPPPAGLLH                                     29

SEQ ID NO: 159           moltype = AA  length = 227
FEATURE                  Location/Qualifiers
source                   1..227
                         mol_type = protein
                         organism = Homo sapiens
SEQUENCE: 159
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 160           moltype = AA  length = 325
FEATURE                  Location/Qualifiers
source                   1..325
                         mol_type = protein
                         organism = Homo sapiens
SEQUENCE: 160
STKGPSVFPL APCSRSTSES TAALGCLVKD YFPEPVTVSW NSGALTSGVH TFPAVLQSSG    60
LYSLSSVVTV PSSNFGTQTY TCNVDHKPSN TKVDKTVERK CCVECPPCPA PPVAGPSVFL   120
FPPKPKDTLM ISRTPEVTCV VVDVSHEDPE VQFNWYVDGV EVHNAKTKPR EEQFNSTFRV   180
VSVLTVVHQD WLNGKEYKCK VSNKGLPAPI EKTISKTKGQ PREPQVYTLP PSREEMTKNQ   240
VSLTCLVKGF YPSDIAVEWE SNGQPENNYK TTPPMLDSDG SFFLYSKLTV DKSRWQQGNV   300
FSCSVMHEAL HNHYTQKSLS LSPGK                                        325

SEQ ID NO: 161           moltype = AA  length = 246
FEATURE                  Location/Qualifiers
source                   1..246
                         mol_type = protein
                         organism = Homo sapiens
SEQUENCE: 161
HKPSNTKVDK RVELKTPLGD TTHTCPPCPA PELLGGPSVF LFPPKPKDTL MISRTPEVTC    60
VVVDVSHEDP EVKFNWYVDG VEVHNAKTKP REEQYNSTYR VVSVLTVLHQ DWLNGKEYKC   120
KVSNKALPAP IEKTISKAKG QPREPQVYTL PPSRDELTKN QVSLTCLVKG FYPSDIAVEW   180
ESNGQPENNY KTTPPVLDSD GSFFLYSKLT VDKSRWQQGN VFSCSVMHEA LHNHYTQKSL   240
SLSPGK                                                             246

SEQ ID NO: 162           moltype = AA  length = 383
FEATURE                  Location/Qualifiers
source                   1..383
                         mol_type = protein
```

```
                            organism = Homo sapiens
SEQUENCE: 162
PTKAPDVFPI ISGCRHPKDN SPVVLACLIT GYHPTSVTVT WYMGTQSQPQ RTFPEIQRRD    60
SYYMTSSQLS TPLQQWRQGE YKCVVQHTAS KSKKEIFRWP ESPKAQASSV PTAQPQAEGS   120
LAKATTAPAT TRNTGRGGEE KKKEKEKEEQ EERETKTPEC PSHTQPLGVY LLTPAVQDLW   180
LRDKATFTCF VVGSDLKDAH LTWEVAGKVP TGGVEEGLLE RHSNGSQSQH SRLTLPRSLW   240
NAGTSVTCTL NHPSLPPQRL MALREPAAQA PVKLSLNLLA SSDPPEAASW LLCEVSGFSP   300
PNILLMWLED QREVNTSGFA PARPPPQPRS TTFWAWSVLR VPAPPSPQPA TYTCVVSHED   360
SRTLLNASRS LEVSYVTDHG PMK                                           383

SEQ ID NO: 163          moltype = AA  length = 276
FEATURE                 Location/Qualifiers
source                  1..276
                        mol_type = protein
                        organism = Homo sapiens
SEQUENCE: 163
VTSTLTIKZS DWLGESMFTC RVDHRGLTFQ QNASSMCVPD QDTAIRVFAI PPSFASIFLT    60
KSTKLTCLVT DLTTYBSVTI SWTREENGAV KTHTNISESH PNATFSAVGE ASICEDBDWS   120
GERFTCTVTH TDLPSPLKQT ISRPKGVALH RPBVYLLPPA RZZLNLRESA TITCLVTGFS   180
PADVFVEWMQ RGEPLSPQKY VTSAPMPEPQ APGRYFAHSI LTVSEEEWNT GGTYTCVVAH   240
EALPNRVTER TVDKSTGKPT LYNVSLVMSD TAGTCY                             276

SEQ ID NO: 164          moltype = AA  length = 353
FEATURE                 Location/Qualifiers
source                  1..353
                        mol_type = protein
                        organism = Homo sapiens
SEQUENCE: 164
ASPTSPKVFP LSLCSTQPDG NVVIACLVQG FFPQEPLSVT WSESGQGVTA RNFPPSQDAS    60
GDLYTTSSQL TLPATQCLAG KSVTCHVKHY TNPSQDVTVP CPVPSTPPTP SPSTPPTPSP   120
SCCHPRLSLH RPALEDLLLG SEANLTCTLT GLRDASGVTF TWTPSSGKSA VQGPPERDLC   180
GCYSVSSVLP GCAEPWNHGK TFTCTAAYPE SKTPLTATLS KSGNTFRPEV HLLPPPSEEL   240
ALNELVTLTC LARGFSPKDV LVRWLQGSQE LPREKYLTWA SRQEPSQGTT TFAVTSILRV   300
AAEDWKKGDT FSCMVGHEAL PLAFTQKTID RLAGKPTHVN VSVVMAEVDG TCY          353

SEQ ID NO: 165          moltype = AA  length = 222
FEATURE                 Location/Qualifiers
source                  1..222
                        mol_type = protein
                        organism = Homo sapiens
SEQUENCE: 165
ADPCDSNPRG VSAYLSRPSP FDLFIRKSPT ITCLVVDLAP SKGTVNLTWS RASGKPVNHS    60
TRKEEKQRNG TLTVTSTLPV GTRDWIEGET YQCRVTHPHL PRALMRSTTK TSGPRAAPEV   120
YAFATPEWPG SRDKRTLACL IQNFMPEDIS VQWLHNEVQL PDARHSTTQP RKTKGSGFFV   180
FSRLEVTRAE WEQKDEFICR AVHEAASPSQ TVQRAVSVNP GK                      222

SEQ ID NO: 166          moltype = AA  length = 327
FEATURE                 Location/Qualifiers
source                  1..327
                        mol_type = protein
                        organism = Homo sapiens
SEQUENCE: 166
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 167          moltype = AA  length = 227
FEATURE                 Location/Qualifiers
source                  1..227
                        mol_type = protein
                        organism = Homo sapiens
SEQUENCE: 167
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 168          moltype = AA  length = 227
FEATURE                 Location/Qualifiers
source                  1..227
                        mol_type = protein
                        organism = Homo sapiens
SEQUENCE: 168
DKTHTCPPCP APEFEGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA SIEKTISKAK   120
GQPREPQVYT LPPSREEMTK NQVSLTCLVK GFYPSDIAVE WESNGQPENN YKTTPPVLDS   180
```

```
DGSFFLYSKL TVDKSRWQQG NVFSCSVMHE ALHNHYTQKS LSLSPGK                  227

SEQ ID NO: 169            moltype = AA  length = 227
FEATURE                   Location/Qualifiers
source                    1..227
                          mol_type = protein
                          organism = Homo sapiens
SEQUENCE: 169
DKTHTCPPCP APELLGGPSV FLFPPKPKDT LMISRTPEVT CVVVDVSHED PEVKFNWYVD    60
GVEVHNAKTK PREEQYASTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 170            moltype = AA  length = 227
FEATURE                   Location/Qualifiers
source                    1..227
                          mol_type = protein
                          organism = Homo sapiens
SEQUENCE: 170
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 171            moltype = AA  length = 189
FEATURE                   Location/Qualifiers
source                    1..189
                          mol_type = protein
                          organism = synthetic construct
SEQUENCE: 171
IKCEHVIIQA EFYLNPDQSG EFMFDFDGDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                           189

SEQ ID NO: 172            moltype = AA  length = 189
FEATURE                   Location/Qualifiers
source                    1..189
                          mol_type = protein
                          organism = synthetic construct
SEQUENCE: 172
IKECHVIIQA EFYLNPDQSG EFMFDFDGDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                           189

SEQ ID NO: 173            moltype = AA  length = 189
FEATURE                   Location/Qualifiers
source                    1..189
                          mol_type = protein
                          organism = synthetic construct
SEQUENCE: 173
IKEEHVIIQA ECYLNPDQSG EFMFDFDGDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                           189

SEQ ID NO: 174            moltype = AA  length = 189
FEATURE                   Location/Qualifiers
source                    1..189
                          mol_type = protein
                          organism = synthetic construct
SEQUENCE: 174
IKEEHVIIQA EFYLNPDQSG EFMFDFDCDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                           189

SEQ ID NO: 175            moltype = AA  length = 189
FEATURE                   Location/Qualifiers
source                    1..189
                          mol_type = protein
                          organism = synthetic construct
SEQUENCE: 175
IKEEHVIIQA EFYLNPDQSG EFMFDFDGDE IFHVDMAKKE TVWRLEEFGR FASFEAQGAL    60
ANIAVDKANL EIMTKRSNYC PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                           189
```

```
SEQ ID NO: 176          moltype = AA  length = 189
FEATURE                 Location/Qualifiers
source                  1..189
                        mol_type = protein
                        organism = synthetic construct
SEQUENCE: 176
IKEEHVIIQA EFYLNPDQSG EFMFDFDGDE IFHVDMAKKE TVWRLEEFGR FASFEAQGAL    60
ANIAVDKANL EIMTKRSNYT PITNVPPEVT VLCNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                          189

SEQ ID NO: 177          moltype = AA  length = 189
FEATURE                 Location/Qualifiers
source                  1..189
                        mol_type = protein
                        organism = synthetic construct
SEQUENCE: 177
IKEEHVIIQA EFYLNPDQSG EFMFDFDGDE IFHVDMAKKE TVWRLEEFGR FASFEAQGAL    60
ANIAVDKANL EIMTKRSNYT PITNVPPEVT VLTCSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                          189

SEQ ID NO: 178          moltype = AA  length = 189
FEATURE                 Location/Qualifiers
source                  1..189
                        mol_type = protein
                        organism = synthetic construct
SEQUENCE: 178
IKEEHVIIQA EFYLNPDQSG EFMFDFDGDE IFHVDMAKKE TVWRLEEFGR FASFEAQGAL    60
ANIAVDKANL EIMTKRSNYT PITNVPPEVT VLTNCPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPET                                                          189

SEQ ID NO: 179          moltype = AA  length = 199
FEATURE                 Location/Qualifiers
source                  1..199
                        mol_type = protein
                        organism = synthetic construct
SEQUENCE: 179
GDTRPRCLEQ VKHECHFFNG TERVRFLDRY FYHQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPASIEVR WFRNGQEEKT GVVSTGLIQN GDWTFQTLVM LETVPRSGEV YTCQVEHPSL   180
TSPLTVEWRA RSESAQSKM                                               199

SEQ ID NO: 180          moltype = AA  length = 199
FEATURE                 Location/Qualifiers
source                  1..199
                        mol_type = protein
                        organism = synthetic construct
SEQUENCE: 180
GDTRPRFLEC VKHECHFFNG TERVRFLDRY FYHQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPASIEVR WFRNGQEEKT GVVSTGLIQN GDWTFQTLVM LETVPRSGEV YTCQVEHPSL   180
TSPLTVEWRA RSESAQSKM                                               199

SEQ ID NO: 181          moltype = AA  length = 199
FEATURE                 Location/Qualifiers
source                  1..199
                        mol_type = protein
                        organism = synthetic construct
SEQUENCE: 181
GDTRPRFLEQ VKHECHFFCG TERVRFLDRY FYHQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPASIEVR WFRNGQEEKT GVVSTGLIQN GDWTFQTLVM LETVPRSGEV YTCQVEHPSL   180
TSPLTVEWRA RSESAQSKM                                               199

SEQ ID NO: 182          moltype = AA  length = 199
FEATURE                 Location/Qualifiers
source                  1..199
                        mol_type = protein
                        organism = synthetic construct
SEQUENCE: 182
GDTRPRFLEQ VKHECHFFNC TERVRFLDRY FYHQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPASIEVR WFRNGQEEKT GVVSTGLIQN GDWTFQTLVM LETVPRSGEV YTCQVEHPSL   180
TSPLTVEWRA RSESAQSKM                                               199

SEQ ID NO: 183          moltype = AA  length = 199
FEATURE                 Location/Qualifiers
```

```
                                     -continued
source              1..199
                    mol_type = protein
                    organism = synthetic construct
SEQUENCE: 183
GDTRPRFLEQ VKHECHFFNG TERVRFLDRY FYCQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPASIEVR WFRNGQEEKT GVVSTGLIQN GDWTFQTLVM LETVPRSGEV YTCQVEHPSL   180
TSPLTVEWRA RSESAQSKM                                                199

SEQ ID NO: 184      moltype = AA   length = 199
FEATURE             Location/Qualifiers
source              1..199
                    mol_type = protein
                    organism = synthetic construct
SEQUENCE: 184
GDTRPRFLEQ VKHECHFFNG TERVRFLDRY FYHQEEYVRF DSDVGEYRAV TELGRPDAEY    60
WNSQKDLLEQ KRAAVDTYCR HNYGVGESFT VQRRVYPEVT VYPAKTQPLQ HHNLLVCSVN   120
GFYPASIEVR WFRNGQEEKT GVVSTGLIQN GCWTFQTLVM LETVPRSGEV YTCQVEHPSL   180
TSPLTVEWRA RSESAQSKM                                                199

SEQ ID NO: 185      moltype = AA   length = 229
FEATURE             Location/Qualifiers
source              1..229
                    mol_type = protein
                    organism = synthetic construct
SEQUENCE: 185
SLQPLALEGS LQSRGGGCGS GGGGSGGGGS GDTRPRFLEQ VKHECHFFNG TERVRFLDRY    60
FYHQEEYVRF DSDVGEYRAV TELGRPDAEY WNSQKDLLEQ KRAAVDTYCR HNYGVGESFT   120
VQRRVYPEVT VYPAKTQPLQ HHNLLVCSVN GFYPASIEVR WFRNGQEEKT GVVSTGLIQN   180
GDWTFQTLVM LETVPRSGEV YTCQVEHPSL TSPLTVEWRA RSESAQSKM               229

SEQ ID NO: 186      moltype = AA   length = 663
FEATURE             Location/Qualifiers
source              1..663
                    mol_type = protein
                    organism = synthetic construct
SEQUENCE: 186
FTVTVPKDLY VVEYGSNMTI ECKFPVEKQL DLAALIVYWE MEDKNIIQFV HGEEDLKVQH    60
SSYRQRARLL KDQLSLGNAA LQITDVKLQD AGVYRCMISY GGADYKRITV KVNAPYNKIN   120
QRILVVDPVT SEHELTCQAE GYPKAEVIWT SSDHQVLSGK TTTTNSKREE KLFNVTSTLR   180
INTTTNEIFY CTFRRLDPEE NHTAELVIPE LPLAHPPNER GGGGSGGGGS GGGGSGGGGS   240
IKEEHVIIQA EFYLNPDQSG EFMFDFDGDE IFHVDMAKKE TVWRLEEFGR FASFEAQGAL   300
ANIAVDKANL EIMTCRSNYT PITNVPPEVT VLTNSPVELR EPNVLICFID KFTPPVVNVT   360
WLRNGKPVTT GVSETVFLPR EDHLFRKFHY LPFLPSTEDV YDCRVEHWGL DEPLLKHWEF   420
DAPSPLPETG GSAAAGGDKT HTCPPCPAPE AAGGPSVFLF PPKPKDTLMI SRTPEVTCVV   480
VDVSHEDPEV KFNWYVDGVE VHNAKTKPRE EQYNSTYRVV SVLTVLHQDW LNGKEYKCKV   540
SNKALPAPIE KTISKAKGQP REPQVYTLPP SREEMTKNQV SLTCLVKGFY PSDIAVEWES   600
NGQPENNYKT TPPVLDSDGS FFLYSKLTVD KSRWQQGNVF SCSVMHEALH NHYTQKSLSL   660
SPG                                                                 663

SEQ ID NO: 187      moltype = AA   length = 229
FEATURE             Location/Qualifiers
source              1..229
                    mol_type = protein
                    organism = synthetic construct
SEQUENCE: 187
SLQPLALEGS LQSRGGGGGS GGGGSGGGGS GDTRPRFLEQ VKHECHFFNG TERVRFLDRY    60
FYHQEEYVRF DSDVGEYRAV TELGRPDAEY WNSQKDLLEQ KRAAVDTYCR HNYGVGESFT   120
VQRRVYPEVT VYPAKTQPLQ HHNLLVCSVN GFYPASIEVR WFRNGQEEKT GVVSTGLIQN   180
GDWTFQTLVM LETVPRSGEV YTCQVEHPSL TSPLTVEWRA RSESAQSKM               229

SEQ ID NO: 188      moltype = AA   length = 663
FEATURE             Location/Qualifiers
source              1..663
                    mol_type = protein
                    organism = synthetic construct
SEQUENCE: 188
IKEEHVIIQA EFYLNPDQSG EFMFDFDGDE IFHVDMAKKE TVWRLEEFGR FASFEAQGAL    60
ANIAVDKANL EIMTCRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPETG GSAAAGGDKT HTCPPCPAPE AAGGPSVFLF PPKPKDTLMI SRTPEVTCVV   240
VDVSHEDPEV KFNWYVDGVE VHNAKTKPRE EQYNSTYRVV SVLTVLHQDW LNGKEYKCKV   300
SNKALPAPIE KTISKAKGQP REPQVYTLPP SREEMTKNQV SLTCLVKGFY PSDIAVEWES   360
NGQPENNYKT TPPVLDSDGS FFLYSKLTVD KSRWQQGNVF SCSVMHEALH NHYTQKSLSL   420
SPGGGGGSGG GGSGGGGSGG GGSFTVTVPK DLYVVEYGSN MTIECKFPVE KQLDLAALIV   480
YWEMEDKNII QFVHGEEDLK VQHSSYRQRA RLLKDQLSLG NAALQITDVK LQDAGVYRCM   540
ISYGGADYKR ITVKVNAPYN KINQRILVVD PVTSEHELTC QAEGYPKAEV IWTSSDHQVL   600
SGKTTTTNSK REEKLFNVTS TLRINTTTNE IFYCTFRRLD PEENHTAELV IPELPLAHPP   660
NER                                                                 663
```

```
SEQ ID NO: 189            moltype = AA   length = 227
FEATURE                   Location/Qualifiers
source                    1..227
                          mol_type = protein
                          organism = synthetic construct
SEQUENCE: 189
NFFRMVISNP AATGGGGSGG GGSGGGGSGD TRPRFLEQVK HECHFFNGTE RVRFLDRYFY   60
HQEEYVRFDS DVGEYRAVTE LGRPDAEYWN SQKDLLEQAA AAVDTYCRHN YGVGESFTVQ  120
RRVYPEVTVY PAKTQPLQHH NLLVCSVNGF YPASIEVRWF RNGQEEKTGV VSTGLIQNGD  180
WTFQTLVMLE TVPRSGEVYT CQVEHPSLTS PLTVEWRARS ESAQSKM                227

SEQ ID NO: 190            moltype = AA   length = 663
FEATURE                   Location/Qualifiers
source                    1..663
                          mol_type = protein
                          organism = synthetic construct
SEQUENCE: 190
FTVTVPKDLY VVEYGSNMTI ECKFPVEKQL DLAALIVYWE MEDKNIIQFV HGEEDLKVQH   60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPE LPLAHPPNER GGGGSGGGGS GGGGSGGGGS  240
IKEEHVIIQA EFYLNPDQSG EFMFDFDGDE IFHVDMAKKE TVWRLEEFGR FASFEAQGAL  300
ANIAVDKANL EIMTKRSNYT PITNVPPEVT VLTNSPVELR EPNVLICFID KFTPPVVNVT  360
WLRNGKPVTT GVSETVFLPR EDHLFRKFHY LPFLPSTEDV YDCRVEHWGL DEPLLKHWEF  420
DAPSPLPETG GSAAAGGDKT HTCPPCPAPE AAGGPSVFLF PPKPKDTLMI SRTPEVTCVV  480
VDVSHEDPEV KFNWYVDGVE VHNAKTKPRE EQYNSTYRVV SVLTVLHQDW LNGKEYKCKV  540
SNKALPAPIE KTISKAKGQP REPQVYTLPP SREEMTKNQV SLTCLVKGFY PSDIAVEWES  600
NGQPENNYKT TPPVLDSDGS FFLYSKLTVD KSRWQQGNVF SCSVMHEALH NHYTQKSLSL  660
SPG                                                                 663

SEQ ID NO: 191            moltype = AA   length = 227
FEATURE                   Location/Qualifiers
source                    1..227
                          mol_type = protein
                          organism = synthetic construct
SEQUENCE: 191
NFIRMVISNP AATGGGGSGG GGSGGGGSGD TRPRFLEQVK HECHFFNGTE RVRFLDRYFY   60
HQEEYVRFDS DVGEYRAVTE LGRPDAEYWN SQKDLLEQKR AAVDTYCRHN YGVGESFTVQ  120
RRVYPEVTVY PAKTQPLQHH NLLVCSVNGF YPASIEVRWF RNGQEEKTGV VSTGLIQNGD  180
WTFQTLVMLE TVPRSGEVYT CQVEHPSLTS PLTVEWRARS ESAQSKM                227

SEQ ID NO: 192            moltype = AA   length = 423
FEATURE                   Location/Qualifiers
source                    1..423
                          mol_type = protein
                          organism = synthetic construct
SEQUENCE: 192
IKEEHVIIQA EFYLNPDQSG EFMFDFDGDE IFHVDMAKKE TVWRLEEFGR FASFEAQGAL   60
ANIAVDKANL EIMTKRSNYT CITNVPPEVT VLTNSPVELR EPNVLICFID KFTPPVVNVT  120
WLRNGKPVTT GVSETVFLPR EDHLFRKFHY LPFLPSTEDV YDCRVEHWGL DEPLLKHWEF  180
DAPSPLPETG GSAAAGGDKT HTCPPCPAPE AAGGPSVFLF PPKPKDTLMI SRTPEVTCVV  240
VDVSHEDPEV KFNWYVDGVE VHNAKTKPRE EQYNSTYRVV SVLTVLHQDW LNGKEYKCKV  300
SNKALPAPIE KTISKAKGQP REPQVYTLPP SREEMTKNQV SLTCLVKGFY PSDIAVEWES  360
NGQPENNYKT TPPVLDSDGS FFLYSKLTVD KSRWQQGNVF SCSVMHEALH NHYTQKSLSL  420
SPG                                                                 423

SEQ ID NO: 193            moltype = AA   length = 7
FEATURE                   Location/Qualifiers
source                    1..7
                          mol_type = protein
                          organism = synthetic construct
SEQUENCE: 193
GGSAAGG                                                               7

SEQ ID NO: 194            moltype = AA   length = 232
FEATURE                   Location/Qualifiers
source                    1..232
                          mol_type = protein
                          organism = synthetic construct
SEQUENCE: 194
GSLQPLALEG SLQSRGIVGG GGSGGGGSGG GGSGDTRPRC LEQVKHECHF FNGTERVRFL   60
DRYFYHQEEY VRFDSDVGEY RAVTELGRPD AEYWNSQKDL LEQKRAAVDT YCRHNYGVGE  120
SFTVQRRVYP EVTVYPAKTQ PLQHHNLLVC SVNGFYPASI EVRWFRNGQE EKTGVVSTGL  180
IQNGDWTFQT LVMLETVPRS GEVYTCQVEH PSLTSPLTVE WRARSESAQS KM          232

SEQ ID NO: 195            moltype = AA   length = 232
FEATURE                   Location/Qualifiers
source                    1..232
```

```
                        mol_type = protein
                        organism = synthetic construct
SEQUENCE: 195
GSLQPLALEG SLQSRGIVGG GGSGGGGSGG GGSGDTRCRF LEQVKHECHF FNGTERVRFL   60
DRYFYHQEEY VRFDSDVGEY RAVTELGRPD AEYWNSQKDL LEQKRAAVDT YCRHNYGVGE  120
SFTVQRRVYP EVTVYPAKTQ PLQHHNLLVC SVNGFYPASI EVRWFRNGQE EKTGVVSTGL  180
IQNGDWTFQT LVMLETVPRS GEVYTCQVEH PSLTSPLTVE WRARSESAQS KM          232

SEQ ID NO: 196          moltype = AA  length = 232
FEATURE                 Location/Qualifiers
source                  1..232
                        mol_type = protein
                        organism = synthetic construct
SEQUENCE: 196
GSLQPLALEG SLQSRGIVGG GGSGGGGSGG GGSGDTRPRF LEQVKHECHF FNGTERVRFL   60
DRYFYCQEEY VRFDSDVGEY RAVTELGRPD AEYWNSQKDL LEQKRAAVDT YCRHNYGVGE  120
SFTVQRRVYP EVTVYPAKTQ PLQHHNLLVC SVNGFYPASI EVRWFRNGQE EKTGVVSTGL  180
IQNGDWTFQT LVMLETVPRS GEVYTCQVEH PSLTSPLTVE WRARSESAQS KM          232

SEQ ID NO: 197          moltype = AA  length = 423
FEATURE                 Location/Qualifiers
source                  1..423
                        mol_type = protein
                        organism = synthetic construct
SEQUENCE: 197
IKECHVIIQA EFYLNPDQSG EFMFDFDGDE IFHVDMAKKE TVWRLEEFGR FASFEAQGAL   60
ANIAVDKANL EIMTKRSNYT PITNVPPEVT VLTNSPVELR EPNVLICFID KFTPPVVNVT  120
WLRNGKPVTT GVSETVFLPR EDHLFRKFHY LPFLPSTEDV YDCRVEHWGL DEPLLKHWEF  180
DAPSPLPETG GSAAAGGDKT HTCPPCPAPE AAGGPSVFLF PPKPKDTLMI SRTPEVTCVV  240
VDVSHEDPEV KFNWYVDGVE VHNAKTKPRE EQYNSTYRVV SVLTVLHQDW LNGKEYKCKV  300
SNKALPAPIE KTISKAKGQP REPQVYTLPP SREEMTKNQV SLTCLVKGFY PSDIAVEWES  360
NGQPENNYKT TPPVLDSDGS FFLYSKLTVD KSRWQQGNVF SCSVMHEALH NHYTQKSLSL  420
SPG                                                                423

SEQ ID NO: 198          moltype = AA  length = 232
FEATURE                 Location/Qualifiers
source                  1..232
                        mol_type = protein
                        organism = synthetic construct
SEQUENCE: 198
GSLQPLALEG SLQSRGIVGG GGSGGGGSGG GGSGDTRPRF LEQVKHECHF FCGTERVRFL   60
DRYFYHQEEY VRFDSDVGEY RAVTELGRPD AEYWNSQKDL LEQKRAAVDT YCRHNYGVGE  120
SFTVQRRVYP EVTVYPAKTQ PLQHHNLLVC SVNGFYPASI EVRWFRNGQE EKTGVVSTGL  180
IQNGDWTFQT LVMLETVPRS GEVYTCQVEH PSLTSPLTVE WRARSESAQS KM          232

SEQ ID NO: 199          moltype = AA  length = 232
FEATURE                 Location/Qualifiers
source                  1..232
                        mol_type = protein
                        organism = synthetic construct
SEQUENCE: 199
GSLQPLALEG SLQSRGIVGG GGSGGGGSGG GGSGDTRPRF LEQVKHECHF FNCTERVRFL   60
DRYFYHQEEY VRFDSDVGEY RAVTELGRPD AEYWNSQKDL LEQKRAAVDT YCRHNYGVGE  120
SFTVQRRVYP EVTVYPAKTQ PLQHHNLLVC SVNGFYPASI EVRWFRNGQE EKTGVVSTGL  180
IQNGDWTFQT LVMLETVPRS GEVYTCQVEH PSLTSPLTVE WRARSESAQS KM          232

SEQ ID NO: 200          moltype = AA  length = 423
FEATURE                 Location/Qualifiers
source                  1..423
                        mol_type = protein
                        organism = synthetic construct
SEQUENCE: 200
IKEEHVIIQA EFYLNPDQSG EFMFDFDGDE IFHVDMAKKE TVWRLEEFGR FASFEAQGAL   60
ANIAVDKANL EIMTKRSNYT PITNVPPEVT VLCNSPVELR EPNVLICFID KFTPPVVNVT  120
WLRNGKPVTT GVSETVFLPR EDHLFRKFHY LPFLPSTEDV YDCRVEHWGL DEPLLKHWEF  180
DAPSPLPETG GSAAAGGDKT HTCPPCPAPE AAGGPSVFLF PPKPKDTLMI SRTPEVTCVV  240
VDVSHEDPEV KFNWYVDGVE VHNAKTKPRE EQYNSTYRVV SVLTVLHQDW LNGKEYKCKV  300
SNKALPAPIE KTISKAKGQP REPQVYTLPP SREEMTKNQV SLTCLVKGFY PSDIAVEWES  360
NGQPENNYKT TPPVLDSDGS FFLYSKLTVD KSRWQQGNVF SCSVMHEALH NHYTQKSLSL  420
SPG                                                                423

SEQ ID NO: 201          moltype = AA  length = 232
FEATURE                 Location/Qualifiers
source                  1..232
                        mol_type = protein
                        organism = synthetic construct
SEQUENCE: 201
GSLQPLALEG SLQSRGIVGG GGSGGGGSGG GGSGDTRPRF LEQVKHECHF FNGTERVRFL   60
DRYFYHQEEY VRFDSDVGEY RAVTELGRPD AEYWNSQKDL LEQKRAAVDT YCRHNYGVGE  120
```

```
SFTVQRRVYP EVTVYPAKTQ PLQHNLLVC SVNGFYPASI EVRWFRNGQE EKTGVVSTGL    180
IQNGDWTFCT LVMLETVPRS GEVYTCQVEH PSLTSPLTVE WRARSESAQS KM          232

SEQ ID NO: 202          moltype = AA   length = 232
FEATURE                 Location/Qualifiers
source                  1..232
                        mol_type = protein
                        organism = synthetic construct
SEQUENCE: 202
GSLQPLALEG SLQSRGIVGG GGSGGGGSGG GGSGDTRPRF LEQVKHECHF FNGTERVRFL    60
DRYFYHQEEY VRFDSDVGEY RAVTELGRPD AEYWNSQKDL LEQKRAAVDT YCRHNYGVGE   120
SFTVQRRVYP EVTVYPAKTQ PLQHNLLVC SVNGFYPASI EVRWFRNGQE EKTGVVSTGL   180
IQNGDCTFQT LVMLETVPRS GEVYTCQVEH PSLTSPLTVE WRARSESAQS KM          232

SEQ ID NO: 203          moltype = AA   length = 423
FEATURE                 Location/Qualifiers
source                  1..423
                        mol_type = protein
                        organism = synthetic construct
SEQUENCE: 203
IKEEHVIIQA ECYLNPDQSG EFMFDFDGDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPETG GSAAAGGDKT HTCPPCPAPE AAGGPSVFLF PPKPKDTLMI SRTPEVTCVV   240
VDVSHEDPEV KFNWYVDGVE VHNAKTKPRE EQYNSTYRVV SVLTVLHQDW LNGKEYKCKV   300
SNKALPAPIE KTISKAKGQP REPQVYTLPP SREEMTKNQV SLTCLVKGFY PSDIAVEWES   360
NGQPENNYKT TPPVLDSDGS FFLYSKLTVD KSRWQQGNVF SCSVMHEALH NHYTQKSLSL   420
SPG                                                                423

SEQ ID NO: 204          moltype = AA   length = 232
FEATURE                 Location/Qualifiers
source                  1..232
                        mol_type = protein
                        organism = synthetic construct
SEQUENCE: 204
GSLQPLALEG SLQSRGIVGG GGSGGGGSGG GGSGDTRPRF LECVKHECHF FNGTERVRFL    60
DRYFYHQEEY VRFDSDVGEY RAVTELGRPD AEYWNSQKDL LEQKRAAVDT YCRHNYGVGE   120
SFTVQRRVYP EVTVYPAKTQ PLQHNLLVC SVNGFYPASI EVRWFRNGQE EKTGVVSTGL   180
IQNGDWTFQT LVMLETVPRS GEVYTCQVEH PSLTSPLTVE WRARSESAQS KM          232

SEQ ID NO: 205          moltype = AA   length = 423
FEATURE                 Location/Qualifiers
source                  1..423
                        mol_type = protein
                        organism = synthetic construct
SEQUENCE: 205
IKEEHVIIQA EFYLNPDQSG EFMFDFDGDE IFHVDMAKKE TVWRLEEFGR FASFEAQGAL    60
ANIAVDKANL EIMTKRSNYC PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPETG GSAAAGGDKT HTCPPCPAPE AAGGPSVFLF PPKPKDTLMI SRTPEVTCVV   240
VDVSHEDPEV KFNWYVDGVE VHNAKTKPRE EQYNSTYRVV SVLTVLHQDW LNGKEYKCKV   300
SNKALPAPIE KTISKAKGQP REPQVYTLPP SREEMTKNQV SLTCLVKGFY PSDIAVEWES   360
NGQPENNYKT TPPVLDSDGS FFLYSKLTVD KSRWQQGNVF SCSVMHEALH NHYTQKSLSL   420
SPG                                                                423

SEQ ID NO: 206          moltype = AA   length = 423
FEATURE                 Location/Qualifiers
source                  1..423
                        mol_type = protein
                        organism = synthetic construct
SEQUENCE: 206
IKEEHVIIQA EFYLNPDQSG EFMFDFDGDE IFHVDMAKKE TVWRLEEFGR FASFEAQGAL    60
ANIAVDKANL EIMTKRSNYT PCTNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPETG GSAAAGGDKT HTCPPCPAPE AAGGPSVFLF PPKPKDTLMI SRTPEVTCVV   240
VDVSHEDPEV KFNWYVDGVE VHNAKTKPRE EQYNSTYRVV SVLTVLHQDW LNGKEYKCKV   300
SNKALPAPIE KTISKAKGQP REPQVYTLPP SREEMTKNQV SLTCLVKGFY PSDIAVEWES   360
NGQPENNYKT TPPVLDSDGS FFLYSKLTVD KSRWQQGNVF SCSVMHEALH NHYTQKSLSL   420
SPG                                                                423

SEQ ID NO: 207          moltype = AA   length = 423
FEATURE                 Location/Qualifiers
source                  1..423
                        mol_type = protein
                        organism = synthetic construct
SEQUENCE: 207
IKEEHVIIQA EFYLNPDQSG EFMFDFDCDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
```

```
DAPSPLPETG GSAAAGGDKT HTCPPCPAPE AAGGPSVFLF PPKPKDTLMI SRTPEVTCVV    240
VDVSHEDPEV KFNWYVDGVE VHNAKTKPRE EQYNSTYRVV SVLTVLHQDW LNGKEYKCKV    300
SNKALPAPIE KTISKAKGQP REPQVYTLPP SREEMTKNQV SLTCLVKGFY PSDIAVEWES    360
NGQPENNYKT TPPVLDSDGS FFLYSKLTVD KSRWQQGNVF SCSVMHEALH NHYTQKSLSL    420
SPG                                                                 423

SEQ ID NO: 208              moltype = AA   length = 232
FEATURE                     Location/Qualifiers
source                      1..232
                            mol_type = protein
                            organism = synthetic construct
SEQUENCE: 208
GSLQPLALEG SLQSRGIVGG GGSGGGGSGG GGSGDTRPRF LEQVKHECHF FNGTERVRFL     60
DRYFYHQEEY VRFDSDVGEY RAVTELGRPD AEYWNSQKDL LEQKRAAVDT YCRHNYGVGE    120
SFTVQRRVYP EVTVYPAKTQ PLQHHNLLVC SVNGFYPASI EVRWFRNGQE EKTGVVSTGL    180
IQNCDWTFQT LVMLETVPRS GEVYTCQVEH PSLTSPLTVE WRARSESAQS KM            232

SEQ ID NO: 209              moltype = AA   length = 232
FEATURE                     Location/Qualifiers
source                      1..232
                            mol_type = protein
                            organism = synthetic construct
SEQUENCE: 209
GSLQPLALEG SLQSRGIVGG GGSGGGGSGG GGSGDTRPRF LEQVKHECHF FNGTERVRFL     60
DRYFYHQEEY VRFDSDVGEY RAVTELGRPD AEYWNSQKDL LEQKRAAVDT YCRHNYGVGE    120
SFTVQRRVYP EVTVYPAKTQ PLQHHNLLVC SVNGFYPASI EVRWFRNGQE EKTGVVSTGL    180
IQNGCWTFQT LVMLETVPRS GEVYTCQVEH PSLTSPLTVE WRARSESAQS KM            232

SEQ ID NO: 210              moltype = AA   length = 423
FEATURE                     Location/Qualifiers
source                      1..423
                            mol_type = protein
                            organism = synthetic construct
SEQUENCE: 210
IKEEHVIIQA EFYLNPDQSG EFMFDFDGDE IPHVDMAKKE TVWRLEEFGR FASFEAQGAL     60
ANIAVDKANL EIMTKRSNYT PITNVPPEVT VLTNSPVELR EPNVLICFID KFTPPVVNVT    120
WLRNGKPVTT GVSETVFLPR EDHLFRKFHY LPFLPSTEDV YDCRVEHWGL DEPLLKHWEF    180
DAPSPLPETG GSAAAGGDKT HTCPPCPAPE AAGGPSVFLF PPKPKDTLMI SRTPEVTCVV    240
VDVSHEDPEV KFNWYVDGVE VHNAKTKPRE EQYNSTYRVV SVLTVLHQDW LNGKEYKCKV    300
SNKALPAPIE KTISKAKGQP REPQVYTLPP SREEMTKNQV SLTCLVKGFY PSDIAVEWES    360
NGQPENNYKT TPPVLDSDGS FFLYSKLTVD KSRWQQGNVF SCSVMHEALH NHYTQKSLSL    420
SPG                                                                 423

SEQ ID NO: 211              moltype = AA   length = 232
FEATURE                     Location/Qualifiers
source                      1..232
                            mol_type = protein
                            organism = synthetic construct
SEQUENCE: 211
GSLQPLALEG SLQSRGIVGG GGSGGGGSGG GGSGDTRPRF LEQVKHECHF FNGTERVRFL     60
DRYFYHQEEY VRFDSDVGEY RAVTELGRPD AEYWNSQKDL LEQKRAAVDT YCRHNYGVGE    120
SFTVQRRVYP EVTVYPAKTQ PLQHHNLLVC SVNGFYPASI EVRWFRNGQE EKTGVVSTGL    180
IQNGDWTFQT LVMLETVPRS GEVYTCQVEH PSLTSPLTVE WRARSESAQS KM            232

SEQ ID NO: 212              moltype = AA   length = 423
FEATURE                     Location/Qualifiers
source                      1..423
                            mol_type = protein
                            organism = synthetic construct
SEQUENCE: 212
IKEEHVIIQA EFYLNPDQSG EFMFDFDGCE IPHVDMAKKE TVWRLEEFGR FASFEAQGAL     60
ANIAVDKANL EIMTKRSNYT PITNVPPEVT VLTNSPVELR EPNVLICFID KFTPPVVNVT    120
WLRNGKPVTT GVSETVFLPR EDHLFRKFHY LPFLPSTEDV YDCRVEHWGL DEPLLKHWEF    180
DAPSPLPETG GSAAAGGDKT HTCPPCPAPE AAGGPSVFLF PPKPKDTLMI SRTPEVTCVV    240
VDVSHEDPEV KFNWYVDGVE VHNAKTKPRE EQYNSTYRVV SVLTVLHQDW LNGKEYKCKV    300
SNKALPAPIE KTISKAKGQP REPQVYTLPP SREEMTKNQV SLTCLVKGFY PSDIAVEWES    360
NGQPENNYKT TPPVLDSDGS FFLYSKLTVD KSRWQQGNVF SCSVMHEALH NHYTQKSLSL    420
SPG                                                                 423

SEQ ID NO: 213              moltype = AA   length = 423
FEATURE                     Location/Qualifiers
source                      1..423
                            mol_type = protein
                            organism = synthetic construct
SEQUENCE: 213
IKEEHVIIQA EFYLNPDQSG EFMFDFDGDE IPHVDMAKKE TVWRLEEFGR FASFEAQGAL     60
ANIAVDKANL EIMTKRSNYT PITNVPPEVT VLTCSPVELR EPNVLICFID KFTPPVVNVT    120
WLRNGKPVTT GVSETVFLPR EDHLFRKFHY LPFLPSTEDV YDCRVEHWGL DEPLLKHWEF    180
DAPSPLPETG GSAAAGGDKT HTCPPCPAPE AAGGPSVFLF PPKPKDTLMI SRTPEVTCVV    240
```

```
VDVSHEDPEV KFNWYVDGVE VHNAKTKPRE EQYNSTYRVV SVLTVLHQDW LNGKEYKCKV    300
SNKALPAPIE KTISKAKGQP REPQVYTLPP SREEMTKNQV SLTCLVKGFY PSDIAVEWES    360
NGQPENNYKT TPPVLDSDGS FFLYSKLTVD KSRWQQGNVF SCSVMHEALH NHYTQKSLSL    420
SPG                                                                 423

SEQ ID NO: 214          moltype = AA   length = 232
FEATURE                 Location/Qualifiers
source                  1..232
                        mol_type = protein
                        organism = synthetic construct
SEQUENCE: 214
GSLQPLALEG SLQSRGIVGG GGSGGGGSGG GGSGDTRPRF LEQVKHECHF FNGTERVRFL    60
DRYFYHQEEY VRFDSDVGEY RAVTELGRPD AEYWNSQKDL LEQKRAAVDT YCRHNYGVGE    120
SFTVQRRVYP EVTVYPAKTQ PLQHHNLLVC SVCGFYPASI EVRWFRNGQE EKTGVVSTGL    180
IQNGDWTFQT LVMLETVPRS GEVYTCQVEH PSLTSPLTVE WRARSESAQS KM            232

SEQ ID NO: 215          moltype = AA   length = 423
FEATURE                 Location/Qualifiers
source                  1..423
                        mol_type = protein
                        organism = synthetic construct
SEQUENCE: 215
IKEEHVIIQA EFYLNPDQSG EFMFDFDGDE IFHVDMAKKE TVWRLEEFGR FASFEAQGAL    60
ANIAVDKANL EIMTKRSNYT PITNVPPEVT VLTNCPVELR EPNVLICFID KFTPPVVNVT    120
WLRNGKPVTT GVSETVFLPR EDHLFRKFHY LPFLPSTEDV YDCRVEHWGL DEPLLKHWEF    180
DAPSPLPETG GSAAAGGDKT HTCPPCPAPE AAGGPSVFLF PPKPKDTLMI SRTPEVTCVV    240
VDVSHEDPEV KFNWYVDGVE VHNAKTKPRE EQYNSTYRVV SVLTVLHQDW LNGKEYKCKV    300
SNKALPAPIE KTISKAKGQP REPQVYTLPP SREEMTKNQV SLTCLVKGFY PSDIAVEWES    360
NGQPENNYKT TPPVLDSDGS FFLYSKLTVD KSRWQQGNVF SCSVMHEALH NHYTQKSLSL    420
SPG                                                                 423

SEQ ID NO: 216          moltype = AA   length = 423
FEATURE                 Location/Qualifiers
source                  1..423
                        mol_type = protein
                        organism = synthetic construct
SEQUENCE: 216
IKCEHVIIQA EFYLNPDQSG EFMFDFDGDE IFHVDMAKKE TVWRLEEFGR FASFEAQGAL    60
ANIAVDKANL EIMTKRSNYT PITNVPPEVT VLTNSPVELR EPNVLICFID KFTPPVVNVT    120
WLRNGKPVTT GVSETVFLPR EDHLFRKFHY LPFLPSTEDV YDCRVEHWGL DEPLLKHWEF    180
DAPSPLPETG GSAAAGGDKT HTCPPCPAPE AAGGPSVFLF PPKPKDTLMI SRTPEVTCVV    240
VDVSHEDPEV KFNWYVDGVE VHNAKTKPRE EQYNSTYRVV SVLTVLHQDW LNGKEYKCKV    300
SNKALPAPIE KTISKAKGQP REPQVYTLPP SREEMTKNQV SLTCLVKGFY PSDIAVEWES    360
NGQPENNYKT TPPVLDSDGS FFLYSKLTVD KSRWQQGNVF SCSVMHEALH NHYTQKSLSL    420
SPG                                                                 423

SEQ ID NO: 217          moltype = AA   length = 423
FEATURE                 Location/Qualifiers
source                  1..423
                        mol_type = protein
                        organism = synthetic construct
SEQUENCE: 217
IKEEHVIIQA EFYLNPDQSG EFMFDFDGDE IFHVDMAKKE TVWRLEEFGR FASFEAQGAL    60
ANIAVDKANL ECMTKRSNYT PITNVPPEVT VLTNSPVELR EPNVLICFID KFTPPVVNVT    120
WLRNGKPVTT GVSETVFLPR EDHLFRKFHY LPFLPSTEDV YDCRVEHWGL DEPLLKHWEF    180
DAPSPLPETG GSAAAGGDKT HTCPPCPAPE AAGGPSVFLF PPKPKDTLMI SRTPEVTCVV    240
VDVSHEDPEV KFNWYVDGVE VHNAKTKPRE EQYNSTYRVV SVLTVLHQDW LNGKEYKCKV    300
SNKALPAPIE KTISKAKGQP REPQVYTLPP SREEMTKNQV SLTCLVKGFY PSDIAVEWES    360
NGQPENNYKT TPPVLDSDGS FFLYSKLTVD KSRWQQGNVF SCSVMHEALH NHYTQKSLSL    420
SPG                                                                 423

SEQ ID NO: 218          moltype = AA   length = 423
FEATURE                 Location/Qualifiers
source                  1..423
                        mol_type = protein
                        organism = synthetic construct
SEQUENCE: 218
IKEEHVIIQA EFYLNPDQSG EFMFDFDGDE IFHVDMAKKE TVWRLEEFGR FASFEAQGAL    60
ANIAVDKANL EIMTCRSNYT PITNVPPEVT VLTNSPVELR EPNVLICFID KFTPPVVNVT    120
WLRNGKPVTT GVSETVFLPR EDHLFRKFHY LPFLPSTEDV YDCRVEHWGL DEPLLKHWEF    180
DAPSPLPETG GSAAAGGDKT HTCPPCPAPE AAGGPSVFLF PPKPKDTLMI SRTPEVTCVV    240
VDVSHEDPEV KFNWYVDGVE VHNAKTKPRE EQYNSTYRVV SVLTVLHQDW LNGKEYKCKV    300
SNKALPAPIE KTISKAKGQP REPQVYTLPP SREEMTKNQV SLTCLVKGFY PSDIAVEWES    360
NGQPENNYKT TPPVLDSDGS FFLYSKLTVD KSRWQQGNVF SCSVMHEALH NHYTQKSLSL    420
SPG                                                                 423

SEQ ID NO: 219          moltype = AA   length = 229
FEATURE                 Location/Qualifiers
source                  1..229
```

```
                        mol_type = protein
                        organism = synthetic construct
SEQUENCE: 219
SLQPLALEGS LQSRGCGGGS GGGGSGGGGS GDTRPRFLEQ VKHECHFFNG TERVRFLDRY    60
FYHQEEYVRF DSDVGEYRAV TELGRPDAEY WNSQKDLLEQ KRAAVDTYCR HNYGVGESFT   120
VQRRVYPEVT VYPAKTQPLQ HHNLLVCSVN GFYPASIEVR WFRNGQEEKT GVVSTGLIQN   180
GDWTFQTLVM LETVPRSGEV YTCQVEHPSL TSPLTVEWRA RSESAQSKM              229

SEQ ID NO: 220          moltype = AA  length = 15
FEATURE                 Location/Qualifiers
source                  1..15
                        mol_type = protein
                        organism = synthetic construct
SEQUENCE: 220
CGGGSGGGGS GGGGS                                                     15

SEQ ID NO: 221          moltype = AA  length = 229
FEATURE                 Location/Qualifiers
source                  1..229
                        mol_type = protein
                        organism = synthetic construct
SEQUENCE: 221
SLQPLALEGS LQSRGGCGGS GGGGSGGGGS GDTRPRFLEQ VKHECHFFNG TERVRFLDRY    60
FYHQEEYVRF DSDVGEYRAV TELGRPDAEY WNSQKDLLEQ KRAAVDTYCR HNYGVGESFT   120
VQRRVYPEVT VYPAKTQPLQ HHNLLVCSVN GFYPASIEVR WFRNGQEEKT GVVSTGLIQN   180
GDWTFQTLVM LETVPRSGEV YTCQVEHPSL TSPLTVEWRA RSESAQSKM              229

SEQ ID NO: 222          moltype = AA  length = 15
FEATURE                 Location/Qualifiers
source                  1..15
                        mol_type = protein
                        organism = synthetic construct
SEQUENCE: 222
GCGGSGGGGS GGGGS                                                     15

SEQ ID NO: 223          moltype = AA  length = 229
FEATURE                 Location/Qualifiers
source                  1..229
                        mol_type = protein
                        organism = synthetic construct
SEQUENCE: 223
SLQPLALEGS LQSRGGGGGC GGGGSGGGGS GDTRPRFLEQ VKHECHFFNG TERVRFLDRY    60
FYHQEEYVRF DSDVGEYRAV TELGRPDAEY WNSQKDLLEQ KRAAVDTYCR HNYGVGESFT   120
VQRRVYPEVT VYPAKTQPLQ HHNLLVCSVN GFYPASIEVR WFRNGQEEKT GVVSTGLIQN   180
GDWTFQTLVM LETVPRSGEV YTCQVEHPSL TSPLTVEWRA RSESAQSKM              229

SEQ ID NO: 224          moltype = AA  length = 15
FEATURE                 Location/Qualifiers
source                  1..15
                        mol_type = protein
                        organism = synthetic construct
SEQUENCE: 224
GGGGCGGGGS GGGGS                                                     15

SEQ ID NO: 225          moltype = AA  length = 229
FEATURE                 Location/Qualifiers
source                  1..229
                        mol_type = protein
                        organism = synthetic construct
SEQUENCE: 225
SLQPLALEGS LQSRGGGGCS GGGGSGGGGS GDTRPRFLEQ VKHECHFFNG TERVRFLDRY    60
FYHQEEYVRF DSDVGEYRAV TELGRPDAEY WNSQKDLLEQ KRAAVDTYCR HNYGVGESFT   120
VQRRVYPEVT VYPAKTQPLQ HHNLLVCSVN GFYPASIEVR WFRNGQEEKT GVVSTGLIQN   180
GDWTFQTLVM LETVPRSGEV YTCQVEHPSL TSPLTVEWRA RSESAQSKM              229

SEQ ID NO: 226          moltype = AA  length = 15
FEATURE                 Location/Qualifiers
source                  1..15
                        mol_type = protein
                        organism = synthetic construct
SEQUENCE: 226
GGGCSGGGGS GGGGS                                                     15

SEQ ID NO: 227          moltype = AA  length = 663
FEATURE                 Location/Qualifiers
source                  1..663
                        mol_type = protein
                        organism = synthetic construct
SEQUENCE: 227
```

```
IKEEHVIIQA EFYLNPDQSG EFMFDFDGDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPETG GSAAAGGDKT HTCPPCPAPE AAGGPSVFLF PPKPKDTLMI SRTPEVTCVV   240
VDVSHEDPEV KFNWYVDGVE VHNAKTKPRE EQYNSTYRVV SVLTVLHQDW LNGKEYKCKV   300
SNKALPAPIE KTISKAKGQP REPQVYTLPP SREEMTKNQV SLTCLVKGFY PSDIAVEWES   360
NGQPENNYKT TPPVLDSDGS FFLYSKLTVD KSRWQQGNVF SCSVMHEALH NHYTQKSLSL   420
SPGGGGGSGG GGSGGGGSGG GGSFTVTVPK DLYVVEYGSN MTIECKFPVE KQLDLAALIV   480
YWEMEDKNII QFVHGEEDLK VQHSSYRQRA RLLKDQLSLG NAALQITDVK LQDAGVYRCM   540
ISYGGADYKR ITVKVNAPCN KINQRILVVD PVTSEHELTC QAECYPKAEV IWTSSDHQVL   600
SGKTTTTNSK REEKLFNVTS TLRINTTTNE IFYCTFRRLD PEENHTAELV IPELPLAHPP   660
NER                                                                663

SEQ ID NO: 228          moltype = AA   length = 387
FEATURE                 Location/Qualifiers
source                  1..387
                        mol_type = protein
                        organism = synthetic construct
SEQUENCE: 228
QAVHAAHAEI NGGGGSGGGG SGGGGSLEQP NVAISLSRTE ALNHHNTLVC SVTDFYPAKI    60
KVRWFRNGQE ETVGVSSTQL IRNGDWTFQV LVMLEMTPHQ GEVYTCHVEH PSLKSPITVE   120
WRAQSESARS KGGGGSGGGG SGGGGSGGGG SGGGGSGGGS SDKTHTCPPC PAPEAAGGPS   180
VFLFPPKPKD TLMISRTPEV TCVVVDVSHE DPEVKFNWYV DGVEVHNAKT KPREEQYNST   240
YRVVSVLTVL HQDWLNGKEY KCKVSNKALP APIEKTISKA KGQPREPQVY TLPPSREEMT   300
KNQVSLTCLV KGFYPSDIAV EWESNGQPEN NYKTTPPVLD SDGSFFLYSK LTVDKSRWQQ   360
GNVFSCSVMH EALHNHYTQK SLSLSPG                                      387

SEQ ID NO: 229          moltype = AA   length = 11
FEATURE                 Location/Qualifiers
source                  1..11
                        mol_type = protein
                        organism = synthetic construct
SEQUENCE: 229
QAVHAAHAEI N                                                        11

SEQ ID NO: 230          moltype = AA   length = 663
FEATURE                 Location/Qualifiers
source                  1..663
                        mol_type = protein
                        organism = synthetic construct
SEQUENCE: 230
FTVTVPKDLY VVEYGSNMTI ECKFPVEKQL DLAALIVYWE MEDKNIIQFV HGEEDLKVQH    60
SSYRQRARLL KDQLSLGNAA LQITDVKLQD AGVYRCMISY GGADYKRITV KVNAPYNKIN   120
QRILVVDPVT SEHELTCQAE GYPKAEVIWT SSDHQVLSGK TTTTNSKREE KLFNVTSTLR   180
INTTTNEIFY CTFRRLDPEE NHTAELVIPE LPLAHPPNER GGGGSGGGGS GGGGSGGGGS   240
IKEEHVIIQA EFYLNPDQSG EFMFDFDGDE IFHVDMAKKE TVWRLEEFGR FASFEAQGAL   300
ANIAVDKANL ECMTKRSNYT PITNVPPEVT VLTNSPVELR EPNVLICFID KFTPPVVNVT   360
WLRNGKPVTT GVSETVFLPR EDHLFRKFHY LPFLPSTEDV YDCRVEHWGL DEPLLKHWEF   420
DAPSPLPETG GSAAAGGDKT HTCPPCPAPE AAGGPSVFLF PPKPKDTLMI SRTPEVTCVV   480
VDVSHEDPEV KFNWYVDGVE VHNAKTKPRE EQYNSTYRVV SVLTVLHQDW LNGKEYKCKV   540
SNKALPAPIE KTISKAKGQP REPQVYTLPP SREEMTKNQV SLTCLVKGFY PSDIAVEWES   600
NGQPENNYKT TPPVLDSDGS FFLYSKLTVD KSRWQQGNVF SCSVMHEALH NHYTQKSLSL   660
SPG                                                                663

SEQ ID NO: 231          moltype = AA   length = 675
FEATURE                 Location/Qualifiers
source                  1..675
                        mol_type = protein
                        organism = synthetic construct
SEQUENCE: 231
IKEEHVIIQA EFYLNPDQSG EFMFDFDGDE IFHVDMAKKE TVWRLEEFGR FASFEAQGAL    60
ANIAVDKANL EIMTKRSNYT PITNVPPEVT VLTNSPVELR EPNVLICFID KFTPPVVNVT   120
WLRNGKPVTT GVSETVFLPR EDHLFRKFHY LPFLPSTEDV YDCRVEHWGL DEPLLKHWEF   180
DAPSPLPETG GGGSGGGGSG GGGSGGGGSF TVTVPKDLYV VEYGSNMTIE CKFPVEKQLD   240
LAALIVYWEM EDKNIIQFVH GEEDLKVQHS SYRQRARLLK DQLSLGNAAL QITDVKLQDA   300
GVYRCMISYG GADYKRITVK VNAPYNKINQ RILVVDPVTS EHELTCQAEG YPKAEVIWTS   360
SDHQVLSGKT TTTNSKREEK LFNVTSTLRI NTTTNEIFYC TFRRLDPEEN HTAELVIPEL   420
PLAHPPNERG GGGSGGGGSG GGSGGGGSD KTHTCPPCPA PEAAGGPSVF LFPPPKPKDTL   480
MISRTPEVTC VVVDVSHEDP EVKFNWYVDG VEVHNAKTKP REEQYNSTYR VVSVLTVLHQ   540
DWLNGKEYKC KVSNKALPAP IEKTISKAKG QPREPQVYTL PPSREEMTKN QVSLTCLVKG   600
FYPSDIAVEW ESNGQPENNY KTTPPVLDSD GSFFLYSKLT VDKSRWQQGN VFSCSVMHEA   660
LHNHYTQKSL SLSPG                                                   675

SEQ ID NO: 232          moltype = AA   length = 462
FEATURE                 Location/Qualifiers
source                  1..462
                        mol_type = protein
                        organism = synthetic construct
SEQUENCE: 232
```

```
FTVTVPKDLY VVEYGSNMTI ECKFPVEKQL DLAALIVYWE MEDKNIIQFV HGEEDLKVQH    60
SSYRQRARLL KDQLSLGNAA LQITDVKLQD AGVYRCMISY GGADYKRITV KVNAPYNKIN   120
QRILVVDPVT SEHELTCQAE GYPKAEVIWT SSDHQVLSGK TTTTNSKREE KLFNVTSTLR   180
INTTTNEIFY CTFRRLDPEE NHTAELVIPE LPLAHPPNER GGGGSGGGGS GGGGSNFFRM   240
VISNPAATGG GGSGGGGSGG GGSGDTRPRF LEQVKHECHF FNGTERVRFL DRYFYHQEEY   300
VRFDSDVGEY RAVTELGRPD AEYWNSQKDL LEQKRAAVDT YCRHNYGVGE SFTVQRRVYP   360
EVTVYPAKTQ PLQHHNLLVC SVNGFYPASI EVRWFRNGQE EKTGVVSTGL IQNGDWTFQT   420
LVMLETVPRS GEVYTCQVEH PSLTSPLTVE WRARSESAQS KM                     462

SEQ ID NO: 233          moltype = AA  length = 462
FEATURE                 Location/Qualifiers
source                  1..462
                        mol_type = protein
                        organism = synthetic construct
SEQUENCE: 233
NFFRMVISNP AATGGGGSGG GGSGGGGSGD TRPRFLEQVK HECHFFNGTE RVRFLDRYFY    60
HQEEYVRFDS DVGEYRAVTE LGRPDAEYWN SQKDLLEQKR AAVDTYCRHN YGVGESFTVQ   120
RRVYPEVTVY PAKTQPLQHH NLLVCSVNGF YPASIEVRWF RNGQEEKTGV VSTGLIQNGD   180
WTFQTLVMLE TVPRSGEVYT CQVEHPSLTS PLTVEWRARS ESAQSKMGGG GSGGGGSGGG   240
GSFTVTVPKD LYVVEYGSNM TIECKFPVEK QLDLAALIVY WEMEDKNIIQ FVHGEEDLKV   300
QHSSYRQRAR LLKDQLSLGN AALQITDVKL QDAGVYRCMI SYGGADYKRI TVKVNAPYNK   360
INQRILVVDP VTSEHELTCQ AEGYPKAEVI WTSSDHQVLS GKTTTTNSKR EEKLFNVTST   420
LRINTTTNEI FYCTFRRLDP EENHTAELVI PELPLAHPPN ER                     462

SEQ ID NO: 234          moltype = AA  length = 5
FEATURE                 Location/Qualifiers
source                  1..5
                        mol_type = protein
                        organism = synthetic construct
SEQUENCE: 234
GGCGS                                                                5

SEQ ID NO: 235          moltype = AA  length = 5
FEATURE                 Location/Qualifiers
source                  1..5
                        mol_type = protein
                        organism = synthetic construct
SEQUENCE: 235
GCGGS                                                                5

SEQ ID NO: 236          moltype = AA  length = 5
FEATURE                 Location/Qualifiers
VARIANT                 4
                        note = X is any amino acid other than proline
source                  1..5
                        mol_type = protein
                        organism = synthetic construct
SEQUENCE: 236
VPGXG                                                                5

SEQ ID NO: 237          moltype = AA  length = 150
FEATURE                 Location/Qualifiers
source                  1..150
                        mol_type = protein
                        organism = synthetic construct
SEQUENCE: 237
IGHPSPPPEK KELRKVAHLT GKSNSRSMPL EWEDTYGIVL LSGVKYKKGG LVINETGLYF    60
VYSKVYFRGQ SCNNLPLSHK VYMRNSKYPQ DLVMMEGKMM SYCTTGQMWA RSSYLGAVFN   120
LTSADHLYVN VSELSLVNFE ESQTFFGLYK                                    150
```